United States Patent
Han et al.

(10) Patent No.: US 12,415,801 B2
(45) Date of Patent: Sep. 16, 2025

(54) ORGANIC LIGHT-EMITTING DEVICE

(71) Applicant: LG CHEM, LTD., Seoul (KR)

(72) Inventors: Miyeon Han, Daejeon (KR); Sung Kil Hong, Daejeon (KR); Dong Hoon Lee, Daejeon (KR); Jungoh Huh, Daejeon (KR); Hyungjin Lee, Daejeon (KR); Dongheon Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 1020 days.

(21) Appl. No.: 17/043,130

(22) PCT Filed: Jun. 7, 2019

(86) PCT No.: PCT/KR2019/006863
§ 371 (c)(1),
(2) Date: Sep. 29, 2020

(87) PCT Pub. No.: WO2019/235873
PCT Pub. Date: Dec. 12, 2019

(65) Prior Publication Data
US 2021/0020842 A1 Jan. 21, 2021

(30) Foreign Application Priority Data
Jun. 8, 2018 (KR) .................. 10-2018-0066125

(51) Int. Cl.
| | | |
|---|---|---|
| *C07D 405/10* | (2006.01) | |
| *C07D 251/24* | (2006.01) | |
| *C07D 307/77* | (2006.01) | |
| *C07D 405/04* | (2006.01) | |
| *C07D 409/04* | (2006.01) | |
| *C07D 493/04* | (2006.01) | |
| *C09K 11/06* | (2006.01) | |
| *H10K 50/11* | (2023.01) | |
| *H10K 50/16* | (2023.01) | |
| *H10K 50/17* | (2023.01) | |
| *H10K 50/18* | (2023.01) | |
| *H10K 85/60* | (2023.01) | |
| *H10K 101/10* | (2023.01) | |

(52) U.S. Cl.
CPC ......... *C07D 405/10* (2013.01); *C07D 251/24* (2013.01); *C07D 307/77* (2013.01); *C07D 405/04* (2013.01); *C07D 409/04* (2013.01); *C07D 493/04* (2013.01); *C09K 11/06* (2013.01); *H10K 85/615* (2023.02); *H10K 85/626* (2023.02); *H10K 85/654* (2023.02); *H10K 85/6574* (2023.02); *H10K 85/6576* (2023.02); *C09K 2211/1018* (2013.01); *H10K 50/11* (2023.02); *H10K 50/16* (2023.02); *H10K 50/171* (2023.02); *H10K 50/18* (2023.02); *H10K 2101/10* (2023.02)

(58) Field of Classification Search
CPC ............... H10K 85/615; H10K 85/654; H10K 85/6574; H10K 85/6576; H10K 85/626; H10K 50/11; C07D 251/24; C07D 307/77; C07D 405/04; C07D 405/10; C07D 409/04; C07D 493/04; C09K 11/06; C09K 2211/1018
See application file for complete search history.

(56) References Cited

U.S. PATENT DOCUMENTS

| | | | |
|---|---|---|---|
| 2004/0251816 A1 | 12/2004 | Leo et al. | |
| 2015/0041773 A1 | 2/2015 | Park et al. | |
| 2016/0276596 A1 | 9/2016 | Jang et al. | |
| 2016/0351817 A1 | 12/2016 | Kim et al. | |
| 2017/0133600 A1 | 5/2017 | Pyo et al. | |
| 2018/0066180 A1 * | 3/2018 | Huh ............ | C07D 251/12 |
| 2018/0337341 A1 * | 11/2018 | Heo ............ | C07D 405/14 |
| 2019/0214571 A1 | 7/2019 | Huh et al. | |
| 2019/0296238 A1 | 9/2019 | Cha et al. | |
| 2019/0393426 A1 * | 12/2019 | Masuda ........ | H10K 85/623 |
| 2020/0181096 A1 * | 6/2020 | Yang ............ | C07D 401/14 |
| 2020/0287142 A1 * | 9/2020 | Huh ............. | H10K 85/6572 |
| 2021/0305516 A1 * | 9/2021 | Heo ............. | C07D 405/10 |

FOREIGN PATENT DOCUMENTS

| | | | |
|---|---|---|---|
| CN | 107068878 | 8/2017 | |
| CN | 106164215 | 2/2023 | |
| KR | 10-2015-0018229 | 2/2015 | |
| KR | 10-1593368 | 2/2016 | |
| KR | 1593368 B1 * | 2/2016 | ........... C07D 251/12 |
| KR | 10-2016-0126862 | 11/2016 | |
| KR | 10-2017-0055411 | 5/2017 | |
| KR | 10-2017-0058618 | 5/2017 | |

(Continued)

OTHER PUBLICATIONS

Ikeda et al., machine translation of WO-2014034891-A1 (Year: 2014).*
Han et al., machine translation of KR-1593368-B1 (Year: 2016).*
Zhang et al., machine translation of WO-2018041123-A1 (2018) pp. 1-31. (Year: 2018).*
Heo D et al., machine translation of WO-2020022771-A1 (2020) pp. 1-201. (Year: 2020).*

*Primary Examiner* — Dylan C Kershner
(74) *Attorney, Agent, or Firm* — Bryan Cave Leighton Paisner LLP

(57) ABSTRACT

Provided is an organic light-emitting device comprising: a first electrode; a second electrode provided to face the first electrode; and a first organic material layer and a second organic material layer provided between the first electrode and the second electrode, in which the first organic material layer includes a compound of Formula 1, and the second organic material layer includes a compound of Formula 2.

8 Claims, 2 Drawing Sheets

(56) References Cited

FOREIGN PATENT DOCUMENTS

| KR | 10-2017-0058619 | | | 5/2017 | |
|----|----|----|----|----|----|
| KR | 10-2017-0134264 | | | 12/2017 | |
| KR | 10-2017-0136916 | | | 12/2017 | |
| KR | 10-2018-0111558 | | | 10/2018 | |
| WO | 2003-012890 | | | 2/2003 | |
| WO | WO-2014034891 | A1 | * | 3/2014 | ............. C09K 11/06 |
| WO | WO-2016171406 | A2 | * | 10/2016 | ........... C07D 251/12 |
| WO | WO-2017146466 | A1 | * | 8/2017 | ........... C07D 251/24 |
| WO | WO-2018041123 | A1 | * | 3/2018 | |
| WO | WO-2018139662 | A1 | * | 8/2018 | ............. C09K 11/06 |
| WO | WO-2018221985 | A1 | * | 12/2018 | ........... C07D 213/16 |
| WO | WO-2019245160 | A1 | * | 12/2019 | ............. C09K 11/06 |
| WO | WO-2020022771 | A1 | * | 1/2020 | ............. H10K 50/11 |
| WO | WO-2020050585 | A1 | * | 3/2020 | ........... C07D 213/16 |

* cited by examiner

[Figure 1]
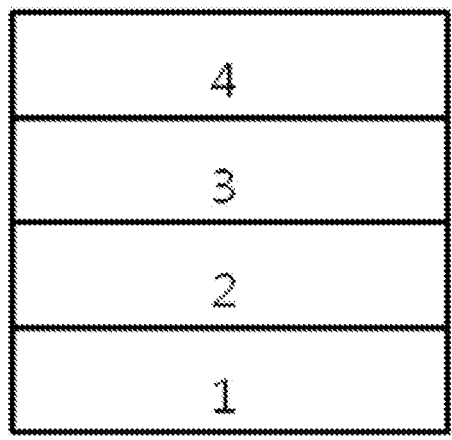
[Figure 2]
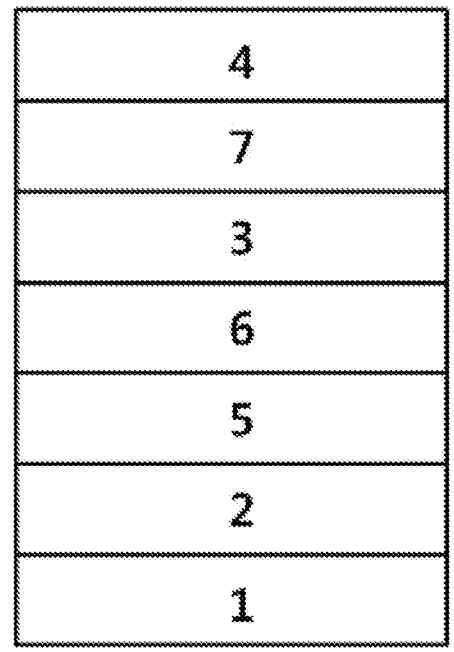

[Figure 3]
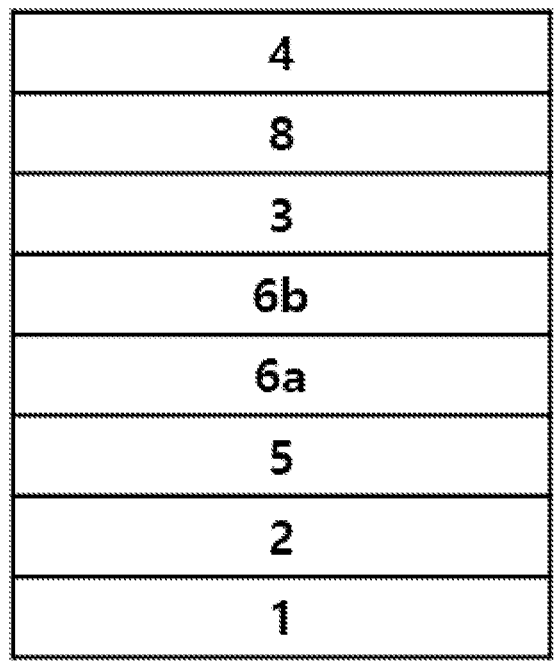

ORGANIC LIGHT-EMITTING DEVICE

CROSS-REFERENCE TO RELATED APPLICATIONS

This application is a National Stage Application of International Application No. PCT/KR2019/006863 filed on Jun. 7, 2019, which claims priority to and the benefit of Korean Patent Application No. 10-2018-0066125 filed in the Korean Intellectual Property Office on Jun. 8, 2018, the entire contents of which are incorporated herein by reference.

TECHNICAL FIELD

The present application relates to an organic light emitting device.

BACKGROUND

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer has in many cases a multi-layered structure composed of different materials in order to improve the efficiency and stability of the organic light emitting device, and for example, can be composed of a hole injection layer, a hole transport layer, a light emitting layer, an electron transport layer, an electron injection layer, and the like. In the structure of the organic light emitting device, if a voltage is applied between the two electrodes, holes are injected from the positive electrode into the organic material layer and electrons are injected from the negative electrode into the organic material layer, and when the injected holes and electrons meet each other, an exciton is formed, and light is emitted when the exciton falls down again to a ground state.

There is a continuous need for developing a new material for the aforementioned organic light emitting device.

BRIEF DESCRIPTION

Technical Problem

The present application has been made in an effort to provide an organic light emitting device.

Technical Solution

The present application provides an organic light emitting device including: a first electrode; a second electrode provided to face the first electrode; and a first organic material layer and a second organic material layer provided between the first electrode and the second electrode,
wherein the first organic material layer includes a compound of the following Formula 1, and
the second organic material layer includes a compound of the following Formula 2:

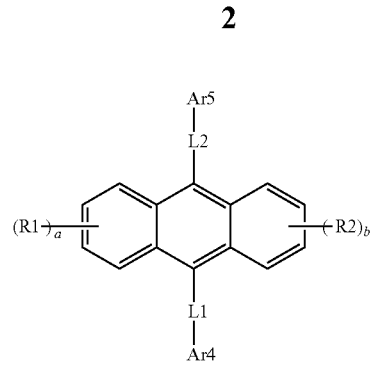

Formula 1 wherein in Formula 1:

R1 and R2 are each independently hydrogen, deuterium, a halogen group, a cyano group, a nitro group, a substituted or unsubstituted alkyl group, a substituted or unsubstituted haloalkyl group, a substituted or unsubstituted haloalkoxy group, a substituted or unsubstituted cycloalkyl group, a substituted or unsubstituted alkenyl group, a substituted or unsubstituted aryl group, or a substituted or unsubstituted heterocyclic group;

L1 and L2 are each independently a single bond, or a substituted or unsubstituted arylene group;

Ar4 is a substituted or unsubstituted aryl group, or a substituted or unsubstituted heterocyclic group;

Ar5 is the following Formula 3;

a and b are each independently an integer from 0 to 4;

when a and b are each independently 2 or more, the substituents in the parenthesis are the same as or different from each other,

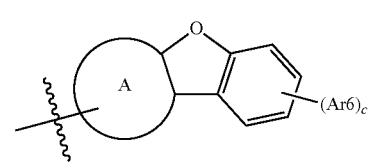

Formula 3 wherein in Formula 3:

A is a substituted or unsubstituted phenyl group, a substituted or unsubstituted naphthyl group, or a substituted or unsubstituted dibenzofuran group;

Ar6 is hydrogen; deuterium, a substituted or unsubstituted aryl group, or a substituted or unsubstituted heterocyclic group;

c is an integer from 0 to 4;

when c is 2 or more, two or more Ar6s are the same as or different from each other, and adjacent Ar6s can be bonded to each other to form a substituted or unsubstituted aryl group or a substituted or unsubstituted heterocyclic group;

when A is a substituted or unsubstituted phenyl group, c is 2 or more and adjacent Ar6s are bonded to each other to form a substituted or unsubstituted aryl group or a substituted or unsubstituted heterocyclic group,

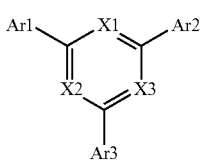

Formula 2 wherein in Formula 2:
at least one of X1 to X3 is N, and the remaining is or are CR;
R is hydrogen, deuterium, a substituted or unsubstituted alkyl group, a substituted or unsubstituted cycloalkyl group, a substituted or unsubstituted alkenyl group, a substituted or unsubstituted aryl group, or a substituted or unsubstituted heterocyclic group, or can be bonded to an adjacent substituent to form a ring;
Ar1 to Ar3 are each independently a substituted or unsubstituted aryl group, or a substituted or unsubstituted heterocyclic group;
at least one of Ar1 to Ar3 includes a cyano group; or
at least one of Ar1 to Ar3 is -L3-Ar201, where L3 is a single bond or a substituted or unsubstituted arylene group, and Ar201 is a substituted or unsubstituted 9-fluorenyl group or a substituted or unsubstituted heterocyclic group including O or S.

Advantageous Effects

An organic light emitting device using the compound according to an exemplary embodiment of the present application can have a low driving voltage, high light emitting efficiency, or a long lifetime.

BRIEF DESCRIPTION OF DRAWINGS

FIG. 1 illustrates an example of an organic light emitting device in which a substrate 1, a positive electrode 2, a light emitting layer 3, and a negative electrode 4 are sequentially stacked.

FIG. 2 illustrates an example of an organic light emitting device in which a substrate 1, a positive electrode 2, a hole injection layer 5, a hole transport layer 6, a light emitting layer 3, an electron transport layer 7, and a negative electrode 4 are sequentially stacked.

FIG. 3 illustrates an example of an organic light emitting device in which a substrate 1, a positive electrode 2, a hole injection layer 5, a first hole transport layer 6a, a second hole transport layer 6b, a light emitting layer 3, an electron injection and transport layer 8, and a negative electrode 4 are sequentially stacked.

EXPLANATION OF REFERENCE NUMERALS AND SYMBOLS

1: Substrate
2: Positive electrode
3: Light emitting layer
4: Negative electrode
5: Hole injection layer
6: Hole transport layer
6a: First hole transport layer
6b: Second hole transport layer
7: Electron transport layer
8: Electron injection and transport layer

DETAILED DESCRIPTION

Hereinafter, the present specification will be described in more detail.

The present application provides an organic light emitting device including: a first electrode; a second electrode provided to face the first electrode; and a first organic material layer and a second organic material layer provided between the first electrode and the second electrode, in which the first organic material layer includes the compound of Formula 1, and the second organic material layer includes the compound of Formula 2.

The compound of Formula 1 has a structure in which a benzonaphthofuran of Ar5 is linked to anthracene. A polycyclic ring benzonaphthofuran is an electron donating group (EDG) which is abundant in electrons, and provides abundant electrons to an anthracene core. When the compound of Formula 1 is applied to a device, the high efficiency and low voltage characteristics of the device are improved.

The compound of Formula 2 includes a cyano group, or includes a polycyclic heterocyclic group or a 9-fluorenyl group.

When the compound of Formula 2 includes a cyano group, the long lifetime characteristic of an organic light emitting device is improved due to an increase in the dipole moment in the molecule when the compound is used as a material for an electron transport layer or electron injection layer. Further, the cyano group acts as an electron withdrawing group (EWG) due to the strong n-type nature. The cyano group can withdraw electrons, thereby controlling the electron mobility in an electron transport layer or electron injection layer. As a result, the hole-electron balance is ultimately improved, so that the long lifetime characteristic of the organic light emitting device is improved.

In addition, the compound of Formula 2 includes a polycyclic heterocyclic group including O or S or a 9-fluorenyl group. The polycyclic heterocyclic group including O or S specifically has a spiro structure in which fluorene and xanthene or fluorene and thioxanthene are fused. The spiro structure is located in a plane in which fluorene and (thio)xanthene are orthogonal to each other in a 3D space. In this case, the compound of Formula 2 has a high glass transition temperature and excellent thermal stability, and exhibits stable blue emission in a solid state.

When the compound of Formula 1 and the compound of Formula 2 are used together in an organic light emitting device, the compound of Formula 2 can control the abundant electron transfer which the compound of Formula 1 has. Furthermore, the aforementioned low voltage and high efficiency characteristics of Formula 1, the aforementioned long lifetime characteristic and the thermal stability due to the high glass transition temperature, of Formula 2 are secured, so that it is possible to obtain an organic light emitting device with improved stability.

In the present specification,

means a moiety to be linked.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent can be substituted, and when two or more are substituted, the two or more substituents can be the same as or different from each other.

In the present specification, the term "substituted or unsubstituted" means being substituted with one or two or more substituents selected from the group consisting of hydrogen, a halogen group, a cyano group, a nitro group, a hydroxyl group, a substituted or unsubstituted alkyl group, a substituted or unsubstituted cycloalkyl group, a substituted or unsubstituted alkenyl group, a substituted or unsubstituted amine group, a substituted or unsubstituted aryl group, and a substituted or unsubstituted heterocyclic group, or being substituted with a substituent to which two or more substituents are linked among the substituents exemplified above, or having no substituent. For example, "the substituent to which two or more substituents are linked" can be a biphenyl group. That is, the biphenyl group can also be an aryl group, and can be interpreted as a substituent to which two phenyl groups are linked.

In the present specification, the fact that two or more substituents are linked indicates that hydrogen of any one substituent is linked to another substituent. For example, an isopropyl group and a phenyl group can be linked to each other to become a substituent of

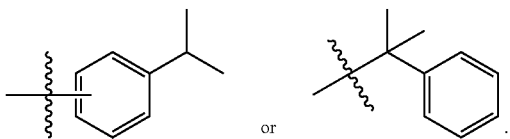

or

In the present specification, the case where three substituents are linked to one another includes not only a case where (Substituent 1)-(Substituent 2)-(Substituent 3) are consecutively linked to one another, but also a case where (Substituent 2) and (Substituent 3) are linked to (Substituent 1). For example, two phenyl groups and an isopropyl group can be linked to each other to become a substituent of

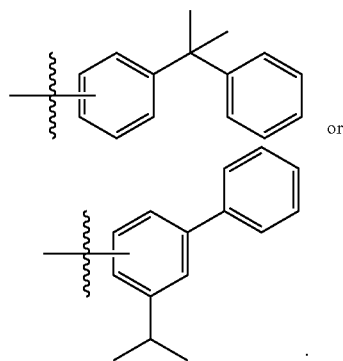

or

The same also applies to the case where four or more substituents are linked to each other.

In the present specification, N % substitution with deuterium means that N % of hydrogen available in the corresponding structure is substituted with deuterium. For example, 25% substitution of dibenzofuran with deuterium means that two of eight hydrogens of dibenzofuran are substituted with two deuteriums.

In the present specification, the degree of deuteration can be confirmed by a publicly-known method such as nuclear magnetic resonance spectroscopy ($^1$H NMR) or GC/MS.

In the present specification, examples of a halogen group include fluorine, chlorine, bromine or iodine.

In the present specification, an alkyl group can be straight-chained or branched, and the number of carbon atoms thereof is not particularly limited, but is preferably 1 to 60. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methyl-pentyl, 3,3-dimethylbutyl, 2-ethylbutyl, heptyl, n-heptyl, 1-methylhexyl, cyclopentylmethyl, cyclohexyl-methyl, octyl, n-octyl, tert-octyl, 1-methylheptyl, 2-ethylhexyl, 2-propyl-pentyl, n-nonyl, 2,2-dimethyl-heptyl, 1-ethyl-propyl, 1,1-dimethyl-propyl, isohexyl, 2-methylpentyl, 4-methylhexyl, 5-methylhexyl, and the like, but are not limited thereto.

In the present specification, the cycloalkyl group is not particularly limited, but is preferably a cycloalkyl group having 3 to 60 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an alkoxy group can be straight-chained, branched, or cyclic. The number of carbon atoms of the alkoxy group is not particularly limited, but is preferably 1 to 20. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methyl-benzyloxy, and the like, but are not limited thereto.

In the present specification, an alkenyl group can be straight-chained or branched, and the number of carbon atoms thereof is not particularly limited, but is preferably 2 to 40. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenyl-vinyl-1-yl, 2-phenylvinyl-1-yl, 2,2-diphenyl-vinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, when an aryl group is a monocyclic aryl group, the number of carbon atoms thereof is not particularly limited, but is preferably 6 to 25. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 24. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group can be substituted, and adjacent substituents can be bonded to each other to form a ring.

When the fluorenyl group is substituted, the substituent can be

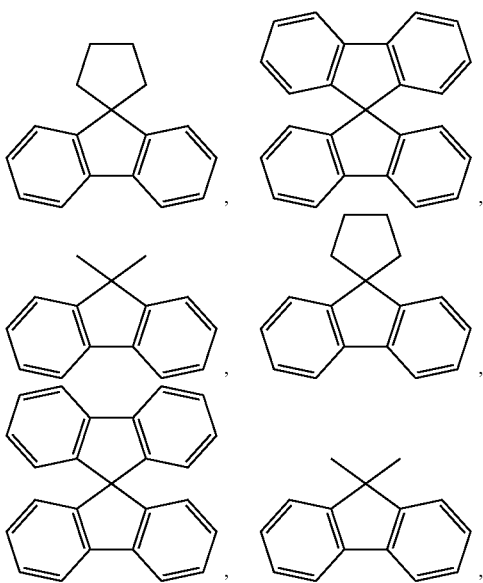

and the like, but is not limited thereto.

In the present specification, the 9-fluorenyl group indicates that the 9th carbon of the fluorenyl group is linked to another substituent. Specifically, the 9-fluorenyl group indicates a form which is

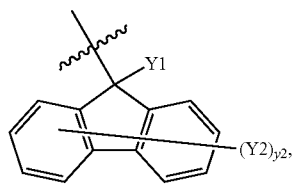

in which Y1 and Y2 are the same as or different from each other, and each can be an alkyl group, an aryl group, or a heterocyclic group. When y2 is an integer from 0 to 8 and 2 or more, the Y2s are the same as or different from each other.

In the present specification, a heterocyclic group includes one or more atoms other than carbon, that is, one or more heteroatoms, and specifically, the hetero-atom can include one or more atoms selected from the group consisting of O, N, Se, S, and the like. The number of carbon atoms of the heterocyclic group is not particularly limited, but is preferably 2 to 60, 2 to 30 or 2 to 20. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzo-carbazole group, a benzothiophene group, a dibenzo-thiophene group, a benzofuranyl group, a phenanthroline group, a thiazolyl group, an isoxazolyl group, an oxadiazolyl group, a thiadiazolyl group, a benzo-thiazolyl group, a phenothiazinyl group, a dibenzofuranyl group, and the like, but are not limited thereto.

In an exemplary embodiment of the present application, R1 and R2 are each independently hydrogen, deuterium, a substituted or unsubstituted alkyl group, a substituted or unsubstituted cycloalkyl group, a substituted or unsubstituted alkenyl group, a substituted or unsubstituted aryl group, or a substituted or unsubstituted heterocyclic group.

In an exemplary embodiment of the present application, R1 and R2 are each independently hydrogen, deuterium, a substituted or unsubstituted aryl group, or a substituted or unsubstituted heterocyclic group.

In an exemplary embodiment of the present application, R1 and R2 are each independently hydrogen, deuterium, or an aryl group having 6 to 30 carbon atoms, which is unsubstituted or substituted with deuterium.

In an exemplary embodiment of the present application, R1 and R2 are each independently hydrogen, deuterium, or an aryl group having 6 to 30 carbon atoms.

In an exemplary embodiment of the present application, R1 and R2 are each independently hydrogen or deuterium.

In an exemplary embodiment of the present application, L1 and L2 are each independently a single bond or a substituted or unsubstituted arylene group having 6 to 60 carbon atoms.

In an exemplary embodiment of the present application, L1 and L2 are each independently a single bond or a substituted or unsubstituted arylene group having 6 to 30 carbon atoms.

In an exemplary embodiment of the present application, L1 and L2 are each independently a single bond or a substituted or unsubstituted arylene group having 6 to 15 carbon atoms.

In an exemplary embodiment of the present application, L1 and L2 are each independently a single bond or an arylene group having 6 to 15 carbon atoms, which is unsubstituted or substituted with deuterium.

In an exemplary embodiment of the present application, L1 and L2 are each independently a single bond; a phenylene group which is unsubstituted or substituted with deuterium; a biphenylene group which is unsubstituted or substituted with deuterium; a terphenylene group which is unsubstituted or substituted with deuterium; or a naphthylene group which is unsubstituted or substituted with deuterium.

In an exemplary embodiment of the present application, L1 and L2 are each independently a single bond, a phenylene group, a biphenylene group, a terphenylene group, or a naphthylene group.

In an exemplary embodiment of the present application, L1 and L2 are the same as or different from each other.

In an exemplary embodiment of the present application, L1 and L2 are substituted with deuterium.

In an exemplary embodiment of the present application, L1 is a single bond.

In an exemplary embodiment of the present application, L2 is a single bond; a phenylene group which is unsubstituted or substituted with deuterium; a biphenylene group which is unsubstituted or substituted with deuterium; or a naphthylene group which is unsubstituted or substituted with deuterium.

In an exemplary embodiment of the present application, L2 is a single bond, a phenylene group, a biphenylene group, or a naphthylene group.

In an exemplary embodiment of the present application, L1 and L2 are each independently a single bond or any one selected from the following structures.

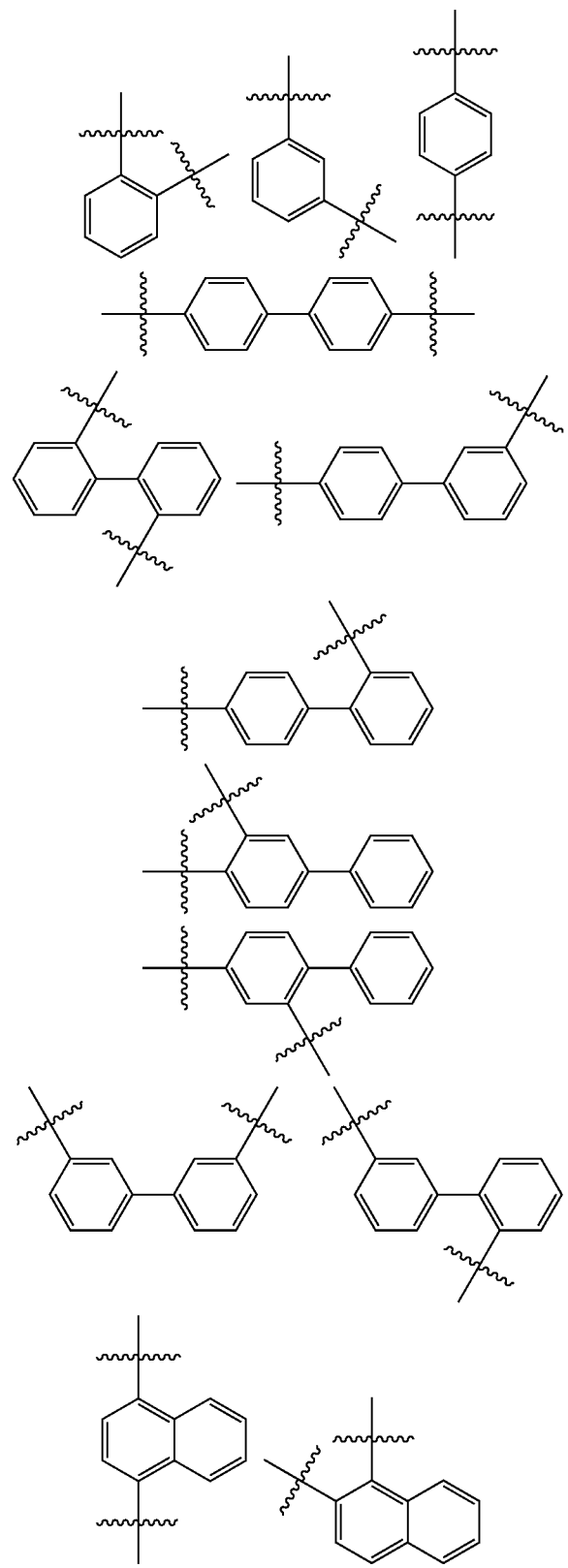

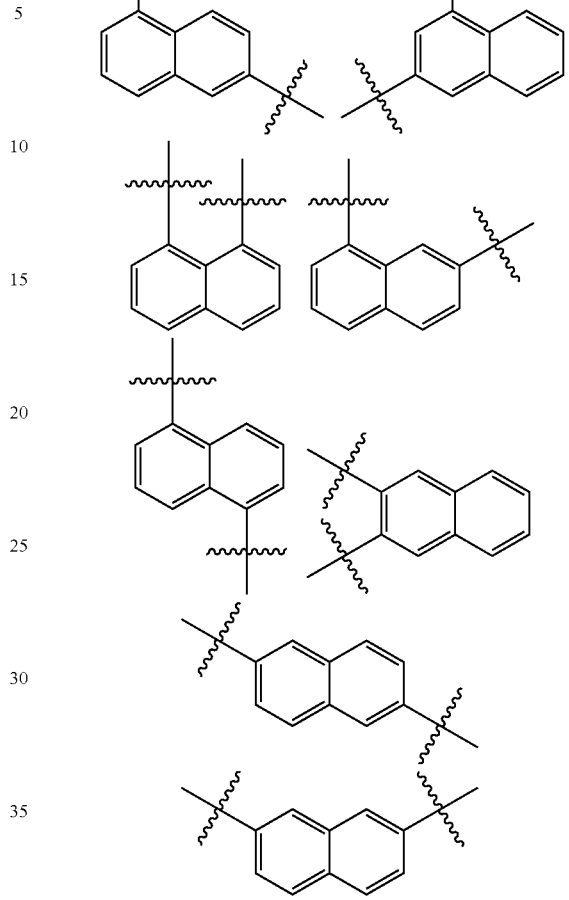

The structures are unsubstituted or substituted with deuterium.

In an exemplary embodiment of the present application, Ar4 is a substituted or unsubstituted aryl group having 6 to 60 carbon atoms, or a substituted or unsubstituted heterocyclic group having 2 to 60 carbon atoms.

In an exemplary embodiment of the present application, Ar4 is a substituted or unsubstituted aryl group having 6 to 30 carbon atoms, or a substituted or unsubstituted heterocyclic group having 2 to 30 carbon atoms.

In an exemplary embodiment of the present application, Ar4 is a substituted or unsubstituted aryl group having 6 to 15 carbon atoms, or a substituted or unsubstituted heterocyclic group having 2 to 15 carbon atoms.

In an exemplary embodiment of the present application, Ar4 is a substituted or unsubstituted aryl group having 6 to 15 carbon atoms.

In an exemplary embodiment of the present application, Ar4 is a phenyl group which is unsubstituted or substituted with deuterium, a biphenyl group which is unsubstituted or substituted with deuterium, a terphenyl group which is unsubstituted or substituted with deuterium, a naphthyl group which is unsubstituted or substituted with deuterium, or a phenanthrene group which is unsubstituted or substituted with deuterium.

In an exemplary embodiment of the present application, Ar4 is a phenyl group, a biphenyl group, a terphenyl group, a naphthyl group, or a phenanthrene group.

In an exemplary embodiment of the present application, a and b are each independently an integer from 0 to 4, and when a and b are each independently 2 or more, substituents in the parenthesis are the same as or different from each other.

In an exemplary embodiment of the present application, Ar5 is Formula 3:

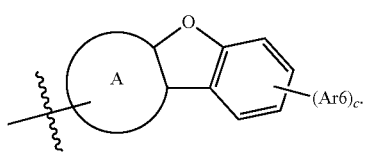

Formula 3

In an exemplary embodiment of the present application, A is a substituted or unsubstituted phenyl group, a substituted or unsubstituted naphthyl group, or a substituted or unsubstituted dibenzofuran group.

In an exemplary embodiment of the present application, Ar6 is hydrogen, deuterium, a substituted or unsubstituted aryl group having 6 to 60 carbon atoms, or a substituted or unsubstituted heterocyclic group having 2 to 60 carbon atoms.

In an exemplary embodiment of the present application, Ar6 is hydrogen, deuterium, a substituted or unsubstituted aryl group having 6 to 30 carbon atoms, or a substituted or unsubstituted heterocyclic group having 2 to 30 carbon atoms.

In an exemplary embodiment of the present application, Ar6 is hydrogen, deuterium, a substituted or unsubstituted aryl group having 6 to 15 carbon atoms, or a substituted or unsubstituted heterocyclic group having 2 to 15 carbon atoms.

In an exemplary embodiment of the present application, Ar6 is hydrogen, deuterium, or a substituted or unsubstituted aryl group having 6 to 15 carbon atoms.

In an exemplary embodiment of the present application, Ar6 is hydrogen, deuterium, or a phenyl group which is unsubstituted or substituted with deuterium.

In an exemplary embodiment of the present application, Ar6 is hydrogen, deuterium, or a phenyl group.

In an exemplary embodiment of the present application, c is an integer from 0 to 4, and when c is 2 or more, two or more Ar6s are the same as or different from each other, and adjacent Ar6s can be bonded to each other to form a substituted or unsubstituted aryl group or a substituted or unsubstituted heterocyclic group.

In an exemplary embodiment of the present application, when A is a substituted or unsubstituted phenyl group, c is 2 or more and adjacent Ar6s are bonded to each other to form a substituted or unsubstituted aryl group or a substituted or unsubstituted heterocyclic group. That is, Formula 3 is provided in a form in which a ring is additionally condensed in a dibenzofuran group.

In an exemplary embodiment of the present application, Formula 3 is any one of the following Formulae 301 to 312:

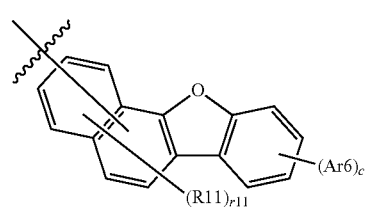

Formula 301

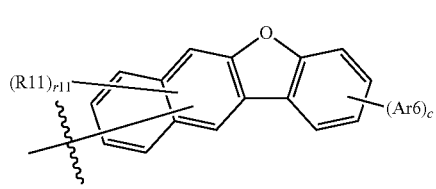

Formula 302

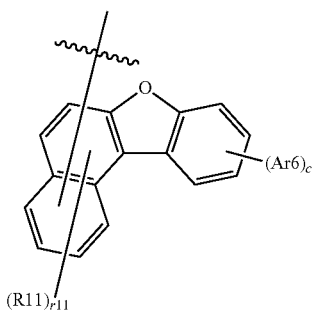

Formula 303

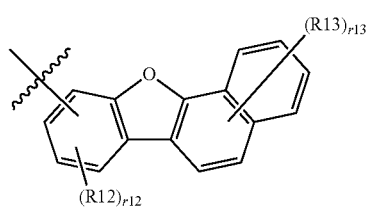

Formula 304

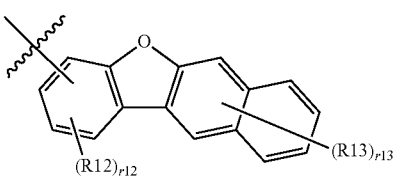

Formula 305

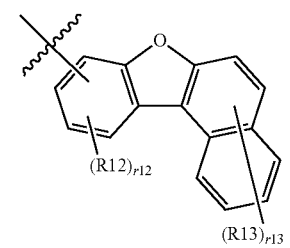

Formula 306

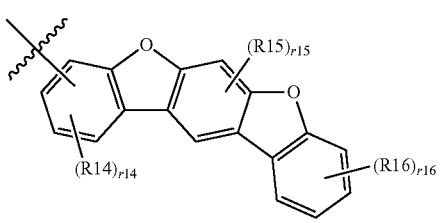

Formula 307

-continued

Formula 308
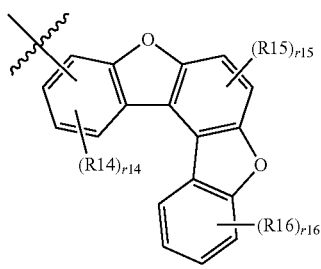

Formula 309
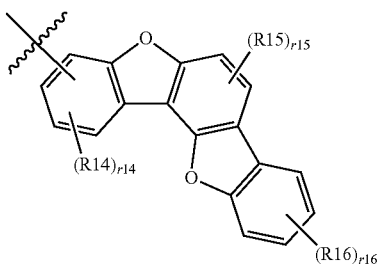

Formula 310
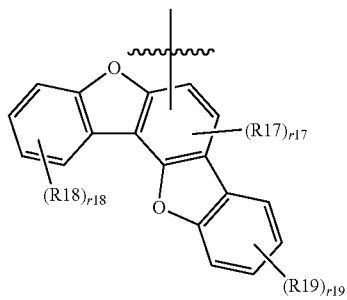

Formula 311
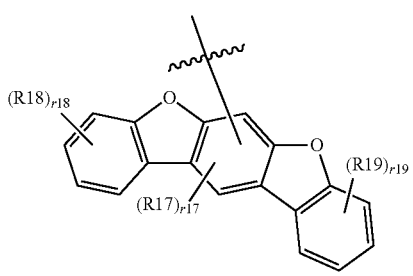

Formula 312
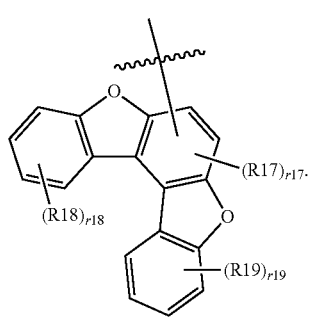

In Formulae 301 to 312, the definitions of Ar6 and c are the same as those defined in Formula 3;

R11 to R19 are each independently hydrogen, deuterium, a substituted or unsubstituted aryl group, or a substituted or unsubstituted heterocyclic group;

r11 to r16, r18 and r19 are each an integer from 0 to 2, and when r11 to r16, r18 and r19 are each 2, the substituents in the parenthesis are the same as or different from each other; and r17 is 0 or 1.

In an exemplary embodiment of the present application, R11 to R19 are the same as or different from each other, and are each independently hydrogen, deuterium, a substituted or unsubstituted aryl group having 6 to 30 carbon atoms, or a substituted or unsubstituted heterocyclic group having 2 to 30 carbon atoms.

In an exemplary embodiment of the present application, R11 to R19 are the same as or different from each other, and are each independently hydrogen, deuterium, or an aryl group having 6 to 30 carbon atoms, which is unsubstituted or substituted with deuterium.

In an exemplary embodiment of the present application, R11 to R19 are the same as or different from each other, and are each independently hydrogen, deuterium, a phenyl group which is unsubstituted or substituted with deuterium, a biphenyl group which is unsubstituted or substituted with deuterium, a terphenyl group which is unsubstituted or substituted with deuterium, a naphthyl group which is unsubstituted or substituted with deuterium, or a phenanthrene group which is unsubstituted or substituted with deuterium.

In an exemplary embodiment of the present application, R11 to R19 are the same as or different from each other, and are each independently hydrogen, deuterium, or a phenyl group which is unsubstituted or substituted with deuterium.

In an exemplary embodiment of the present application, R11 to R19 are the same as or different from each other, and are each independently hydrogen, deuterium, or a phenyl group.

In an exemplary embodiment of the present application, R12 is an aryl group having 6 to 30 carbon atoms, which is unsubstituted or substituted with deuterium.

In an exemplary embodiment of the present application, R12 is a phenyl group which is unsubstituted or substituted with deuterium.

In an exemplary embodiment of the present application, R12 is a phenyl group.

In an exemplary embodiment of the present application, R15 is an aryl group having 6 to 30 carbon atoms, which is unsubstituted or substituted with deuterium.

In an exemplary embodiment of the present application, R15 is a phenyl group which is unsubstituted or substituted with deuterium.

In an exemplary embodiment of the present application, R15 is a phenyl group.

In an exemplary embodiment of the present application, r11 to r16 are each 0 or 1.

In an exemplary embodiment of the present application, Formula 1 includes deuterium. Specifically, Formula 1 includes a structure in which hydrogen is substituted with deuterium. As long as the site has a site to which hydrogen can be linked, deuterium can be linked to the site regardless of the position.

In an embodiment, when the structure of Formula 1 is substituted with deuterium, 30% or more of the structure is substituted with deuterium. In another exemplary embodiment, 40% or more of the structure of Formula 1 is substituted with deuterium. In still another exemplary embodiment, 60% or more of the structure of Formula 1 is substituted with deuterium. In yet another exemplary embodiment, 80% or more of the structure of Formula 1 is substituted with deuterium. In still yet another exemplary embodiment, 100% of the structure of Formula 1 is substituted with deuterium.

In an exemplary embodiment of the present application, when the structure of Formula 1 is substituted with deuterium, the corresponding structural formula can be

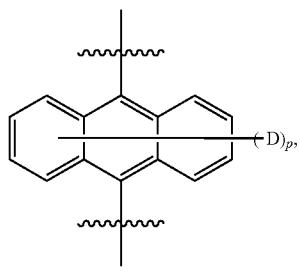

where D is deuterium, and p is (total number of available hydrogens of the corresponding structural formula)*an integer of 0.3 or more. A position where deuterium is substituted is not limited to the anthracene core, and any hydrogen that can be substituted throughout the structure can be substituted with deuterium regardless of the position.

In an exemplary embodiment of the present specification, p is an integer of 2 or more. In another exemplary embodiment, p is an integer of 4 or more. In still another exemplary embodiment, p is 8 or more. In yet another exemplary embodiment, p is 10 or more.

In an exemplary embodiment of the present specification, p is an integer of 35 or less. In another exemplary embodiment, p is 30 or less. In still another exemplary embodiment, p is 25 or less. In yet another exemplary embodiment, p is 20 or less. In still yet another exemplary embodiment, p is 16 or less. In the present specification, even though p is omitted, that means being substituted with two or more deuteriums.

When Formula 1 includes deuterium, the efficiency and lifetime of the device are improved. Specifically, when hydrogen is replaced with deuterium, chemical properties of the compound are rarely changed. However, since the atomic weight of deuterium is twice that of hydrogen, physical properties of a deuterated compound can be changed. As an example, a compound substituted with deuterium has a lower level of vibrational energy. The compound substituted with deuterium can prevent a decrease in quantum efficiency caused by a decrease in intermolecular Van der Waals force or a collision due to intermolecular vibration. Further, the C-D bond can improve stability of a compound. Thus, the compound of Formula 1 can include deuterium to improve the efficiency and lifetime of a device.

The compound of Formula 1 including deuterium can be prepared by a publicly-known deuterated reaction. According to an exemplary embodiment of the present specification, the compound of Formula 1 can be formed using a deuterated compound as a precursor, or deuterium can also be introduced into a compound via a hydrogen-deuterium exchange reaction in the presence of an acid catalyst using a deuterated solvent.

In an exemplary embodiment of the present application, at least one of X1 to X3 is N, and the remaining is or are CR.

In an exemplary embodiment of the present application, two of X1 to X3 are N, and the remaining one is CR.

In an exemplary embodiment of the present application, X1 and X2 are N, and X3 is CR.

In an exemplary embodiment of the present application, X1 and X3 are N, and X2 is CR.

In an exemplary embodiment of the present application, X2 and X3 are N, and X1 is CR.

In an exemplary embodiment of the present application, X1 to X3 are each N.

In an exemplary embodiment of the present application, R is hydrogen, deuterium, a substituted or unsubstituted alkyl group, a substituted or unsubstituted cycloalkyl group, a substituted or unsubstituted alkenyl group, a substituted or unsubstituted aryl group, or a substituted or unsubstituted heterocyclic group, or can be bonded to an adjacent substituent to form a ring.

In an exemplary embodiment of the present application, R is hydrogen, deuterium, a substituted or unsubstituted aryl group, or a substituted or unsubstituted heterocyclic group, or can be bonded to an adjacent substituent to form a ring.

In an exemplary embodiment of the present application, R is hydrogen, or deuterium, or can be bonded to an adjacent substituent to form a ring.

In an exemplary embodiment of the present application, R is hydrogen or deuterium.

In an exemplary embodiment of the present application, Ar1 to Ar3 are each independently a substituted or unsubstituted aryl group, or a substituted or unsubstituted heterocyclic group.

In an exemplary embodiment of the present application, at least one of Ar1 to Ar3 includes a cyano group; or
  at least one of Ar1 to Ar3 is -L3-Ar201, where L3 is a single bond or a substituted or unsubstituted arylene group, and Ar201 is a substituted or unsubstituted 9-fluorenyl group or a substituted or unsubstituted heterocyclic group including O or S.

In an exemplary embodiment of the present application, Ar1 to Ar3 are each independently a substituted or unsubstituted aryl group having 6 to 60 carbon atoms, or a substituted or unsubstituted heterocyclic group having 2 to 60 carbon atoms.

In an exemplary embodiment of the present application, Ar1 to Ar3 are each independently a substituted or unsubstituted aryl group having 6 to 35 carbon atoms, or a substituted or unsubstituted heterocyclic group having 2 to 30 carbon atoms.

In an exemplary embodiment of the present application, at least two of Ar1 to Ar3 are each independently a substituted or unsubstituted aryl group having 6 to 35 carbon atoms, and at least one of Ar1 to Ar3 includes a cyano group.

In an exemplary embodiment of the present application, at least two of Ar1 to Ar3 are each independently a substituted or unsubstituted aryl group having 6 to 30 carbon atoms, and at least one of Ar1 to Ar3 includes a cyano group.

In an exemplary embodiment of the present application, at least two of Ar1 to Ar3 are each independently an aryl group having 6 to 20 carbon atoms, which is unsubstituted or substituted with an aryl group, and at least one of Ar1 to Ar3 includes a cyano group.

In an exemplary embodiment of the present application, at least two of Ar1 to Ar3 are each independently a phenyl group which is unsubstituted or substituted with an aryl group, a biphenyl group which is unsubstituted or substituted with an aryl group, or a naphthyl group which is unsubstituted or substituted with an aryl group, and at least one of Ar1 to Ar3 includes a cyano group.

In an exemplary embodiment of the present application, at least one of Ar1 to Ar3 is an aryl group having 6 to 35 carbon atoms, which is substituted with a cyano group; or a heterocyclic group having 2 to 30 carbon atoms, which is substituted with a cyano group.

In an exemplary embodiment of the present application, at least one of Ar1 to Ar3 is a phenyl group which is substituted with a cyano group; a biphenyl group which is substituted with a cyano group; a naphthyl group which is substituted with a cyano group; a terphenyl group which is substituted with a cyano group; a fluorenyl group which is substituted with a cyano group; or a group including a cyano group and any one of the following Formulae 203 to 205.

In an exemplary embodiment of the present application, at least one of Ar1 to Ar3 is selected from the following Formulae 201 to 205:

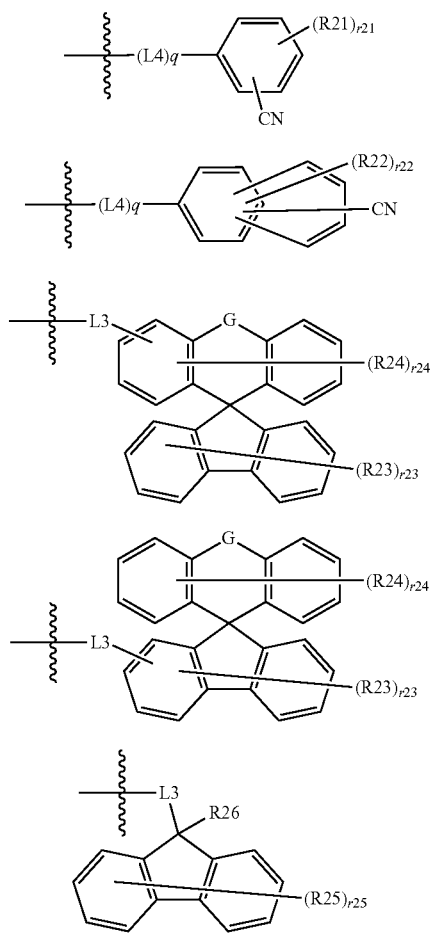

Formula 201

Formula 202

Formula 203

Formula 204

Formula 205

In Formulae 201 to 205:
L3 and L4 are the same as or different from each other, and are each independently a single bond, or a substituted or unsubstituted arylene group;
G is O or S;
R21 to R25 are the same as or different from each other, and are each independently hydrogen, deuterium, a cyano group, a substituted or unsubstituted aryl group, or a substituted or unsubstituted heterocyclic group;
R26 is a substituted or unsubstituted alkyl group, a substituted or unsubstituted aryl group, or a substituted or unsubstituted heterocyclic group;
q is an integer from 0 to 3, and when q is 2 or more, the L4s are the same as or different from each other; and r21 to r25 are an integer from 0 to 4, and when r21 to r25 are each 2 or more, the substituents in the parenthesis are the same as or different from each other.

In an exemplary embodiment of the present application, L4 is a single bond or a substituted or unsubstituted arylene group.

In an exemplary embodiment of the present application, L4 is a single bond or a substituted or unsubstituted arylene group having 6 to 30 carbon atoms.

In an exemplary embodiment of the present application, L4 is a single bond or a substituted or unsubstituted arylene group having 6 to 15 carbon atoms.

In an exemplary embodiment of the present application, L4 is a single bond; a phenylene group which is unsubstituted or substituted with a cyano group or an aryl group; a biphenylene group which is unsubstituted or substituted with a cyano group or an aryl group; a terphenylene group which is unsubstituted or substituted with a cyano group or an aryl group; a naphthylene group which is unsubstituted or substituted with a cyano group or an aryl group; or a fluorenylene group which is unsubstituted or substituted with a cyano group or an aryl group.

In an exemplary embodiment of the present application, L4 is a single bond, a phenylene group, a biphenylene group, a terphenylene group, a naphthylene group, a diphenylfluorenylene group, or a dimethylfluorenylene group.

In an exemplary embodiment of the present application, L4 is a single bond, a phenylene group, a biphenylene group, or a naphthylene group.

In an exemplary embodiment of the present application, q is an integer from 0 to 2.

In an exemplary embodiment of the present application, q is 0 or 1.

In an exemplary embodiment of the present application, L3 is a single bond or a substituted or unsubstituted arylene group.

In an exemplary embodiment of the present application, L3 is a single bond or a substituted or unsubstituted arylene group having 6 to 30 carbon atoms.

In an exemplary embodiment of the present application, L3 is a single bond or a substituted or unsubstituted arylene group having 6 to 15 carbon atoms.

In an exemplary embodiment of the present application, L3 is a single bond; a phenylene group which is unsubstituted or substituted with a cyano group or an aryl group; a biphenylene group which is unsubstituted or substituted with a cyano group or an aryl group; a terphenylene group which is unsubstituted or substituted with a cyano group or an aryl group; a naphthylene group which is unsubstituted or substituted with a cyano group or an aryl group; or a fluorenylene group which is unsubstituted or substituted with a cyano group or an aryl group.

In an exemplary embodiment of the present application, L3 is a single bond, a phenylene group, a biphenylene group, a terphenylene group, a naphthylene group, or a fluorenylene group.

In an exemplary embodiment of the present application, L3 is a single bond, a phenylene group, or a biphenylene group.

In an exemplary embodiment of the present application, L3 and L4 are each independently a single bond or any one selected from the following structures.

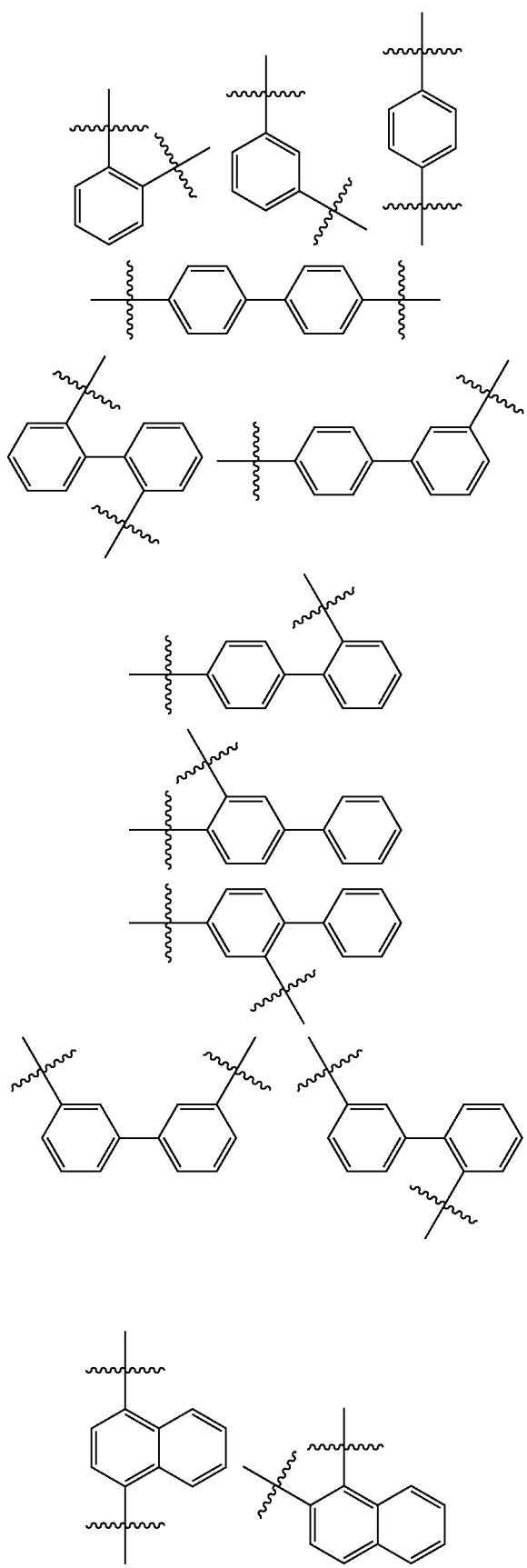
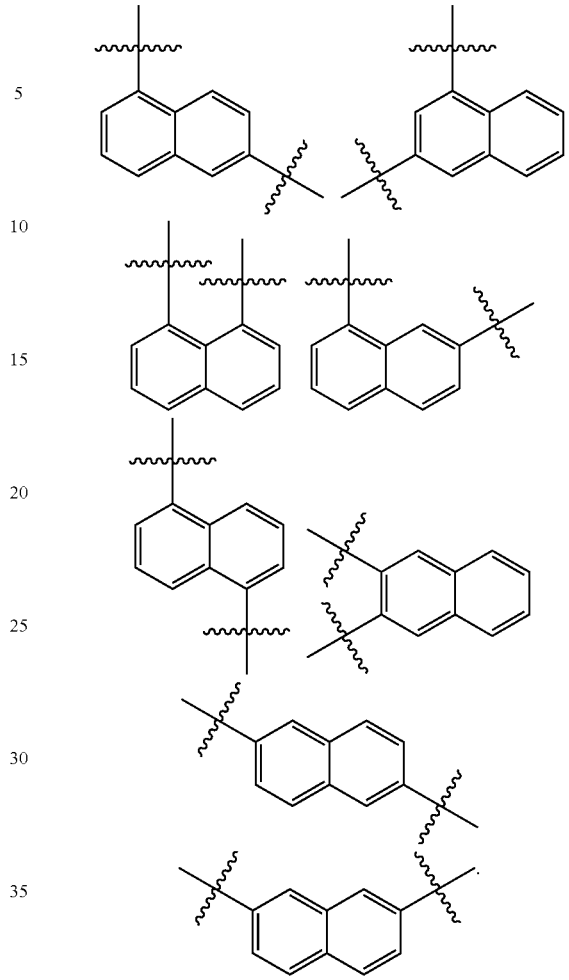

In an exemplary embodiment of the present application, R21 to R25 are each independently hydrogen, deuterium, a cyano group, a substituted or unsubstituted aryl group having 6 to 30 carbon atoms, or a substituted or unsubstituted heterocyclic group having 2 to 30 carbon atoms.

In an exemplary embodiment of the present application, R21 to R25 are each independently hydrogen, deuterium, a cyano group, a substituted or unsubstituted aryl group having 6 to 15 carbon atoms, or a substituted or unsubstituted heterocyclic group having 2 to 15 carbon atoms.

In an exemplary embodiment of the present application, R21 to R25 are each independently hydrogen, deuterium, a cyano group, or an aryl group having 6 to 15 carbon atoms, which is unsubstituted or substituted with a cyano group.

In an exemplary embodiment of the present application, R21 to R25 are each independently hydrogen; deuterium; a cyano group; a phenyl group which is unsubstituted or substituted with a cyano group; a biphenyl group which is unsubstituted or substituted with a cyano group; a terphenyl group which is unsubstituted or substituted with a cyano group; a 1-naphthyl group which is unsubstituted or substituted with a cyano group; or a 2-naphthyl group which is unsubstituted or substituted with a cyano group.

In an exemplary embodiment of the present application, R21 to R25 are each independently hydrogen, deuterium, a cyano group, or a phenyl group which is unsubstituted or substituted with a cyano group.

In an exemplary embodiment of the present application, R23 is a cyano group or a phenyl group which is unsubstituted or substituted with a cyano group.

In an exemplary embodiment of the present application, R24 is a cyano group or a phenyl group which is unsubstituted or substituted with a cyano group.

In an exemplary embodiment of the present application, R25 is a cyano group or a phenyl group which is unsubstituted or substituted with a cyano group.

In an exemplary embodiment of the present application, R26 is a substituted or unsubstituted alkyl group having 1 to 6 carbon atoms; a substituted or unsubstituted aryl group having 6 to 30 carbon atoms; or a substituted or unsubstituted heterocyclic group having 2 to 30 carbon atoms.

In an exemplary embodiment of the present application, R26 is an aryl group having 6 to 15 carbon atoms, which is unsubstituted or substituted with a cyano group or an aryl group.

In an exemplary embodiment of the present application, R26 is a phenyl group which is unsubstituted or substituted with a cyano group; a biphenyl group which is unsubstituted or substituted with a cyano group; a terphenyl group which is unsubstituted or substituted with a cyano group; a 1-naphthyl group which is unsubstituted or substituted with a cyano group; or a 2-naphthyl group which is unsubstituted or substituted with a cyano group.

In an exemplary embodiment of the present application, R26 is a phenyl group which is unsubstituted or substituted with a cyano group.

In an exemplary embodiment of the present application, R26 is a phenyl group.

In an exemplary embodiment of the present application, r21 to r25 are each an integer from 0 to 2.

In an exemplary embodiment of the present application, r21 to r25 are each 1.

Further, in an exemplary embodiment of the present application, Formula 1 is selected from among the following compounds:

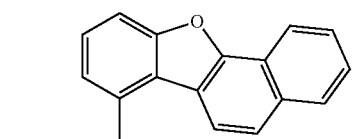

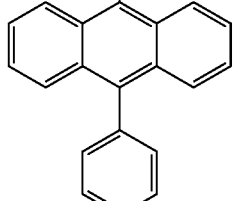

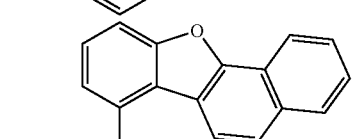

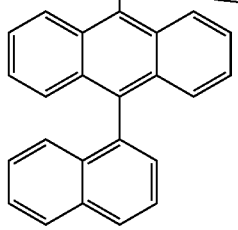

-continued

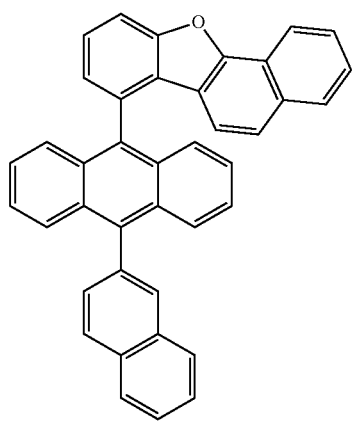

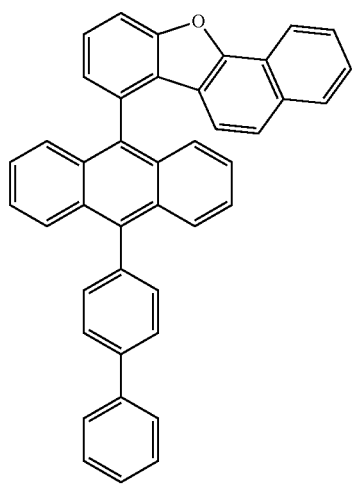

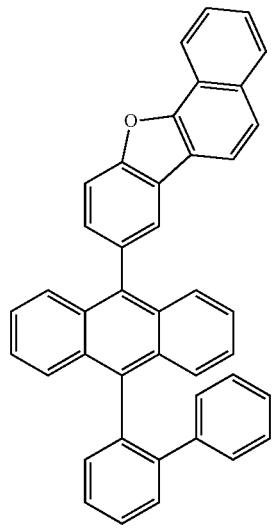

-continued
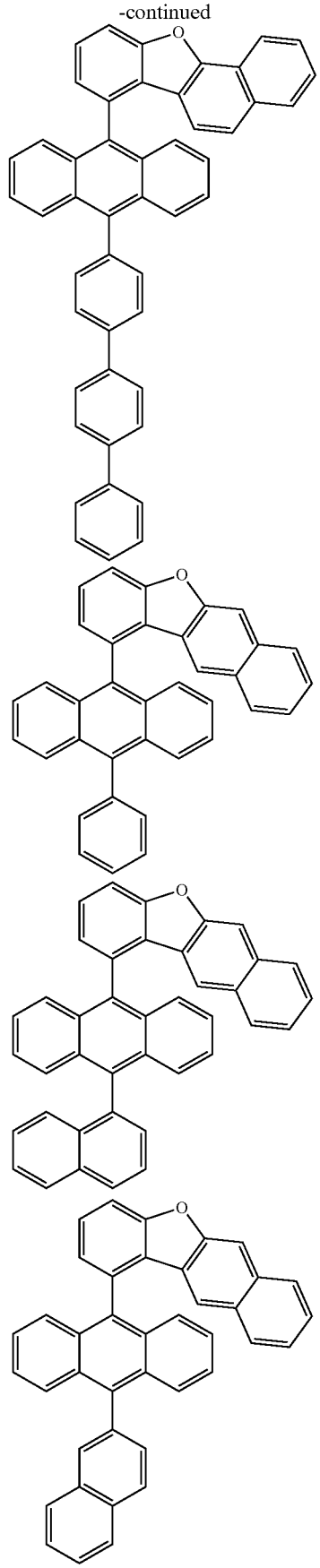
-continued
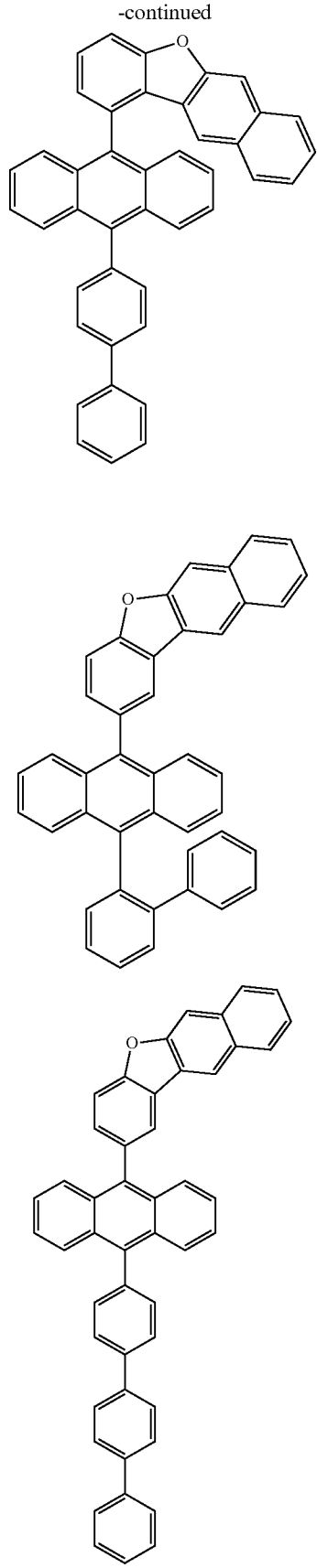

-continued
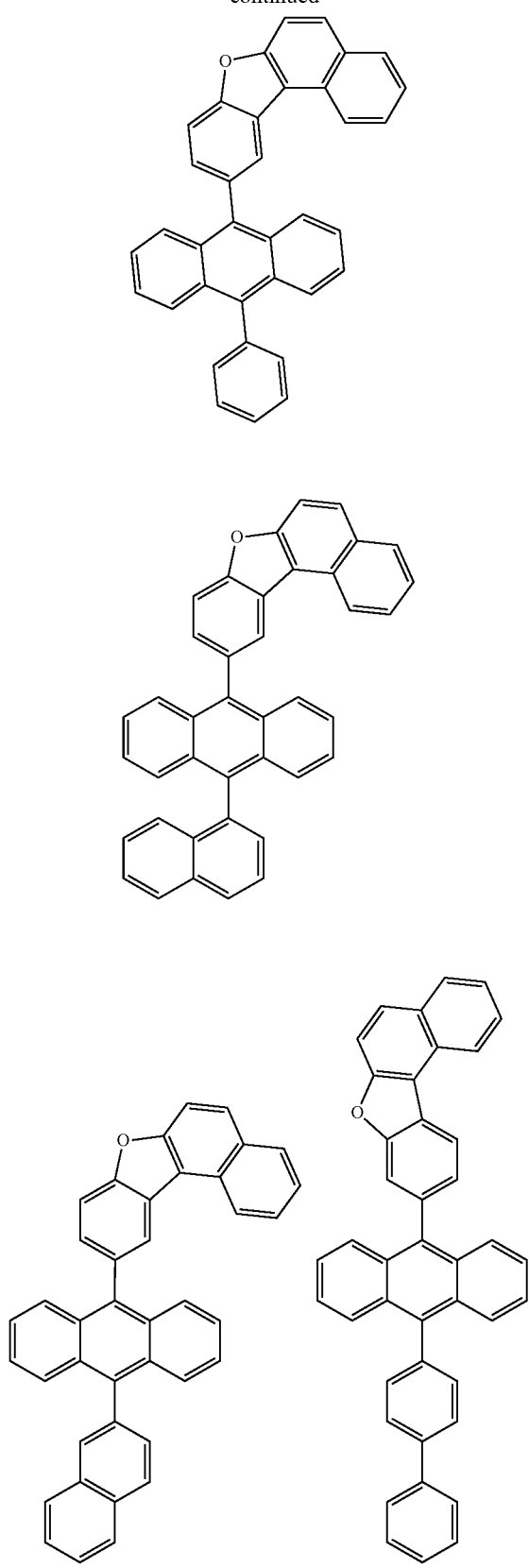
-continued
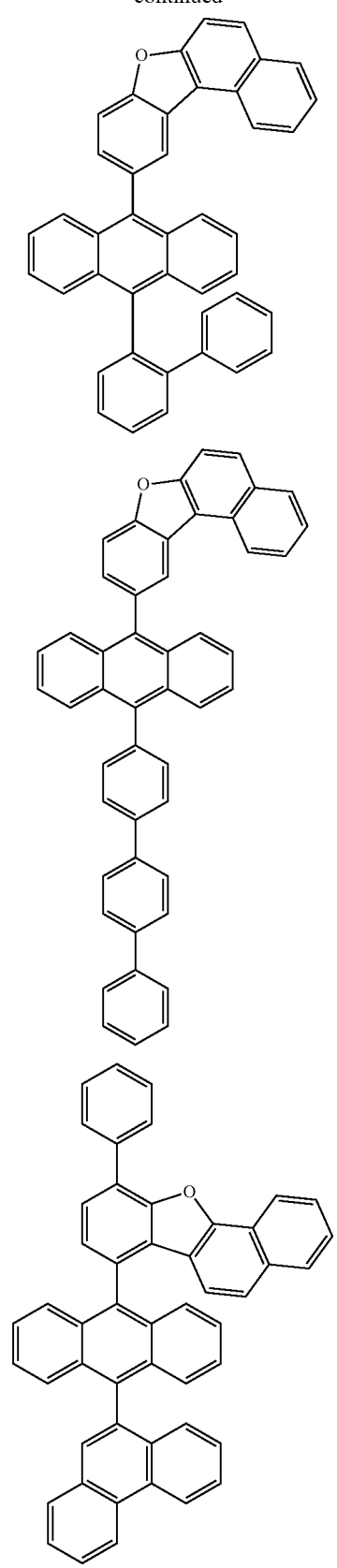

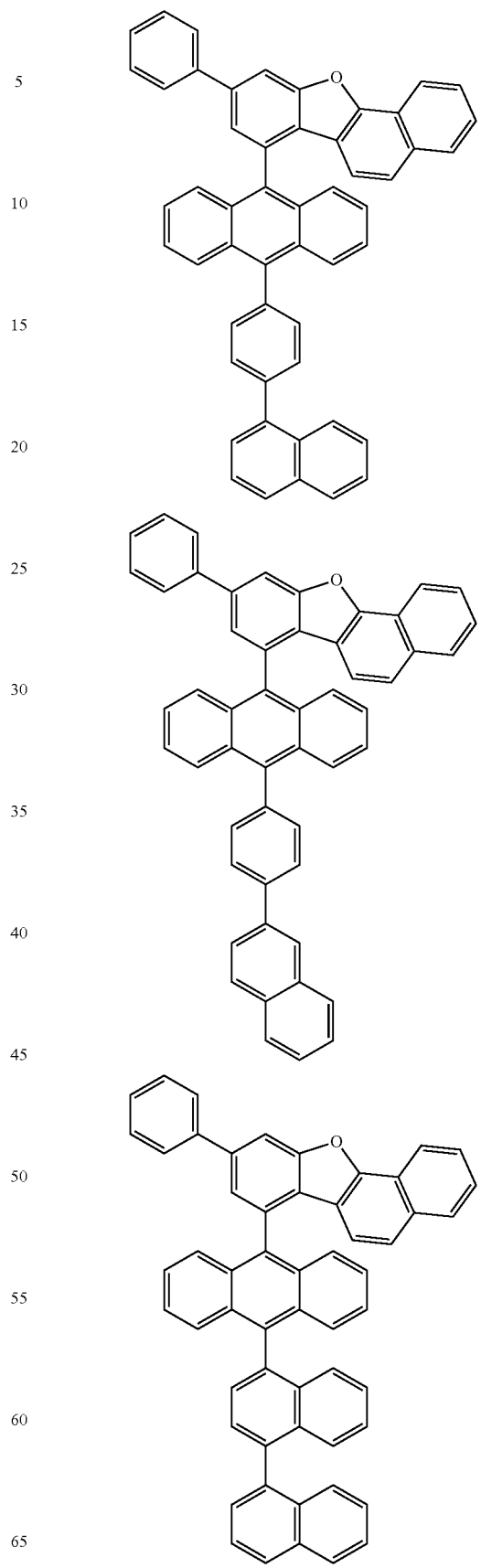

-continued
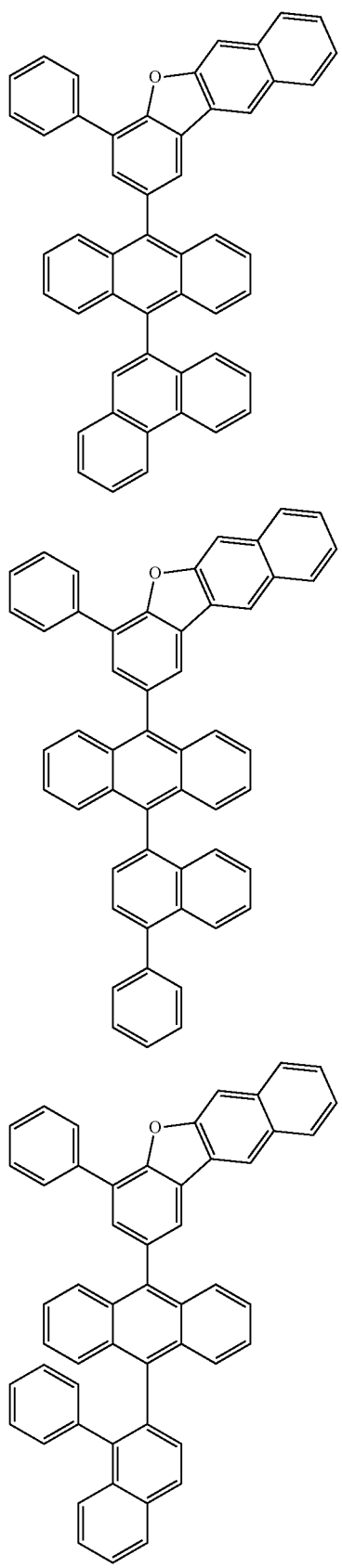 [SMILES: c1ccc(-c2cc(-c3c4ccccc4c(-c4cc5ccccc5c5ccccc45)c4ccccc34)cc3c2oc2cc4ccccc4cc23)cc1 ; c1ccc(-c2ccc(-c3c4ccccc4c(-c4cc(-c5ccccc5)c5oc6cc7ccccc7cc6c5c4)c4ccccc34)c3ccccc23)cc1 ; c1ccc(-c2c(-c3c4ccccc4c(-c4cc(-c5ccccc5)c5oc6cc7ccccc7cc6c5c4)c4ccccc34)ccc3ccccc23)cc1]
-continued
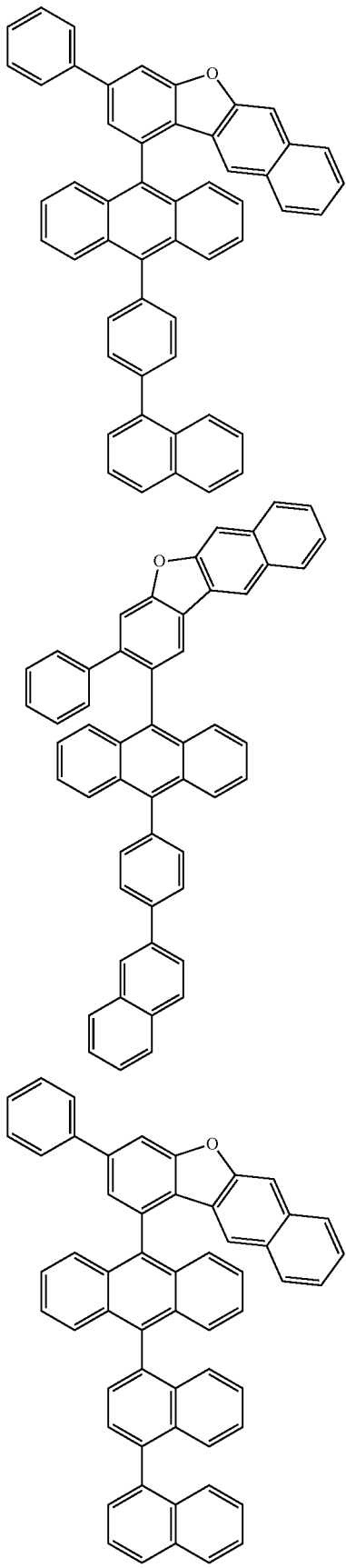

31
-continued
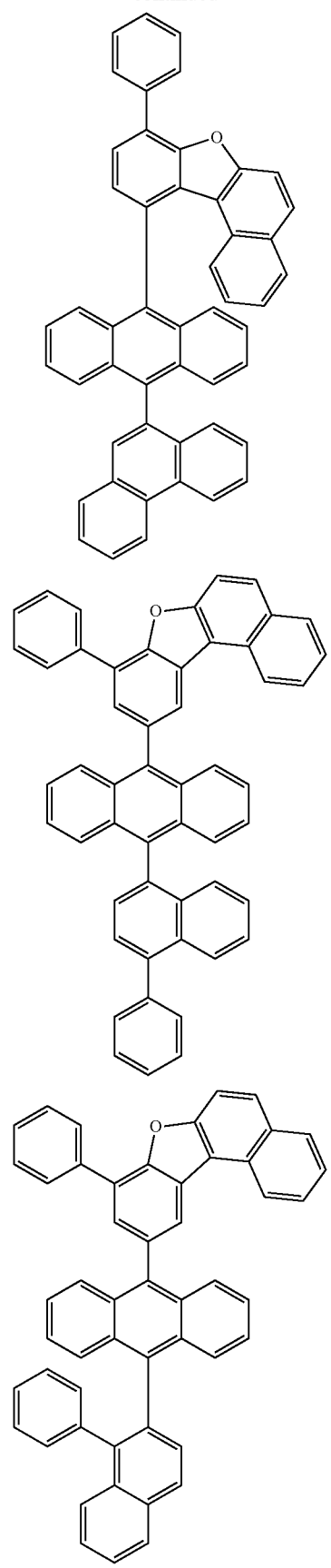 [SMILES: c1ccc(-c2ccc(-c3c4ccccc4c(-c4cc5ccccc5c5ccccc45)c4ccccc34)c3c2oc2ccc4ccccc4c23)cc1 ; c1ccc(-c2ccc(-c3c4ccccc4c(-c4cc(-c5ccccc5)c5oc6ccc7ccccc7c6c5c4)c4ccccc34)c3ccccc23)cc1 ; c1ccc(-c2c(-c3c4ccccc4c(-c4cc(-c5ccccc5)c5oc6ccc7ccccc7c6c5c4)c4ccccc34)ccc3ccccc23)cc1]
32
-continued

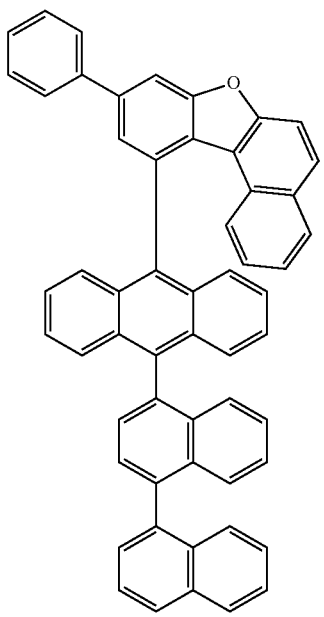
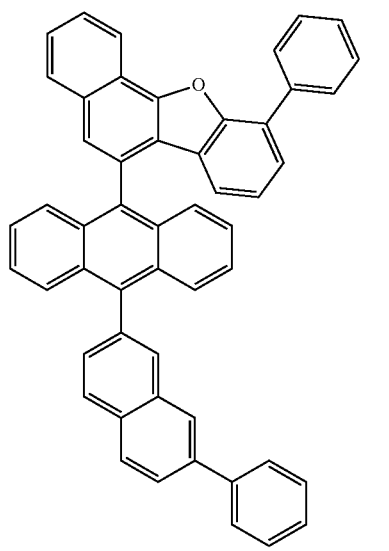
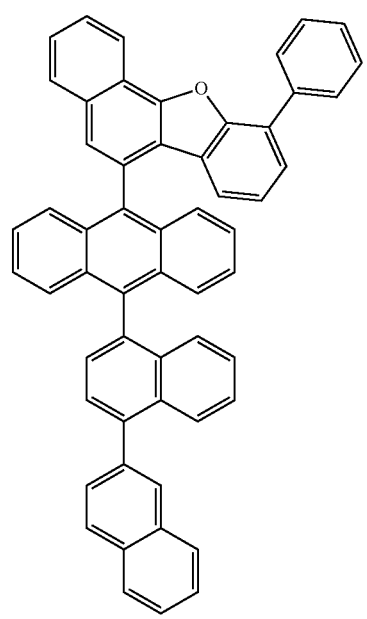

35
-continued
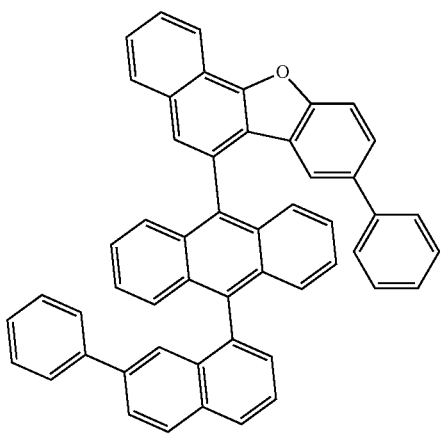
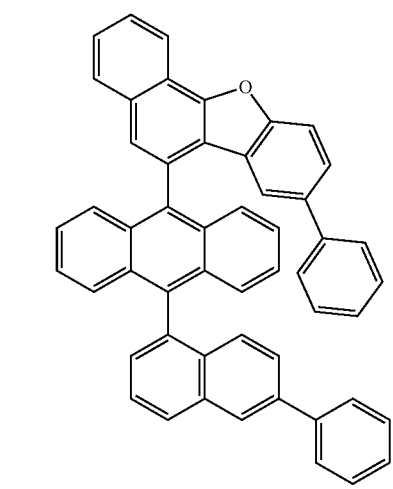
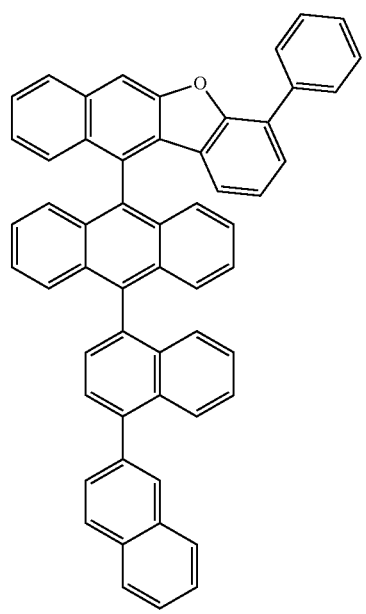
36
-continued
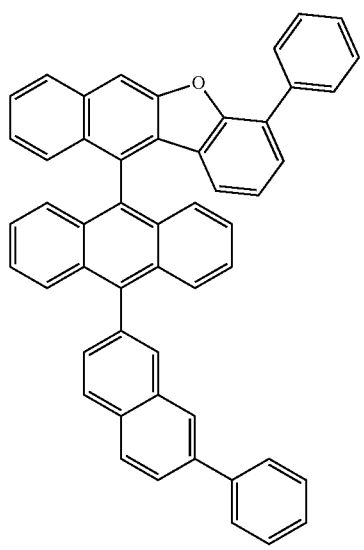
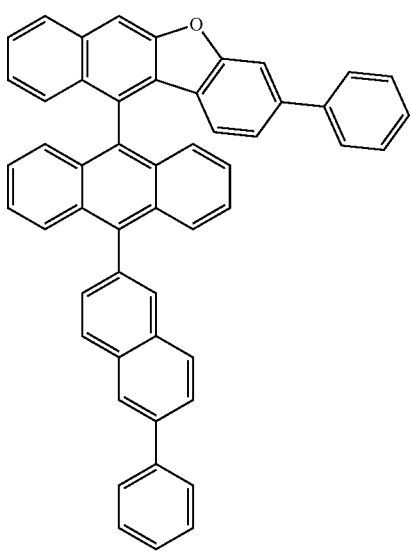
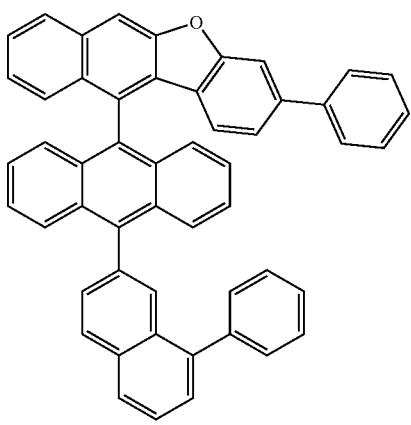

37
-continued
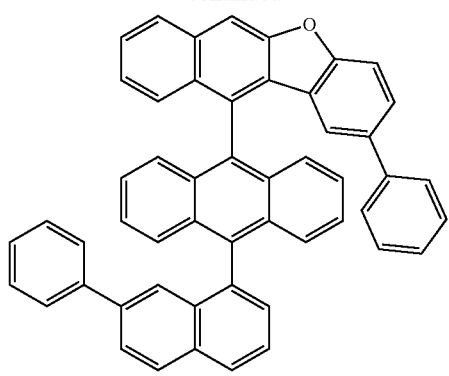
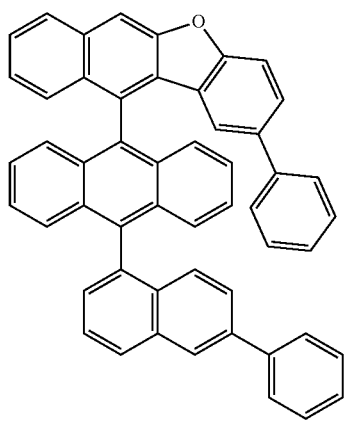
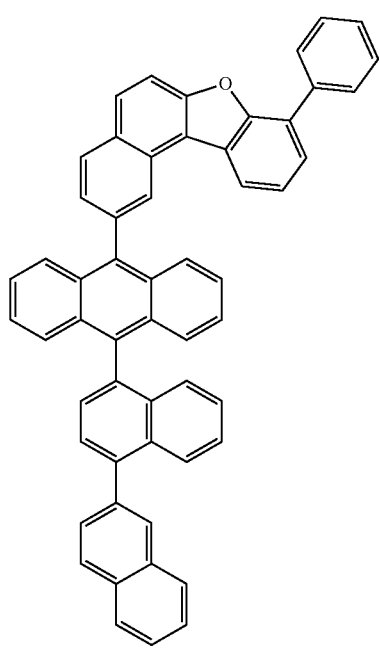
38
-continued
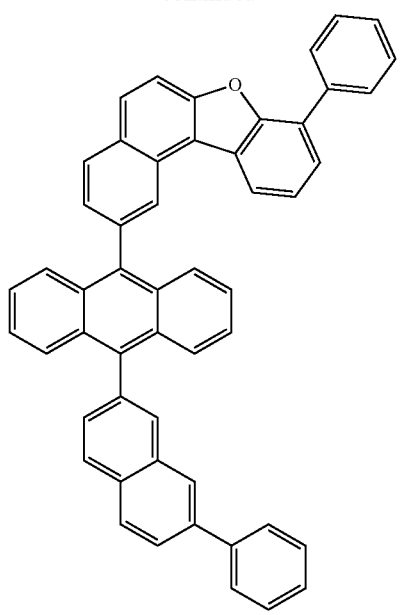
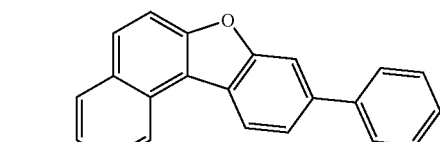
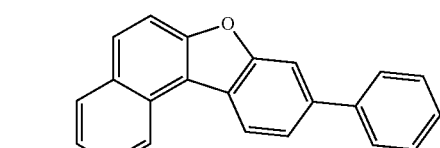

-continued
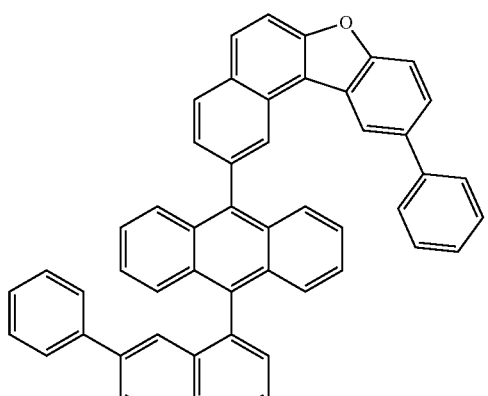
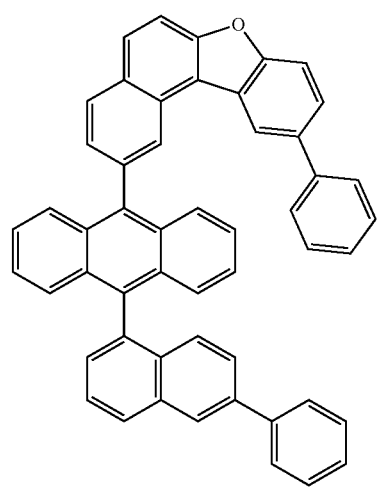
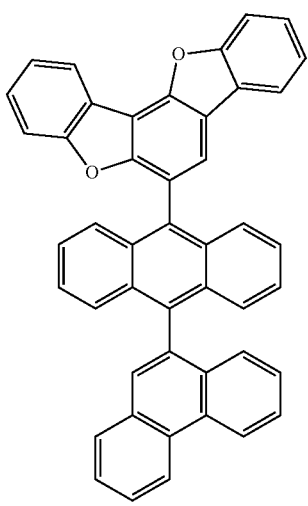
-continued
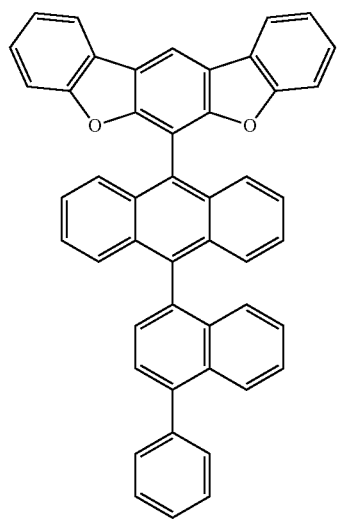
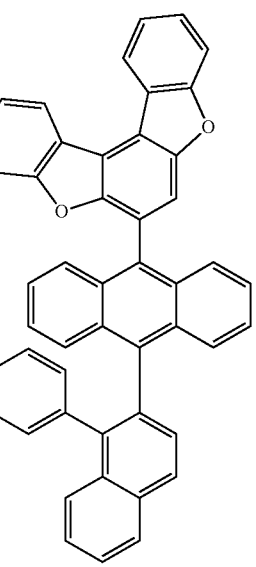
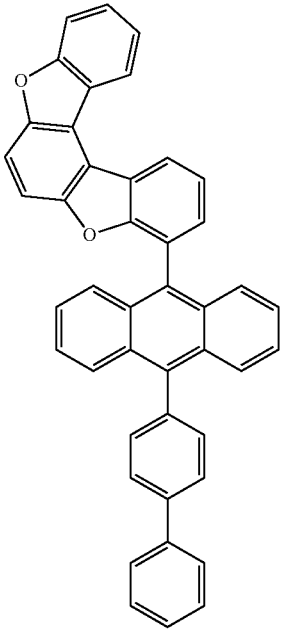

-continued
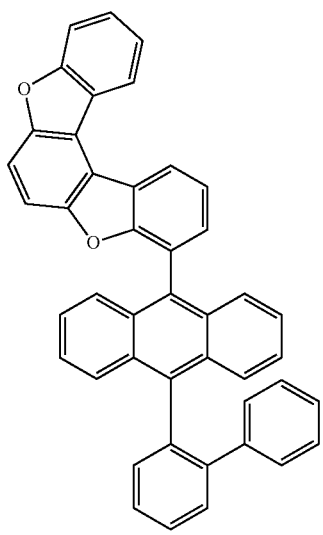
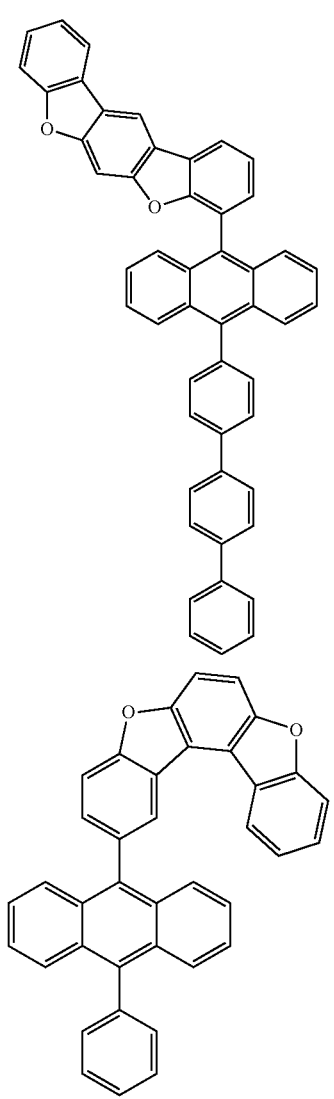
-continued
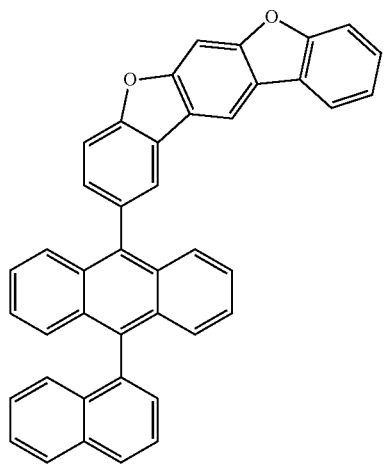
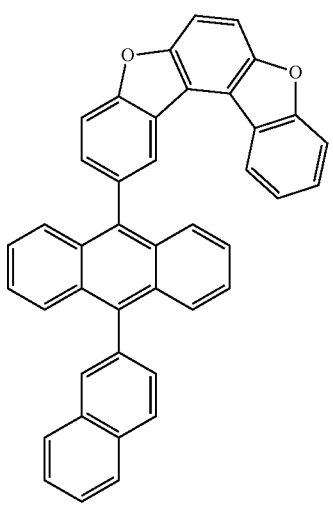
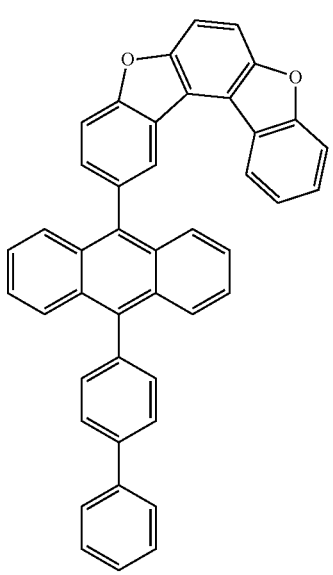

43
-continued
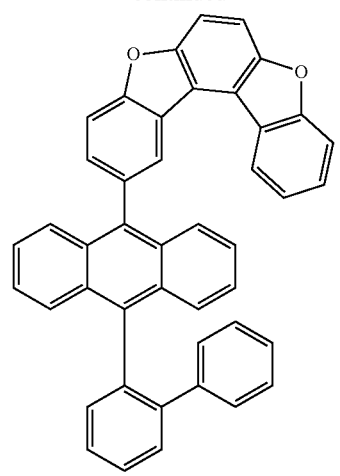
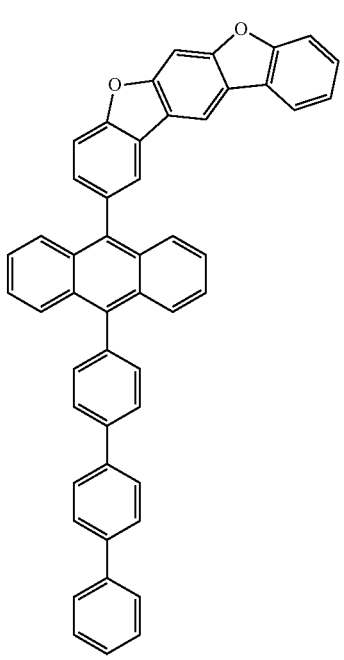
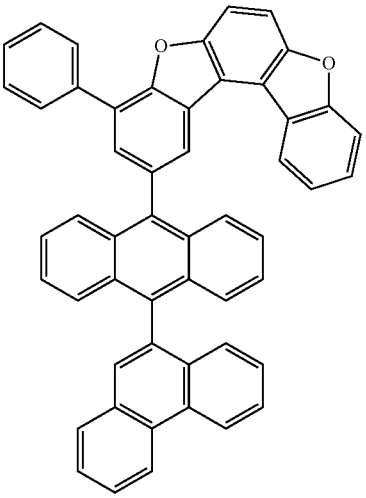
44
-continued
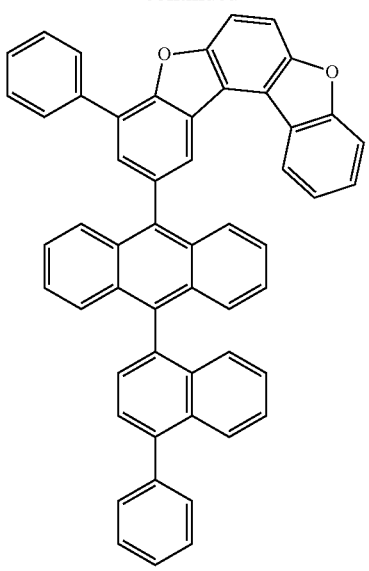
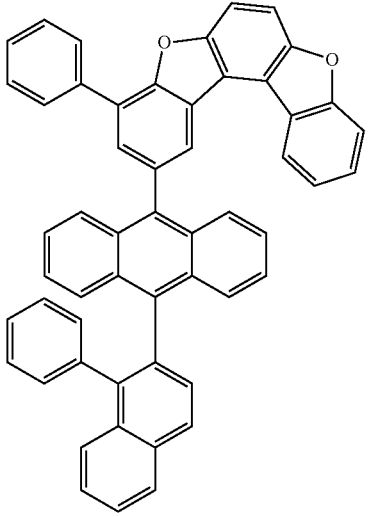
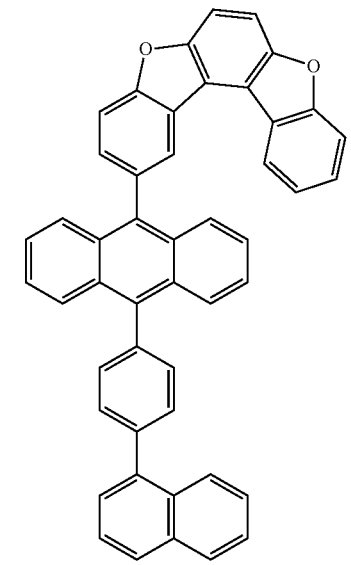

-continued
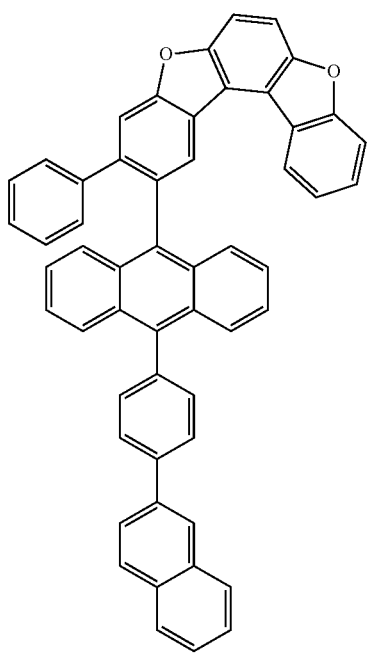
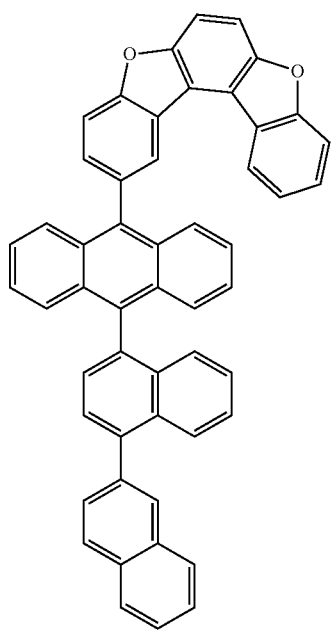
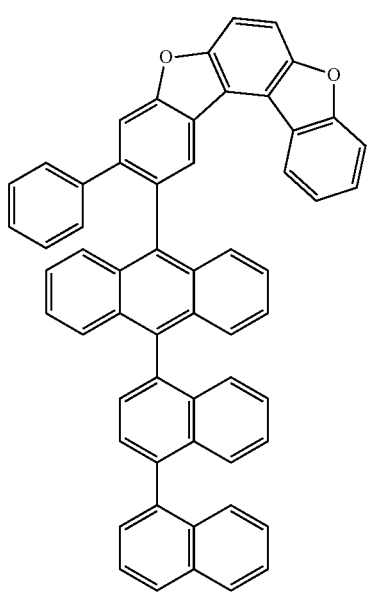
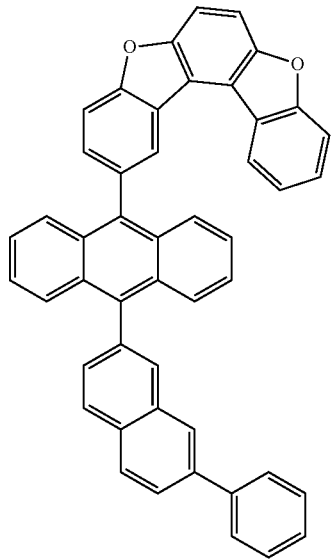

-continued
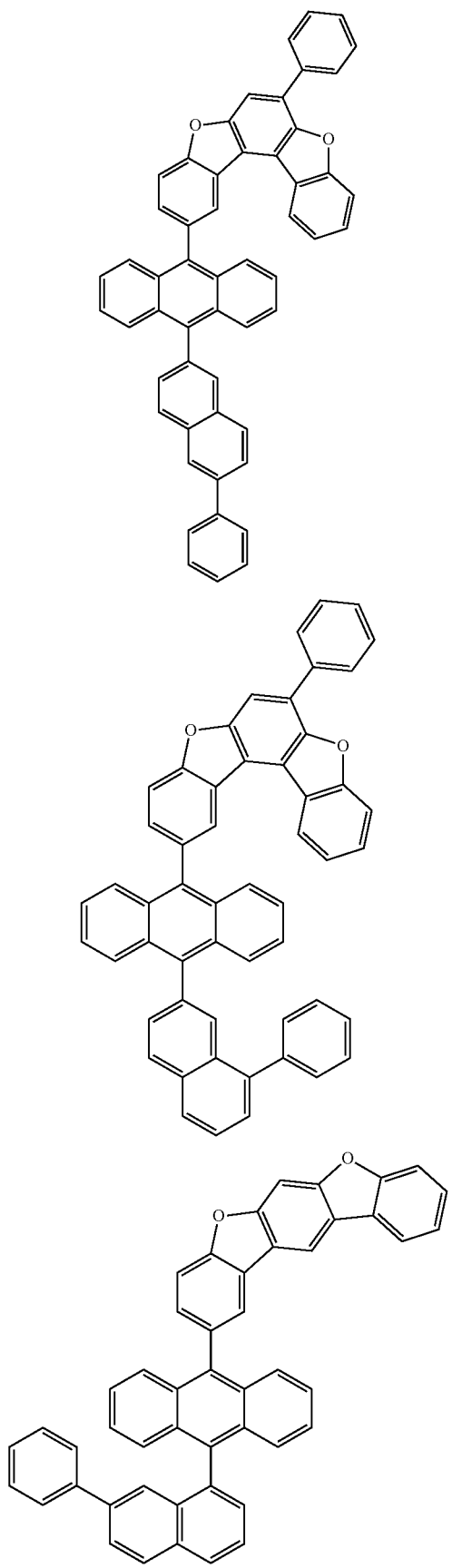
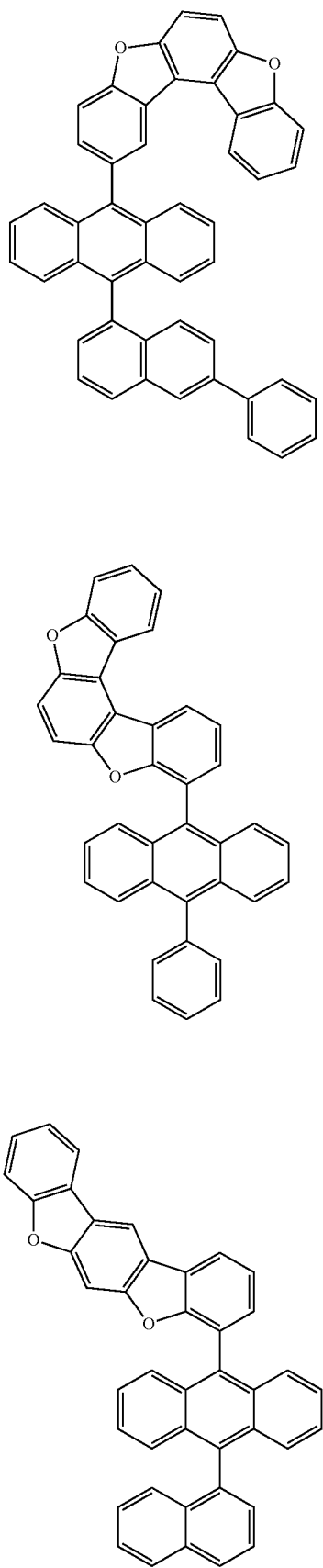

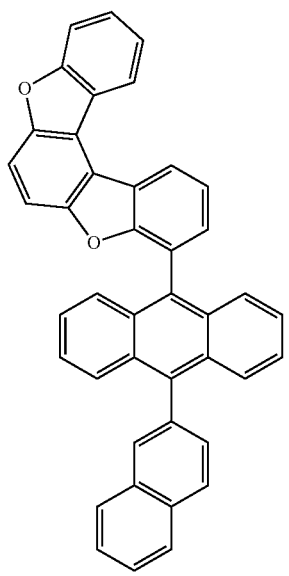
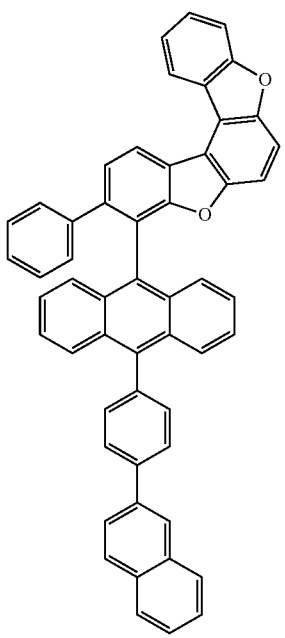
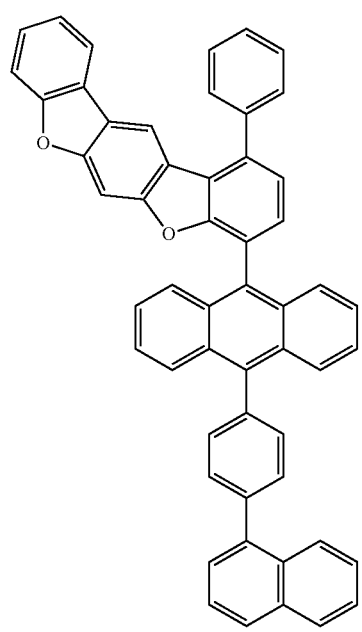
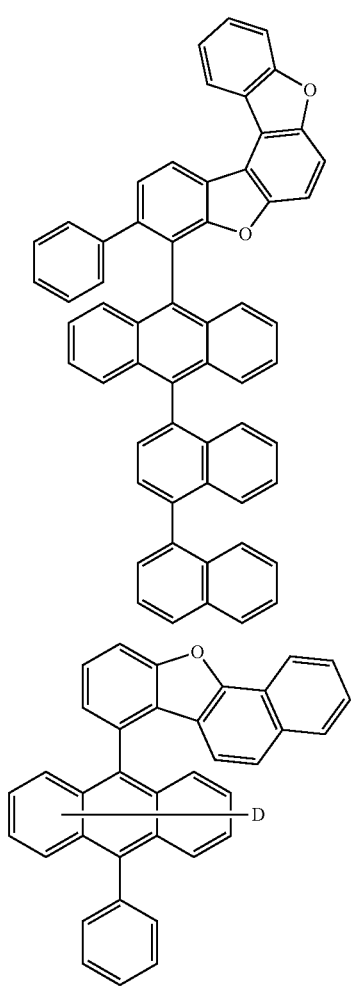

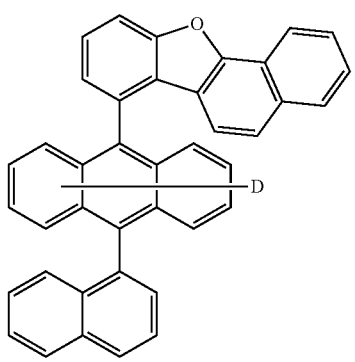
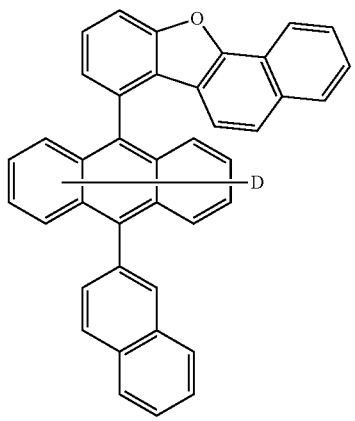
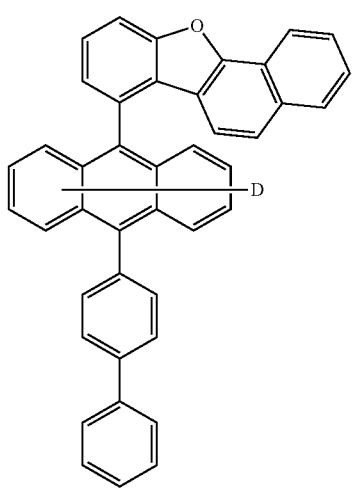
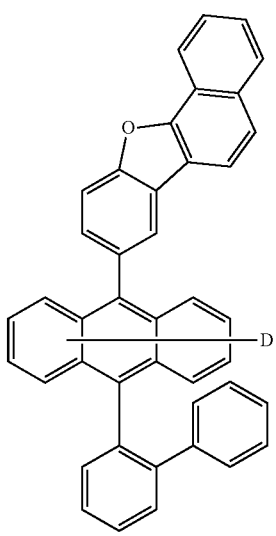
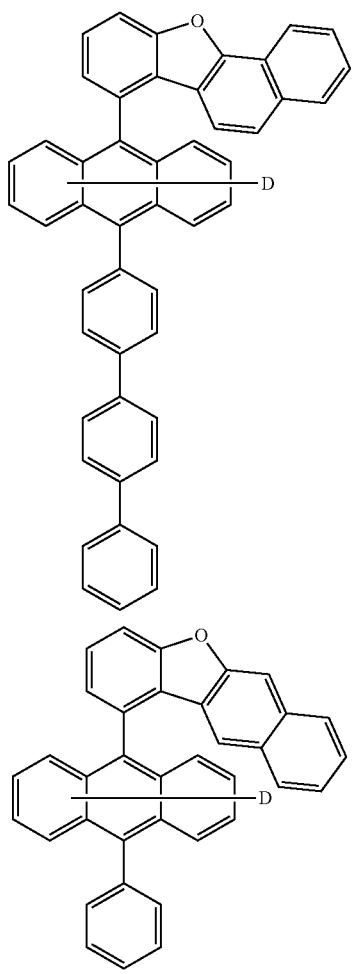

-continued
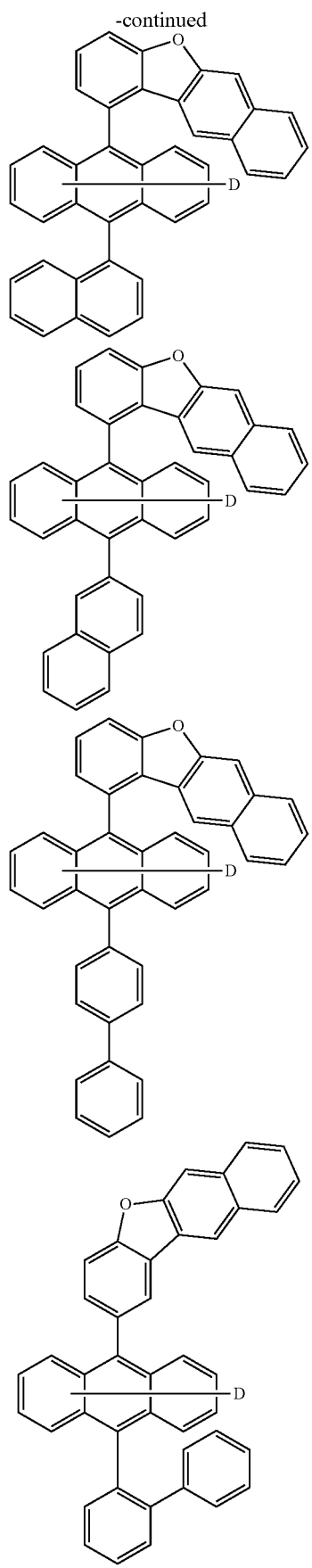
-continued
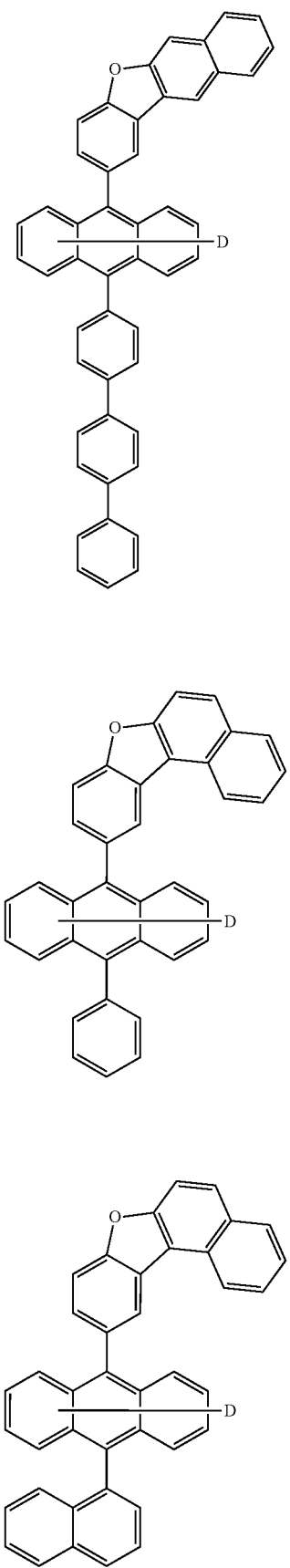

-continued
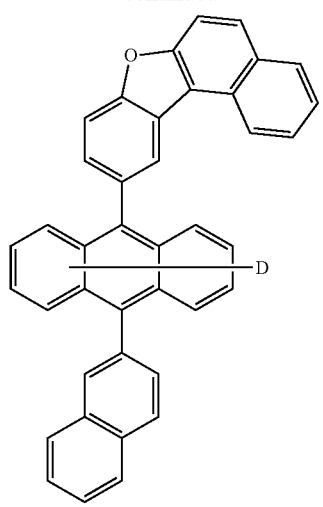
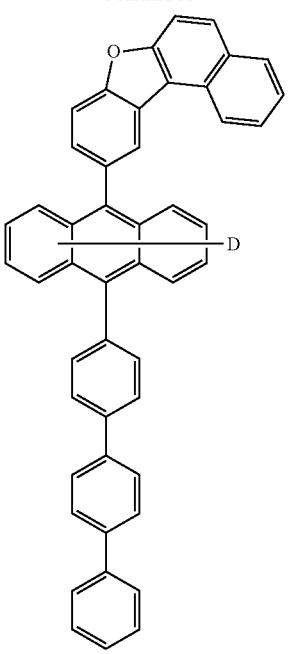
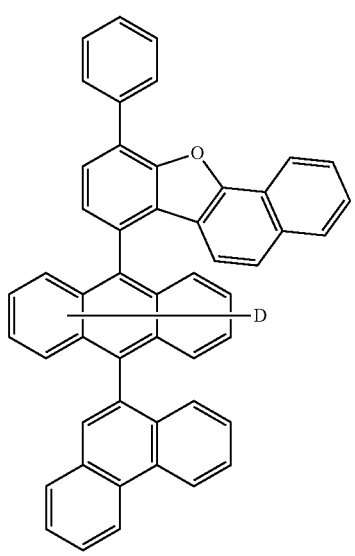

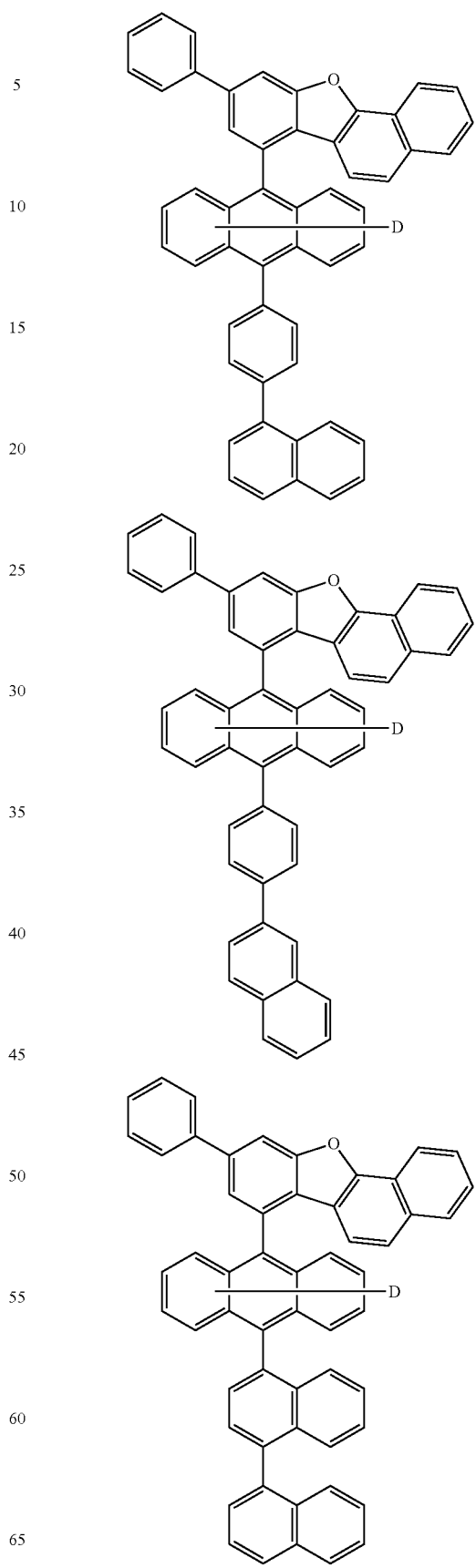

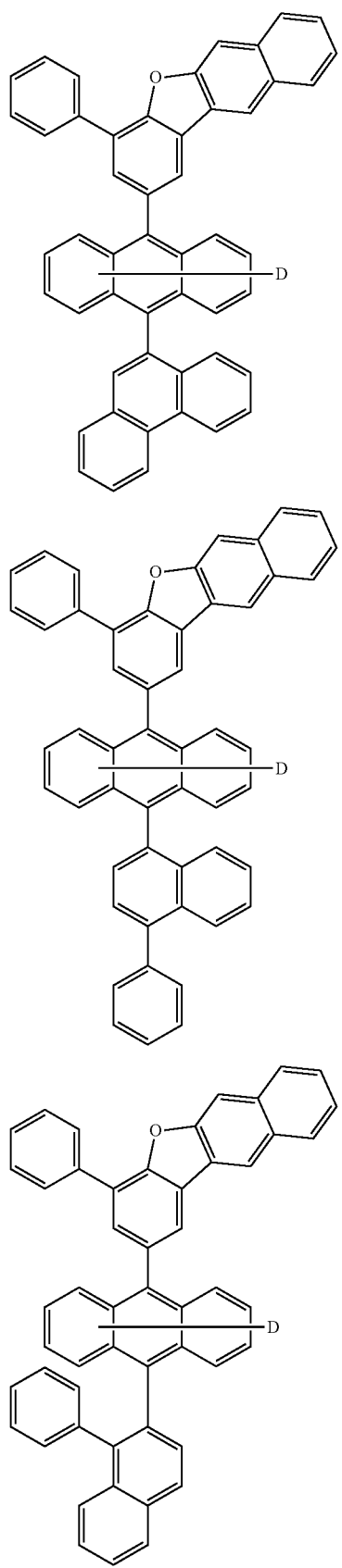
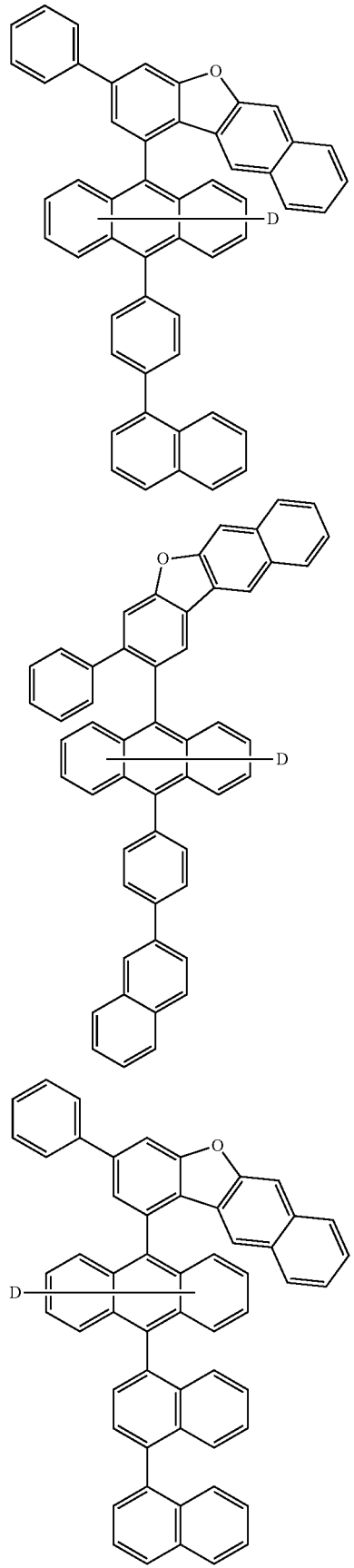

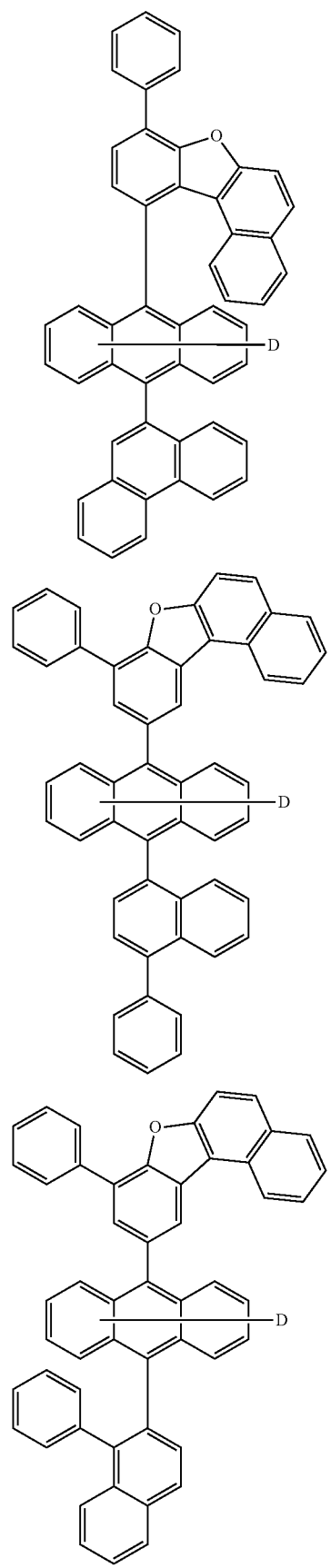

63
-continued
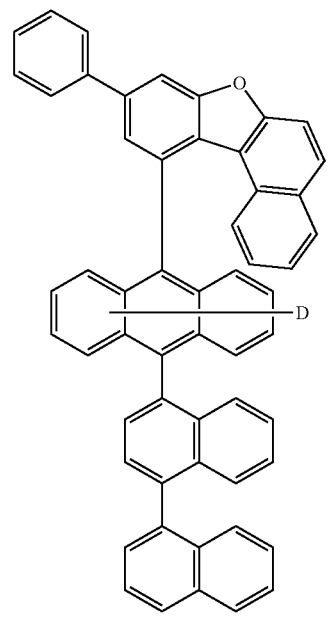
64
-continued
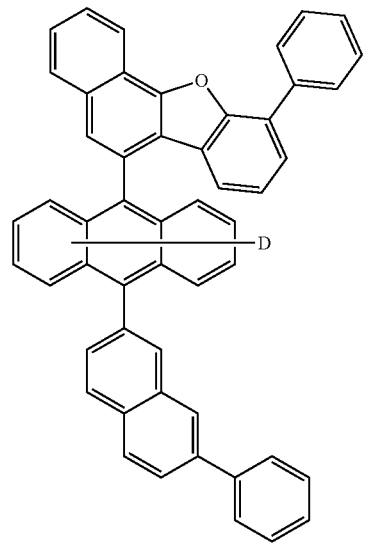
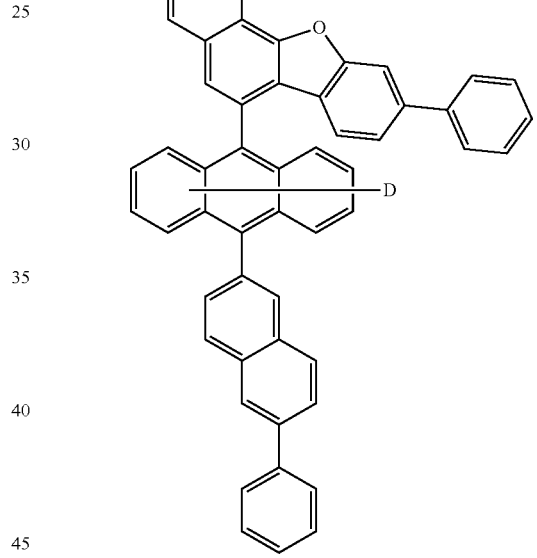
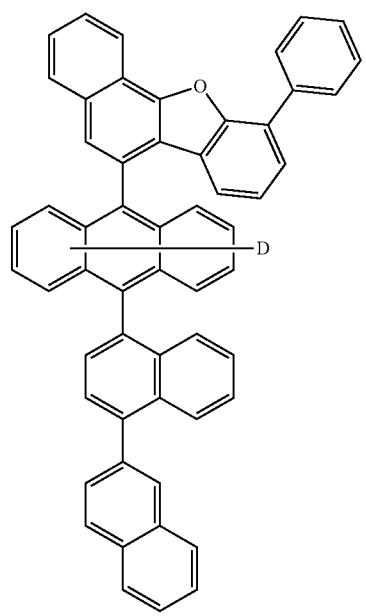

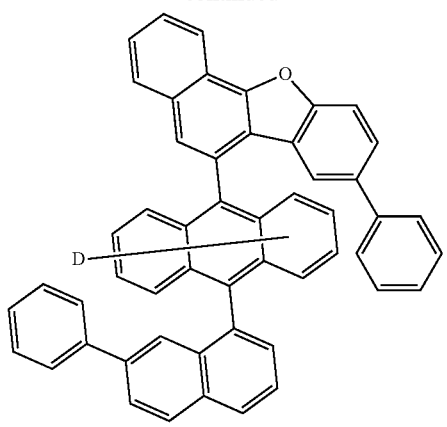
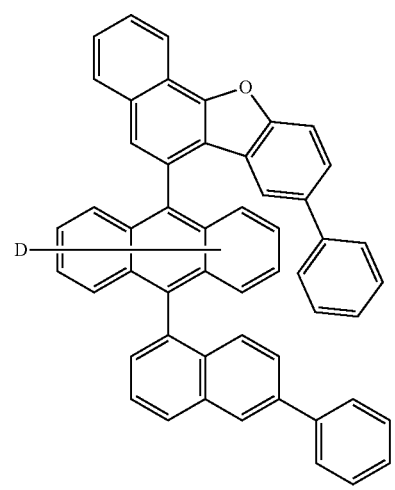
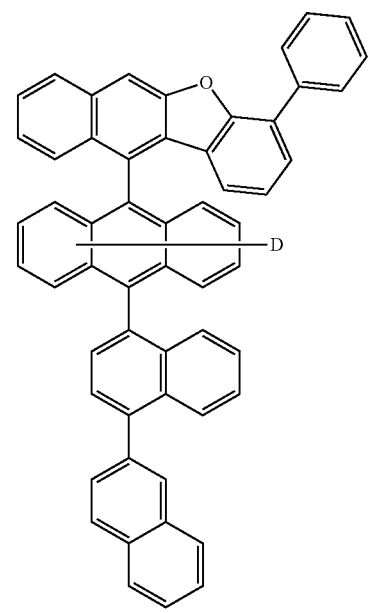
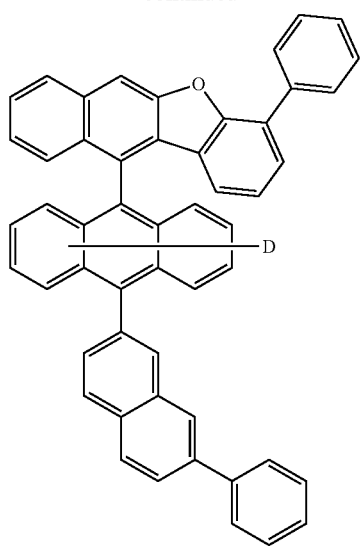
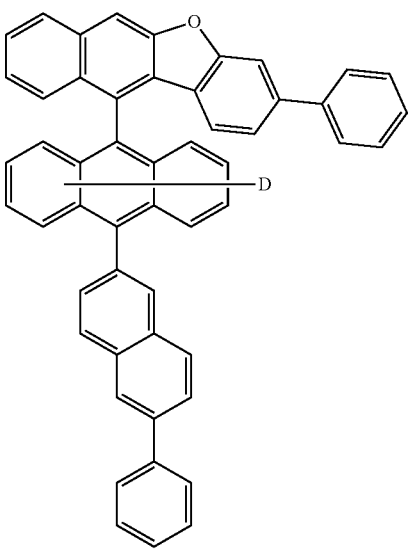
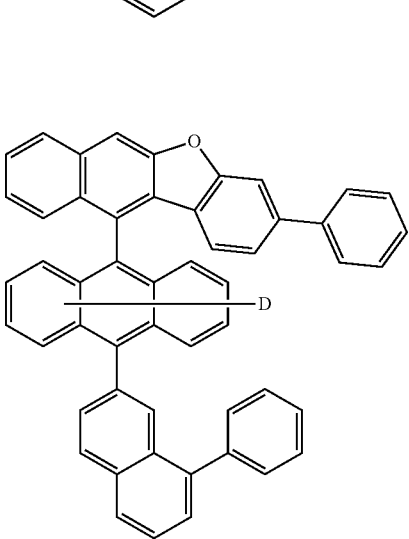

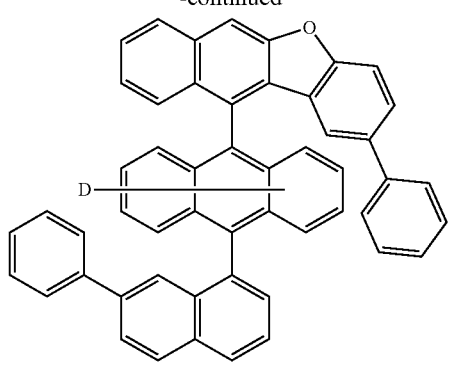
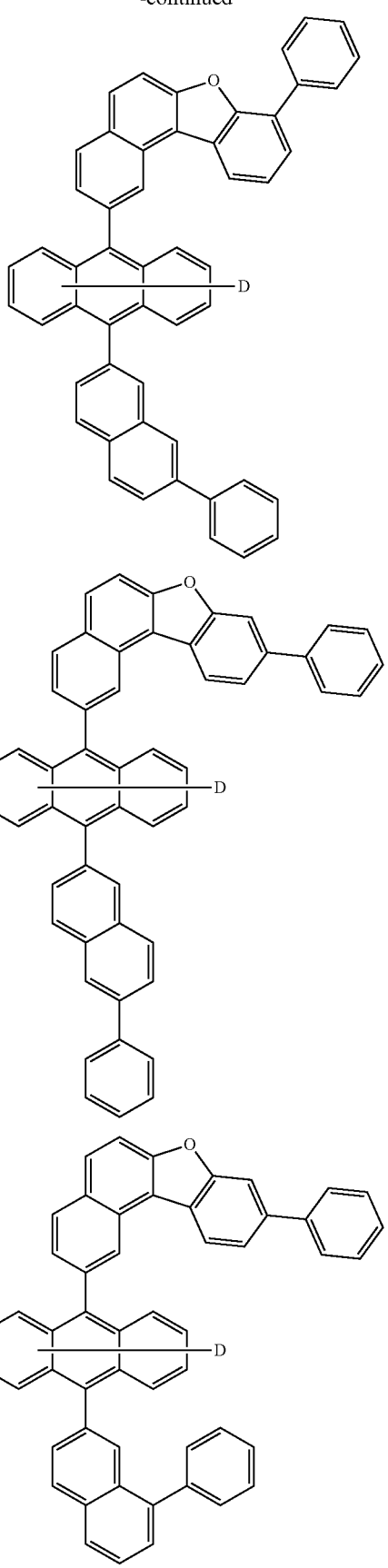

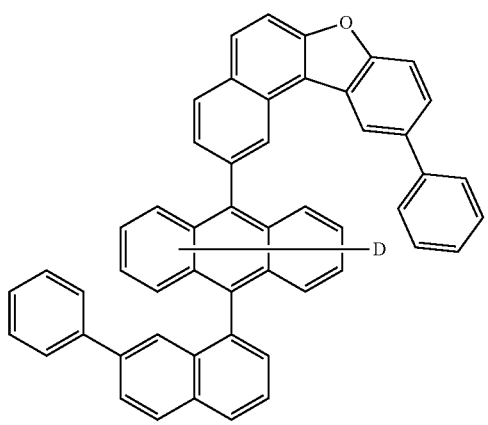
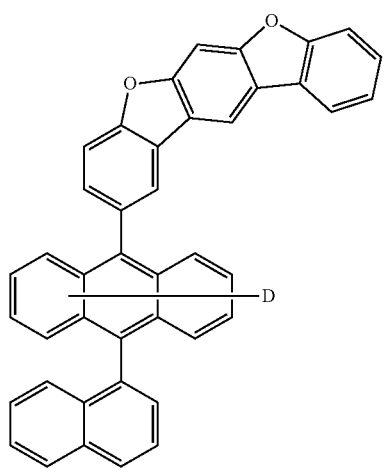
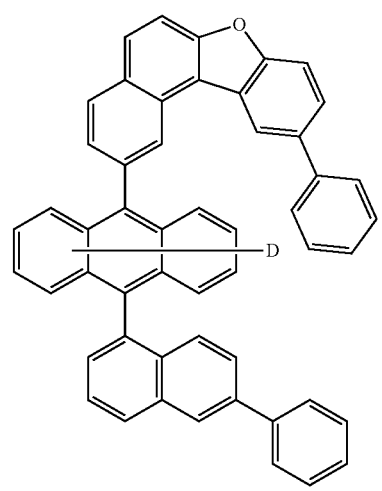
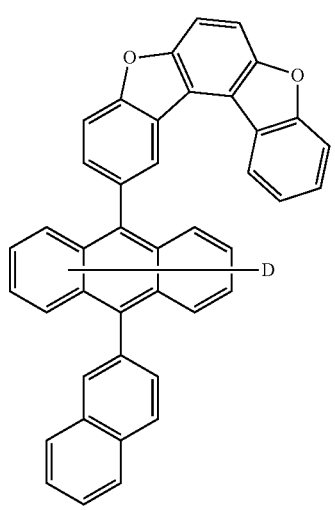
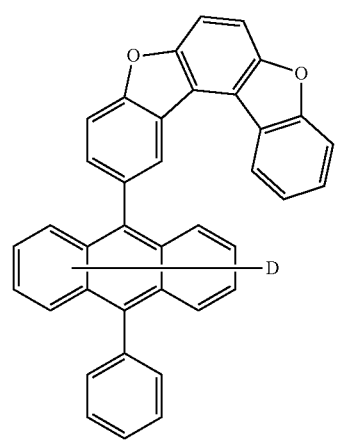
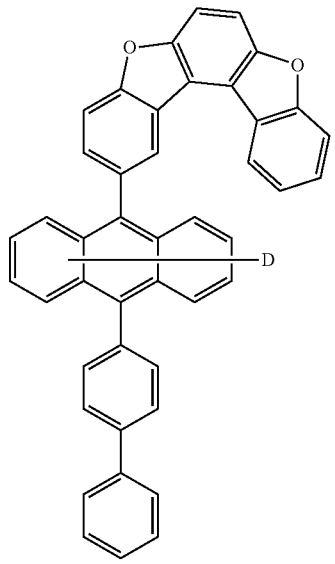

-continued
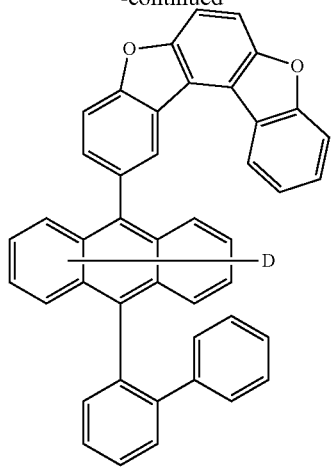
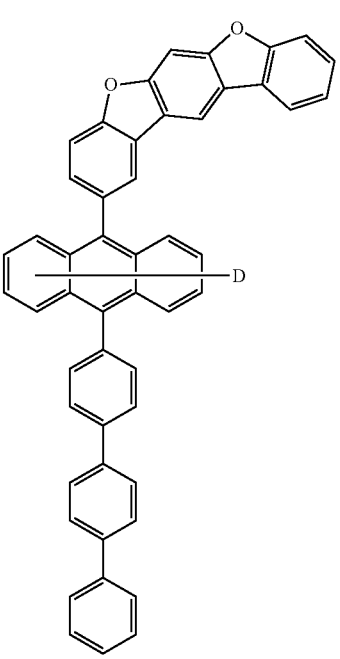
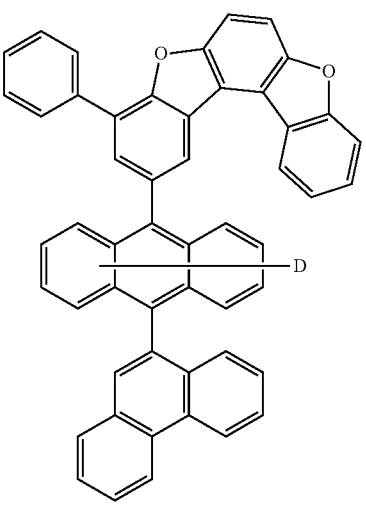
-continued
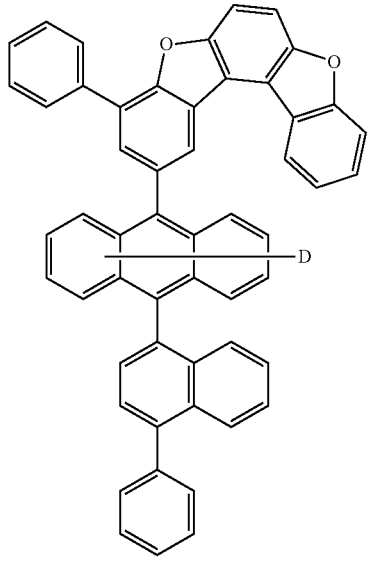
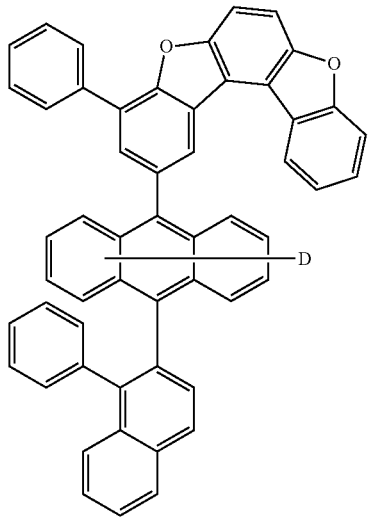
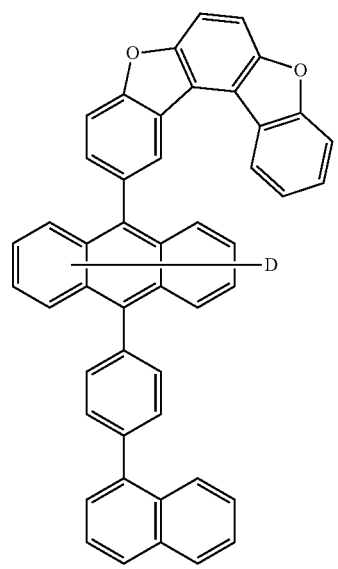

-continued
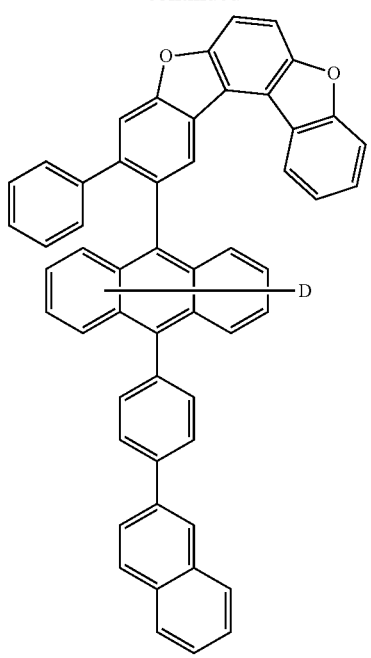
-continued
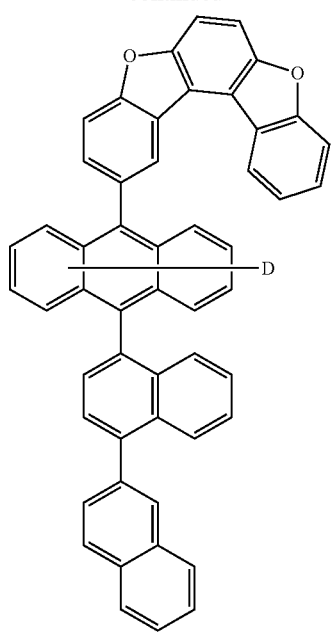
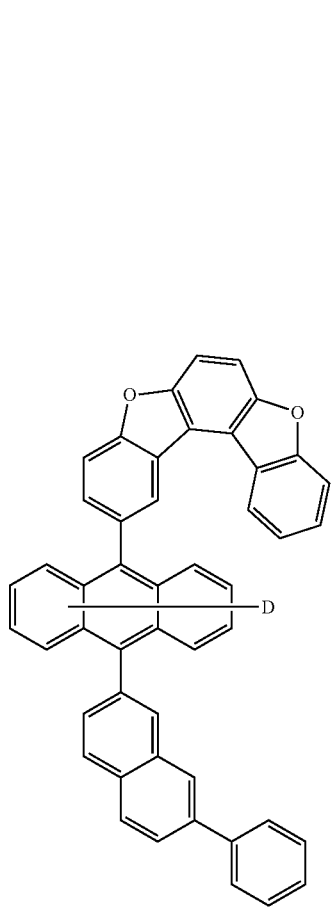

-continued
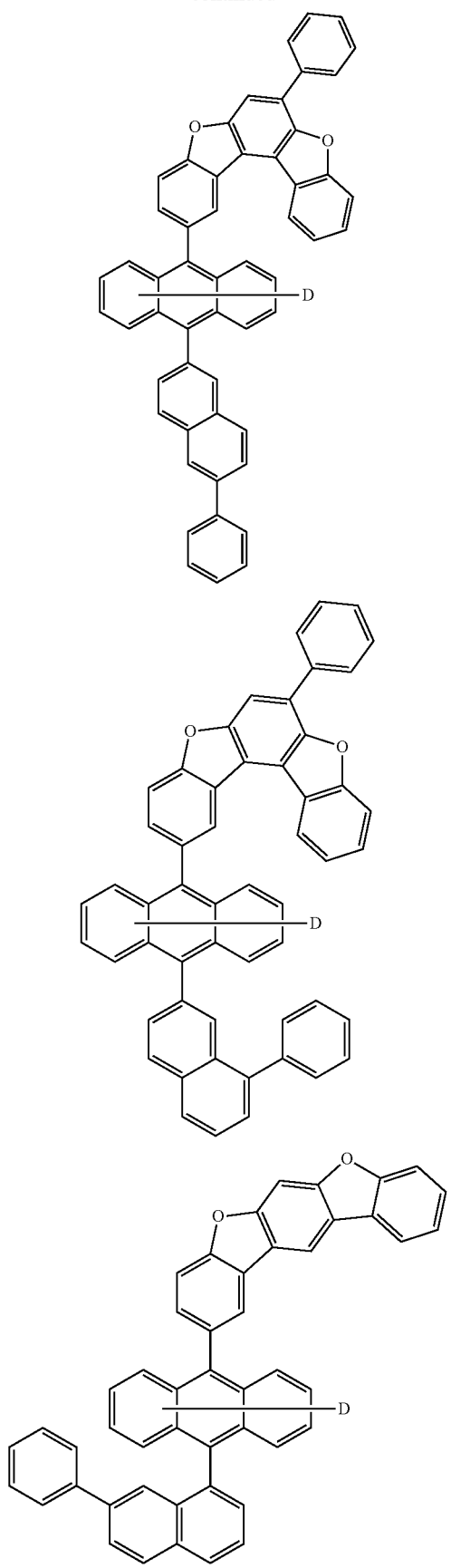
-continued
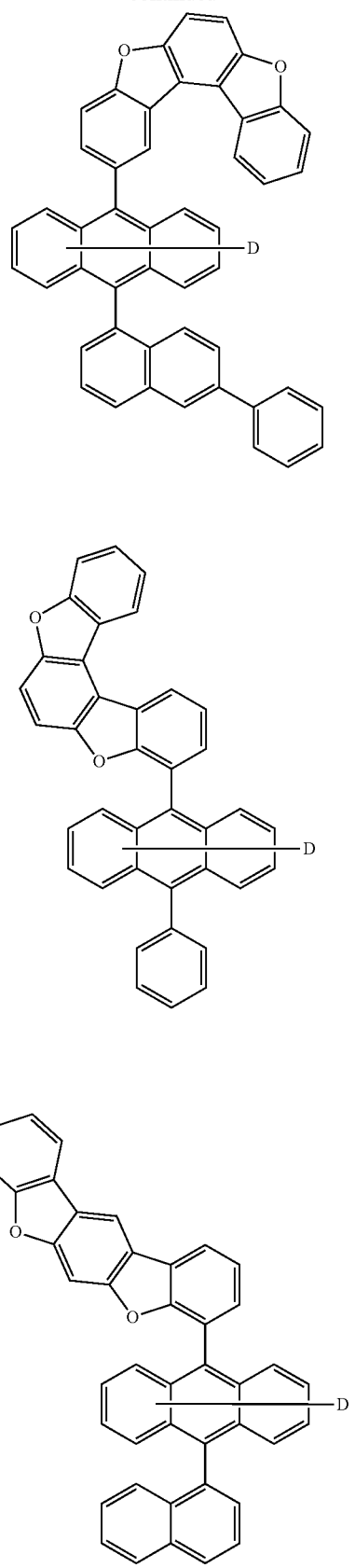

77
-continued
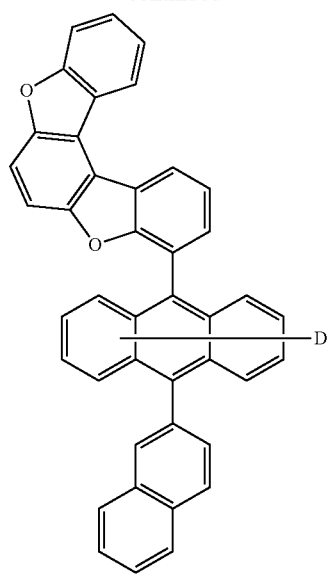
78
-continued
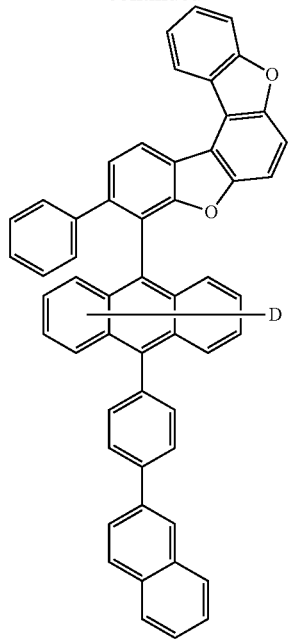
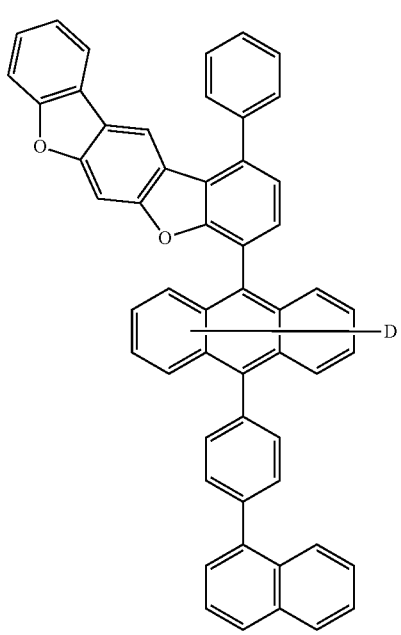
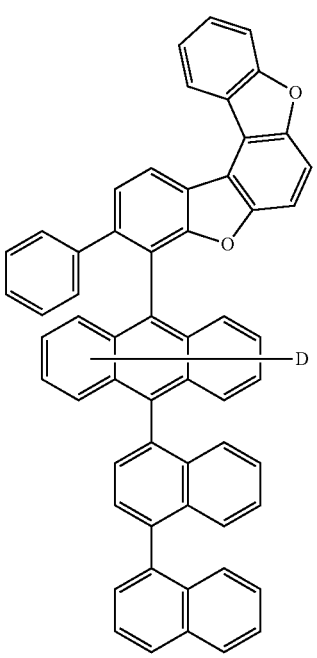

79
-continued
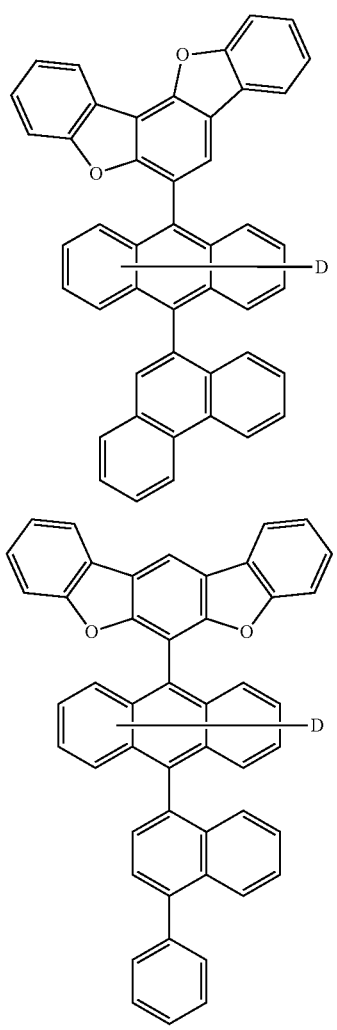
80
-continued
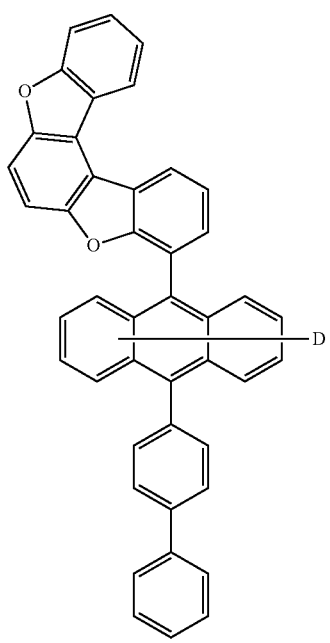
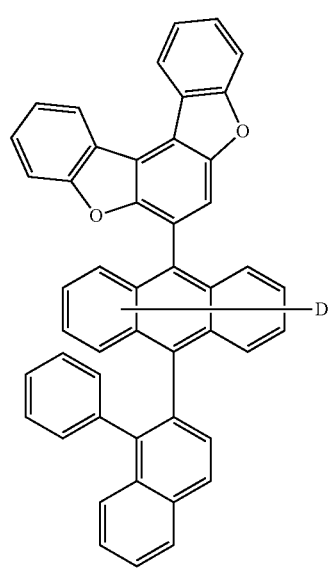
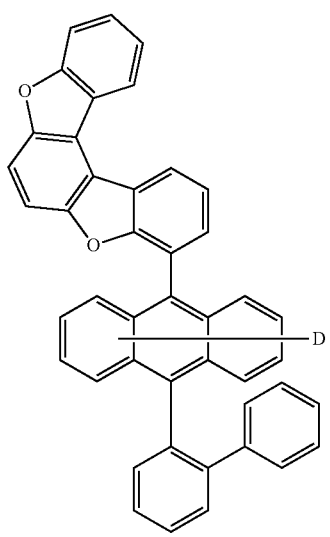

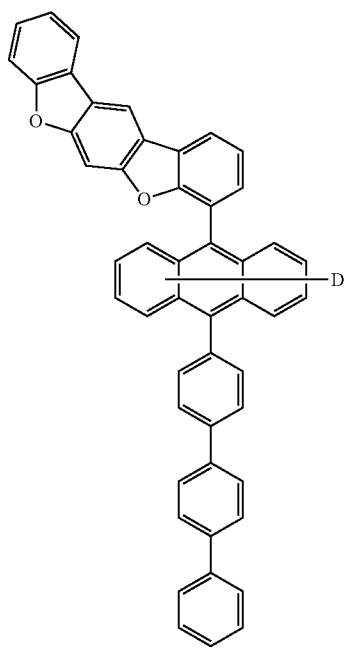
In the compounds, D means deuterium, and when the corresponding structure is substituted with deuterium, 30% or more of the corresponding structure is substituted with deuterium.
In addition, in an exemplary embodiment of the present application, Formula 2 is selected from among the following compounds:
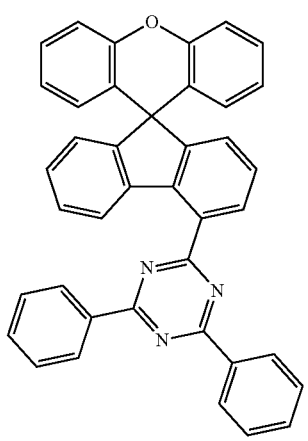
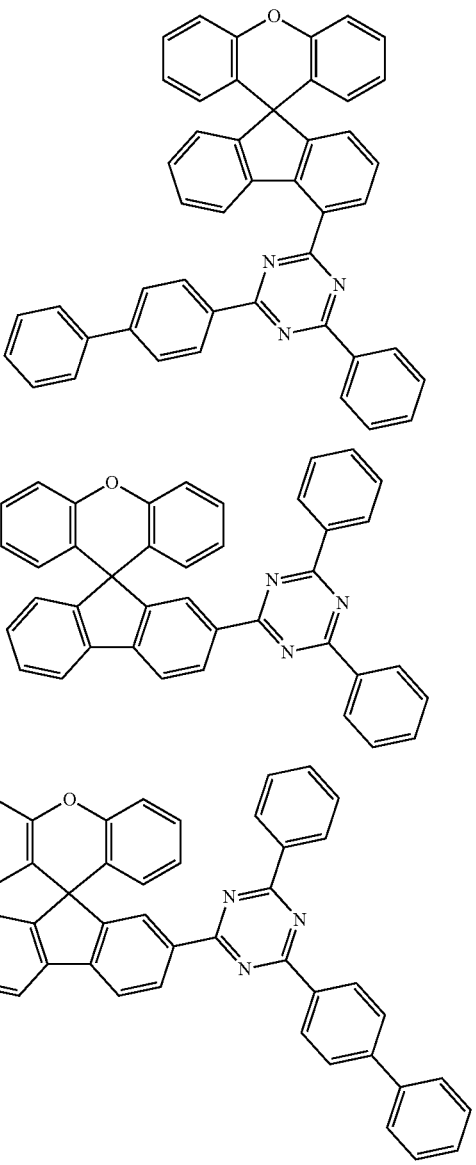

-continued
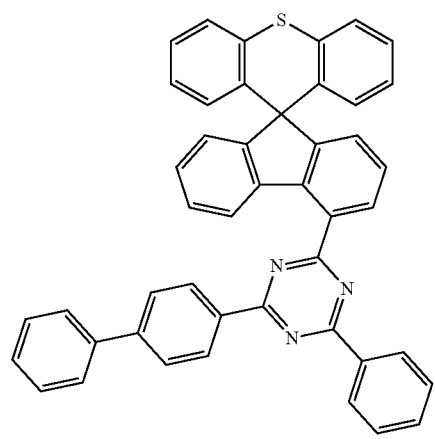
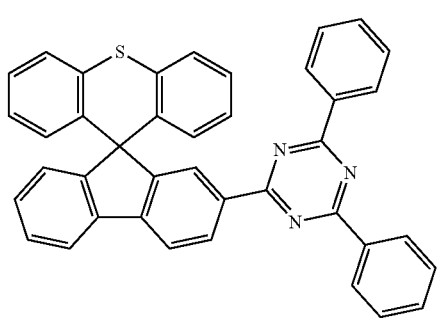
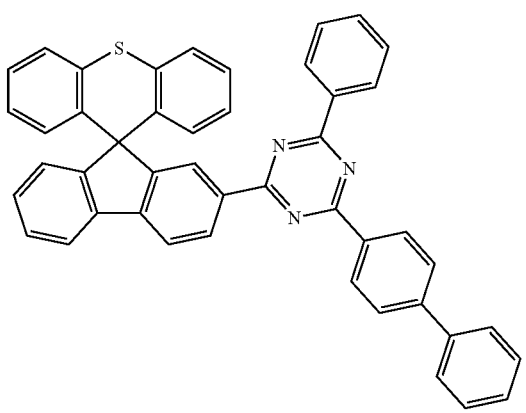
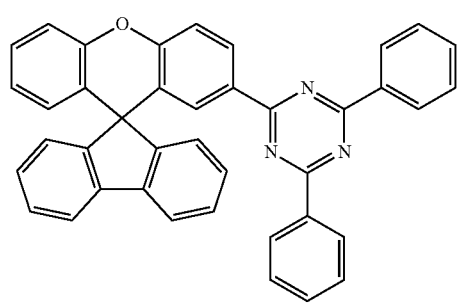
-continued
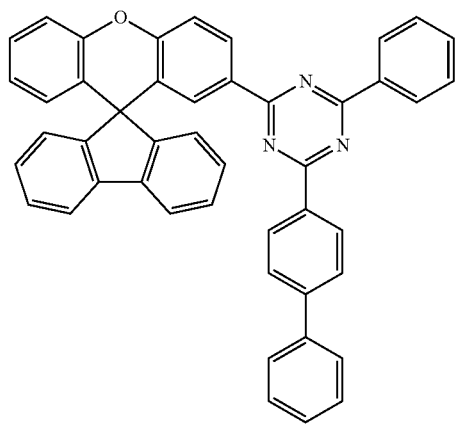
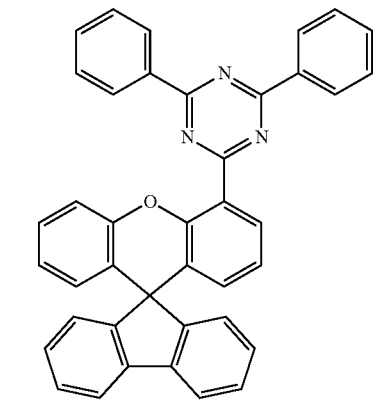
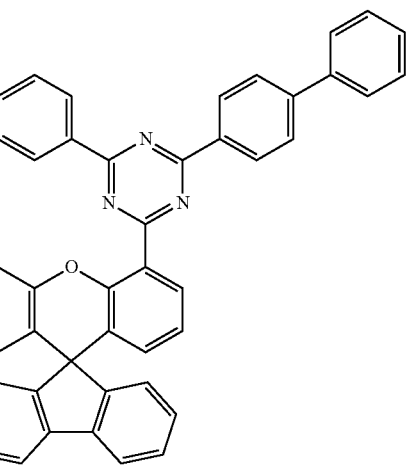
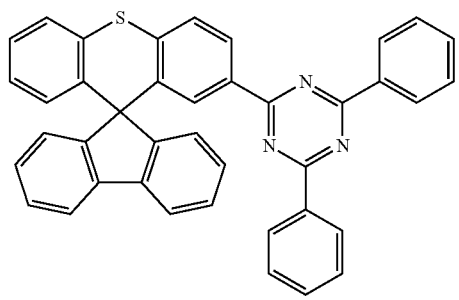

85
-continued
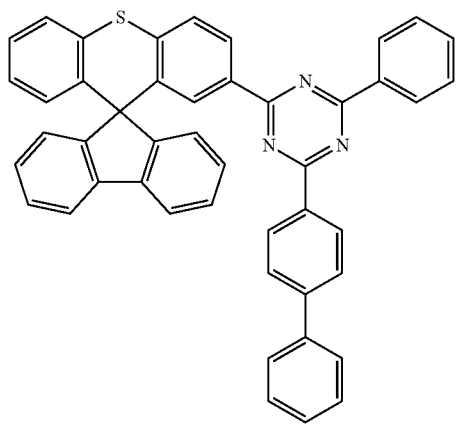
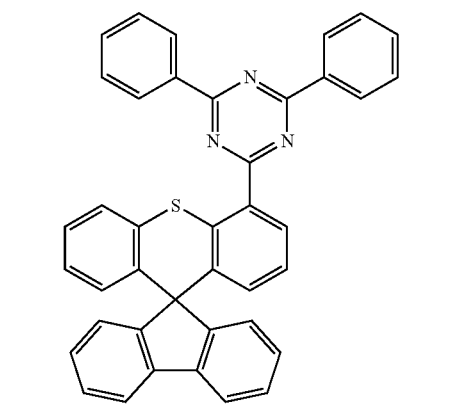
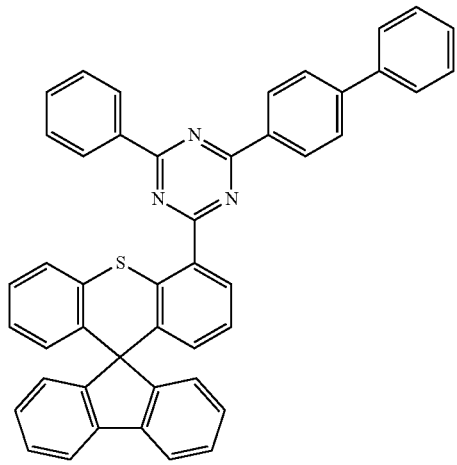
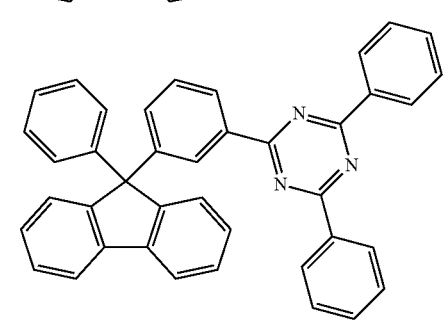
86
-continued
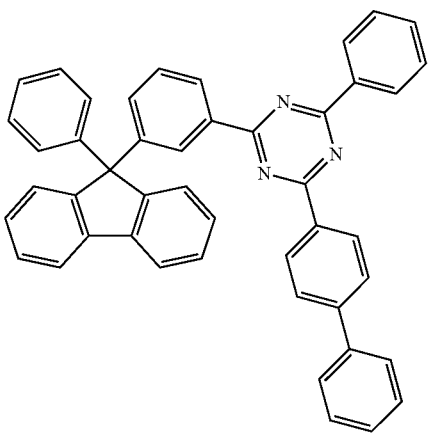
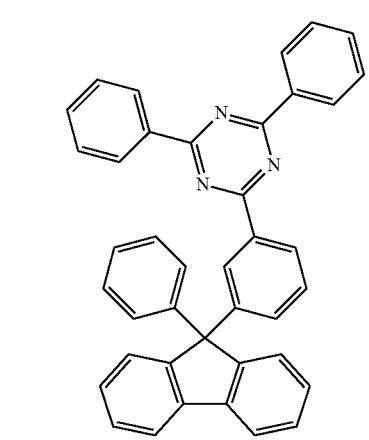
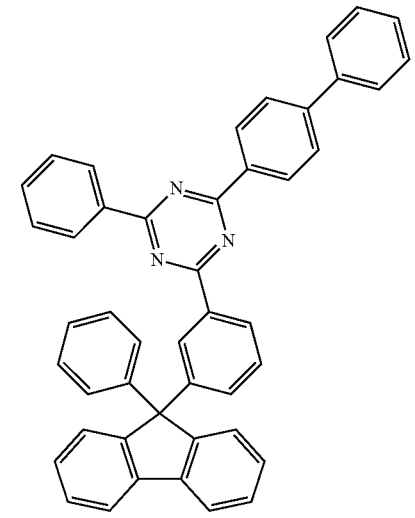

87
-continued
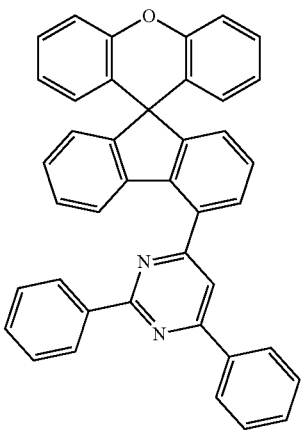
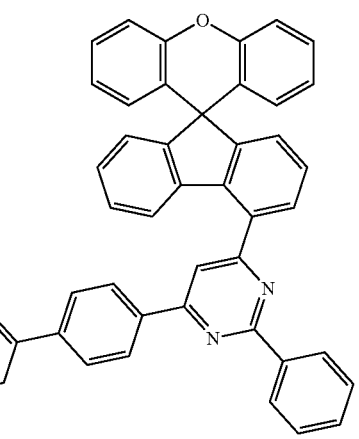
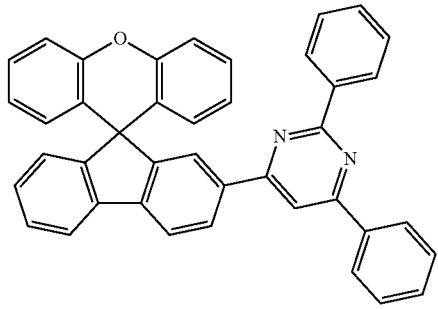
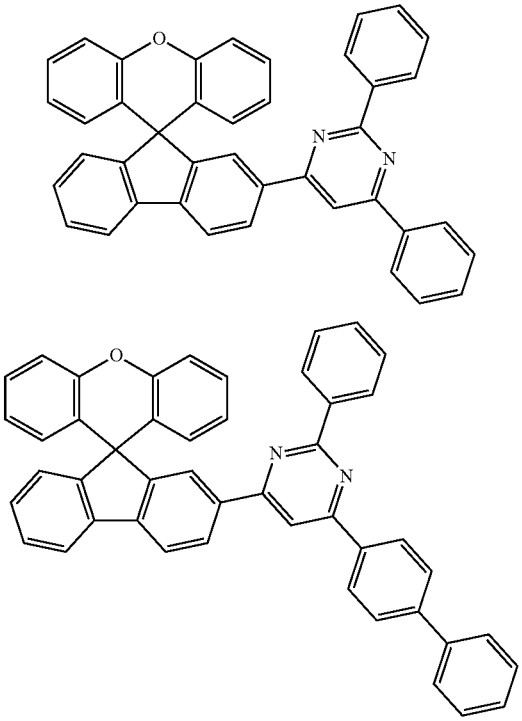
88
-continued
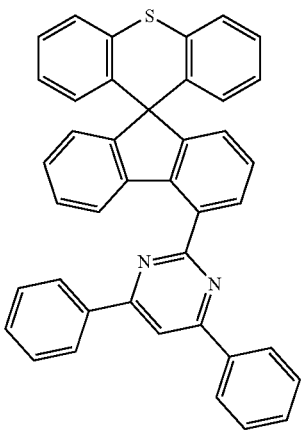
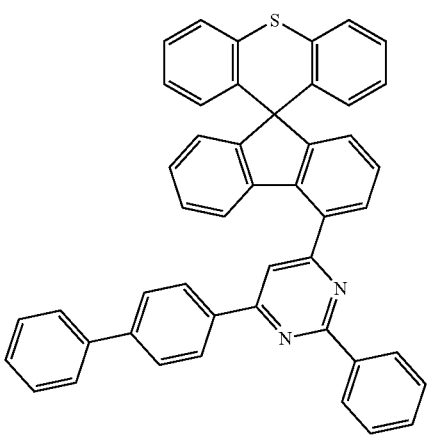
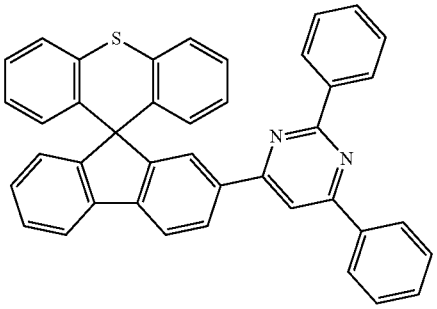

89
-continued
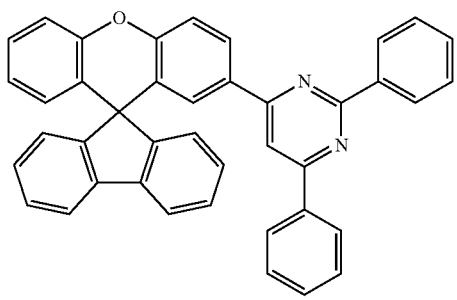
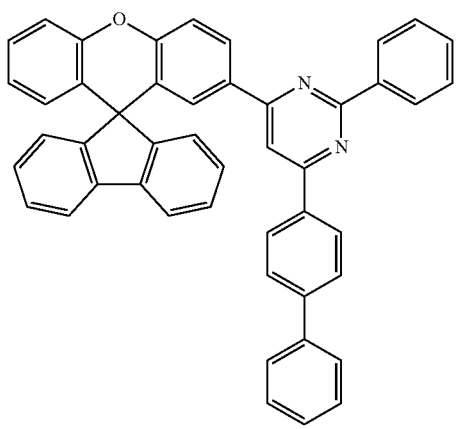
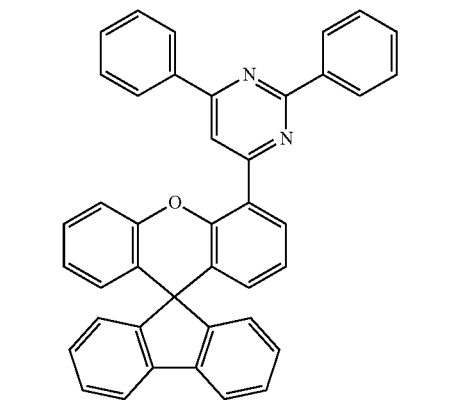
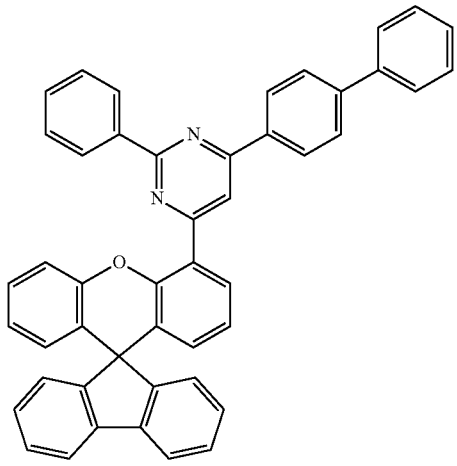
90
-continued
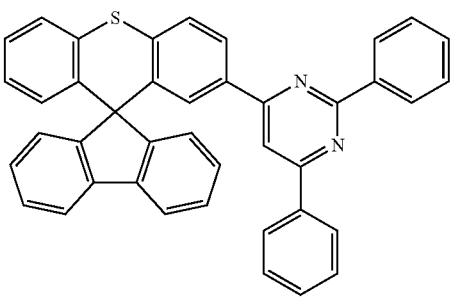
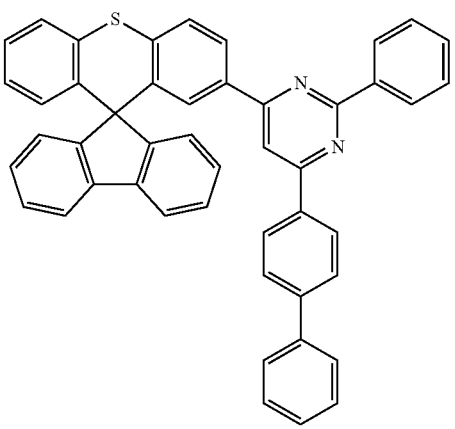
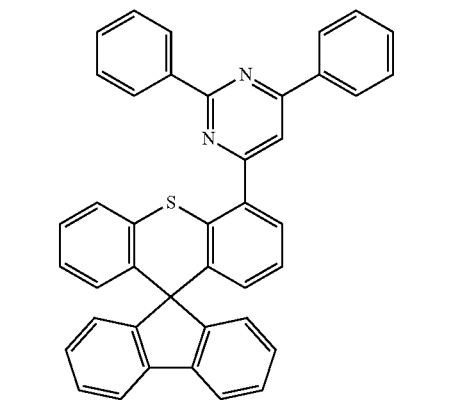
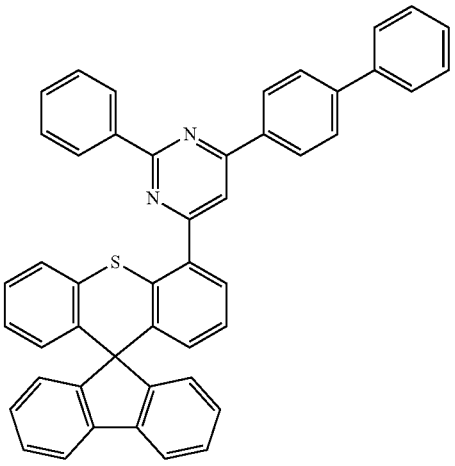

91
-continued
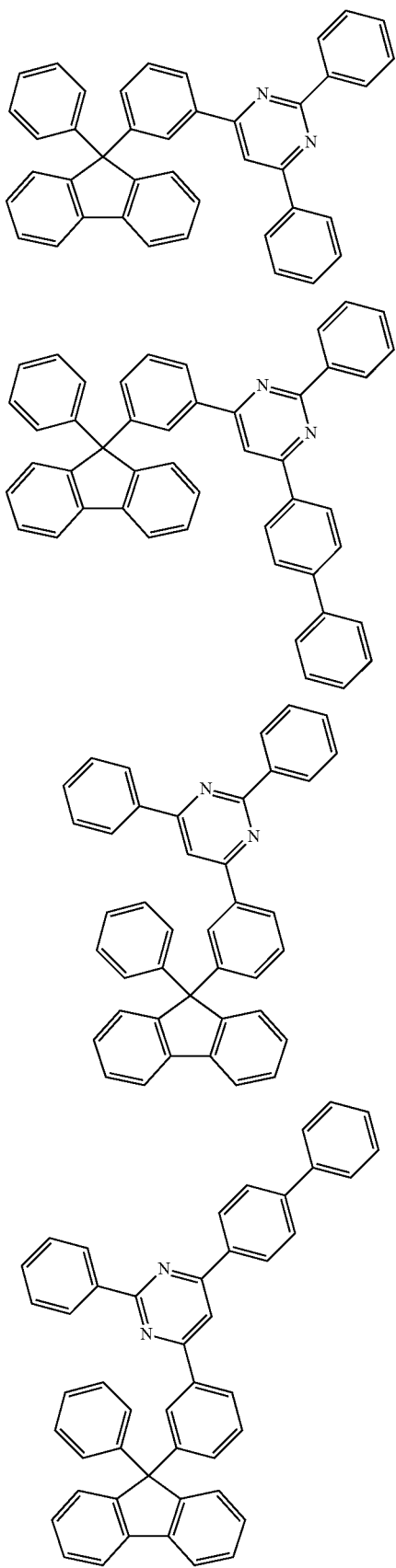
92
-continued
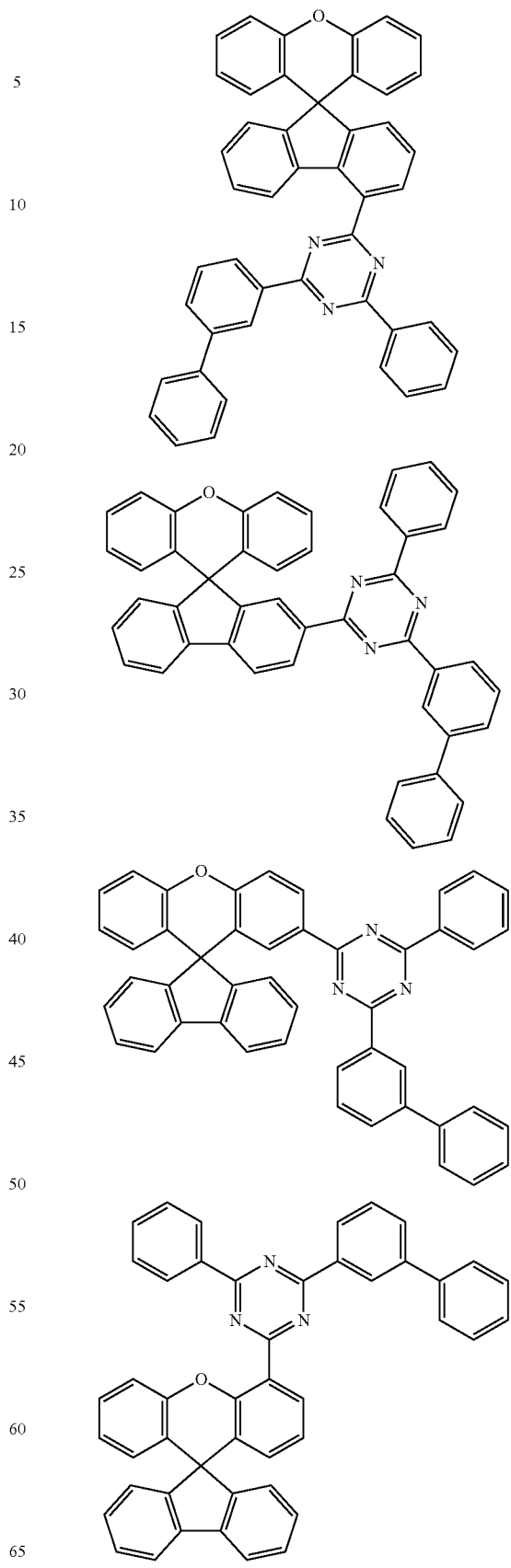

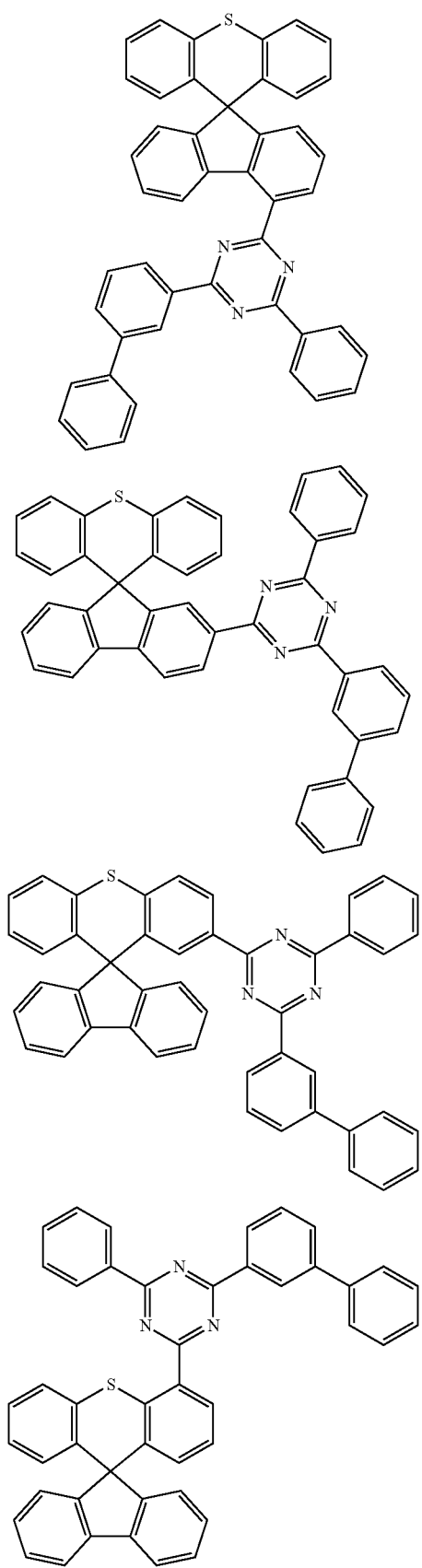

95
-continued
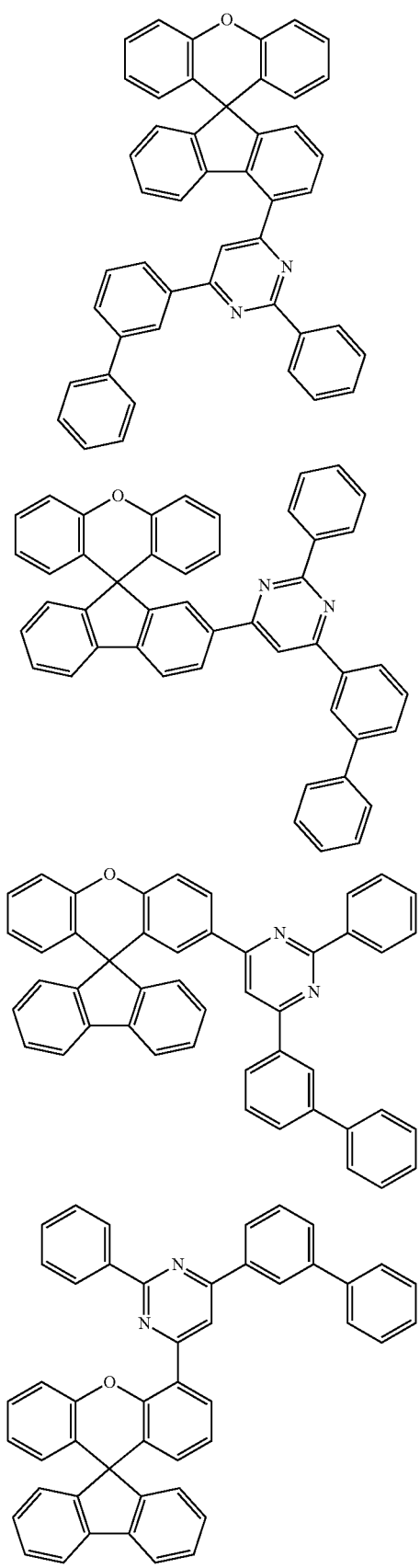
96
-continued
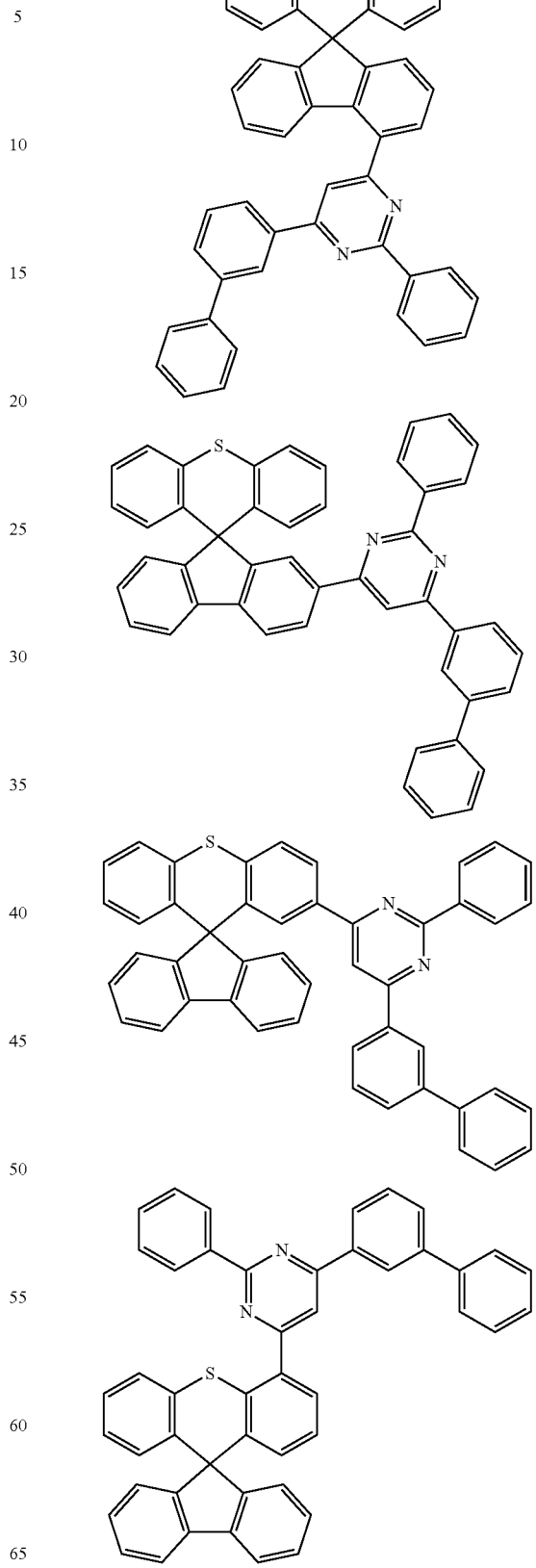

97
-continued
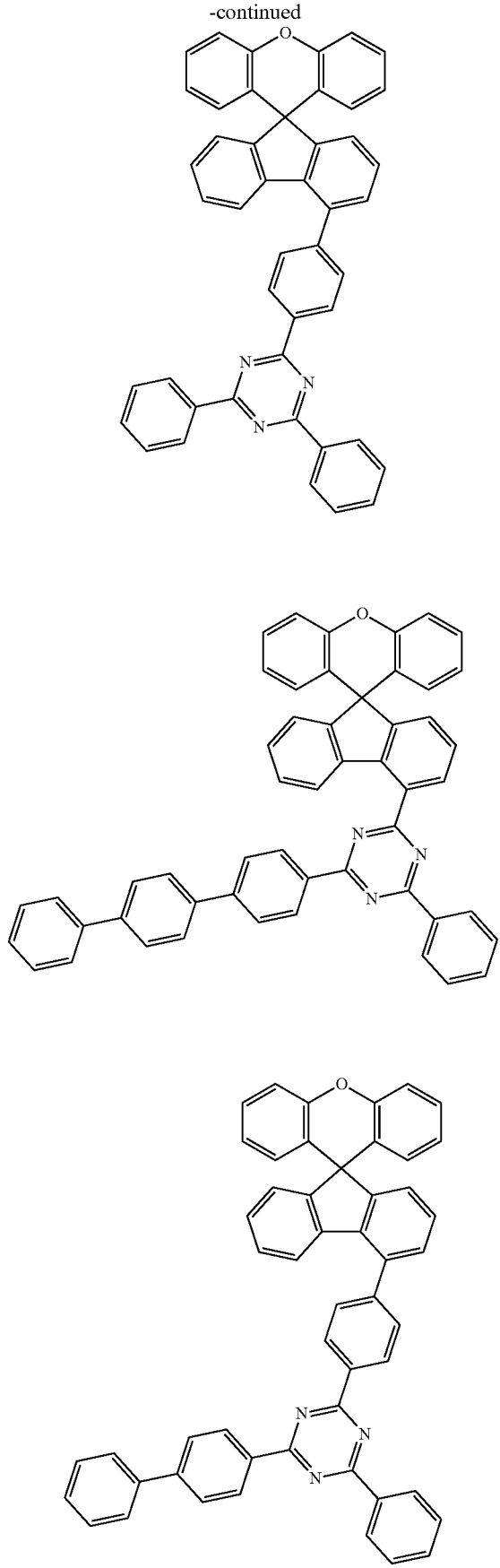
98
-continued
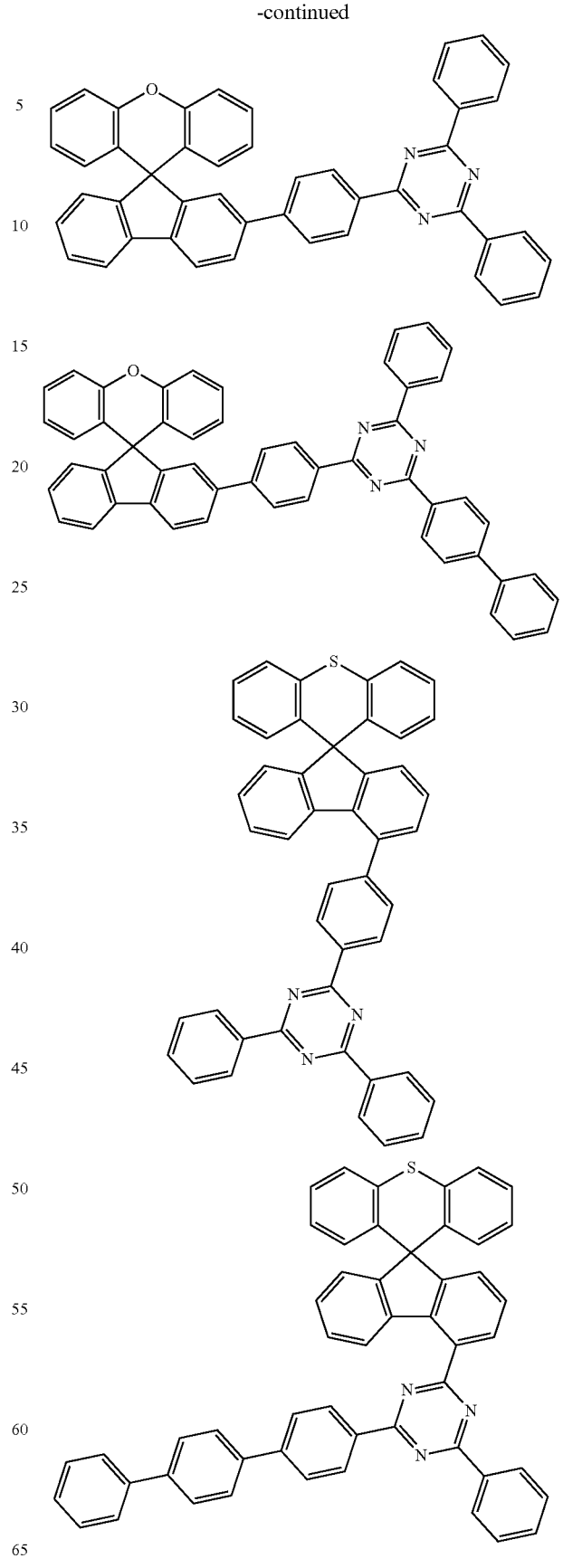

99
-continued
100
-continued
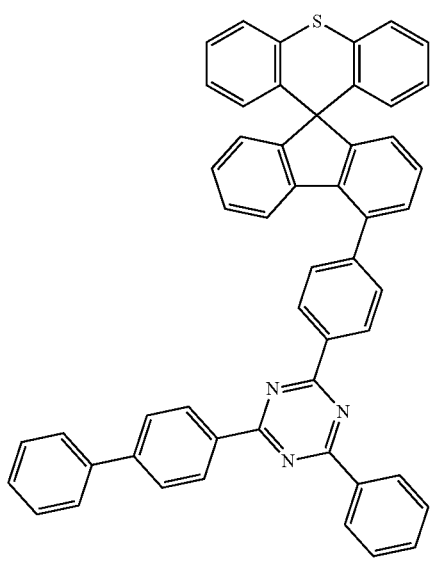
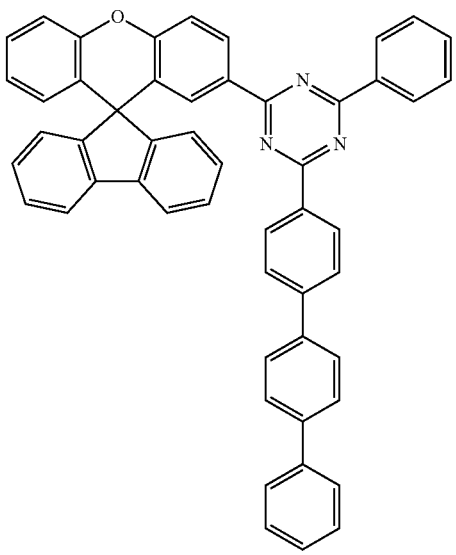
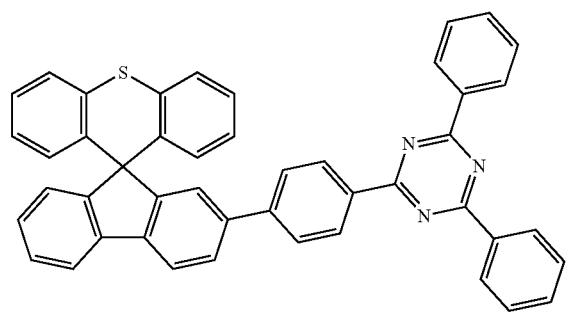
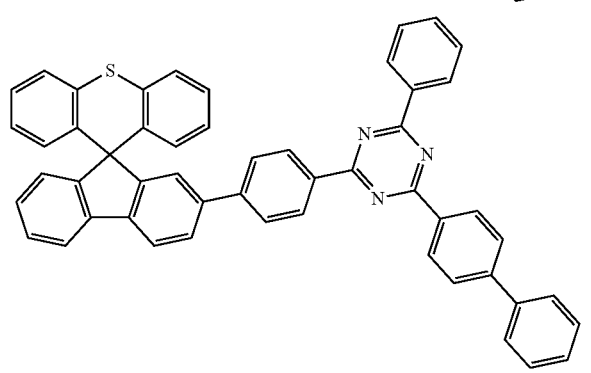
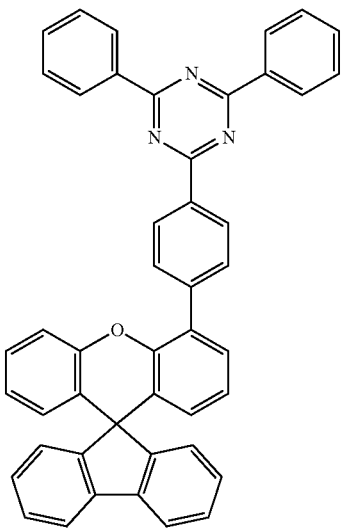

101
-continued
102
-continued
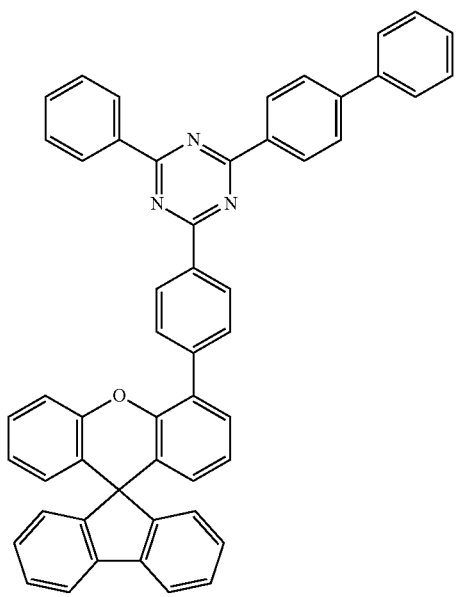
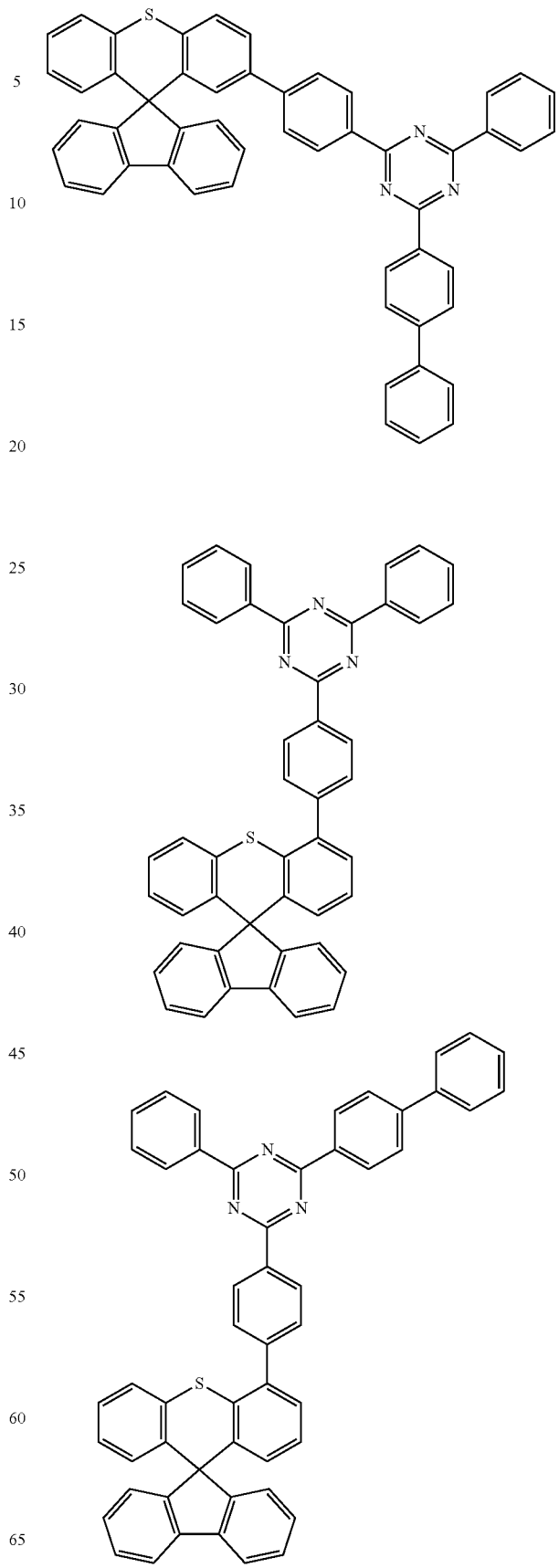

103
-continued
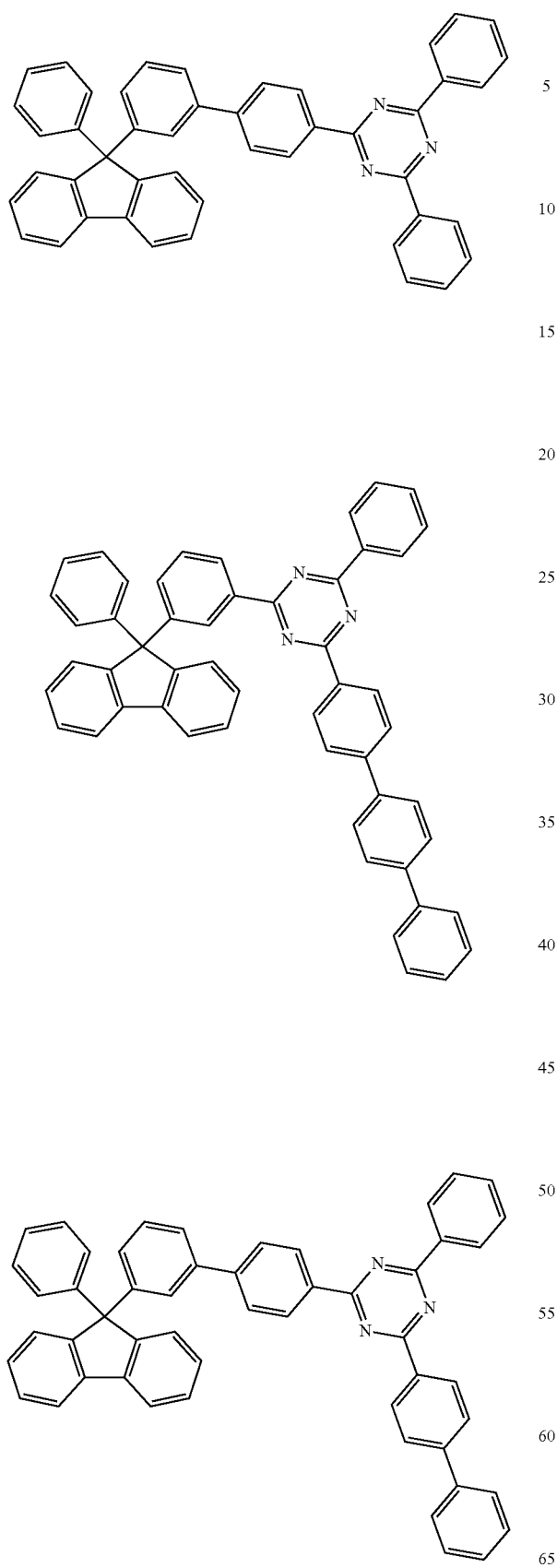
104
-continued

105
-continued
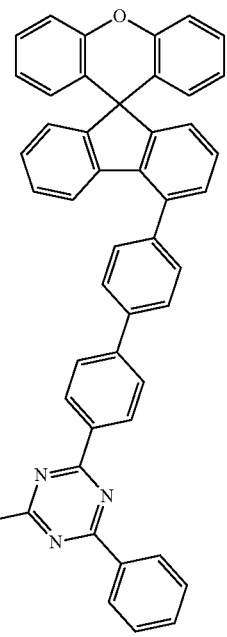
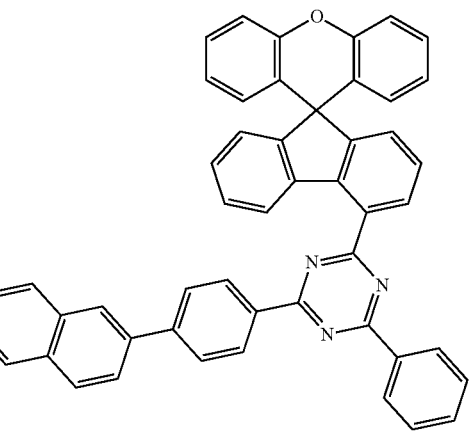
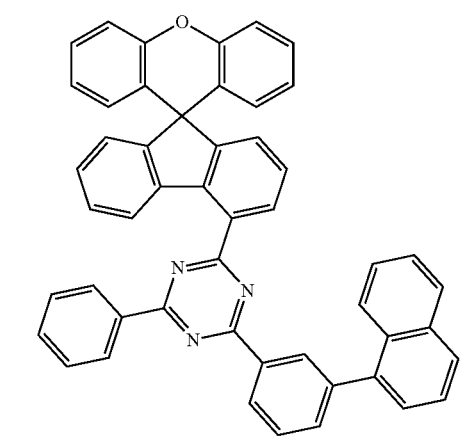
106
-continued
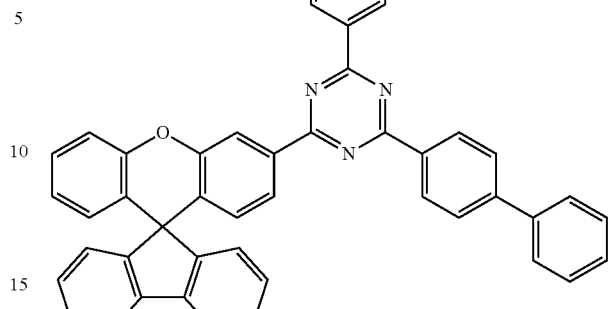
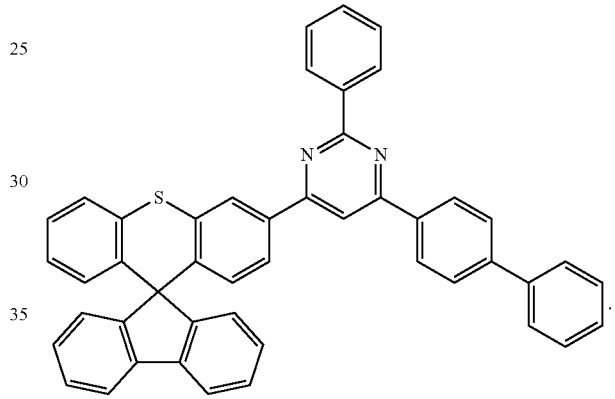
Furthermore, in an exemplary embodiment of the present application, Formula 2 is selected from the following compounds. Specifically, Formula 2 is a compound including a cyano group:
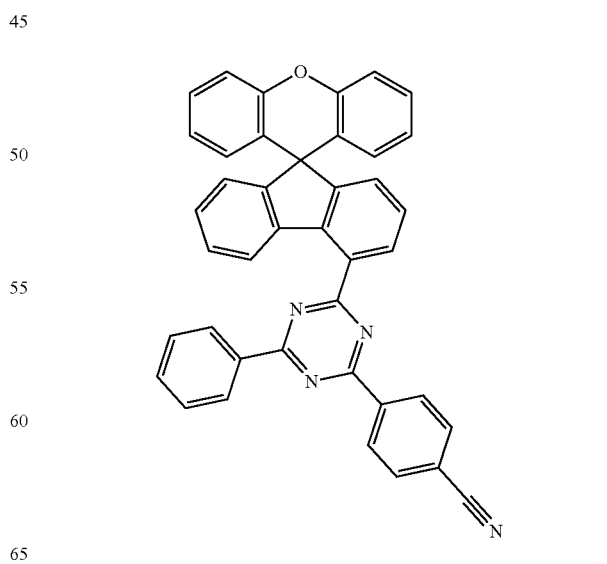

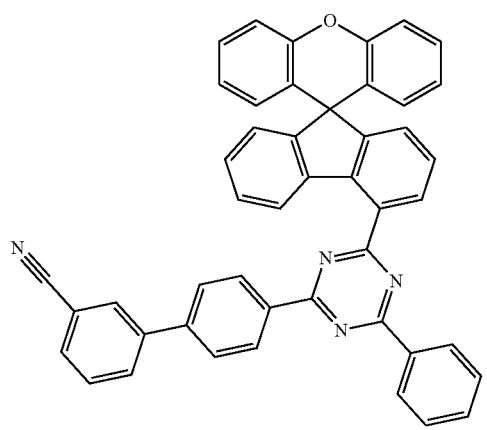
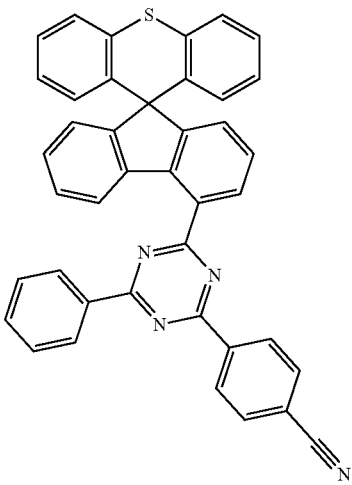
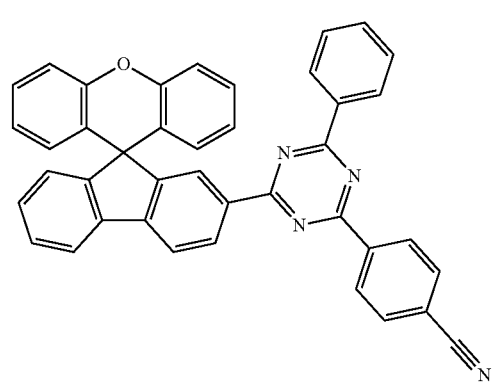
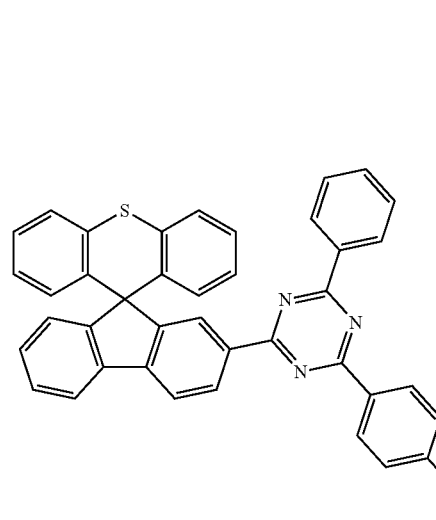
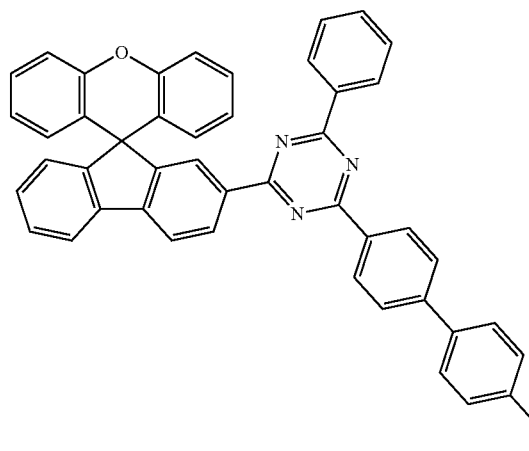

109
-continued
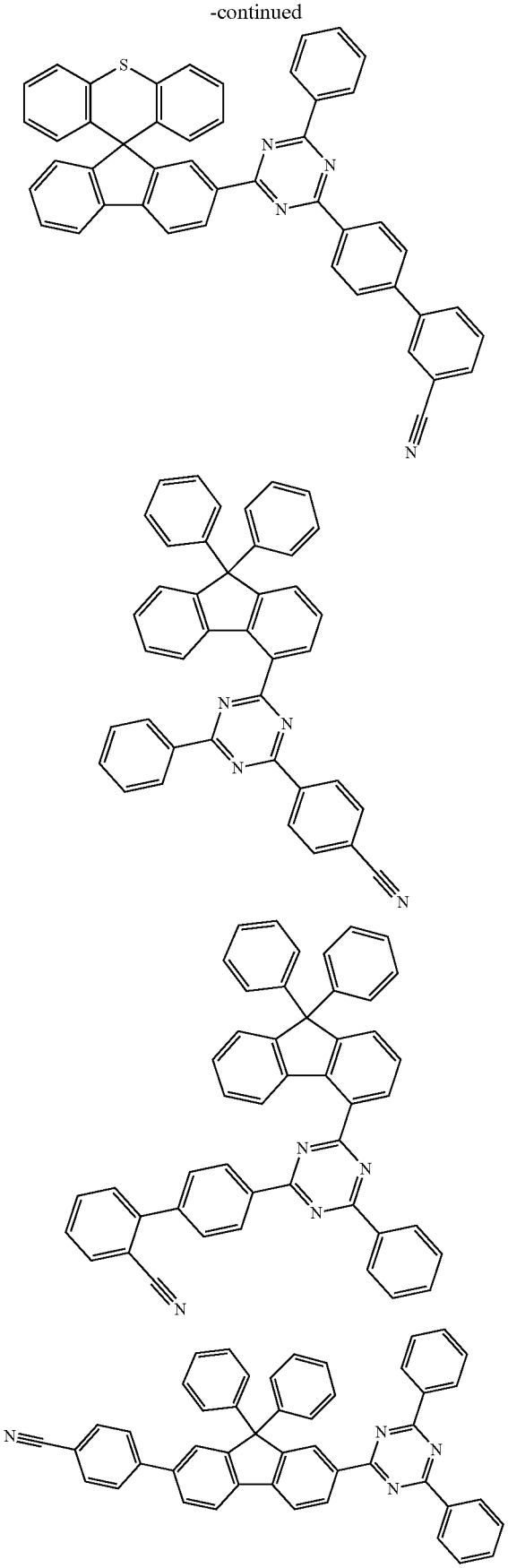
110
-continued
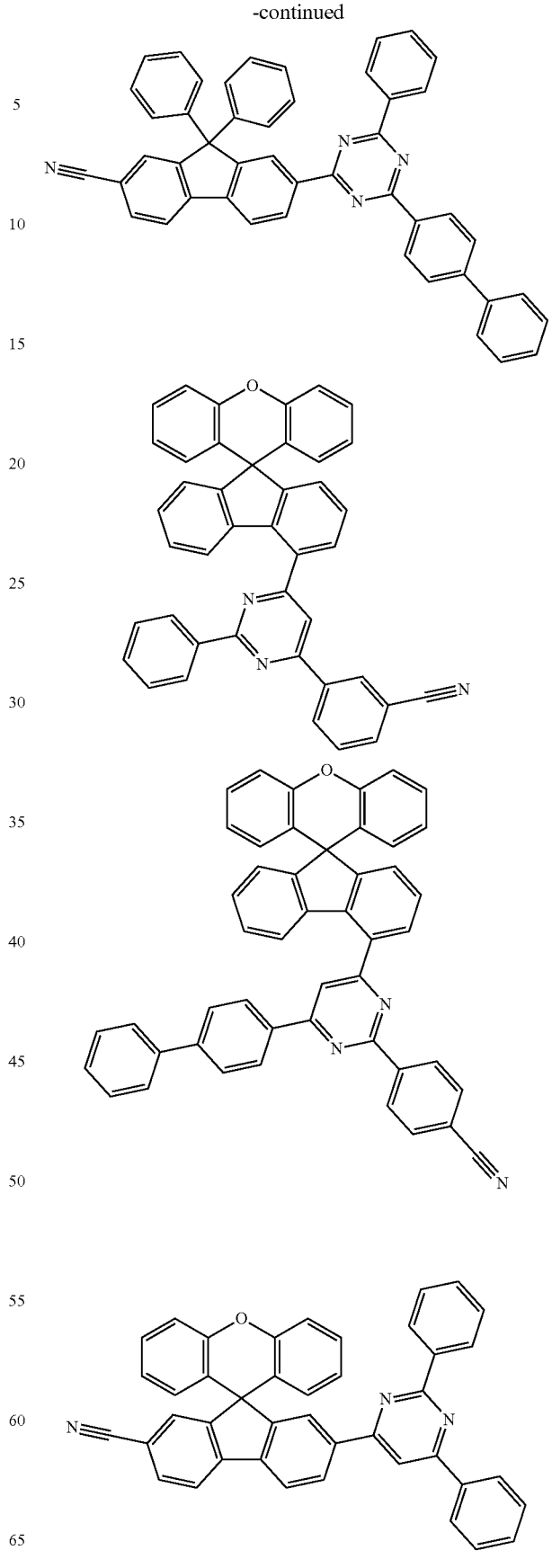

111
-continued
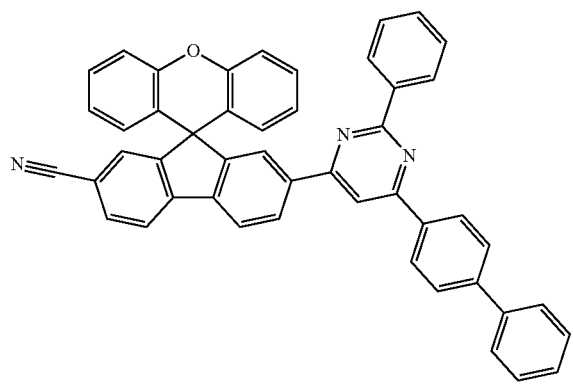
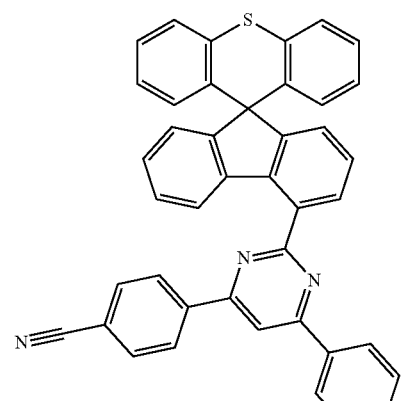
112
-continued
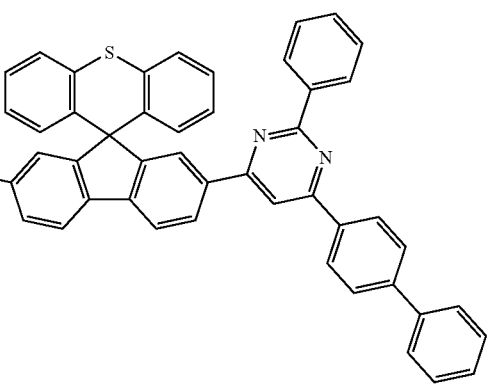
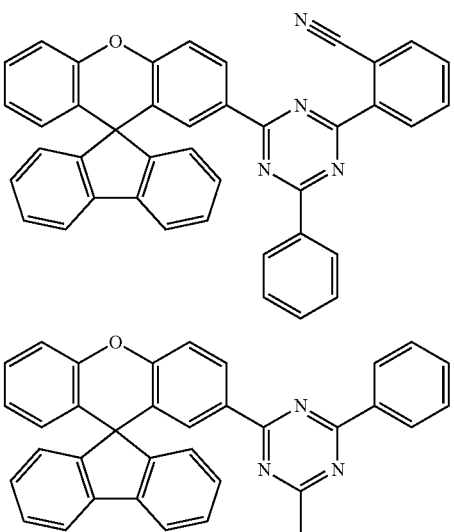
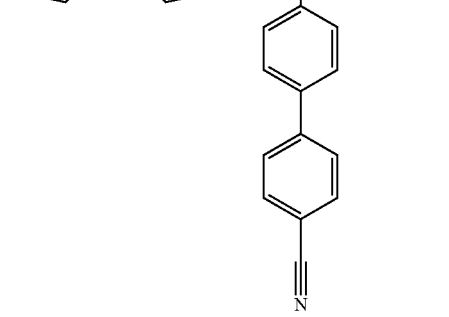
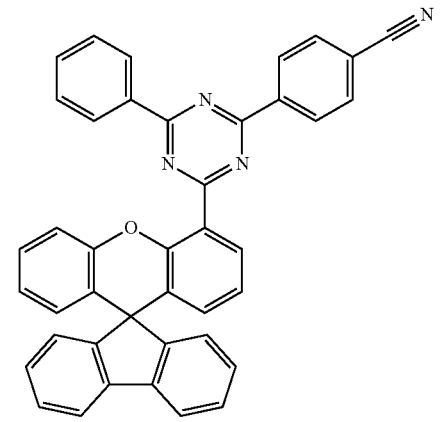

113
-continued
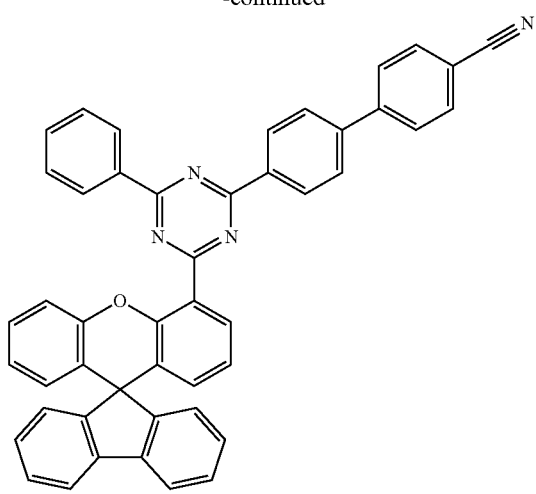
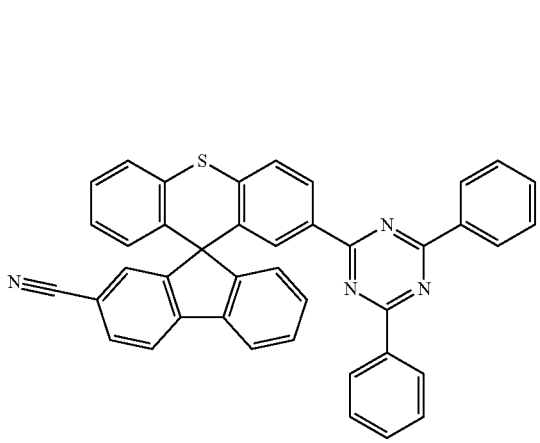
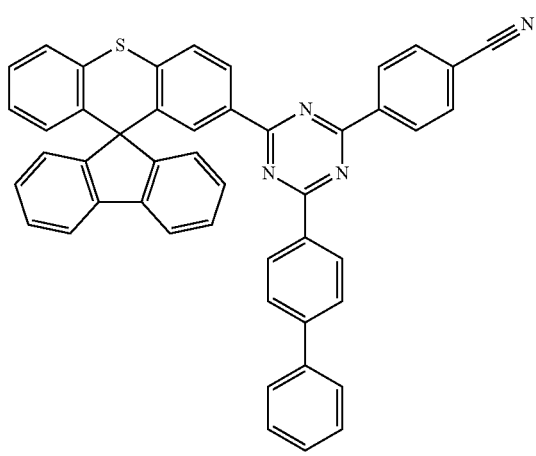
114
-continued
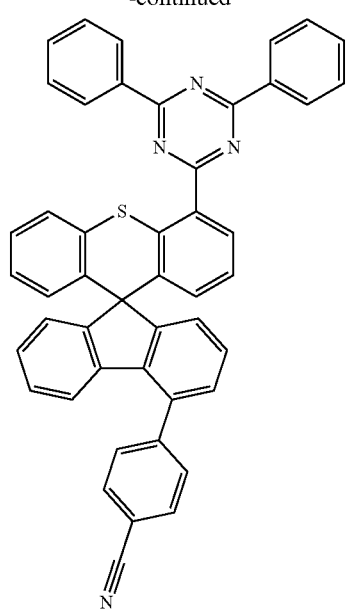
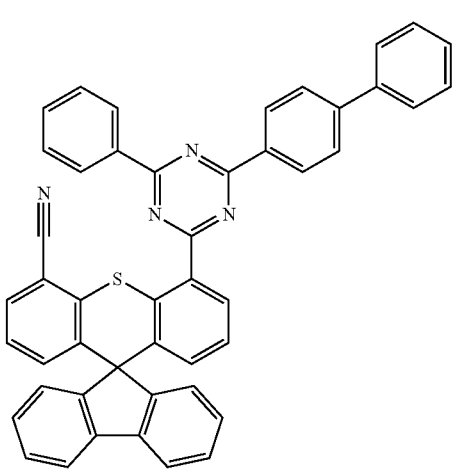
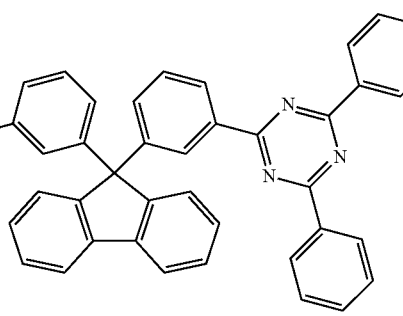

115
-continued
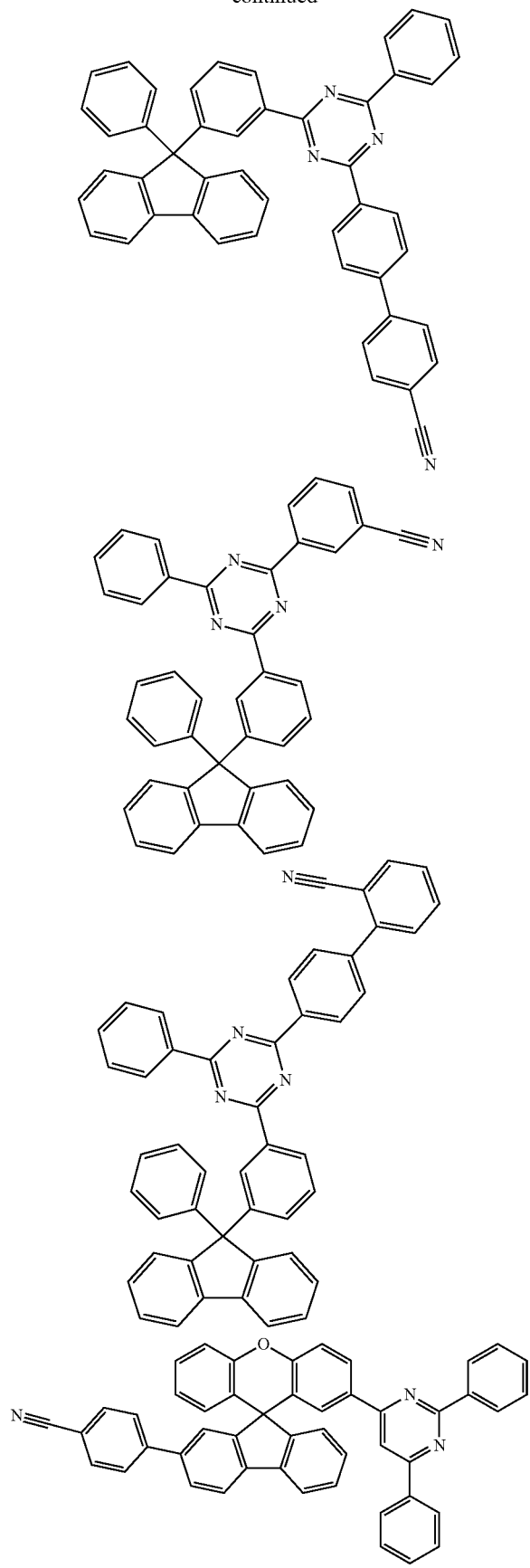
116
-continued
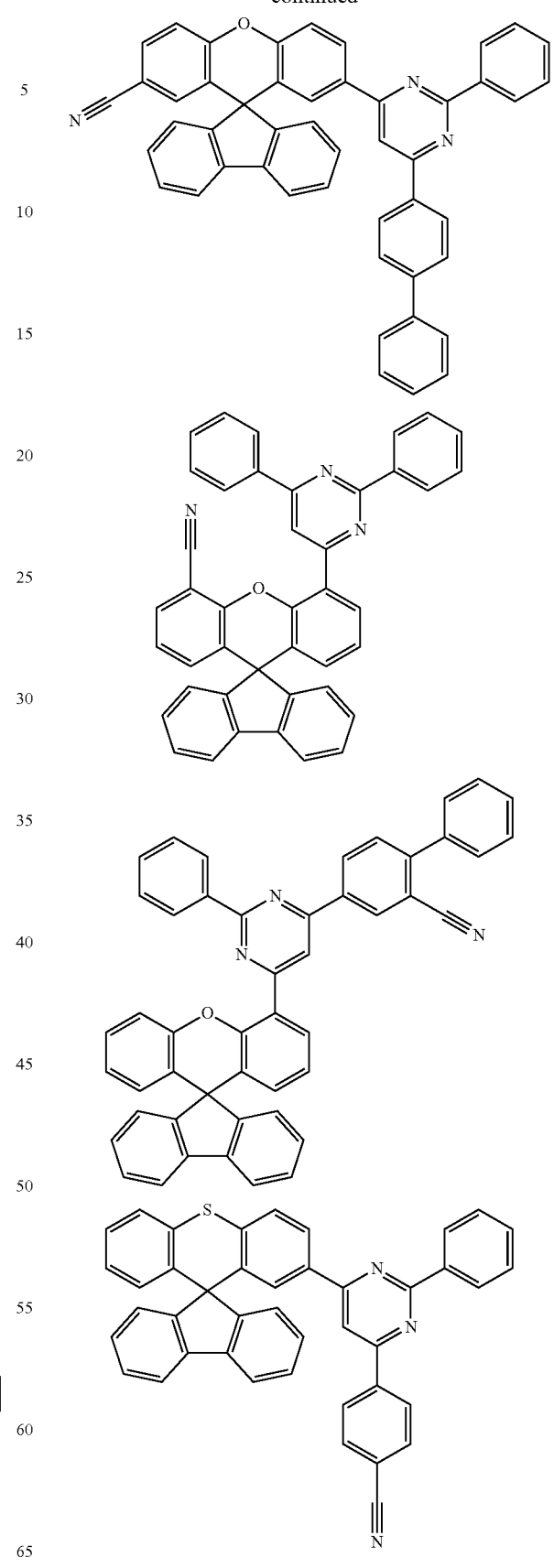

117
-continued
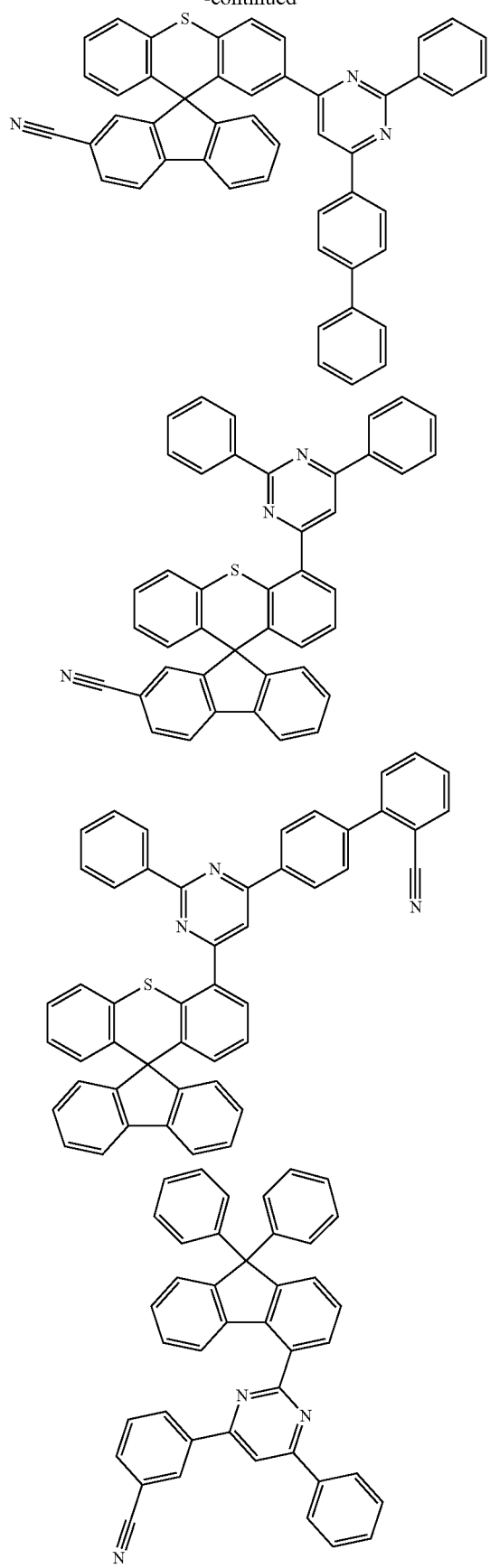
118
-continued
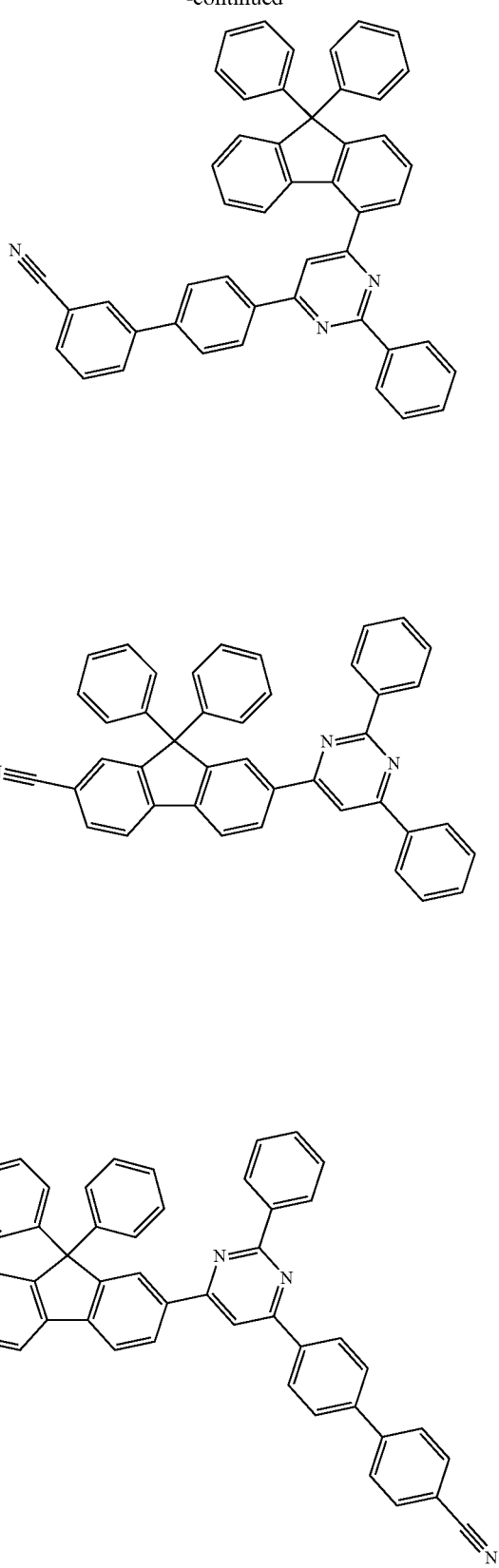

119
-continued
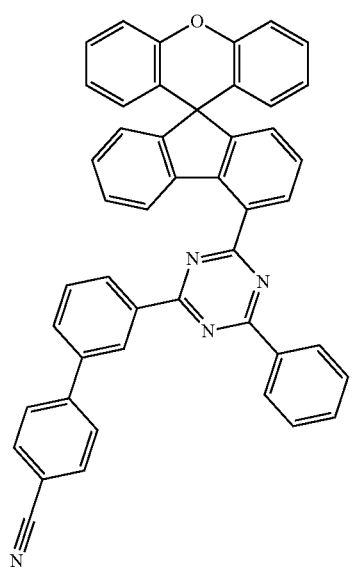
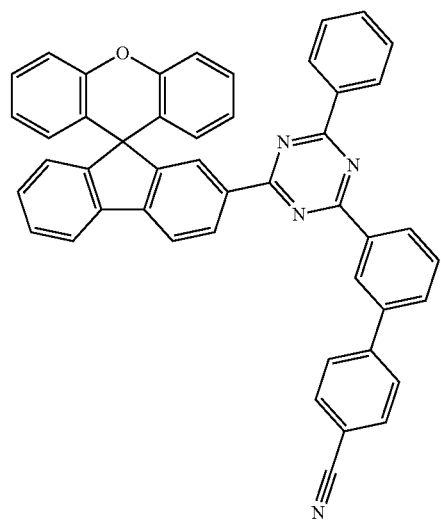
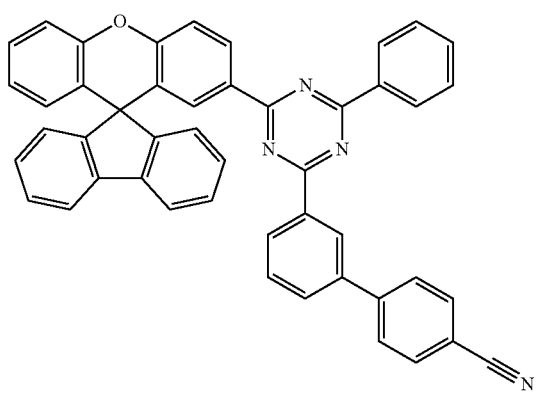
120
-continued
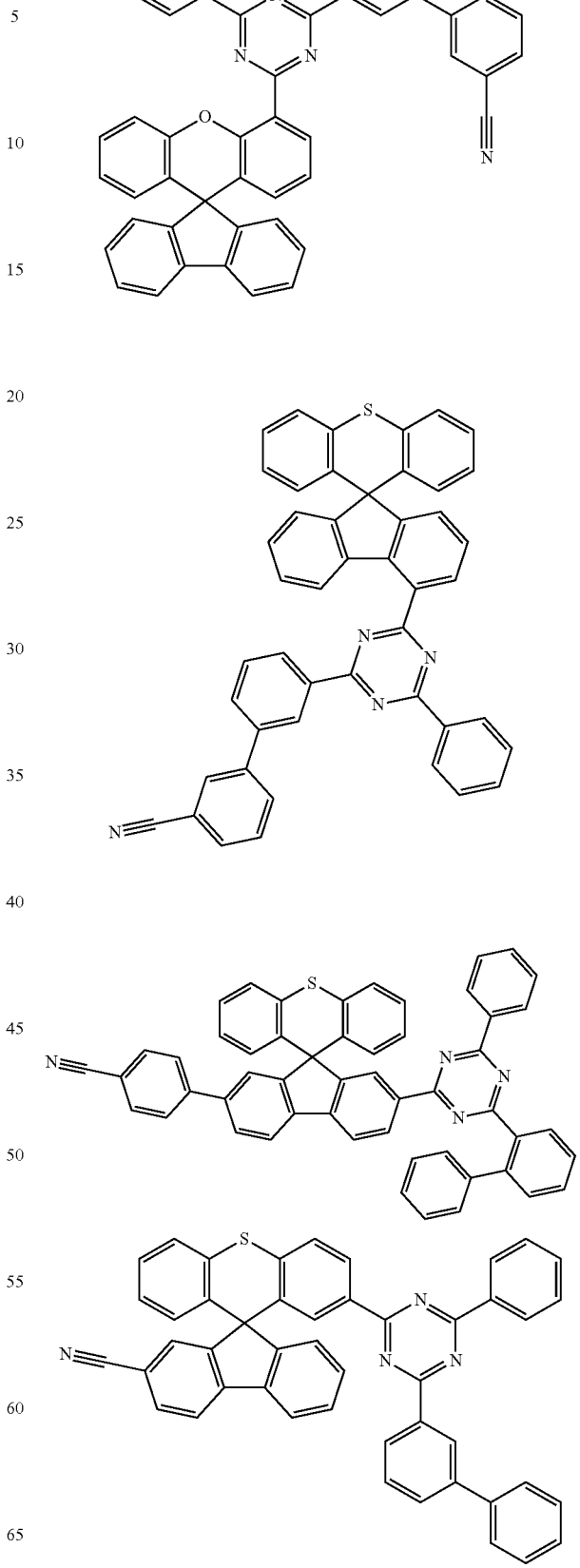

121
-continued
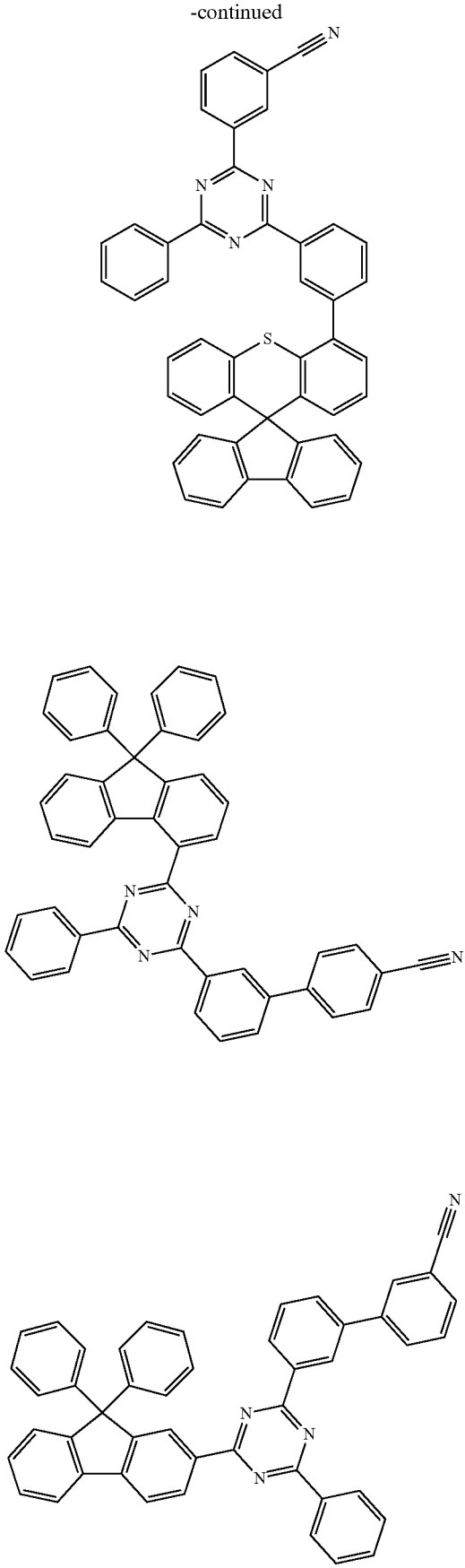
122
-continued
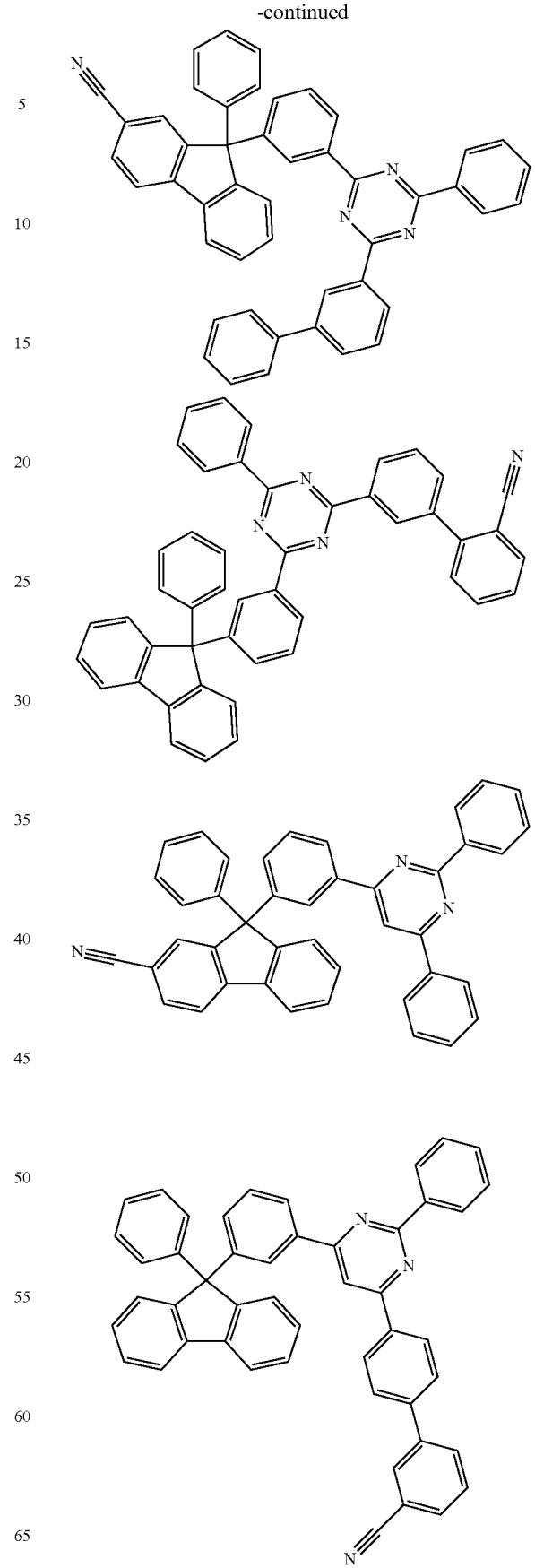

123
-continued
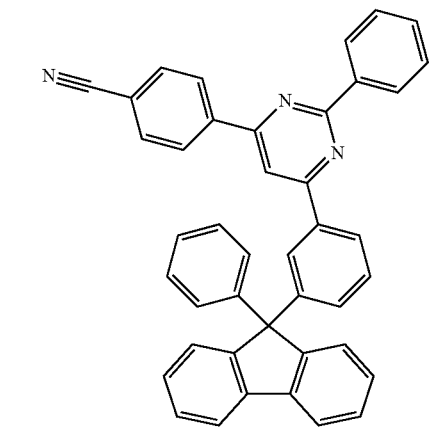
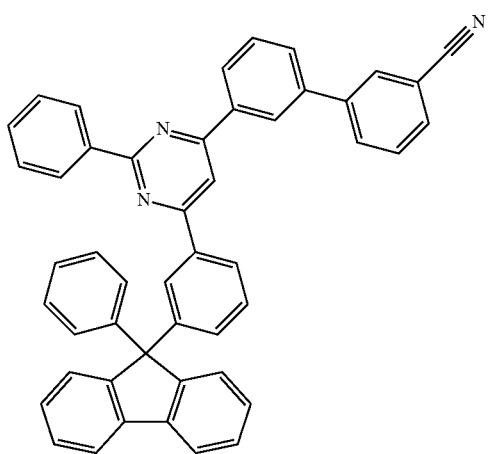
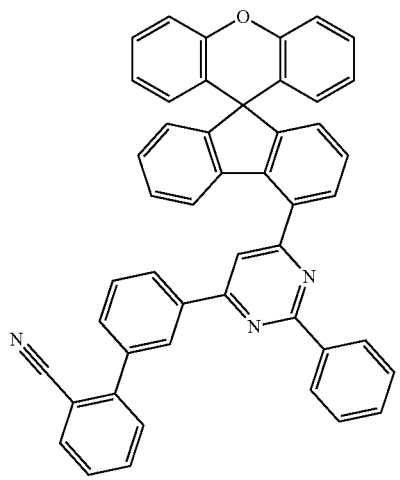
124
-continued
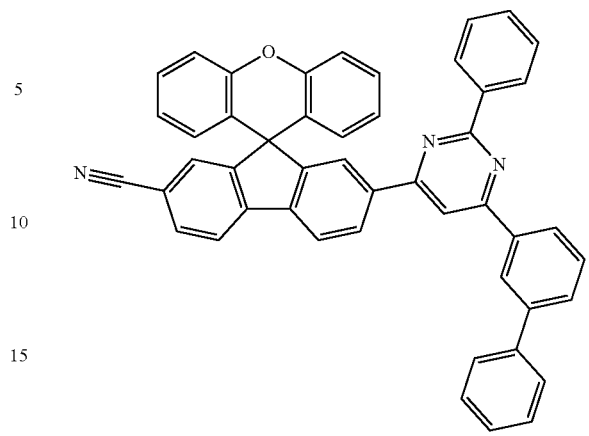
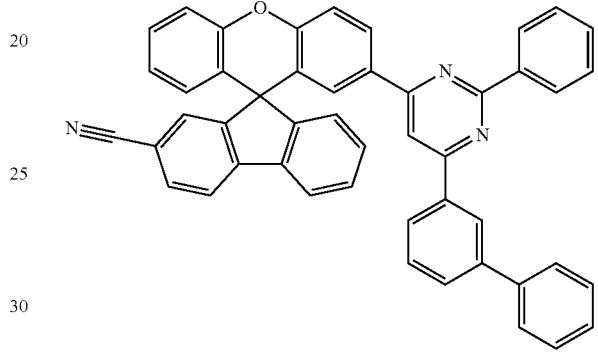
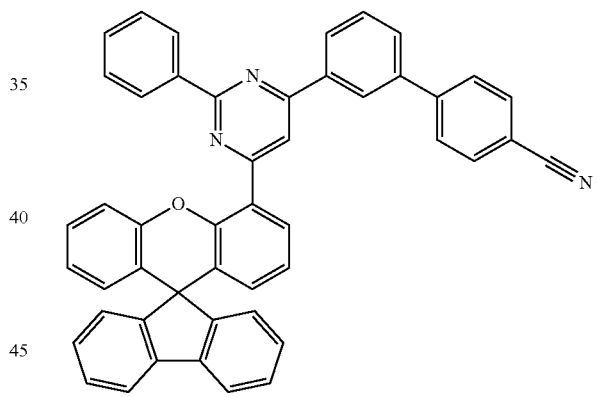
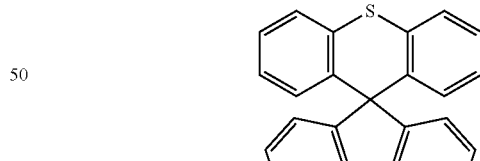
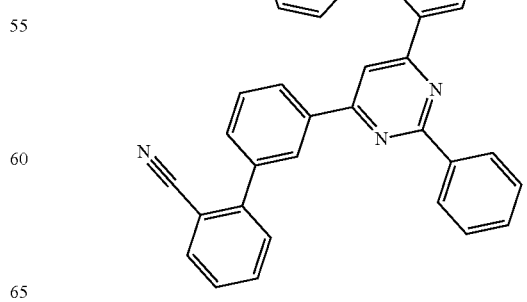

125
-continued
126
-continued
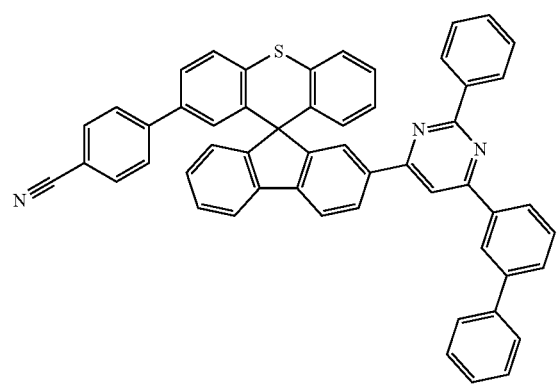
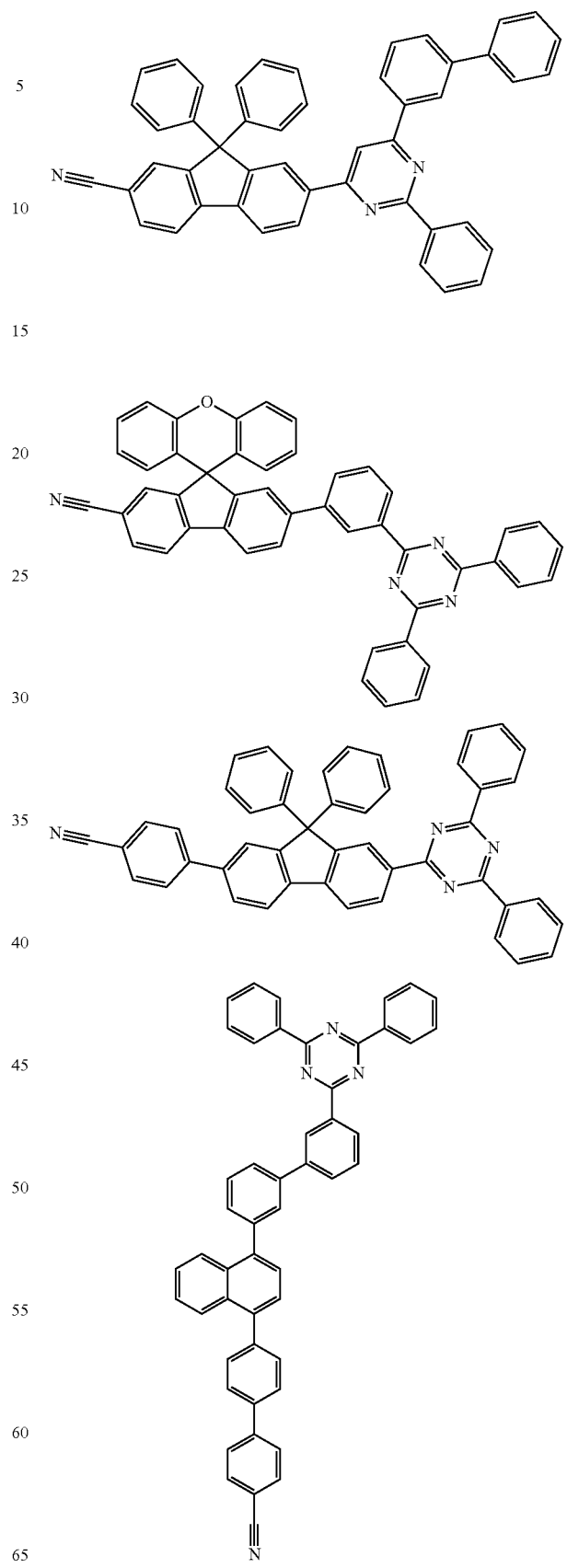

127
-continued
128
-continued
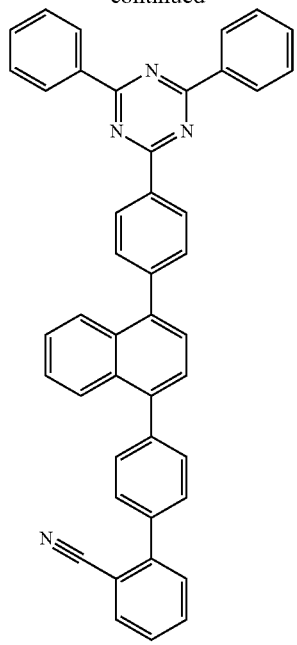
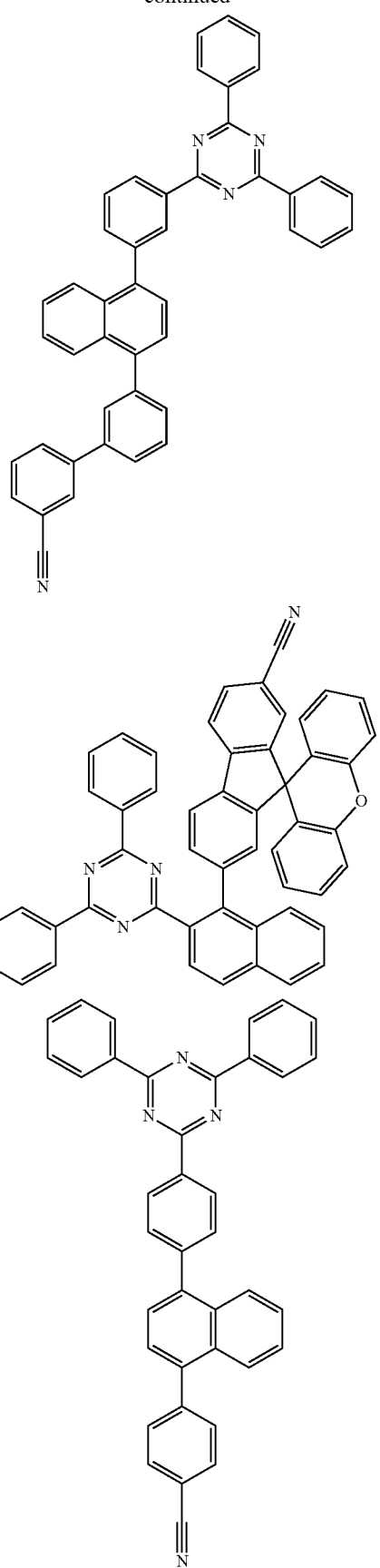

129
-continued
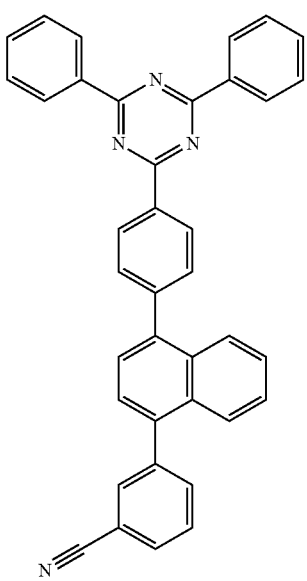
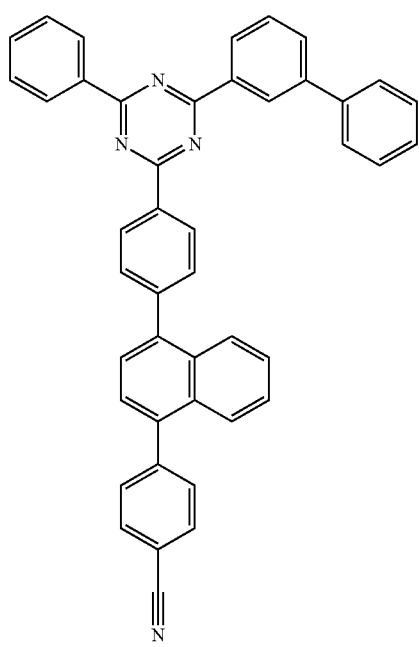
130
-continued
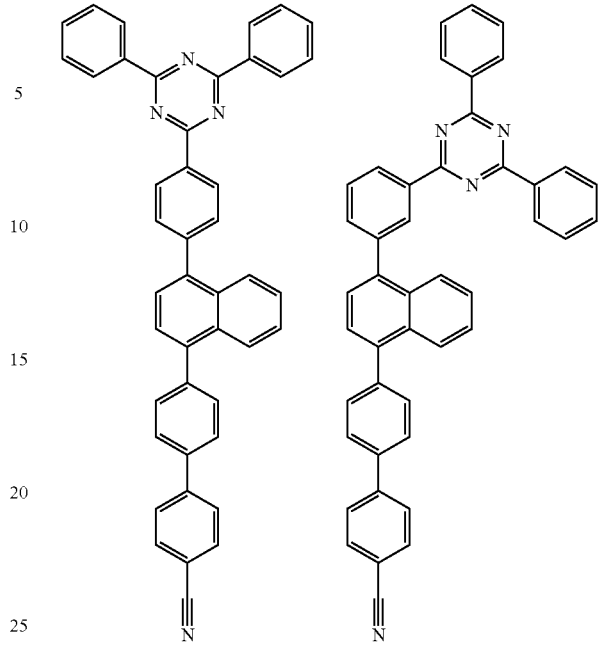
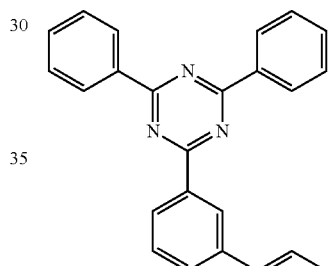
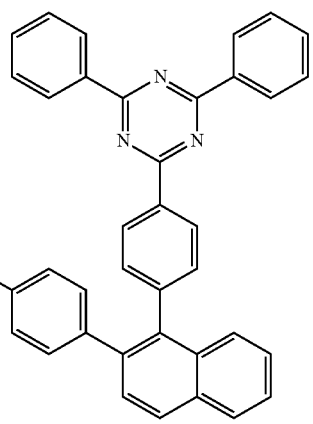

131
-continued
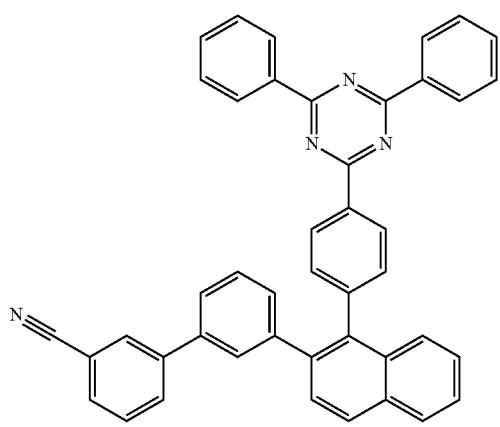
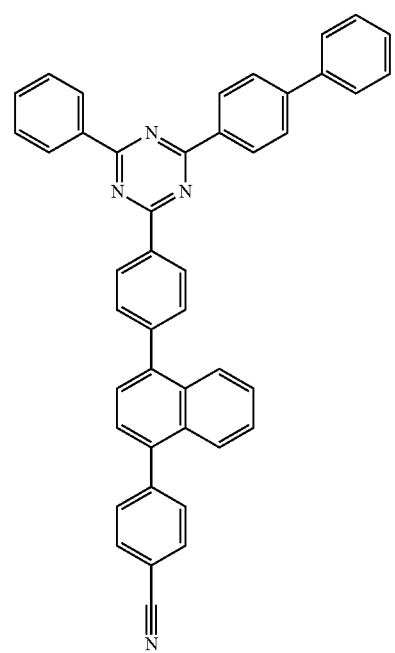
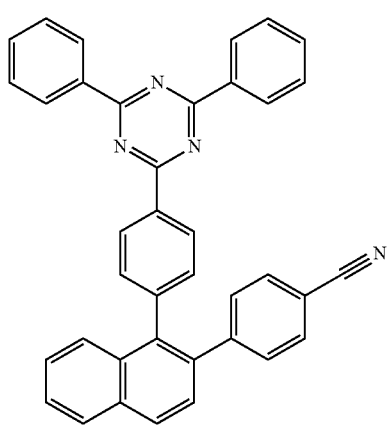
132
-continued
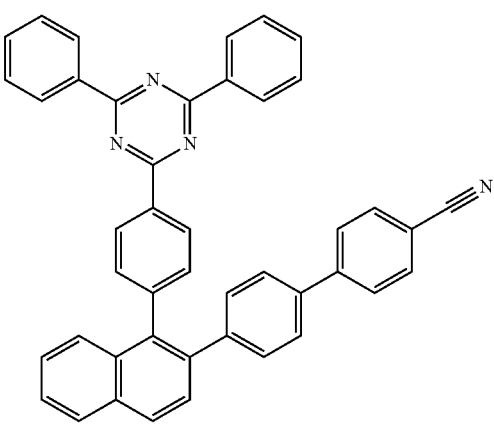
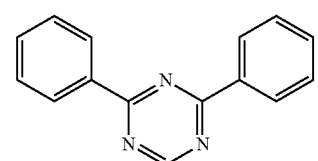
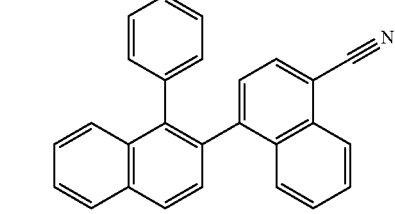
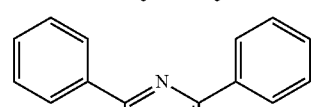
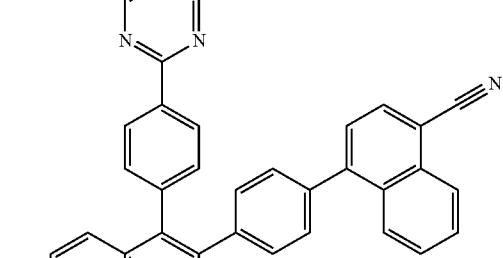
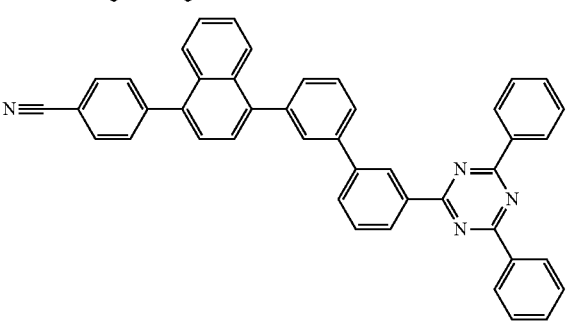

-continued
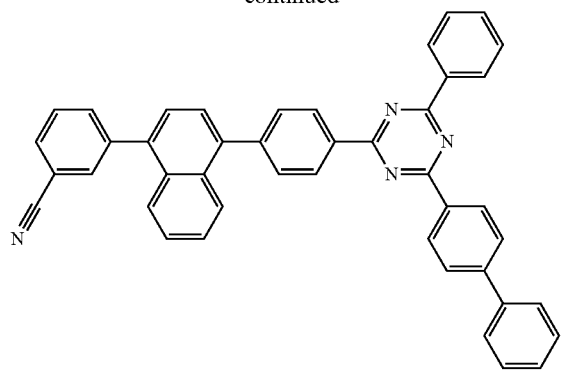
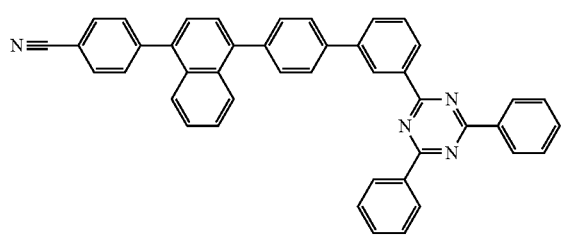
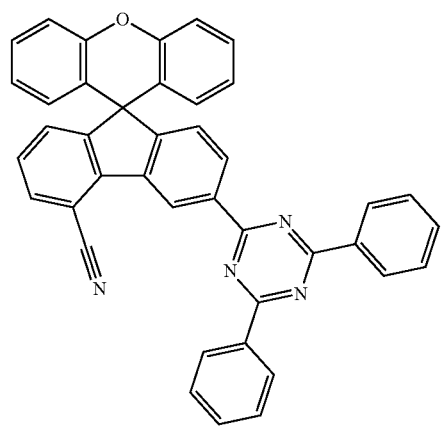
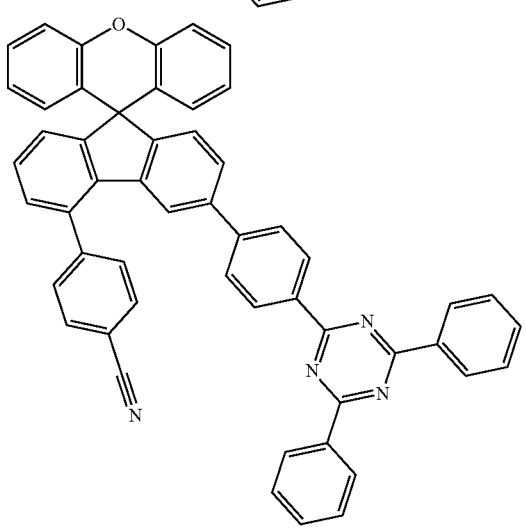
-continued
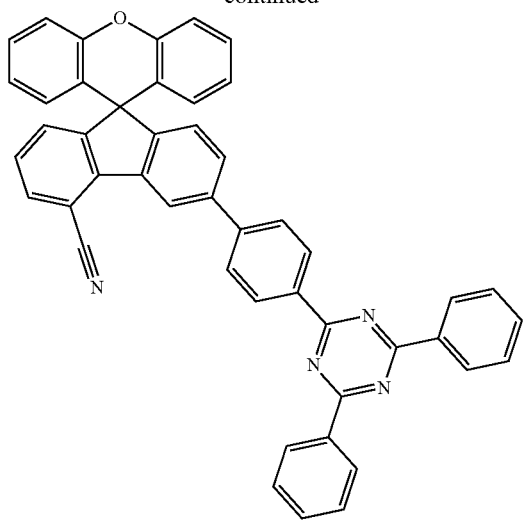
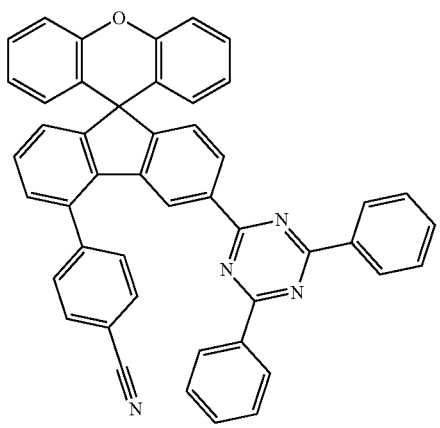
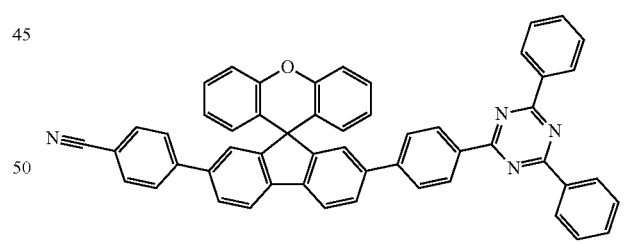
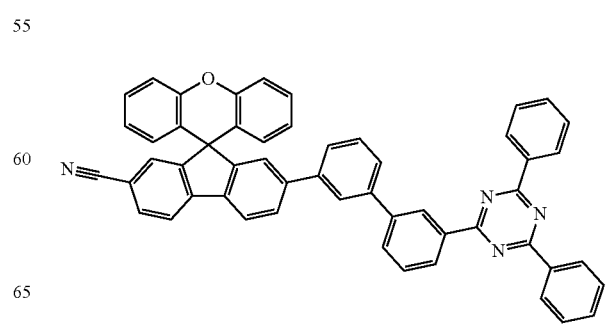

-continued

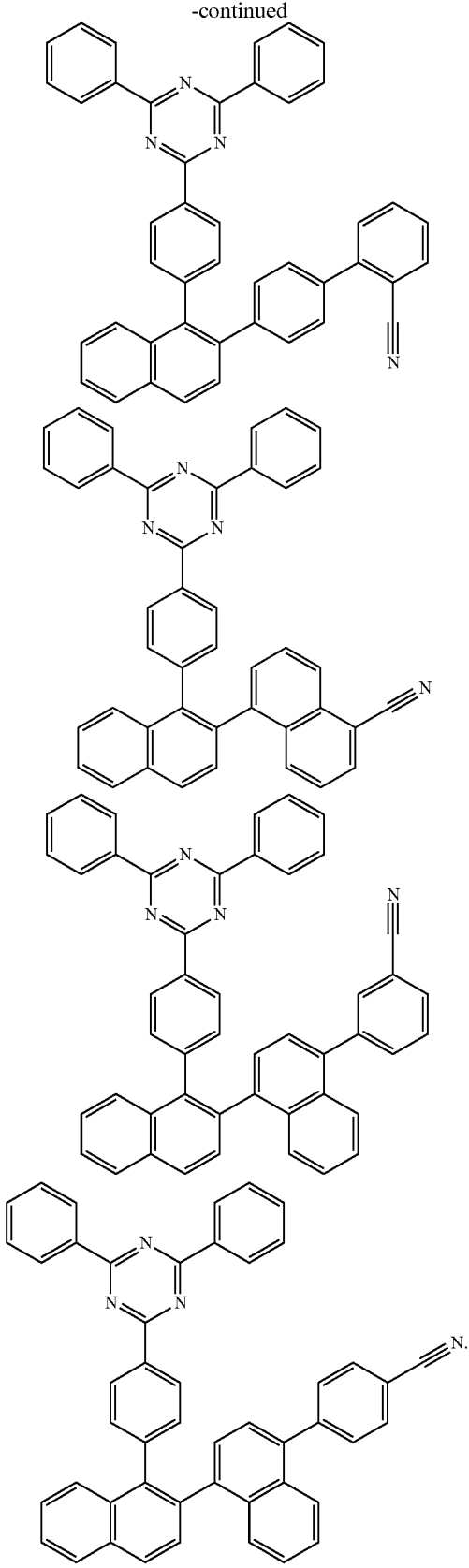

When one member is disposed "on" another member in the present application, this includes not only a case where the one member is brought into contact with another member, but also a case where still another member is present between the two members.

When one part "includes" one constituent element in the present application, unless otherwise specifically described, this does not mean that another constituent element is excluded, but means that another constituent element can be further included.

The first and second organic material layers of the organic light emitting device of the present application can also be composed of a single-layered structure, but can be composed of a multi-layered structure in which organic material layers having two or more layers are stacked. For example, the first organic material layer of the present application can be composed of one to three layers. In addition, the organic light emitting device of the present application can have a structure including a hole injection layer, a light emitting layer, an electron transport layer, and the like as organic material layers. However, the structure of the organic light emitting device is not limited thereto, and can include a greater or fewer number of organic layers.

In an exemplary embodiment of the present application, the organic light emitting device further includes one or two or more layers selected from the group consisting of a hole injection layer, a hole transport layer, an electron blocking layer, a hole blocking layer, an electron transport layer, and an electron injection layer.

In an exemplary embodiment of the present application, the organic light emitting device includes: a first electrode; a second electrode provided to face the first electrode; and a first organic material layer and a second organic material layer each having two or more layers, provided between the first electrode and the second electrode, in which the first organic material layer includes the compound of Formula 1, and the second organic material layer includes the compound of Formula 2.

In an exemplary embodiment of the present application, the first organic material layer includes a light emitting layer, and the light emitting layer can include the compound of Formula 1.

In an exemplary embodiment of the present application, the compound of Formula 1 is a host of the light emitting layer.

In an exemplary embodiment of the present application, the first organic material layer includes a light emitting layer, the light emitting layer can use the compound of Formula 1 as a single layer, and the compound of Formula 1 and another organic material can be used in mixtures.

In an exemplary embodiment of the present application, the light emitting layer is a blue light emitting layer.

In an exemplary embodiment of the present application, the light emitting layer has a maximum light emission peak of 400 nm to 500 nm.

In an exemplary embodiment of the present application, the light emitting layer can further include one host material in addition to the compound of Formula 1. In this case, examples of the further included host material (mixed host compound) include a fused aromatic ring derivative, a hetero ring-containing compound, or the like. Specific examples of the fused aromatic ring derivative include an anthracene derivative, a pyrene derivative, a naphthalene derivative, a pentacene derivative, a phenanthrene compound, a fluoranthene compound, and the like, and specific examples of the hetero ring-containing compound include a dibenzofuran derivative, a ladder-type furan compound, a pyrimidine derivative, and the like, but the examples are not limited thereto.

In an exemplary embodiment of the present application, the mixed host material is an anthracene derivative.

In an exemplary embodiment of the present application, a mixing ratio of the compound of Formula 1 to the mixed host compound is 95:5 to 5:95, and more preferably 30:70 to 70:30.

In an exemplary embodiment of the present application, the light emitting layer includes one compound or two or more compounds of Formula 1.

In an exemplary embodiment of the present application, the light emitting layer includes a dopant and a host, the host includes the compound of Formula 1, and the dopant is a phosphorescent dopant or a fluorescent dopant.

In an exemplary embodiment of the present application, the dopant in the light emitting layer can be included in an amount of 0.1 part by weight to 50 parts by weight, preferably 1 part by weight to 30 parts by weight or 1 part by weight to 15 parts by weight, based on 100 parts by weight of the host.

In an exemplary embodiment of the present application, the fluorescent dopant can be selected from the following compounds, but is not limited thereto:

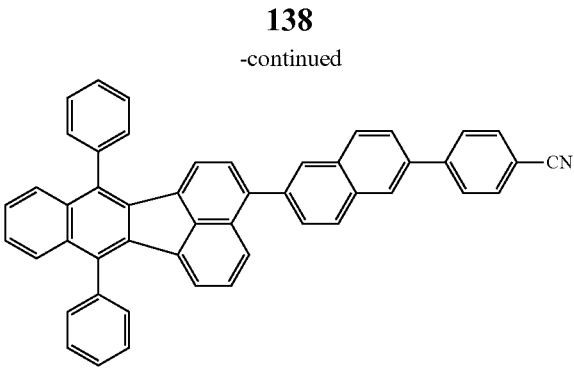

-continued

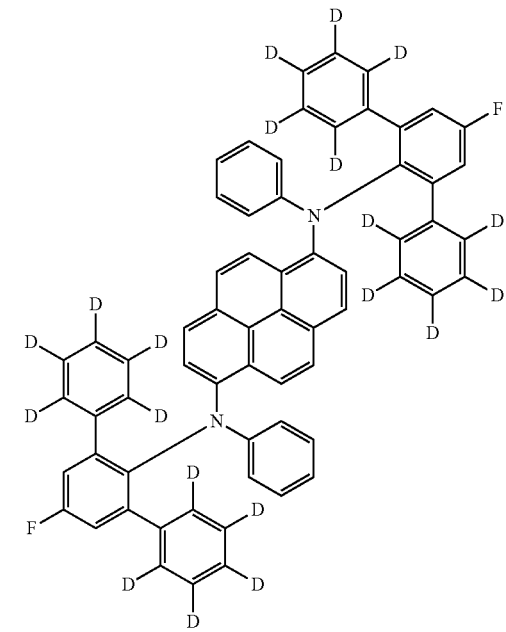

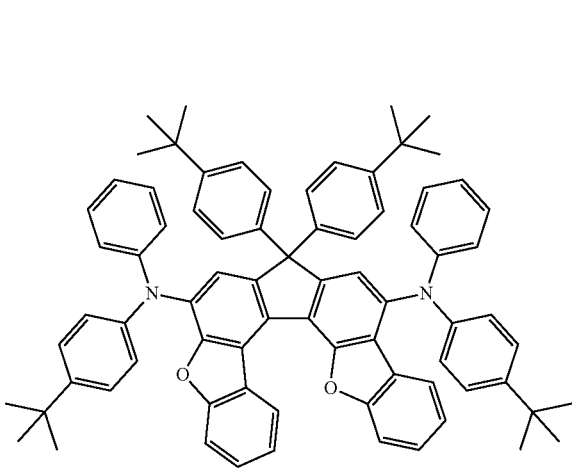

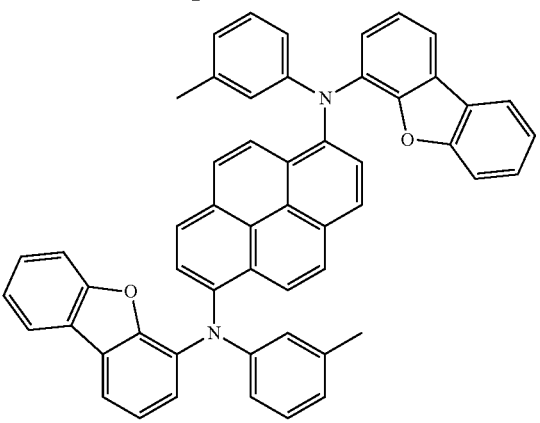

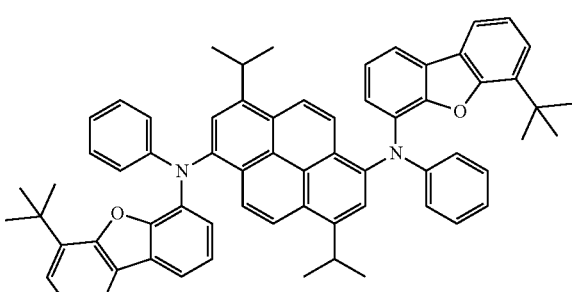

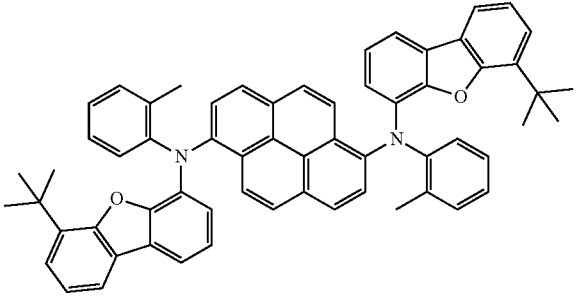

139
-continued
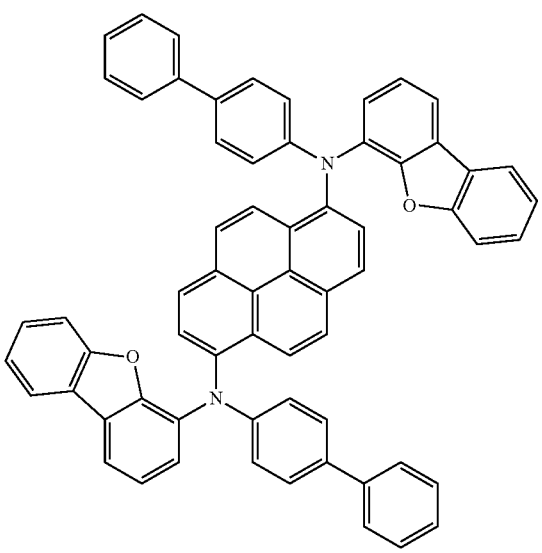
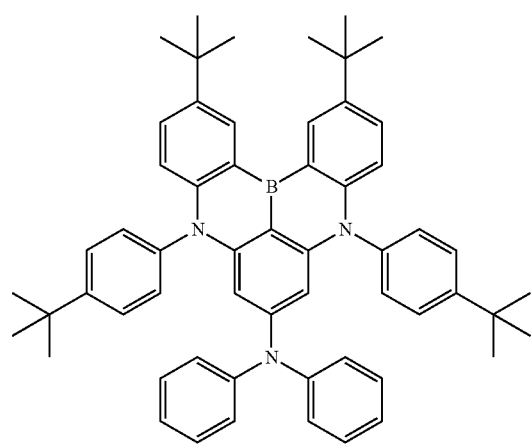
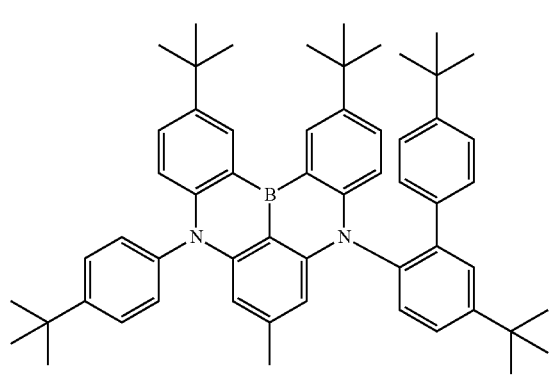
140
-continued
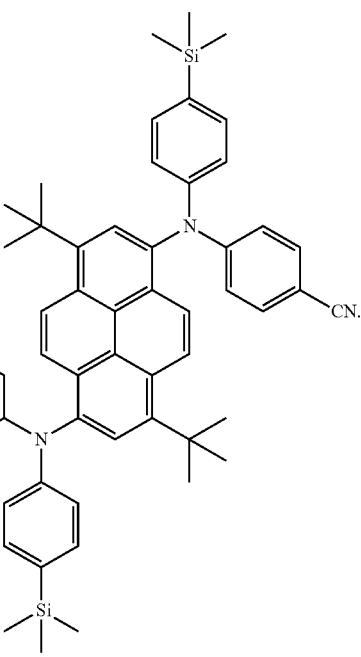
In an exemplary embodiment of the present application, an Ir complex can be used as the phosphorescent dopant, and as an example thereof, any one of the following compounds can be used, but the phosphorescent dopant is not limited thereto:
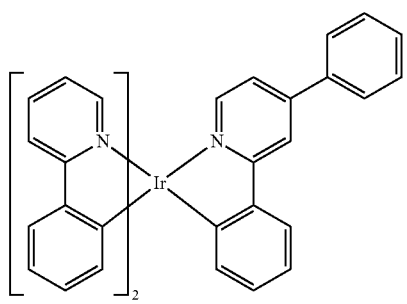
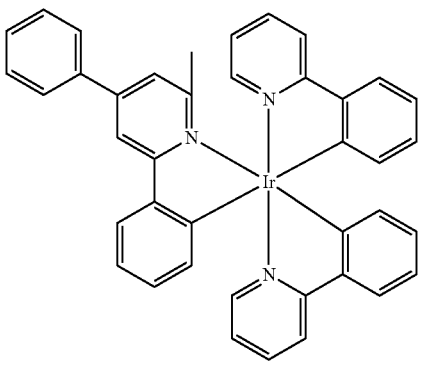

-continued
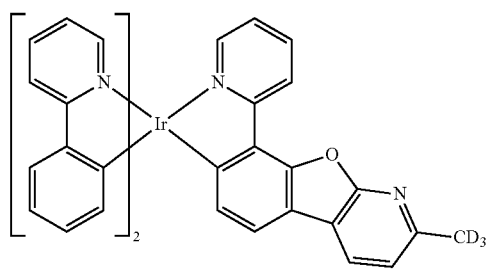
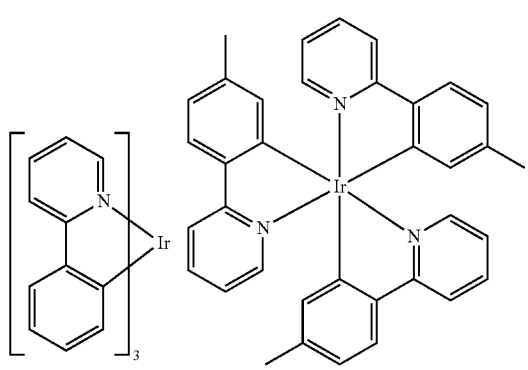
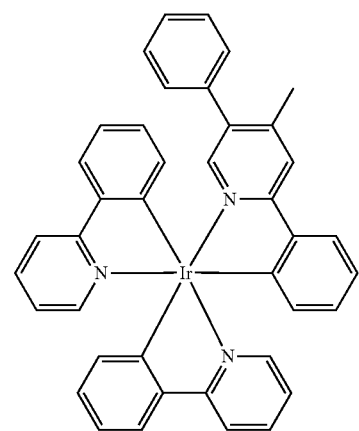
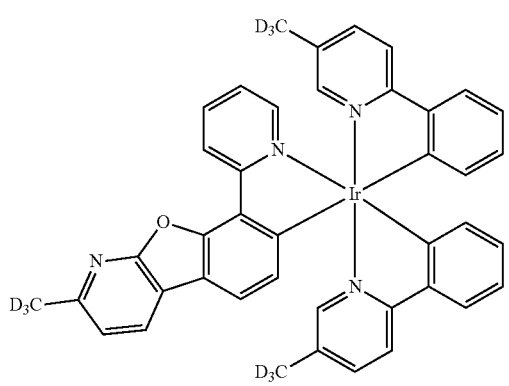
-continued
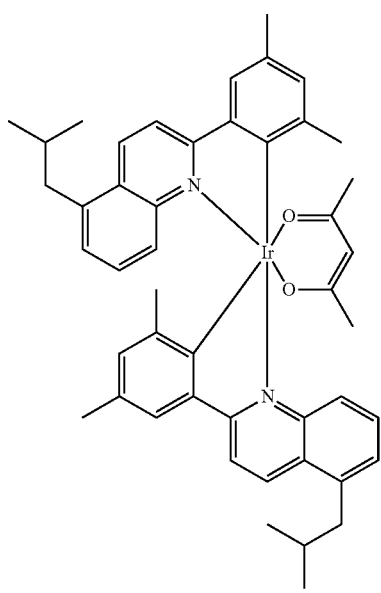
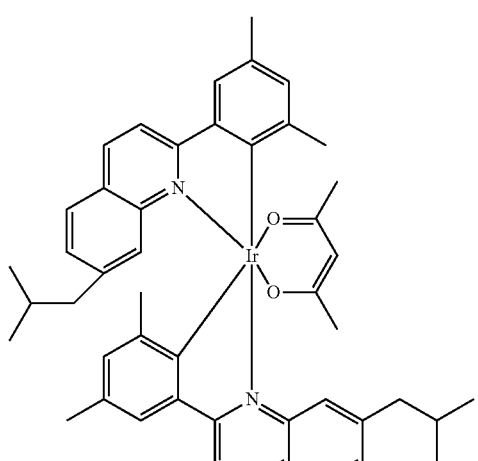
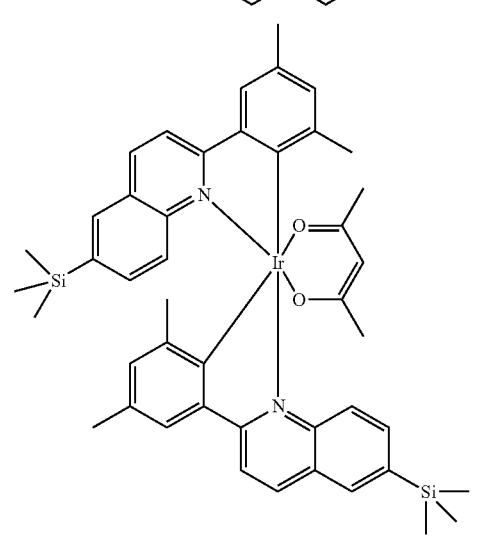

-continued

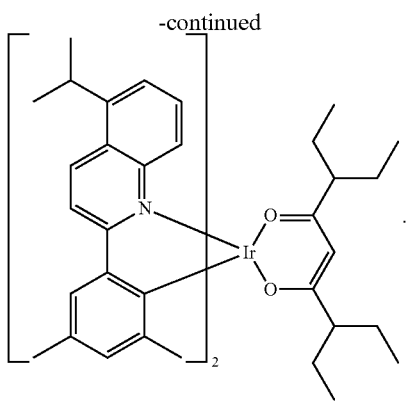

Further, according to an exemplary embodiment of the present application, the second organic material layer can include a hole blocking layer, an electron transport layer, an electron injection layer, or an electron injection and transport layer, and the hole blocking layer, the electron transport layer, the electron injection layer, or the electron injection and transport layer can include the compound of Formula 2.

According to an exemplary embodiment of the present application, the second organic material layer is provided to be brought into contact with the first organic material layer. In this case, an additional organic material layer is not provided between the first organic material layer and the second organic material layer.

In an exemplary embodiment of the present application, a negative electrode is provided to be brought into contact with the second organic material layer.

In another exemplary embodiment, the second organic material layer is provided to be brought into contact with the first organic material layer, and the negative electrode is provided to be brought into contact with the second organic material layer.

In an exemplary embodiment of the present application, the second organic material layer is provided between the first organic material layer and the negative electrode.

In an exemplary embodiment of the present specification, the second organic material layer further includes one n-type dopant or two or more n-type dopants selected from alkali metals and alkaline earth metals.

When the organic alkali metal compound or the organic alkaline earth metal compound is used as an n-type dopant, the stability for holes can be secured from the light emitting layer, so that the lifetime of the organic light emitting device can be improved. In addition, for the electron mobility of the electron transport layer, the balance of holes and electrons in the light emitting layer can be maximized by controlling the ratio of the organic alkali metal compound or the organic alkaline earth metal compound, thereby increasing the light emitting efficiency.

In the present specification, LiQ is preferred as an n-type dopant used for the second organic material layer, but the n-type dopant is not limited thereto.

The second organic material layer can include the compound of Formula 2 and the n-type dopant at a weight ratio of 1:9 to 9:1. Preferably, the second organic material layer can include the compound of Formula 2 and the n-type dopant at a weight ratio of 2:8 to 8:2, and more preferably at a weight ratio of 3:7 to 7:3.

In an exemplary embodiment of the present application, the organic light emitting device further includes one layer or two or more layers selected from the group consisting of a hole injection layer, a hole transport layer, an electron blocking layer, a light emitting layer, a hole blocking layer, an electron transport layer, and an electron injection layer. Specifically, in an exemplary embodiment of the present application, the compound of Formula 1 can also be included in one layer of a light emitting layer having two or more layers, and can be included in each light emitting layer having two or more layers, and the compound of Formula 2 can also be included in one layer of an electron transport layer having two or more layers, and can be included in the respective layers of the light emitting layer having two or more layers.

In an exemplary embodiment of the present application, the organic light emitting device can include an additional light emitting layer in addition to a light emitting layer including the compound of Formula 1. The maximum light emission peak of the additional light emitting layer is the same as or different from the maximum light emission peak of the light emitting layer including the compound of Formula 1.

In addition, in an exemplary embodiment of the present application, when the compound of Formula 1 or 2 is included in each of the light emitting layer or electron transport layer having two or more layers, the other materials except for the compound can be the same as or different from each other.

In an exemplary embodiment of the present application, the organic material layer further includes a hole injection layer or a hole transport layer, which includes a compound including an arylamino group, a carbazole group, or a benzocarbazole group, in addition to the organic material layer including the compound.

In another exemplary embodiment, the organic light emitting device can be a normal type organic light emitting device in which a positive electrode, an organic material layer having one or more layers, and a negative electrode are sequentially stacked on a substrate.

In still another exemplary embodiment, the organic light emitting device can be an inverted type organic light emitting device in which a negative electrode, an organic material layer having one or more layers, and a positive electrode are sequentially stacked on a substrate.

For example, the structure of the organic light emitting device according to an exemplary embodiment of the present application is exemplified in FIGS. 1 and 3.

FIG. 1 exemplifies a structure of a general organic light emitting device in which a substrate 1, a positive electrode 2, a light emitting layer 3, and a negative electrode 4 are sequentially stacked.

FIG. 2 exemplifies a structure of an organic light emitting device in which a substrate 1, a positive electrode 2, a hole injection layer 5, a hole transport layer 6, a light emitting layer 3, an electron transport layer 7, and a negative electrode 4 are sequentially stacked. In such structures, the compound of Formula 1 can be included in the light emitting layer 3, and the compound of Formula 2 can be included in the electron transport layer 7.

FIG. 3 exemplifies a structure of an organic light emitting device in which a substrate 1, a positive electrode 2, a hole injection layer 5, a first hole transport layer 6a, a second hole transport layer 6b, a light emitting layer 3, an electron injection and transport layer 8, and a negative electrode 4 are sequentially stacked. In such a structure, the compound of Formula 1 can be included in the light emitting layer 3, and the compound of Formula 2 can be included in the electron injection and transport layer 8.

The organic light emitting device of the present application can be manufactured by the materials and methods known in the art, except that one or more layers of the first or second organic material layer include the compound of the present application, that is, the compound.

When the organic light emitting device includes a plurality of first or second organic material layers, the organic material layers can be formed of the same material or different materials.

The organic light emitting device of the present application can be manufactured by the materials and methods known in the art, except that one or more layers of the first or second organic material layer include the compound, that is, the compound of Formulae 1 and 2.

For example, the organic light emitting device of the present application can be manufactured by sequentially stacking a first electrode, first and second organic material layers, and a second electrode on a substrate. In this case, the organic light emitting device can be manufactured by depositing a metal or a metal oxide having conductivity, or an alloy thereof on a substrate to form a positive electrode, forming an organic material layer including a hole injection layer, a hole transport layer, a light emitting layer, and an electron transport layer thereon, and then depositing a material, which can be used as a negative electrode, thereon, by using a physical vapor deposition (PVD) method such as sputtering or e-beam evaporation. In addition to the method described above, an organic light emitting device can be made by sequentially depositing a negative electrode material, an organic material layer, and a positive electrode material on a substrate.

Further, the compounds of Formulae 1 and 2 can be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method described above, an organic light emitting device can also be made by sequentially depositing a negative electrode material, an organic material layer, and a positive electrode material on a substrate (International Publication No. WO2003/012890). However, the manufacturing method is not limited thereto.

In an exemplary embodiment of the present application, the first electrode is a positive electrode, and the second electrode is a negative electrode.

In another exemplary embodiment, the first electrode is a negative electrode, and the second electrode is a positive electrode.

As the positive electrode material, materials having a high work function are usually preferred so as to facilitate the injection of holes into a first or second organic material layer. Specific examples of the positive electrode material which can be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or SnO$_2$:Sb; a conductive polymer such as poly(3-methylthiophene), poly[3,4-(ethylene-1,2-dioxy)thiophene](PEDOT), polypyrrole, and polyaniline; and the like, but are not limited thereto.

As the negative electrode material, materials having a low work function are usually preferred so as to facilitate the injection of electrons. Specific examples of the negative electrode material include: a metal such as magnesium, calcium, sodium, potassium, titanium, indium, yttrium, lithium, gadolinium, aluminum, silver, tin, and lead, or an alloy thereof; a multi-layer structured material, such as LiF/Al or LiO$_2$/Al, and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. The highest occupied molecular orbital (HOMO) of the hole injection material is preferably a value between the work function of the positive electrode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

The hole transport layer is a layer which accepts holes from a hole injection layer and transports the holes to a light emitting layer, and a hole transport material is suitably a material having high hole mobility which can accept holes from a positive electrode or a hole injection layer and transfer the holes to a light emitting layer. Specific examples thereof include arylamine-based organic material, conductive polymers, block copolymers having both conjugated portions and non-conjugated portions, and the like, but are not limited thereto.

The light emitting material is a material which can emit light in a visible light region by accepting and combining holes and electrons from a hole transport layer and an electron transport layer, respectively, and preferably a material having high quantum efficiency for fluorescence or phosphorescence. Specific examples thereof include: 8-hydroxy-quinoline aluminum complexes (Alq$_3$) except for the compound of Formula 1 of the present application; carbazole-based compounds; dimerized styryl compounds; BAlq; 10-hydroxybenzoquinoline-metal compounds; benzoxazole-based, benzothiazole-based and benzimidazole-based compounds; poly(p-phenylene-vinylene) (PPV)-based polymers; spiro compounds; polyfluorene, rubrene, and the like, but are not limited thereto.

The electron transport layer is a layer which accepts electrons from an electron injection layer and transports the electrons to a light emitting layer, and an electron transport material is suitably a material having high electron mobility which can proficiently accept electrons from a negative electrode and transfer the electrons to a light emitting layer. Specific examples thereof include: Al complexes of 8-hydroxy-quinoline except for the compound of Formula 2 of the present application; complexes including Alq$_3$; organic radical compounds; hydroxyflavone-metal complexes; and the like, but are not limited thereto. The electron transport layer can be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, an effect of injecting electrons from a negative electrode, and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, metal complex compounds, nitrogen-containing 5-membered ring derivatives, and the like, but are not limited thereto.

Examples of the metal complex compounds include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris (2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato)(o-cresolato) gallium, bis(2-methyl-8-quinolinato)(1-naphtholato) aluminum, bis(2-methyl-8-quinolinato)(2-naphtholato) gallium, and the like, but are not limited thereto.

The hole blocking layer can be disposed between a light emitting layer and an electron transport layer or between a light emitting layer and an electron injection and transport layer, thereby preventing holes, which are not combined with electrons in a light emitting layer among holes transferred from a positive electrode and remain, from passing through the light emitting layer and moving to a negative electrode. It is possible to improve the lifetime and efficiency of the device by including a hole blocking layer. A material for a hole blocking layer is preferably a compound having an ability to prevent the influx of holes from a light emitting layer to a negative electrode and to control the flow of electrons to be injected into a light emitting layer or a light emitting material, and the hole blocking layer can be generally formed under the condition which is the same as that of the electron transport layer. Specific examples thereof include oxadiazole derivatives or triazole derivatives, phenanthroline derivatives, BCP, aluminum complexes, and the like, but are not limited thereto.

The electron blocking layer can be disposed between a light emitting layer and a hole injection layer, thereby preventing electrons, which are not combined with holes in a light emitting layer among electrons transferred from a negative electrode and remain, from passing through the light emitting layer and entering a positive electrode. It is possible to improve the lifetime and efficiency of the device by including an electron blocking layer. The publicly-known material can be used without limitation, and a material for the electron blocking layer is preferably a compound having an ability to prevent the influx of electrons from a light emitting layer to a positive electrode and to control the flow of holes to be injected into a light emitting layer or a light emitting material.

The organic light emitting device according to the present application can be a top emission type, a bottom emission type, or a dual emission type according to the material to be used.

EXAMPLES

Hereinafter, the present specification will be described in detail with reference to Examples for specifically describing the present specification. However, the Examples according to the present specification can be modified in various forms, and it is not interpreted that the scope of the present specification is limited to the Examples described below. The Examples of the present specification are provided to more completely explain the present specification to a person with ordinary skill in the art.

Synthesis Example 1

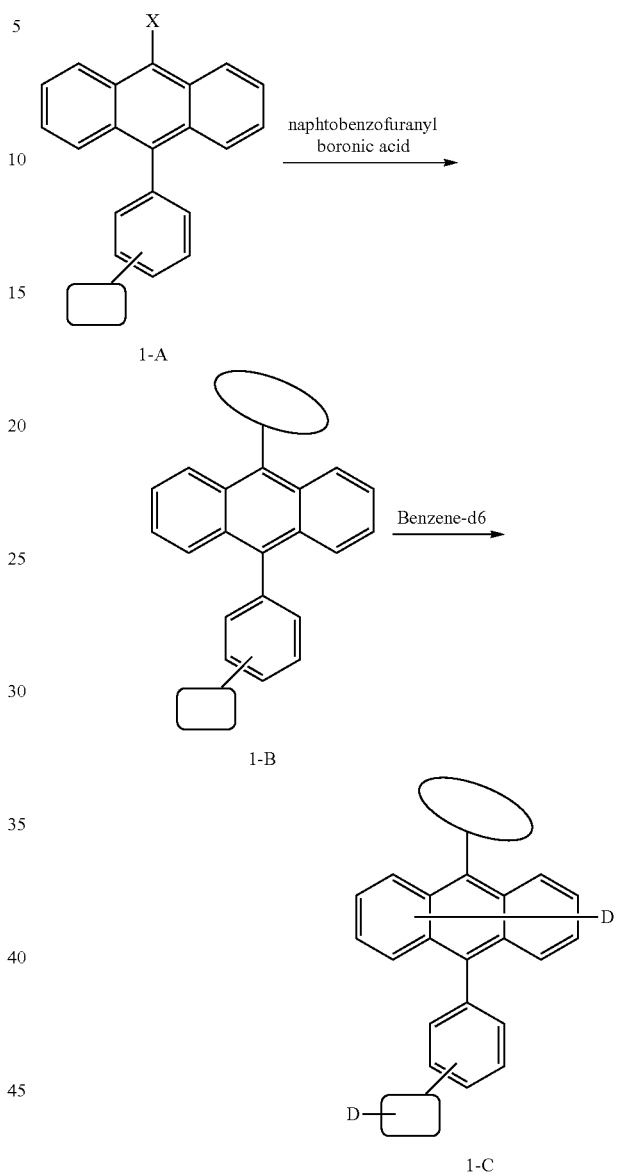

(X=I, Br, Cl, ONf, OTf, and the like)

[Compound 1-B] was synthesized from [Compound 1-A] and naphthobenzofuranyl boronic acid via a coupling reaction using a palladium catalyst and a base in an organic solvent.

When a compound substituted with deuterium is synthesized, a deuterium substitution reaction is additionally performed. Deuterium was introduced into the molecule via a hydrogen-deuterium exchange reaction using TfOH as an acid catalyst in a deuterated solvent such as [Compound 1-B] and Benzene-d6, and [Compound 1-C] was obtained by additional purification and drying using an organic solvent.

[BH 1] to [BH 6] were synthesized using the following [Compound 1-A] and naphthobenzofuranyl boronic acid. [BH 4] to [BH 6] were even subjected to the deuterium substitution reaction after the coupling reaction. The method of synthesizing the compound of Formula 1 is not limited to the following methods.

| [Compound 1-A] | Naphthobenzofuranyl boronic acid | Formula 1 | MS [M + H] |
|---|---|---|---|
| 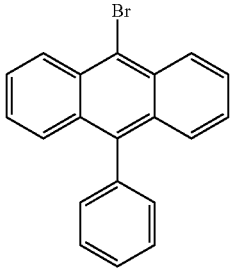 [SMILES: Brc1c2ccccc2c(-c2ccccc2)c2ccccc12] | 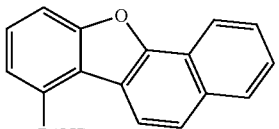 | 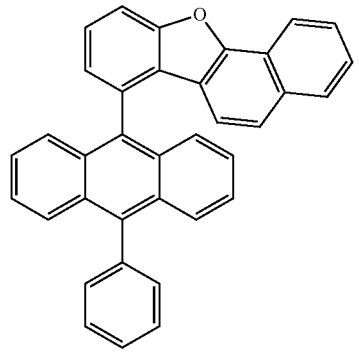 [SMILES: c1ccc(-c2c3ccccc3c(-c3cccc4oc5c6ccccc6ccc5c34)c3ccccc23)cc1] [BH 1] | 471 |
| 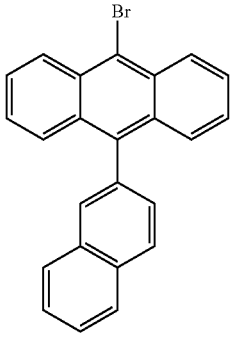 [SMILES: Brc1c2ccccc2c(-c2ccc3ccccc3c2)c2ccccc12] | 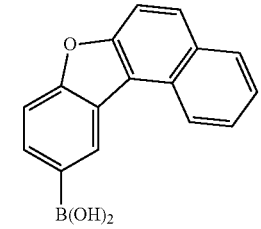 [SMILES: OB(O)c1ccc2oc3ccc4ccccc4c3c2c1] | 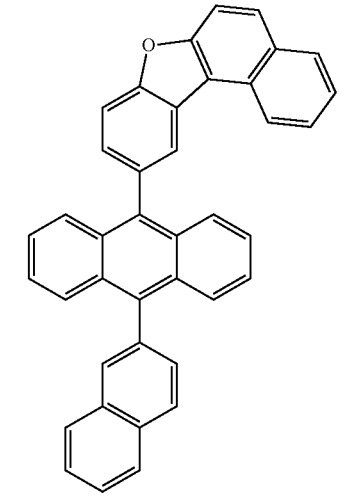 [SMILES: c1ccc2cc(-c3c4ccccc4c(-c4ccc5oc6ccc7ccccc7c6c5c4)c4ccccc34)ccc2c1] [BH 2] | 522 |
| 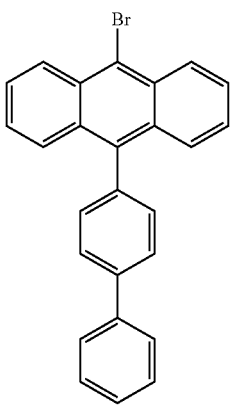 [SMILES: Brc1c2ccccc2c(-c2ccc(-c3ccccc3)cc2)c2ccccc12] | 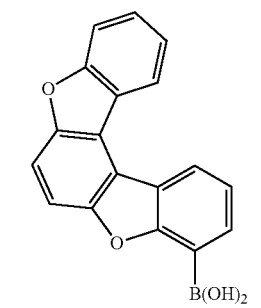 [SMILES: OB(O)c1cccc2c1oc1ccc3oc4ccccc4c3c12] | 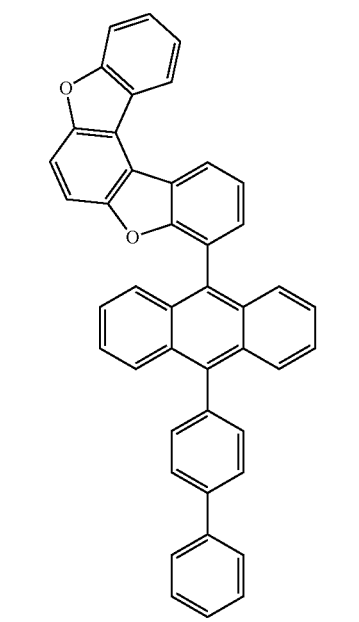 [SMILES: c1ccc(-c2ccc(-c3c4ccccc4c(-c4cccc5c4oc4ccc6oc7ccccc7c6c45)c4ccccc34)cc2)cc1] [BH 3] | 588 |

| [Compound 1-A] | Naphthobenzofuranyl boronic acid | Formula 1 | MS [M + H] |
|---|---|---|---|
| 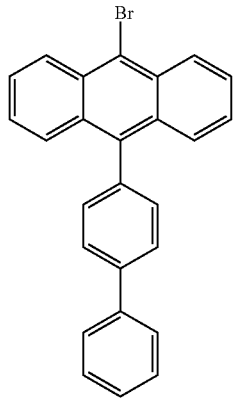 [SMILES: Brc1c2ccccc2c(-c2ccc(-c3ccccc3)cc2)c2ccccc12] | 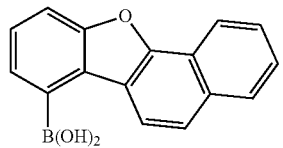 [SMILES: OB(O)c1cccc2oc3c4ccccc4ccc3c12] | 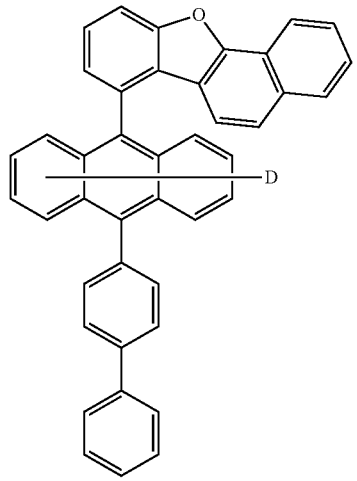
[BH 4] | 555 |
| 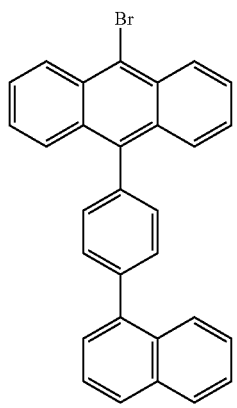 [SMILES: Brc1c2ccccc2c(-c2ccc(-c3cccc4ccccc34)cc2)c2ccccc12] | 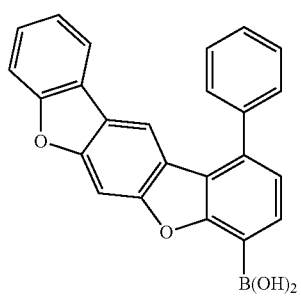 [SMILES: OB(O)c1ccc(-c2ccccc2)c2c1oc1cc3oc4ccccc4c3cc12] | 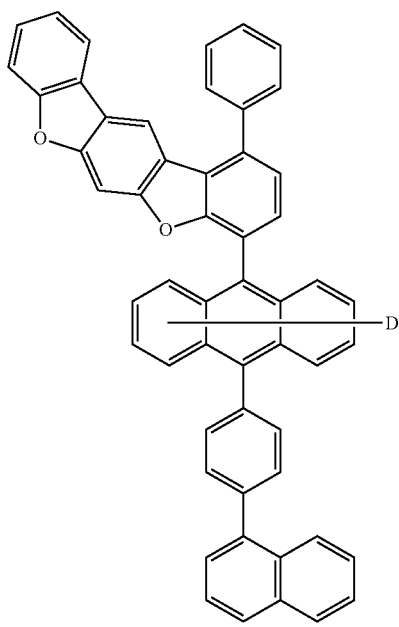
[BH 5] | 725 |
| 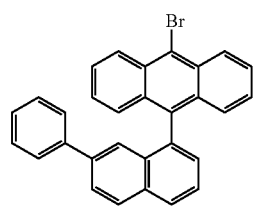 [SMILES: Brc1c2ccccc2c(-c2cccc3ccc(-c4ccccc4)cc23)c2ccccc12] | 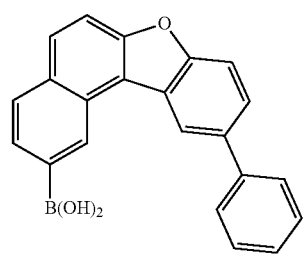 [SMILES: OB(O)c1ccc2ccc3oc4ccc(-c5ccccc5)cc4c3c2c1] | 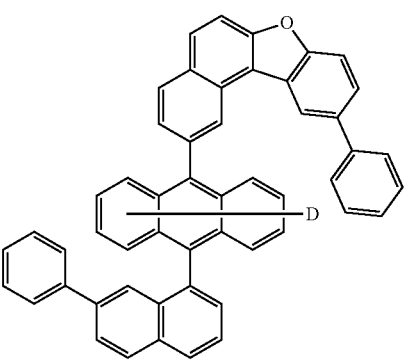
[BH 6] | 674 |

Synthesis Example 2

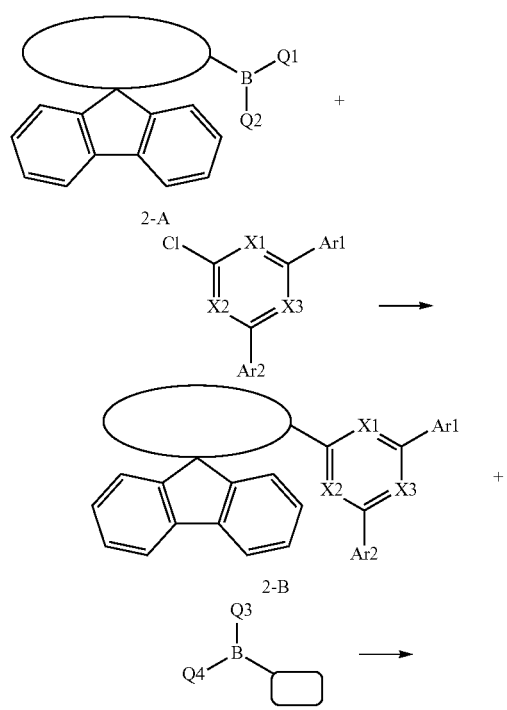

2-A

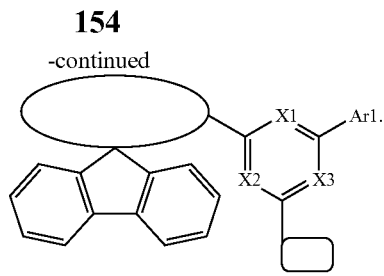

2

(Q1 to Q4=OH, substituted or unsubstituted alkyl, alkoxy, aryl, aryloxy, heteroaryl, and the like)

[Compound 2-B] was synthesized from [Compound 2-A] including boronic acid and a heterocyclic compound including halide via a coupling reaction using a palladium catalyst and a base in an organic solvent.

[Compound 2] of Formula 2 was obtained by a coupling reaction of [Compound 2-B] with a substituent of boronic acid and additional purification and drying using an organic solvent.

When [Compound 2-A] is a compound including a cyano group, Compound 2 in which Ar3 includes a cyano group can be obtained.

[ET 1] to [ET 16] were synthesized using the following [Compound 2-A] and a heterocyclic compound. The method of synthesizing the compound of Formula 2 is not limited to the following methods.

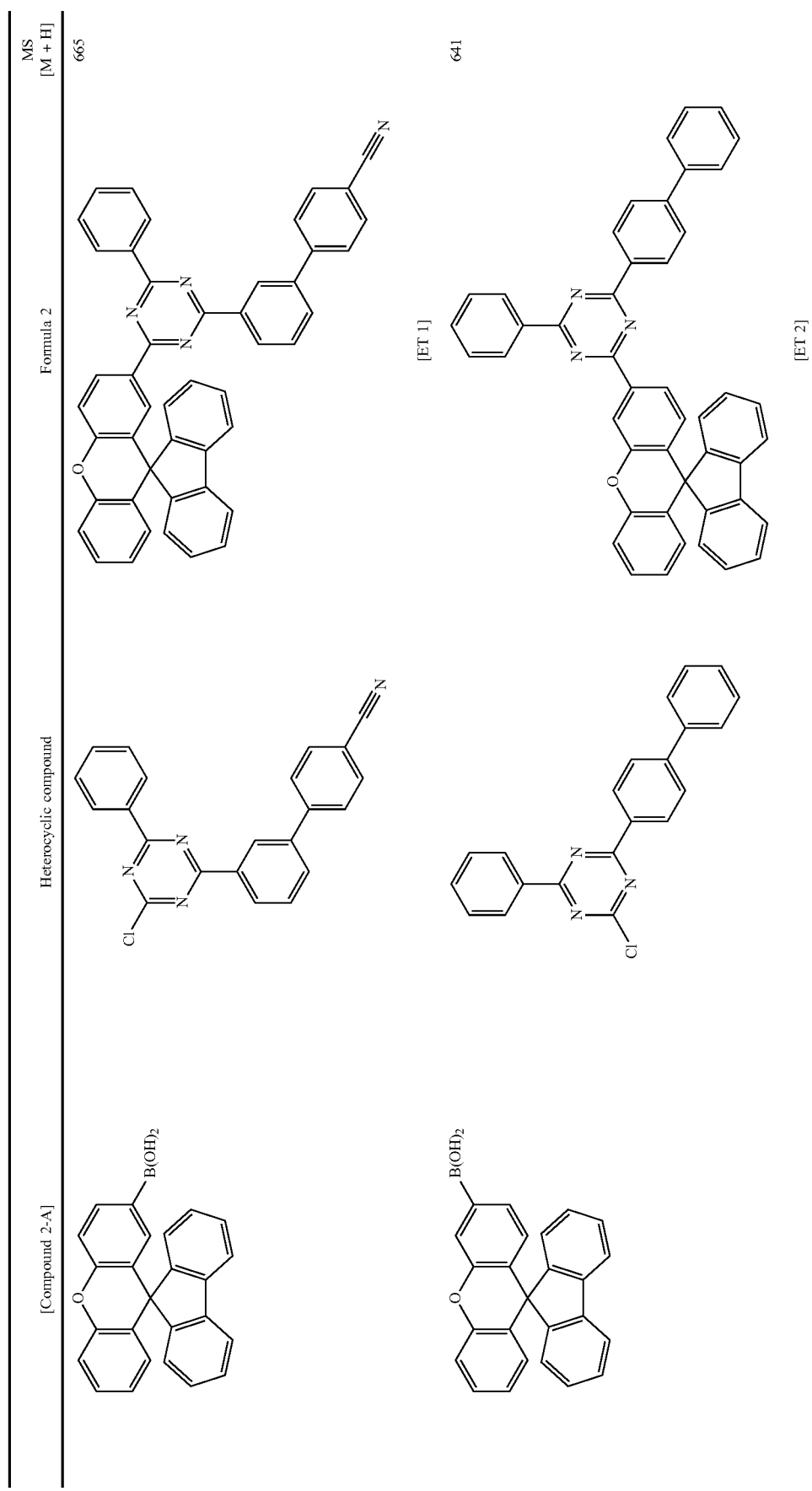

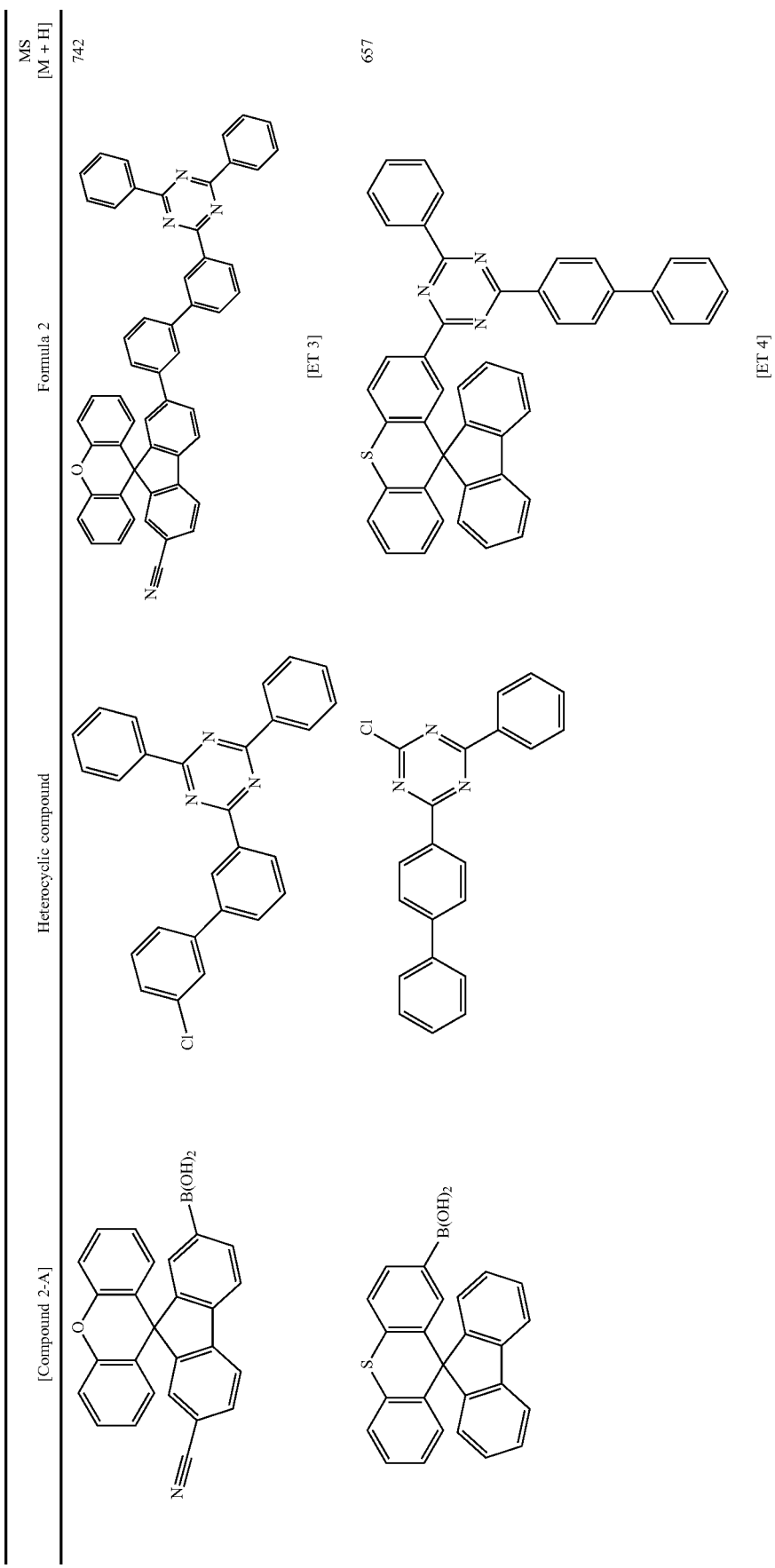

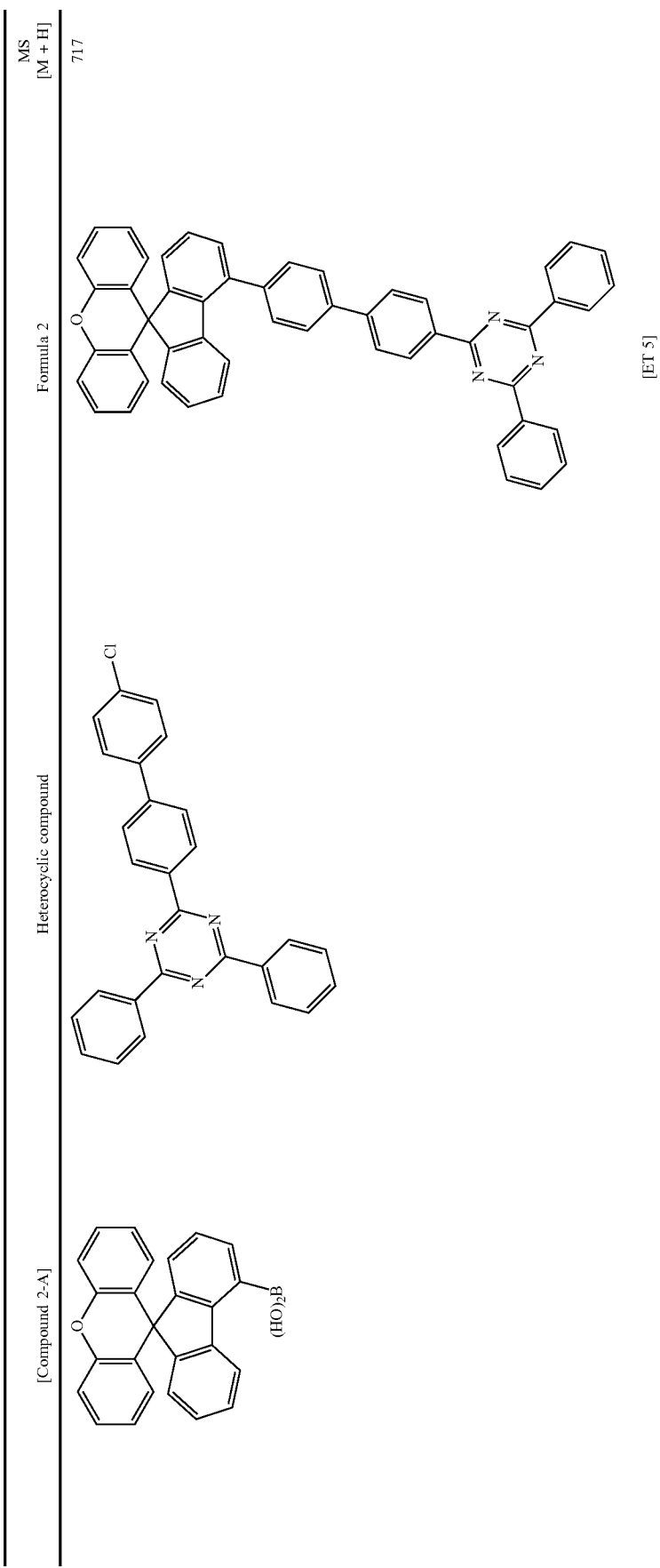

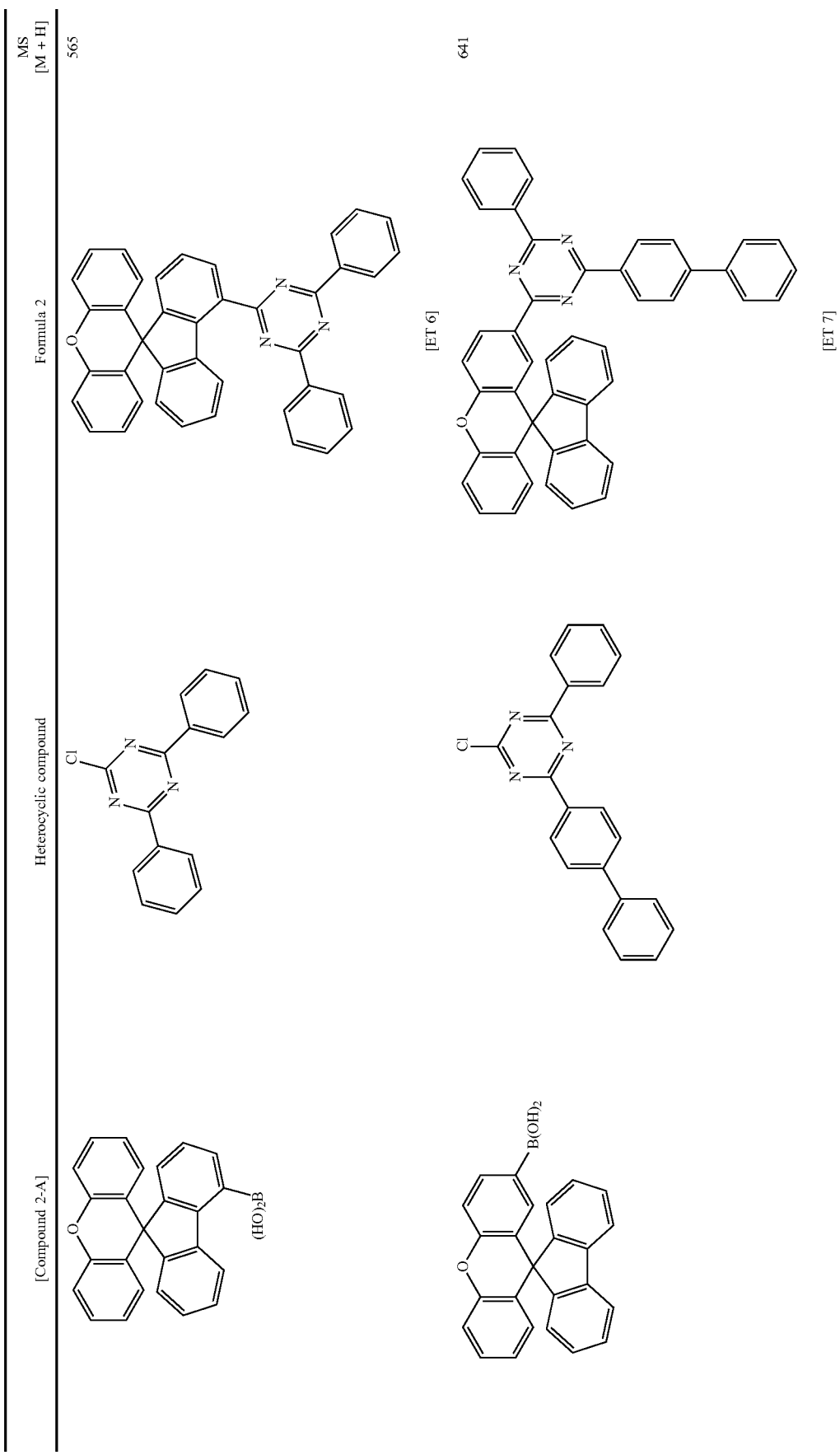

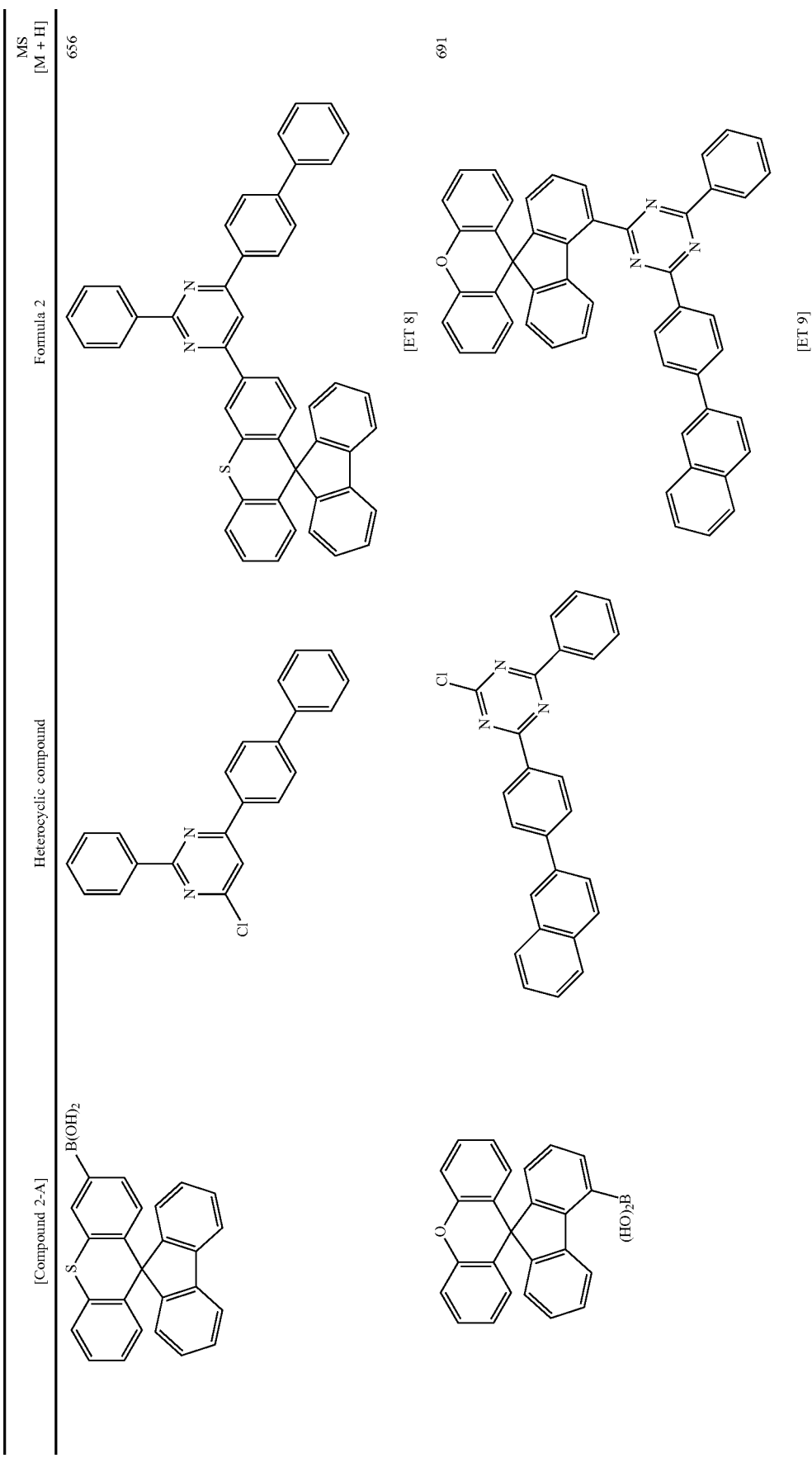

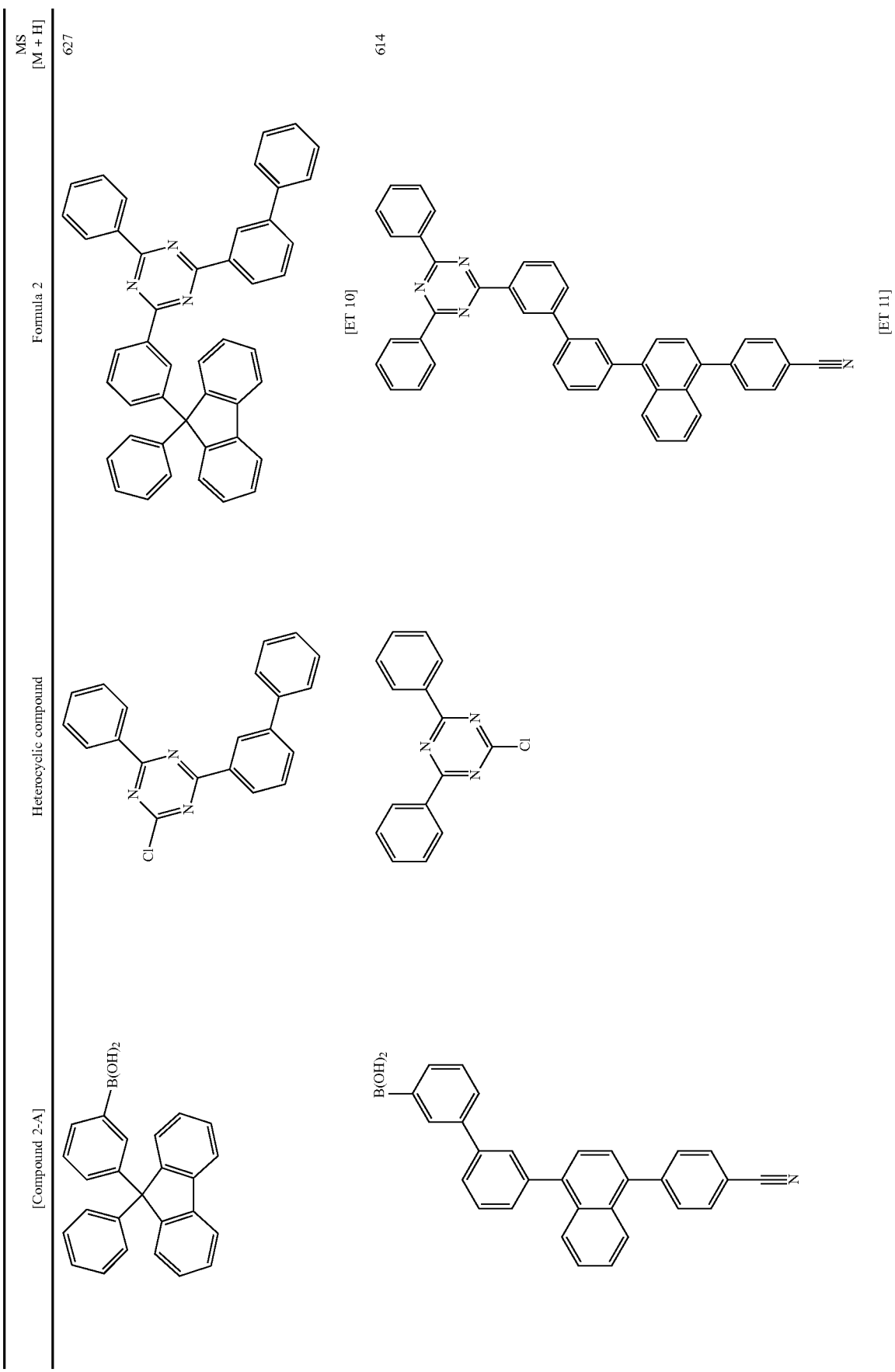

-continued
| [Compound 2-A] | Heterocyclic compound | Formula 2 | MS [M + H] |
|---|---|---|---|
| 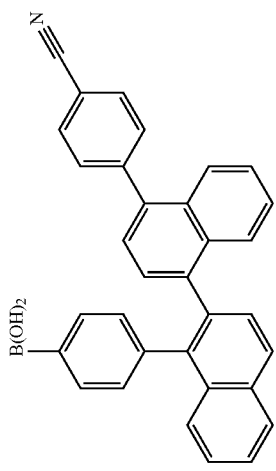 | 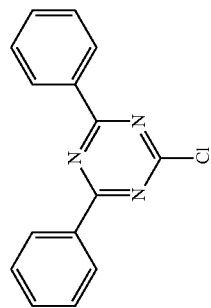 | 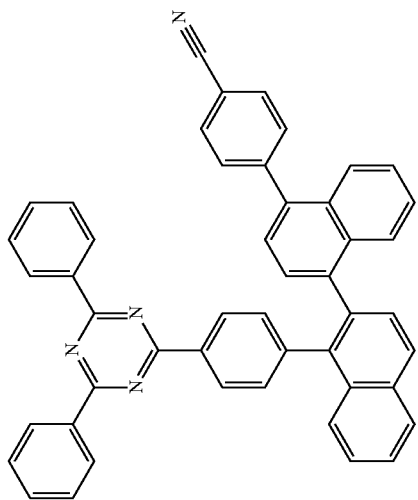 [ET 12] | 664 |

| [Compound 2-A] | Heterocyclic compound | Formula 2 | MS [M + H] |
|---|---|---|---|
| 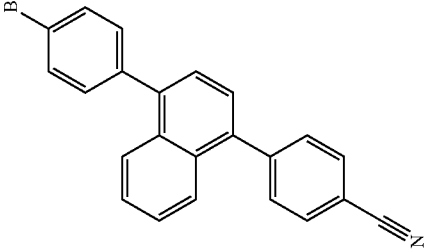 | 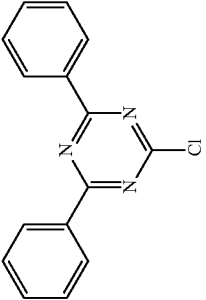 | 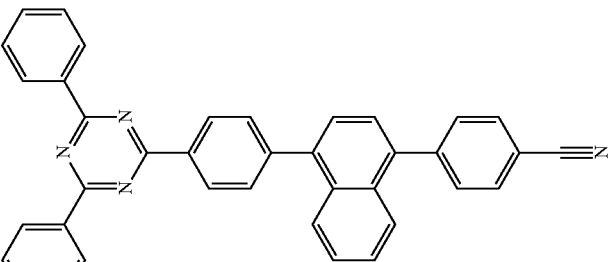 | 538 |
| | | [ET 13] | |
| 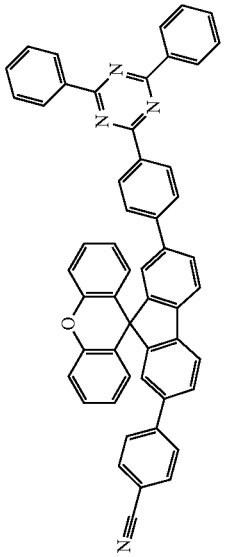 | | | 742 |
| | | [ET 14] | |

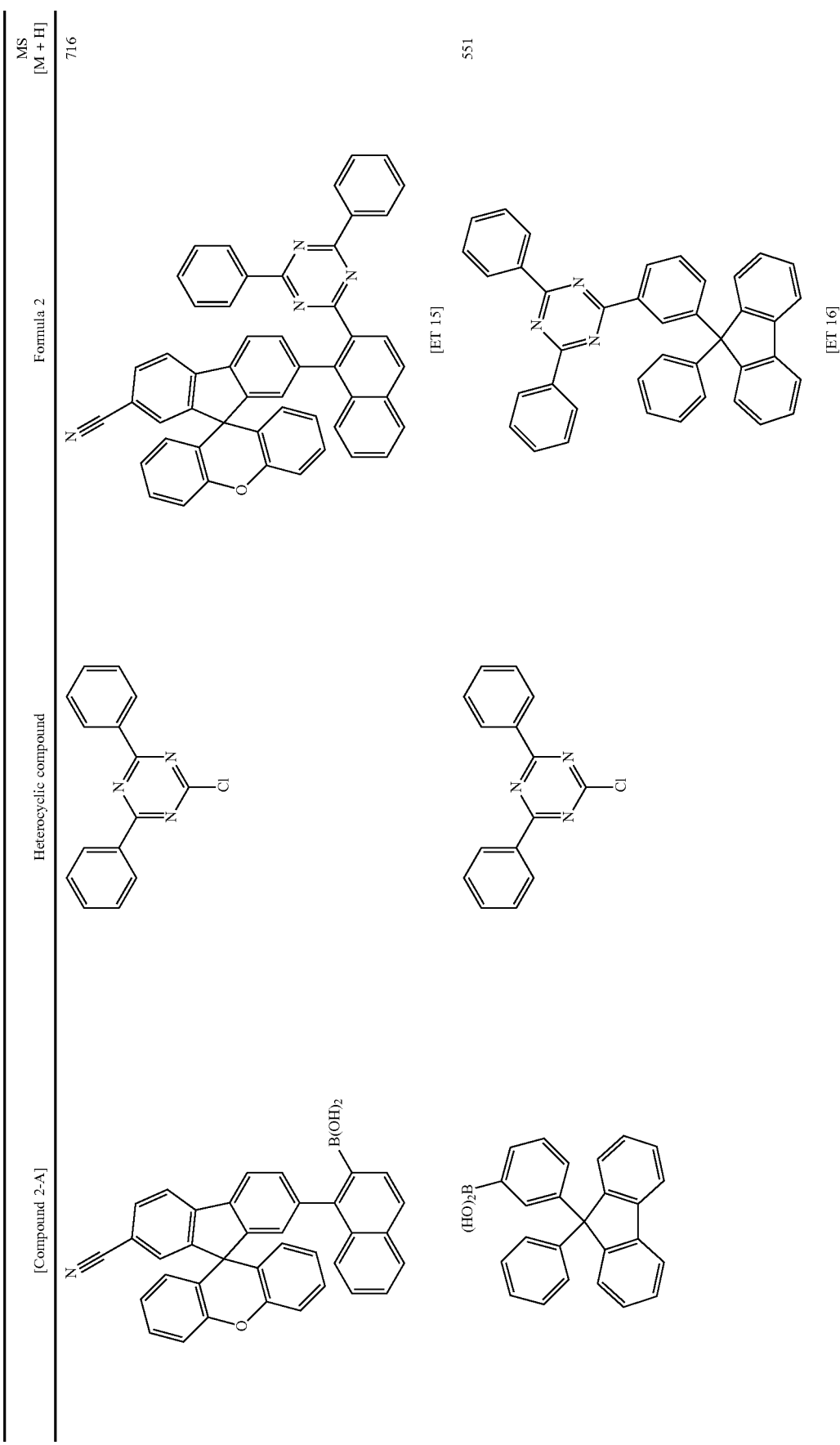

Example 1

A glass substrate thinly coated with indium tin oxide (ITO) to have a thickness of 1000 Å was put into distilled water in which a detergent was dissolved, and ultrasonically washed. In this case, a product manufactured by the Fischer Co., was used as the detergent, and distilled water twice filtered using a filter manufactured by Millipore Co., was used as the distilled water. After the ITO was washed for 30 minutes, ultrasonic washing was repeated twice by using distilled water for 10 minutes. After the washing using distilled water was completed, ultrasonic washing was conducted by using isopropyl alcohol, acetone, and methanol solvents, and the resulting product was dried and then transported to a plasma washing machine. The substrate was washed by using oxygen plasma for 5 minutes, and then was transported to a vacuum deposition machine.

The following HI-A compound was thermally vacuum-deposited to have a thickness of 600 Å on the ITO transparent electrode thus prepared, thereby forming a hole injection layer. The following HAT compound and the following HT-A compound were sequentially vacuum-deposited to have a thickness of 50 Å and 60 Å, respectively, on the hole injection layer, thereby forming a first hole transport layer and a second hole transport layer.

Subsequently, the following [BH 1] compound and BD compound were vacuum-deposited at a weight ratio of 25:1 to have a film thickness of 200 Å on the second hole transport layer, thereby forming a light emitting layer.

Compound [ET 1] in Preparation Example 2 and the following LiQ compound were vacuum-deposited at a weight ratio of 1:1 on the light emitting layer, thereby forming an electron injection and transport layer having a thickness of 350 Å. Lithium fluoride (LiF) and aluminum were sequentially deposited to have a thickness of 10 Å and 1000 Å, respectively, on the electron injection and transport layer, thereby forming a negative electrode.

In the aforementioned procedure, the deposition rate of the organic material was maintained at 0.4 to 0.9 Å/sec, the deposition rates of lithium fluoride and aluminum of the negative electrode were maintained at 0.3 Å/sec and at 2 Å/sec, respectively, and the degree of vacuum during the deposition was maintained at $1\times10^{-7}$ to $5\times10^{-8}$ torr, thereby manufacturing an organic light emitting device.

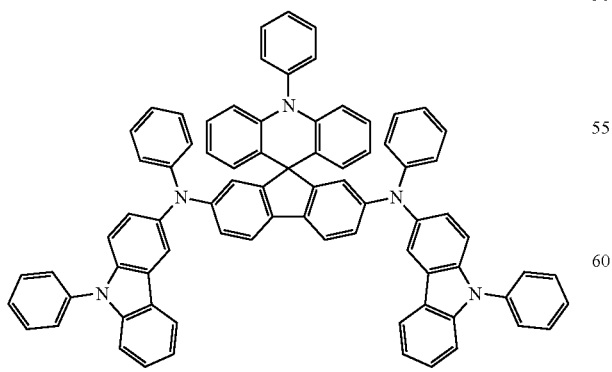

HI-A

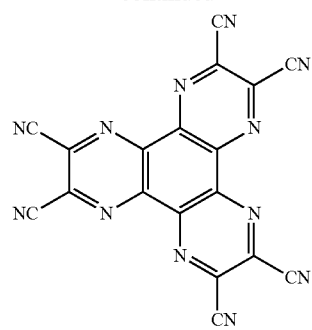

HAT

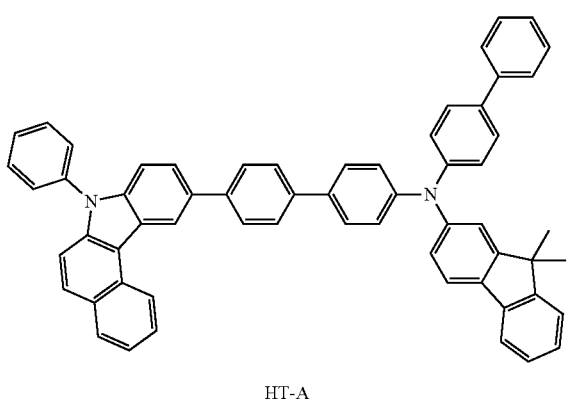

HT-A

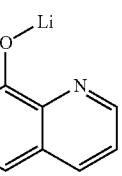

LiQ

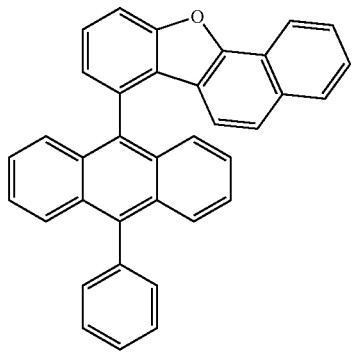

[BH 1]

-continued
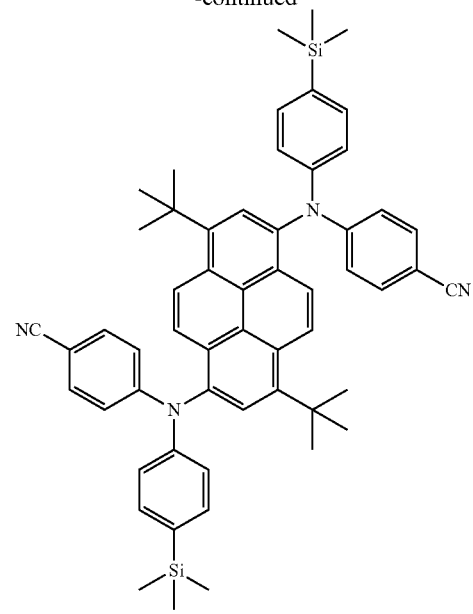
BD
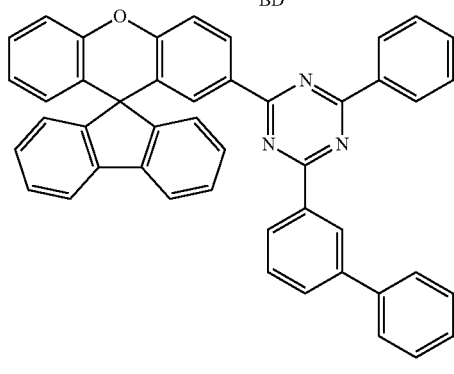
[ET 1]
Examples 2 to 17
Organic light emitting devices were manufactured in the same manner as in Example 1, except that the compounds described in the following Table 1 were each used instead of Compound [BH 1] and Compound [ET 1].
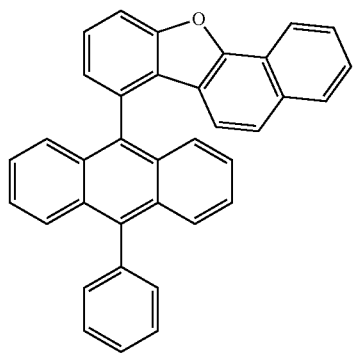
[BH 1]
-continued
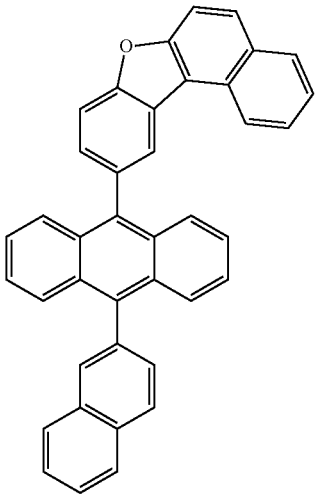
[BH 2]
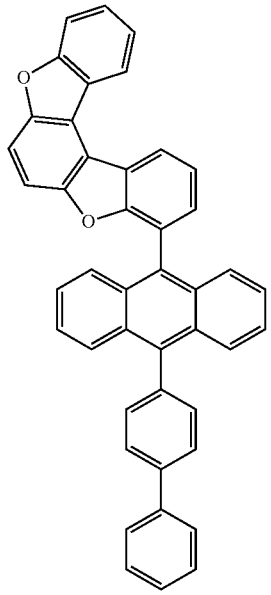
[BH 3]
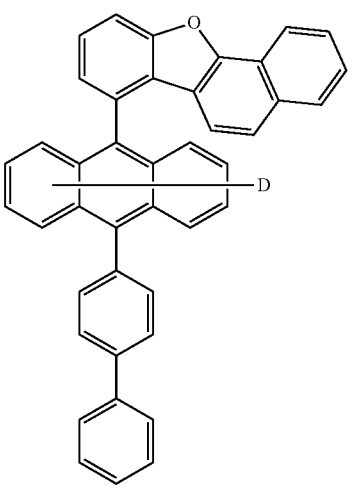
[BH 4]

[BH 5]
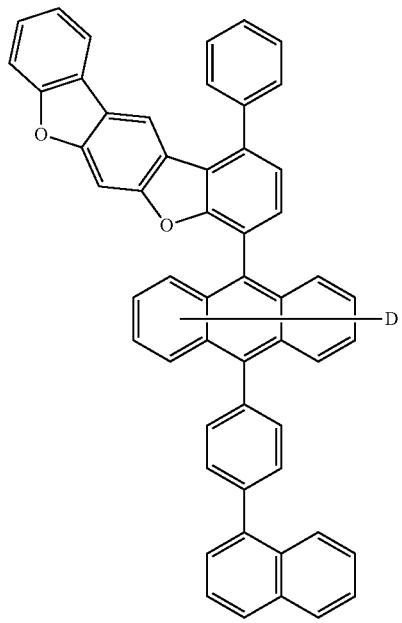
[BH 6]
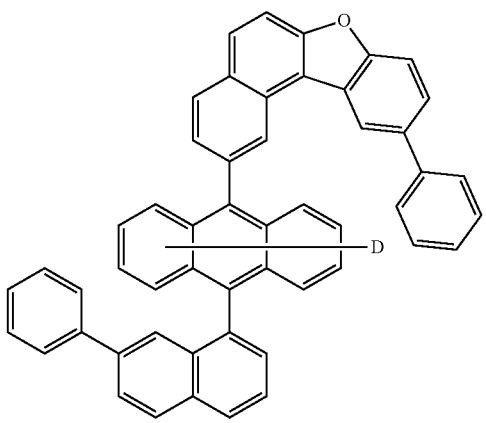
[ET 1]
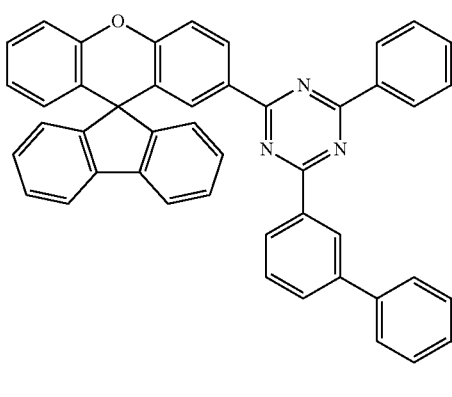
[ET 2]
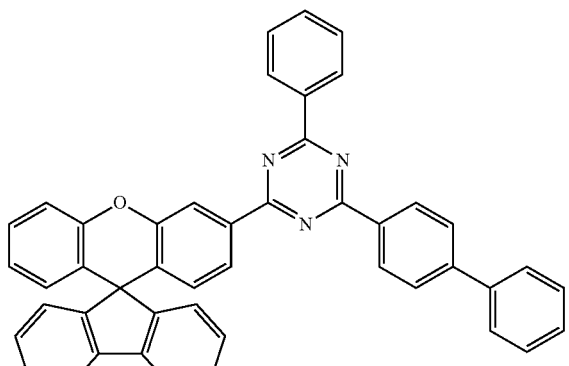
[ET 3]
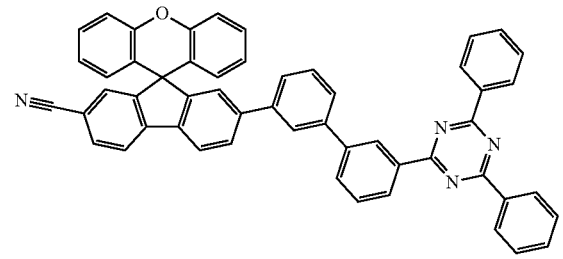
[ET 4]
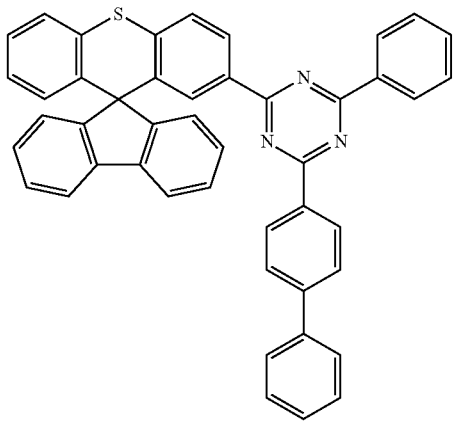 [SMILES: c1ccc(-c2ccc(-c3nc(-c4ccccc4)nc(-c4ccc5c(c4)C4(c6ccccc6O5)c5ccccc5-c5ccccc54)n3)cc2)cc1]

[ET 5]
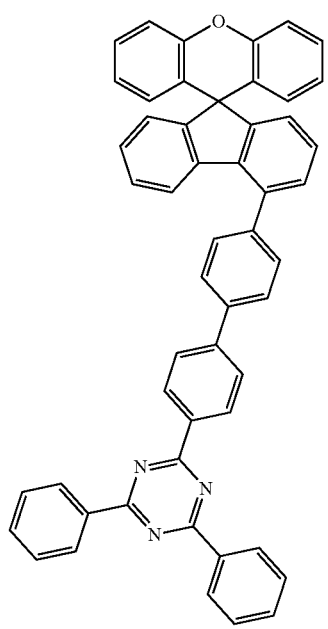
[ET 6]
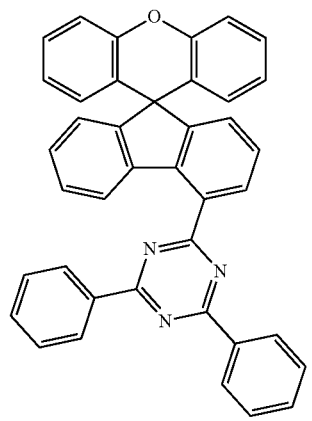
[ET 7]
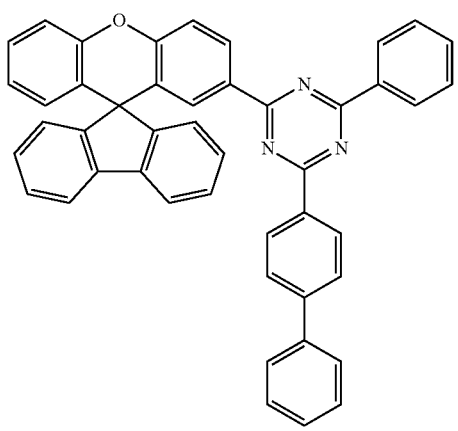
[ET 8]
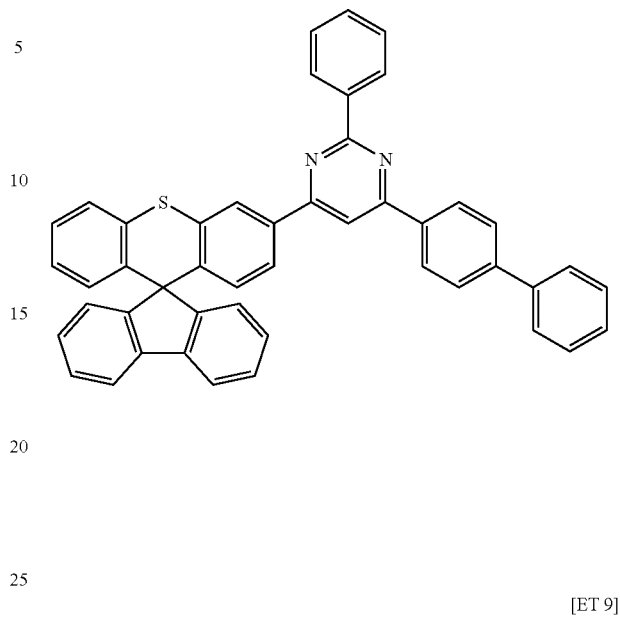
[ET 9]
[ET 10]
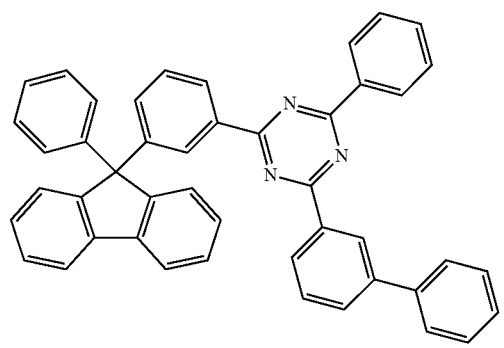 [SMILES: c1ccc(-c2cccc(-c3nc(-c4ccccc4)nc(-c4cccc(C5(c6ccccc6)c6ccccc6-c6ccccc65)c4)n3)c2)cc1]

[ET 11]
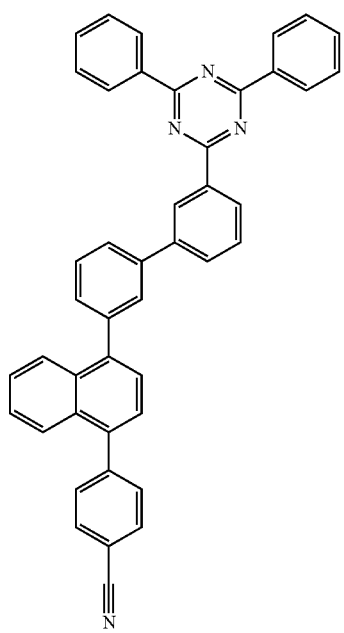 [SMILES: N#Cc1ccc(-c2ccc(-c3cccc(-c4cccc(-c5nc(-c6ccccc6)nc(-c6ccccc6)n5)c4)c3)c3ccccc23)cc1]
[ET 12]
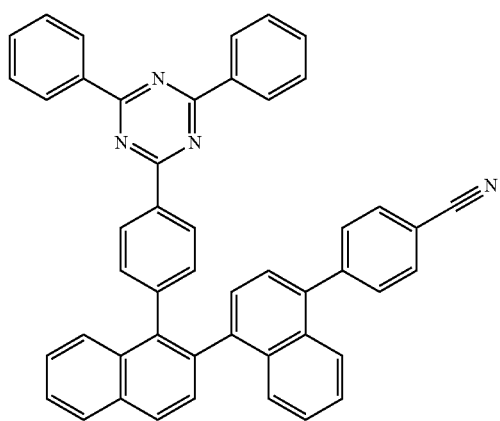 [SMILES: N#Cc1ccc(-c2ccc(-c3ccc4ccccc4c3-c3ccc(-c4nc(-c5ccccc5)nc(-c5ccccc5)n4)cc3)c3ccccc23)cc1]
[ET 13]
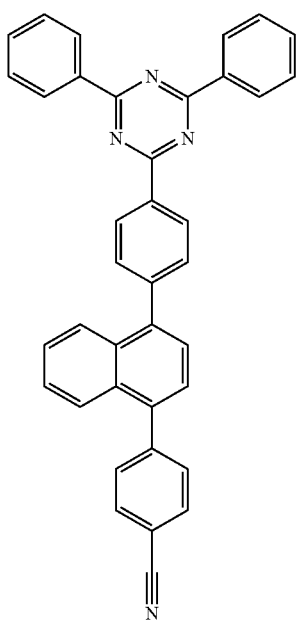 [SMILES: N#Cc1ccc(-c2ccc(-c3ccc(-c4nc(-c5ccccc5)nc(-c5ccccc5)n4)cc3)c3ccccc23)cc1]
[ET 14]
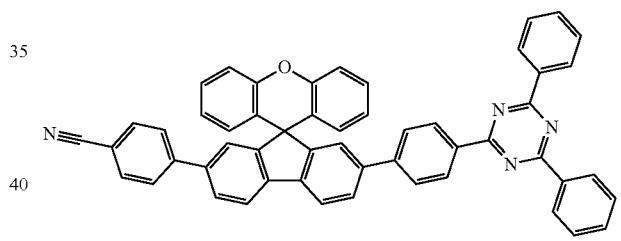
[ET 15]
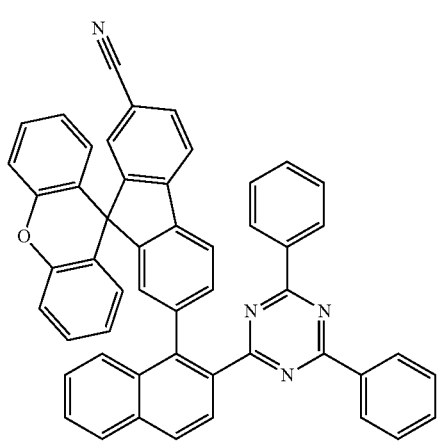

[ET 16]
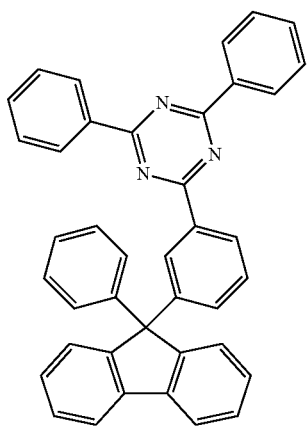 [SMILES: c1ccc(-c2nc(-c3ccccc3)nc(-c3cccc(C4(c5ccccc5)c5ccccc5-c5ccccc54)c3)n2)cc1]
[BH C]
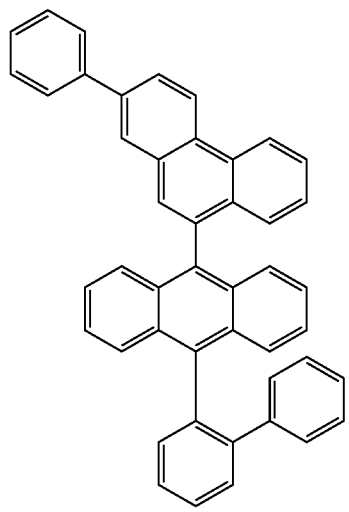
Comparative Examples 1 to 10
Organic light emitting devices were manufactured in the same manner as in Example 1, except that the compounds described in the following Table 1 were each used instead of Compound [BH 1] and Compound [ET 1].
[BH A]
[ET A]
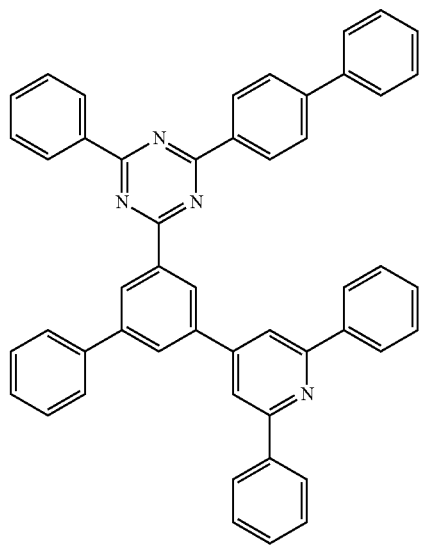
[BH B]
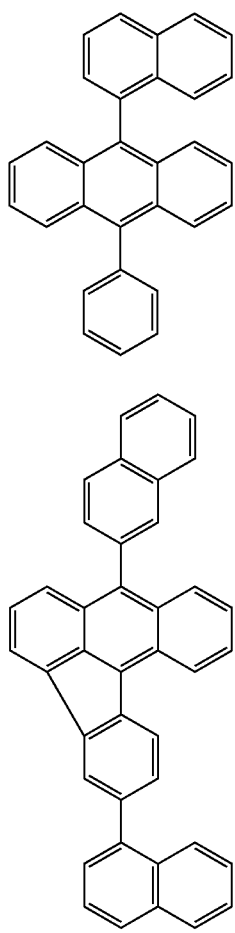
[ET B]
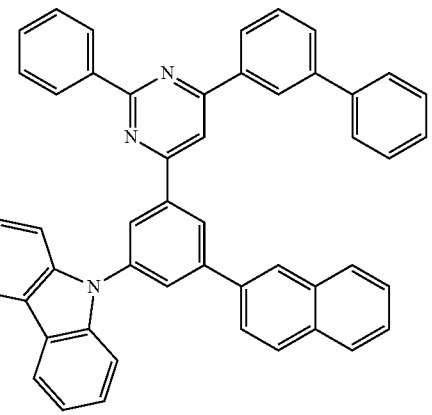

[ET C]
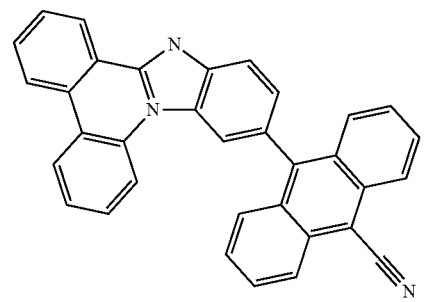
[ET D]
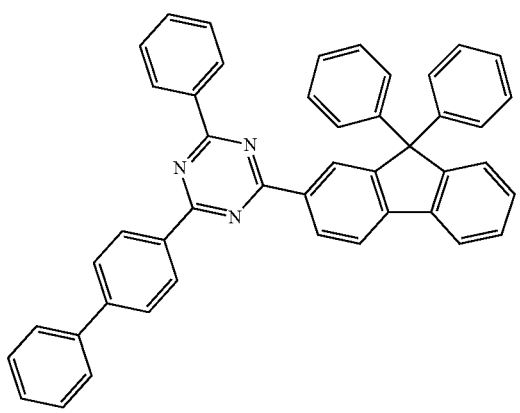
[ET E]
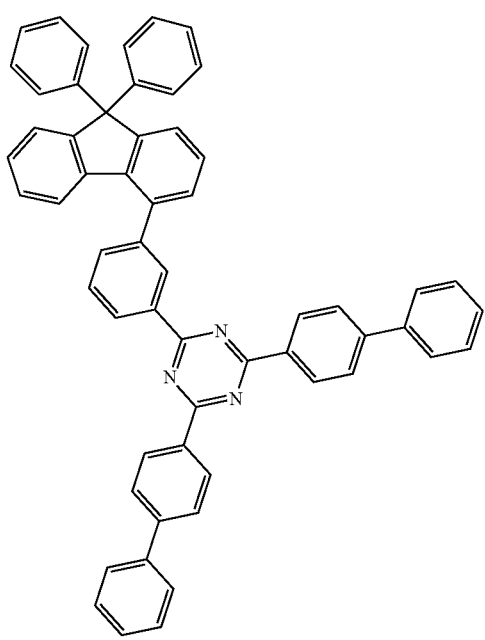
[ET F]
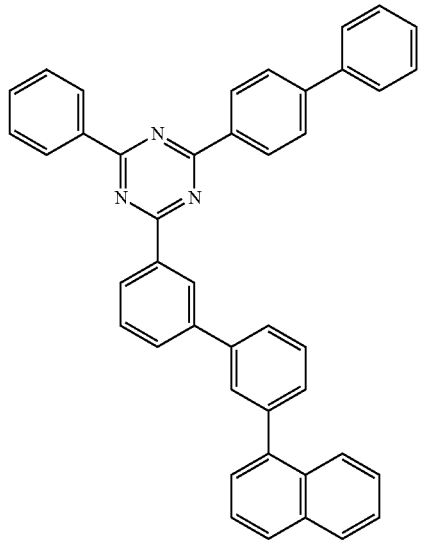
[ET G]
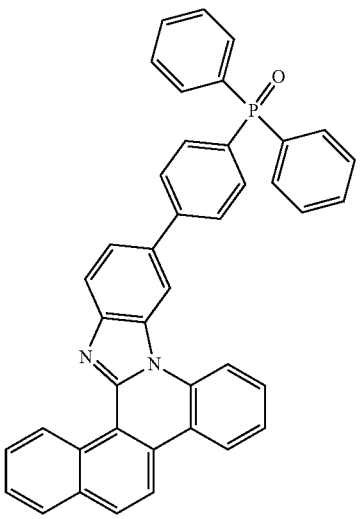
[ET H]
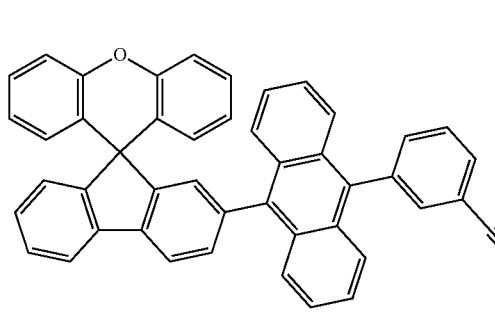

-continued

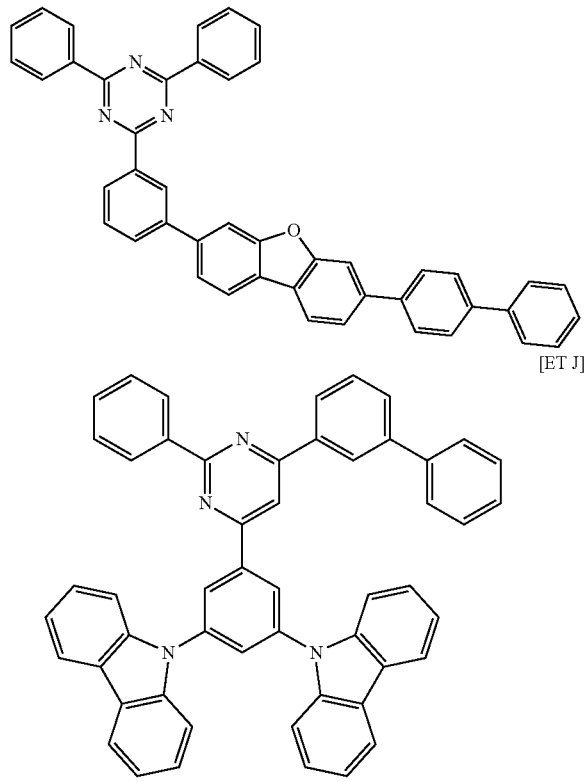

[ET I]

[ET J]

For the organic light emitting devices manufactured in the Examples and the Comparative Examples, the driving voltage and the light emitting efficiency were measured at a current density of 10 mA/cm², and a time (LT95) for reaching a 95% value compared to the initial luminance was measured at a current density of 20 mA/cm². The results are shown in the following Table 1.

TABLE 1

| | Compound | Voltage (V) | Current efficiency (cd/A) | Color coordinate (x, y) | Lifetime (95% at 20 mA/cm²) |
|---|---|---|---|---|---|
| Example 1 | [BH 1]/[ET 1] | 3.65 | 7.67 | (0.136, 0.130) | 207 |
| Example 2 | [BH 1]/[ET 2] | 3.70 | 8.04 | (0.136, 0.128) | 176 |
| Example 3 | [BH 2]/[ET 2] | 3.72 | 7.97 | (0.136, 0.128) | 181 |
| Example 4 | [BH 2]/[ET 3] | 3.72 | 7.82 | (0.136, 0.130) | 169 |
| Example 5 | [BH 3]/[ET 4] | 3.67 | 7.68 | (0.136, 0.131) | 171 |
| Example 6 | [BH 4]/[ET 5] | 3.70 | 7.89 | (0.135, 0.130) | 221 |
| Example 7 | [BH 4]/[ET 6] | 3.68 | 8.01 | (0.136, 0.129) | 165 |
| Example 8 | [BH 5]/[ET 7] | 3.77 | 7.88 | (0.136, 0.130) | 157 |
| Example 9 | [BH 6]/[ET 8] | 3.71 | 7.57 | (0.136, 0.130) | 158 |
| Example 10 | [BH 1]/[ET 9] | 3.82 | 7.44 | (0.136, 0.131) | 230 |
| Example 11 | [BH 1]/[ET 10] | 3.63 | 7.60 | (0.136, 0.130) | 160 |
| Example 12 | [BH 4]/[ET 11] | 3.65 | 7.74 | (0.136, 0.130) | 206 |

TABLE 1-continued

| | Compound | Voltage (V) | Current efficiency (cd/A) | Color coordinate (x, y) | Lifetime (95% at 20 mA/cm²) |
|---|---|---|---|---|---|
| Example 13 | [BH 2]/[ET 12] | 3.67 | 7.63 | (0.136, 0.131) | 189 |
| Example 14 | [BH 3]/[ET 13] | 3.73 | 7.06 | (0.135, 0.130) | 251 |
| Example 15 | [BH 5]/[ET 14] | 3.72 | 7.14 | (0.136, 0.129) | 279 |
| Example 16 | [BH 1]/[ET 15] | 3.77 | 7.62 | (0.136, 0.130) | 219 |
| Example 17 | [BH 4]/[ET 16] | 3.63 | 7.59 | (0.136, 0.130) | 163 |
| Comparative Example 1 | [BH A]/[ET A] | 4.02 | 6.67 | (0.134, 0.132) | 124 |
| Comparative Example 2 | [BH A]/[ET 1] | 4.09 | 6.67 | (0.134, 0.130) | 128 |
| Comparative Example 3 | [BH B]/[ET C] | 4.24 | 6.09 | (0.134, 0.131) | 117 |
| Comparative Example 4 | [BH A]/[ET D] | 3.98 | 6.85 | (0.135, 0.130) | 131 |
| Comparative Example 5 | [BH 3]/[ET E] | 4.33 | 6.50 | (0.135, 0.134) | 125 |
| Comparative Example 6 | [BH 5]/[ET F] | 4.04 | 6.63 | (0.136, 0.130) | 119 |
| Comparative Example 7 | [BH A]/[ET G] | 4.19 | 6.36 | (0.136, 0.130) | 148 |
| Comparative Example 8 | [BH 2]/[ET H] | 4.03 | 5.98 | (0.135, 0.130) | 110 |
| Comparative Example 9 | [BH B]/[ET I] | 4.12 | 6.47 | (0.136, 0.130) | 119 |
| Comparative Example 10 | [BH C]/[ET 9] | 4.17 | 6.67 | (0.136, 0.131) | 142 |

As described in Table 1, the devices in Examples 1 to 17 in which the compound of Formula 1 according to the present invention is used as a host of the light emitting layer and the compound of Formula 2 according to the present invention is used in the electron injection and transport layer have the long lifetime, low voltage, and high efficiency characteristics.

The device in Comparative Example 2 has a configuration which is the same as that of the device in Example 1 of the present application except for only a host compound, and the device in Comparative Example 10 has a configuration which is the same as that of the device in Example 9 of the present application except for a host compound. Host compounds BH A and BH C in Comparative Examples 2 and 10 are compounds which do not include naphthobenzofuran or naphthobenzothiophene. Examples 1 and 9 according to the present invention have the long lifetime, low voltage and high efficiency characteristics as compared to Comparative Examples 2 and 10.

The device in Comparative Example 5 has a configuration which is the same as those of Examples 5 and 14 except for the compound of the electron injection and transport layer. Compound ET E in Comparative Example 5 is a compound which does not include a cyano group or a 9-fluorenyl group. Examples 5 and 14 according to the present invention have the long lifetime, low voltage and high efficiency characteristics as compared to Comparative Example 6.

The device in Comparative Example 6 has a configuration which is the same as those of Examples 8 and 15 except for the compound of the electron injection and transport layer. Compound ET F in Comparative Example 6 is a compound which does not include a cyano group or a spiro structure. Examples 8 and 15 according to the present invention have the long lifetime, low voltage and high efficiency characteristics as compared to Comparative Example 6.

The device in Comparative Example 8 has a configuration which is the same as those of Examples 3, 4, and 14 except for the compound of the electron injection and transport layer. Compound ET H in Comparative Example 8 has a cyano group, but is a compound which does not include the N-containing heterocycle of Formula 2 of the present application. Examples 3, 4, and 14 according to the present invention have the long lifetime, low voltage and high efficiency characteristics as compared to Comparative Example 8.

Therefore, it can be seen that when the compound of Formula 1 of the present invention is used as a host of the light emitting layer and the compound of Formula 2 of the present invention is used for the electron transport layer, the electron injection layer or the electron injection and transport layer, the low voltage and high efficiency characteristics of Formula 1, and the aforementioned long lifetime characteristic and thermal stability due to the high glass transition temperature, of Formula 2 are secured, so that an organic light emitting device with improved stability can be obtained.

The invention claimed is:
1. An organic light emitting device, comprising:
a first electrode;
a second electrode provided to face the first electrode; and
a first organic material layer and a second organic material layer provided between the first electrode and the second electrode,
wherein the first organic material layer comprises a compound of the following Formula 1, and
the second organic material layer comprises a compound of the following Formula 2:

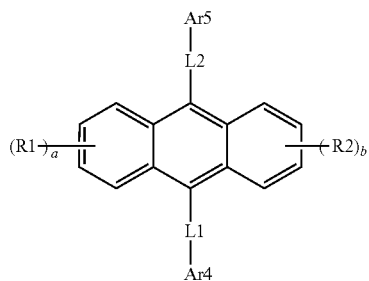

Formula 1 wherein in Formula 1:
R1 and R2 are each independently hydrogen, deuterium, a halogen group, a cyano group, a nitro group, a substituted or unsubstituted alkyl group, a substituted or unsubstituted haloalkyl group, a substituted or unsubstituted haloalkoxy group, a substituted or unsubstituted cycloalkyl group, a substituted or unsubstituted alkenyl group, a substituted or unsubstituted aryl group, or a substituted or unsubstituted heterocyclic group;
L1 and L2 are each independently a single bond or a substituted or unsubstituted arylene group;
Ar4 is a substituted or unsubstituted aryl group or a substituted or unsubstituted heterocyclic group;
Ar5 is a substituent of the following Formula 3;
a and b are each independently an integer from 0 to 4;
when a and b are each independently 2 or more, the substituents in the parentheses are the same as or different from each other;

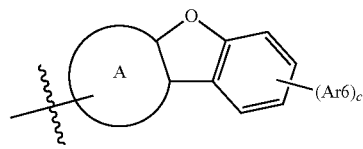

Formula 3 wherein in Formula 3:
A is a substituted or unsubstituted phenyl group, a substituted or unsubstituted naphthyl group, or a substituted or unsubstituted dibenzofuran group;
Ar6 is hydrogen, deuterium, a substituted or unsubstituted aryl group, or a substituted or unsubstituted heterocyclic group;
c is an integer from 0 to 4;
when c is 2 or more, two or more Ar6s are the same as or different from each other, and adjacent Ar6s are optionally bonded to each other to form a substituted or unsubstituted aryl group or a substituted or unsubstituted heterocyclic group;
when A is a substituted or unsubstituted phenyl group, c is 2 or more and adjacent Ar6s are bonded to each other to form a substituted or unsubstituted aryl group or a substituted or unsubstituted heterocyclic group;

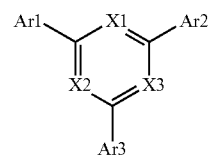

Formula 2 wherein in Formula 2:
at least one of X1 to X3 is N, and the remaining is or are CR;
R is hydrogen, deuterium, a substituted or unsubstituted alkyl group, a substituted or unsubstituted cycloalkyl group, a substituted or unsubstituted alkenyl group, a substituted or unsubstituted aryl group, or a substituted or unsubstituted heterocyclic group, or is optionally bonded to an adjacent substituent to form a ring;
Ar1 to Ar3 are each independently a substituted or unsubstituted aryl group or a substituted or unsubstituted heterocyclic group; and
at least one of Ar1 to Ar3 is Formula 205:

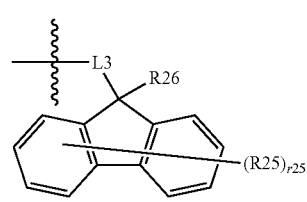

Formula 205 wherein in Formula 205:
L3 is a single bond or a substituted or unsubstituted arylene group;
R25 is a cyano group or a phenyl group that is unsubstituted or substituted with a cyano group, r25 is an integer from 1 to 4, and when r25 is 2 or more, the substituents in the parentheses are the same as or different from each other; and R26 is a substituted or unsubstituted alkyl group, a substituted or unsubstituted aryl group, or a substituted or unsubstituted heterocyclic group.

2. The organic light emitting device of claim 1, wherein Formula 3 is any one selected from the following Formulae 301 to 312:

Formula 301
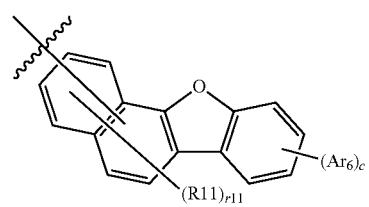

Formula 302
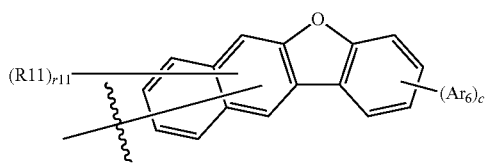

Formula 303
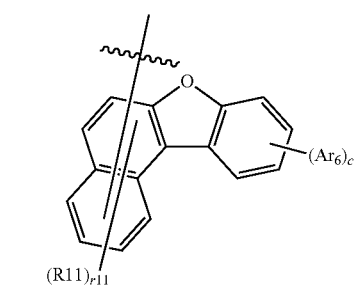

Formula 304
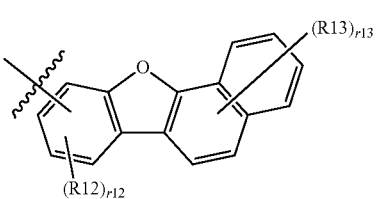

Formula 305
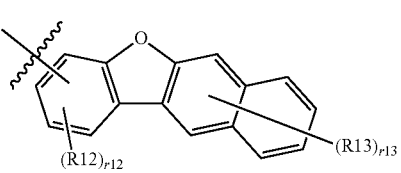

Formula 306
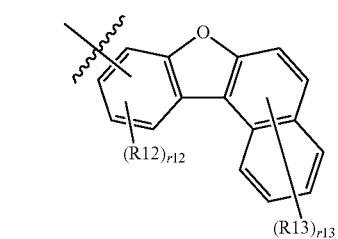

Formula 307
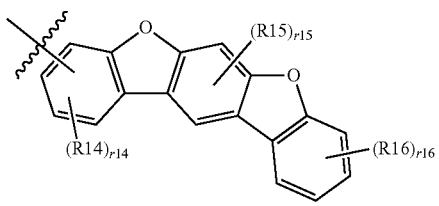

Formula 308
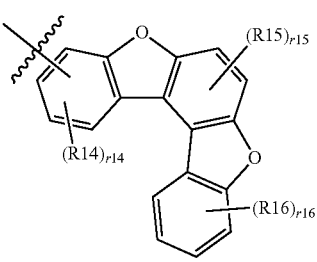

Formula 309
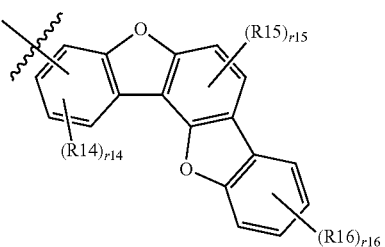

Formula 310
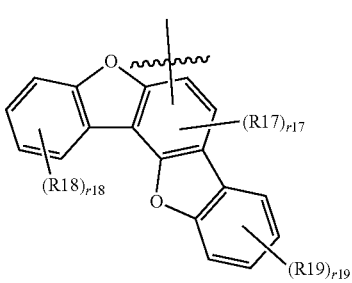

Formula 311
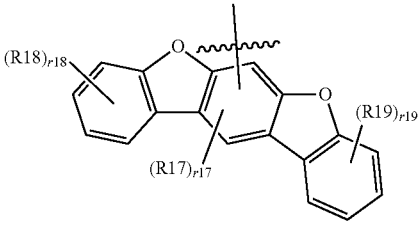

Formula 312
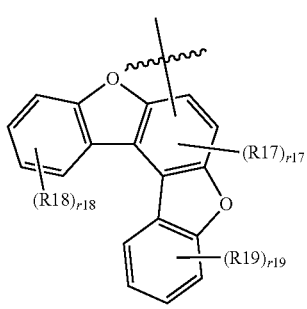

wherein in Formulae 301 to 312, the definitions of Ar6 and c are the same as those defined in Formula 3;

R11 to R19 are each independently hydrogen, deuterium, a substituted or unsubstituted aryl group, or a substituted or unsubstituted heterocyclic group;

r11 to r16, r18 and r19 are each an integer from 0 to 2, and when r11 to r16, r18 and r19 are each 2, the substituents in the parentheses are the same as or different from each other, and r17 is 0 or 1.

3. The organic light emitting device of claim 1, wherein the first organic material layer comprises a light emitting layer, and the light emitting layer comprises the compound of Formula 1.

4. The organic light emitting device of claim 1, wherein the second organic material layer comprises a hole blocking layer, an electron transport layer, an electron injection layer, or an electron injection and transport layer, and the hole blocking layer, the electron transport layer, the electron injection layer, or the electron injection and transport layer comprises the compound of Formula 2.

5. The organic light emitting device of claim 1, wherein the second organic material layer is in contact with the first organic material layer.

6. The organic light emitting device of claim 3, wherein the compound of Formula 1 is a host of the light emitting layer.

7. The organic light emitting device of claim 1, wherein the compound of Formula 1 is selected from the following compounds:

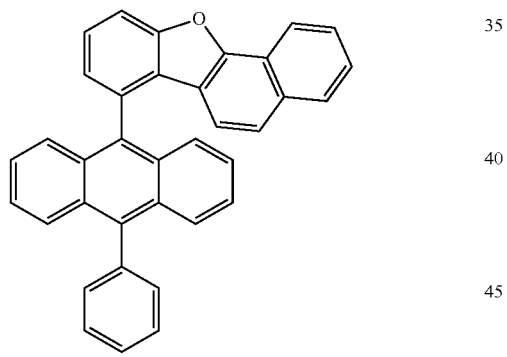

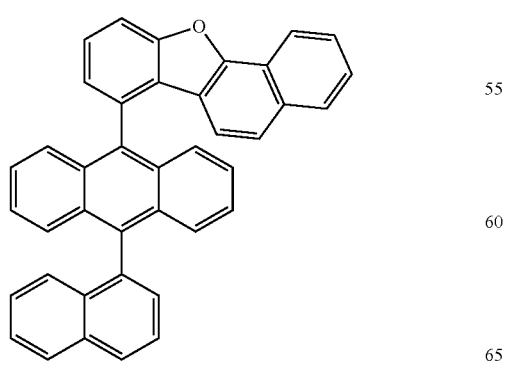

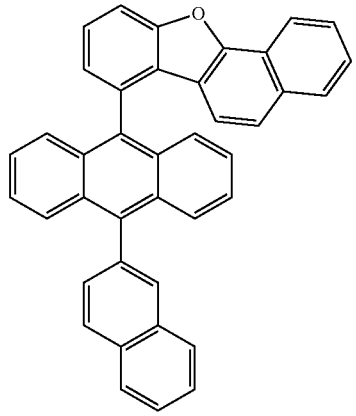

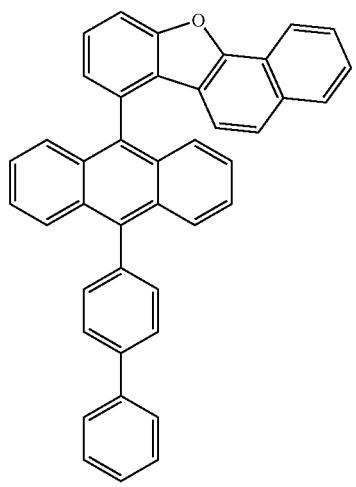

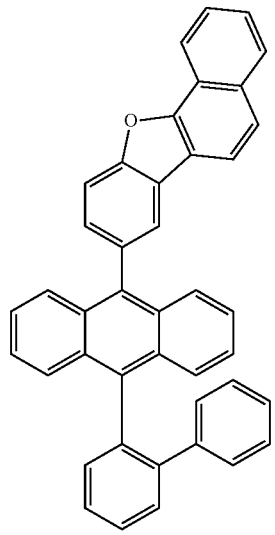

195
-continued
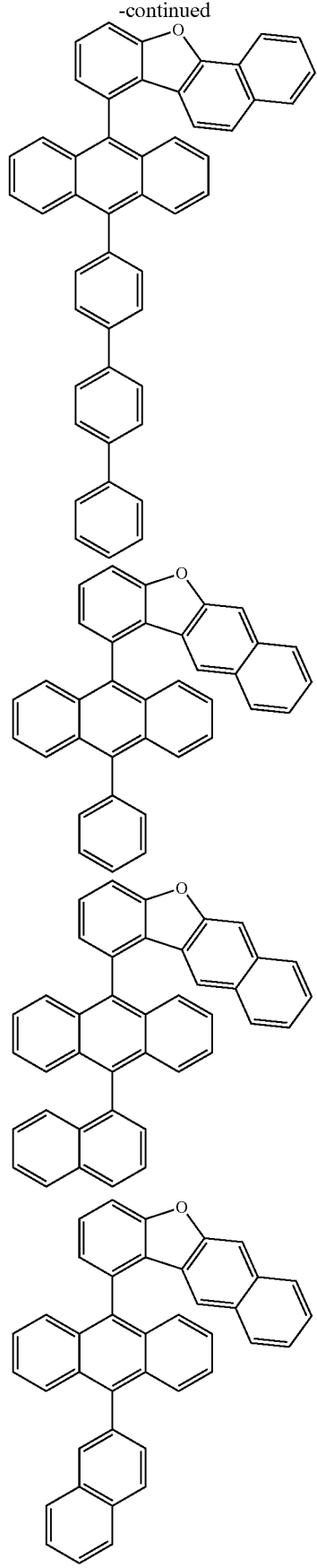
196
-continued
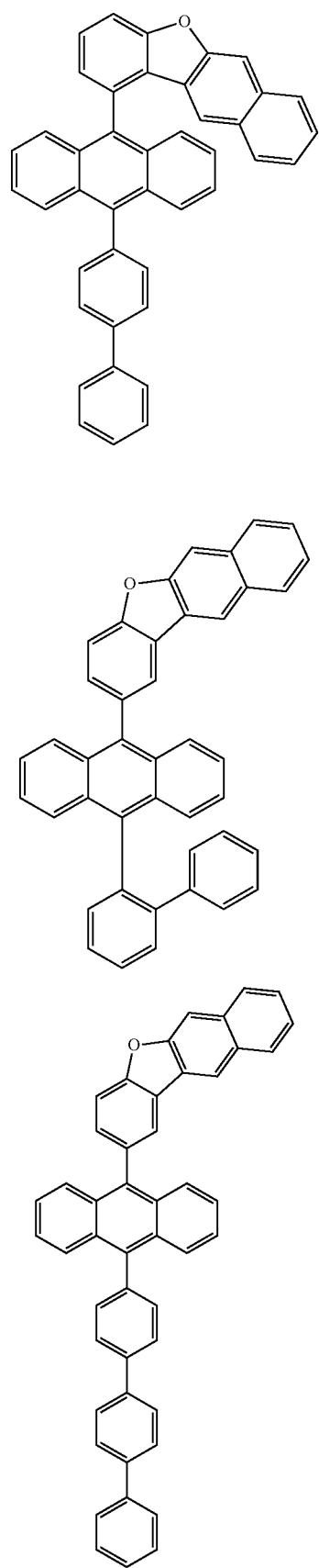

197
-continued
198
-continued
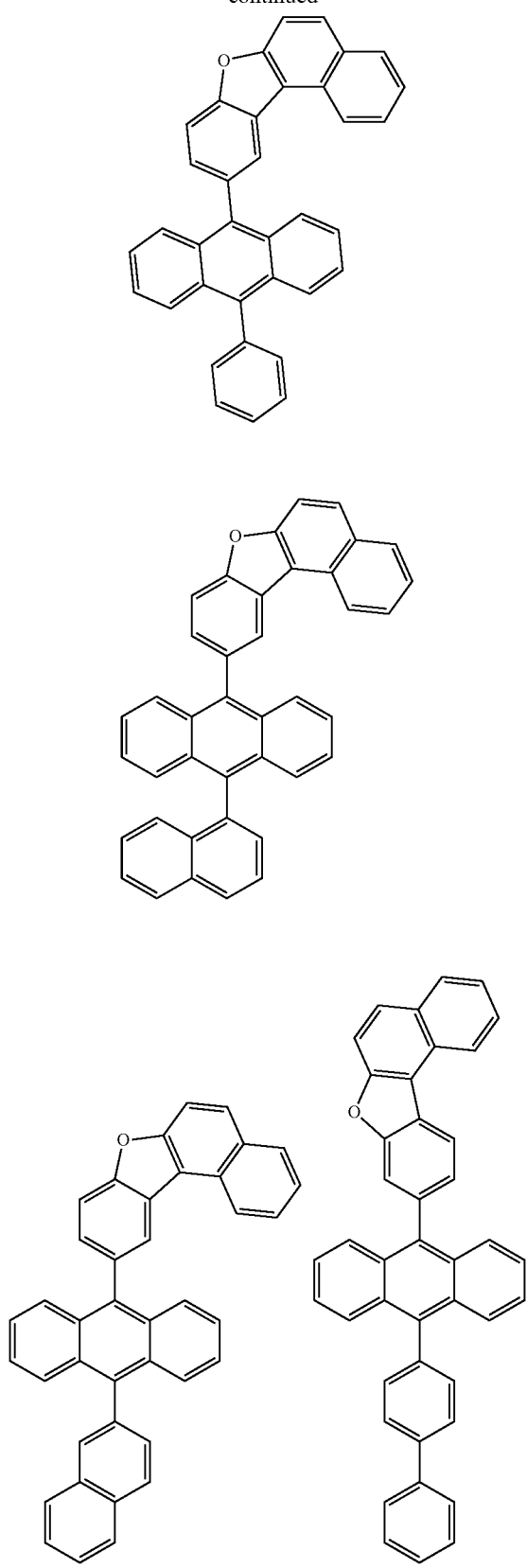
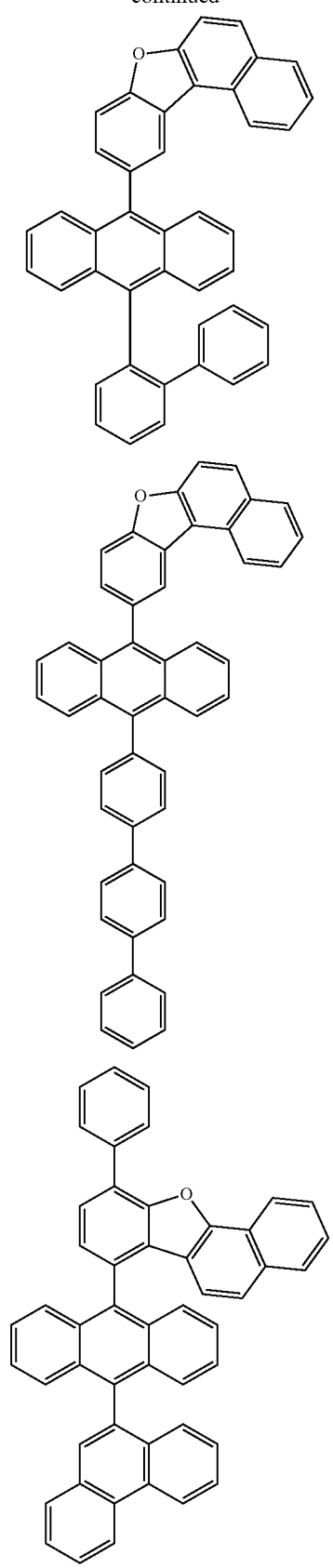

199
-continued
200
-continued
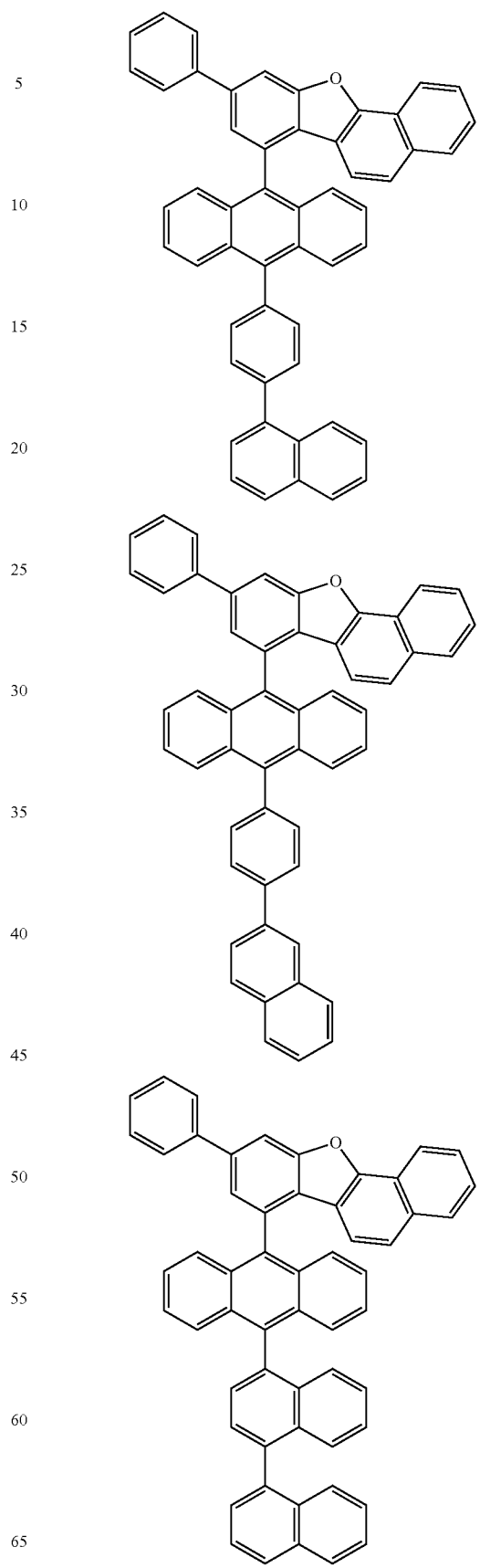

201
-continued
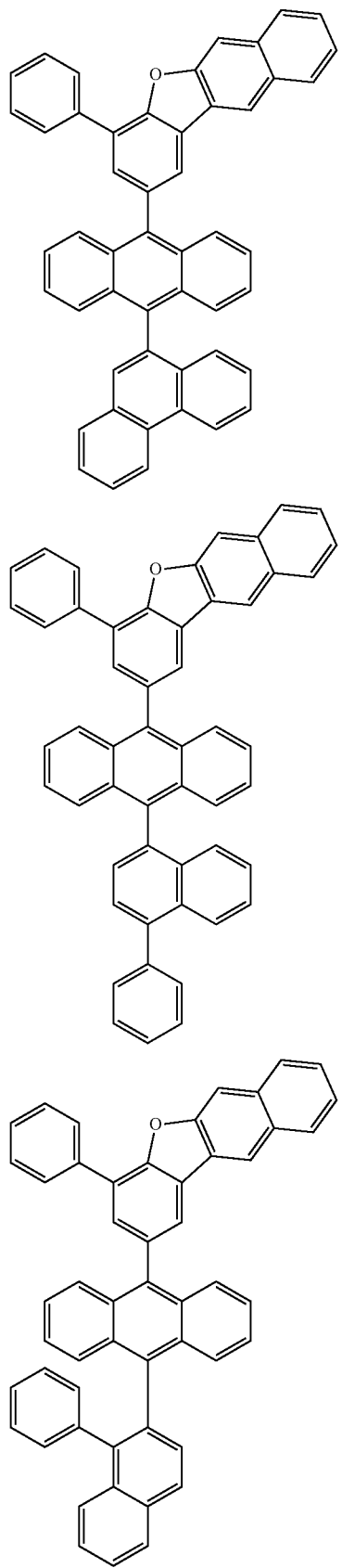
202
-continued
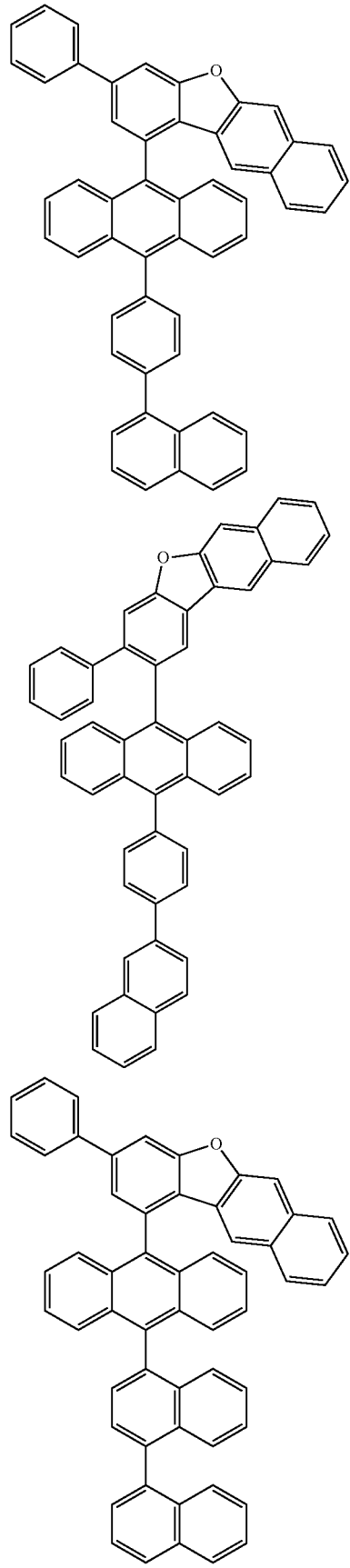

203
-continued
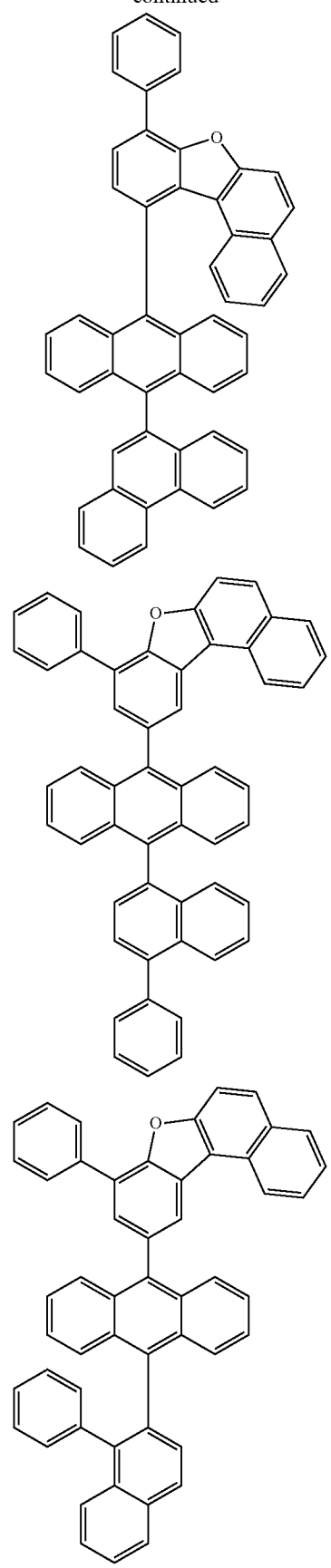
204
-continued

205
-continued
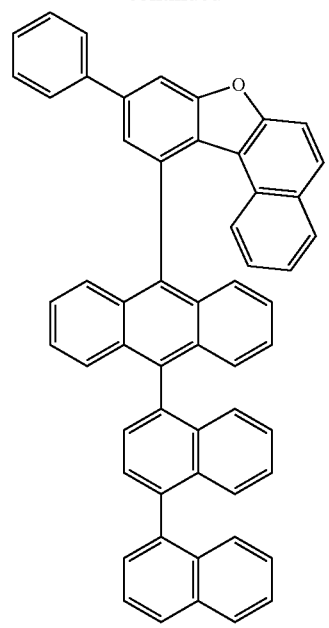
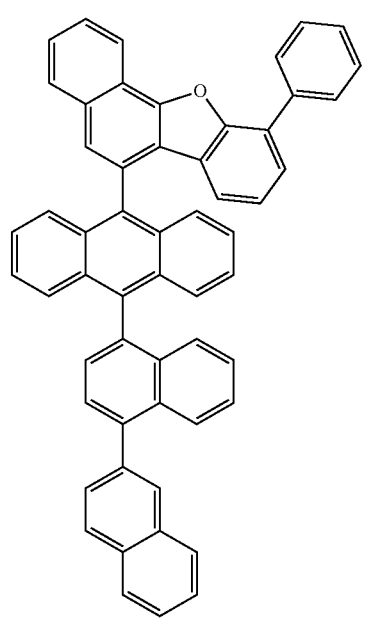
206
-continued
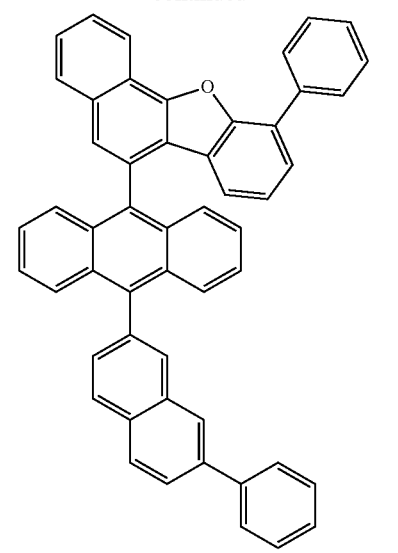
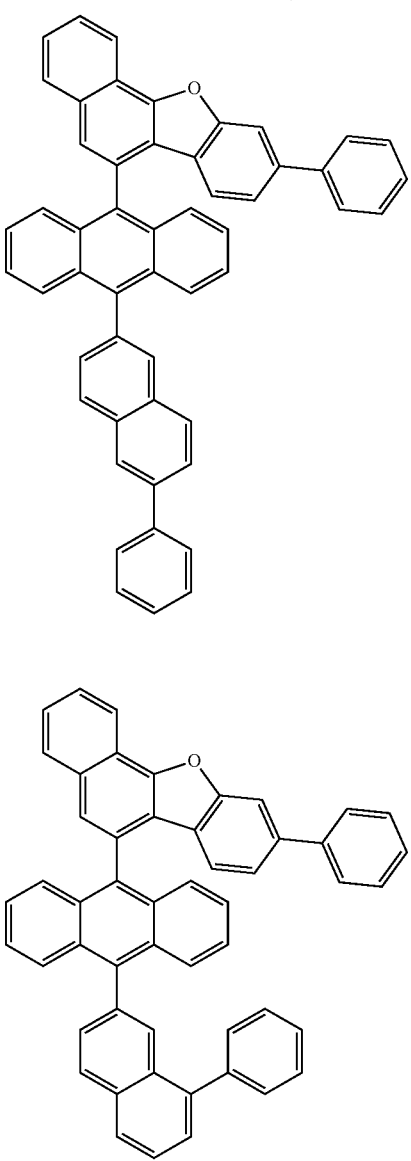

207
-continued
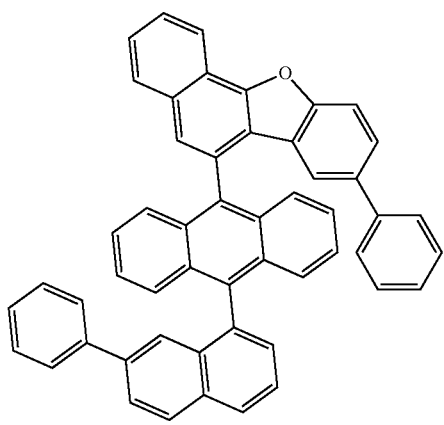
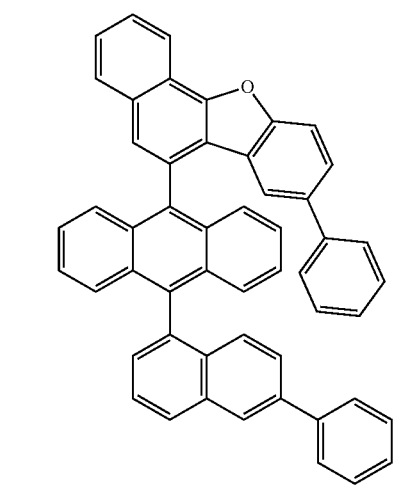
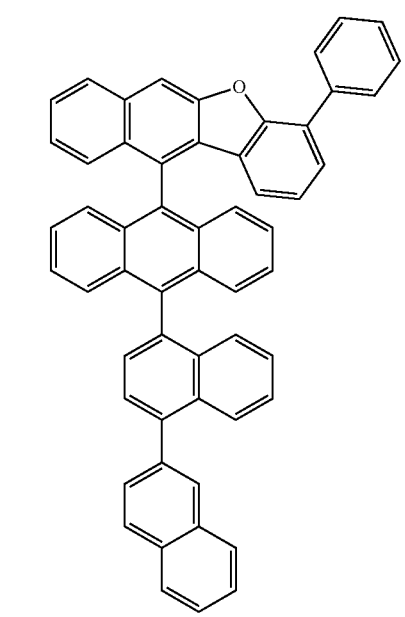
208
-continued
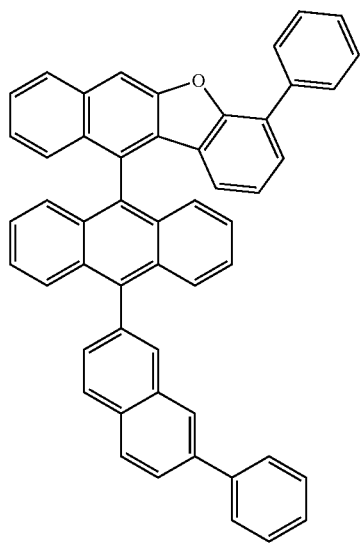
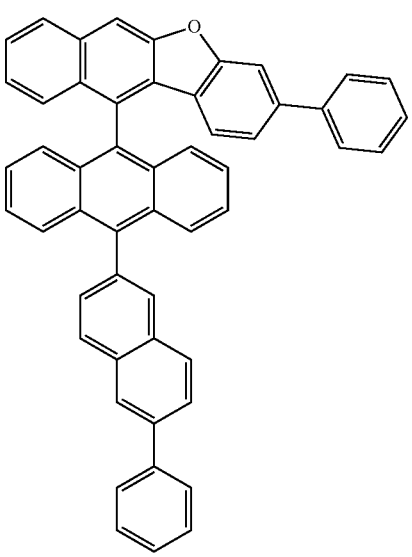
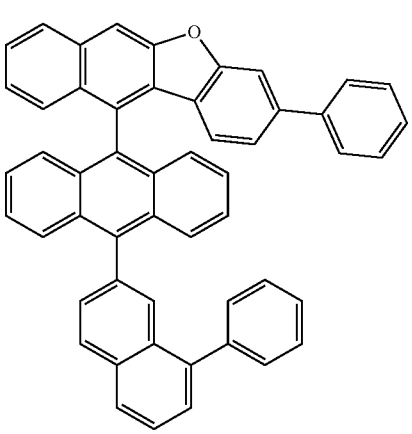

209
-continued
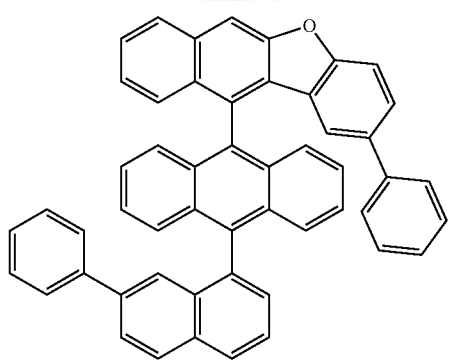
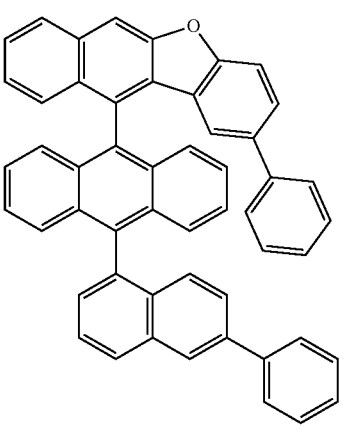
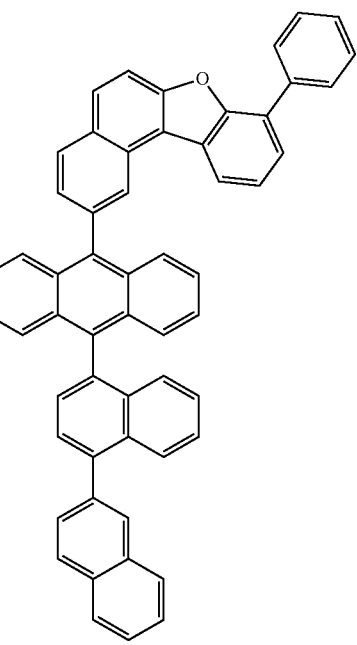
210
-continued
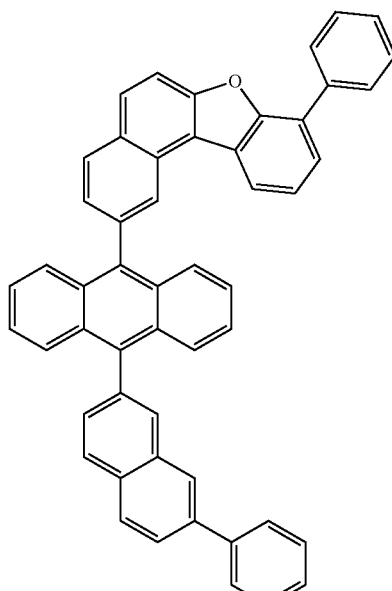
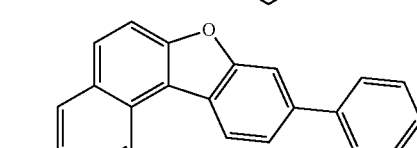
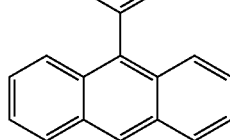
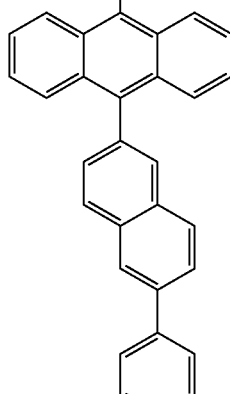
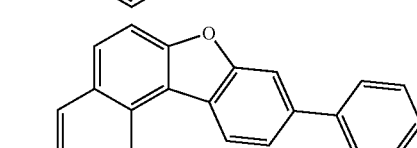
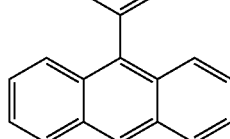
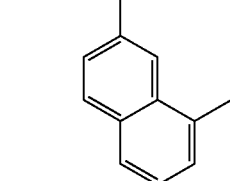

211
-continued
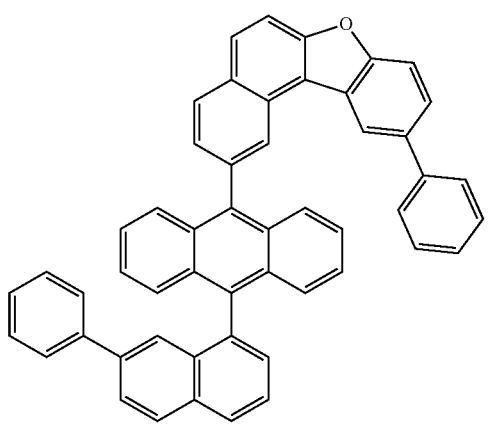
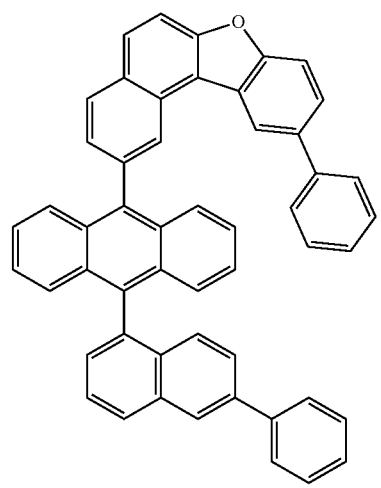
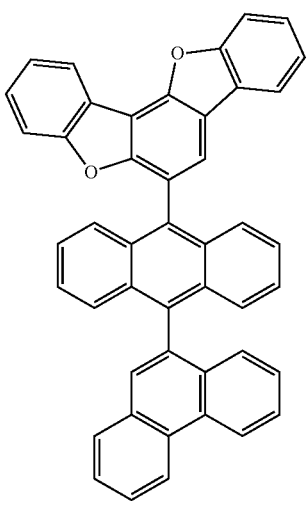
212
-continued
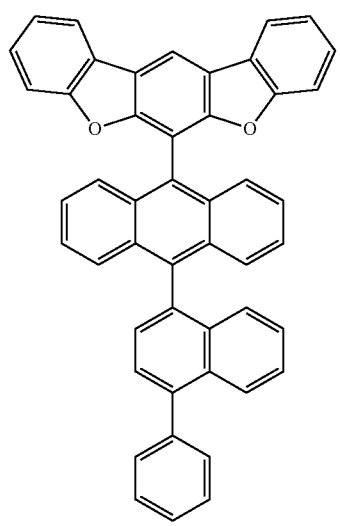
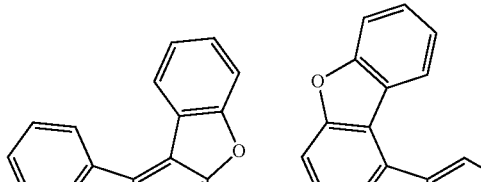
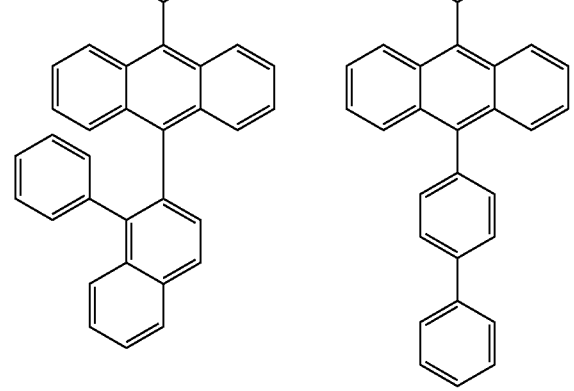
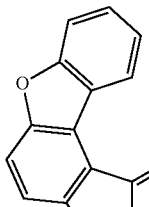
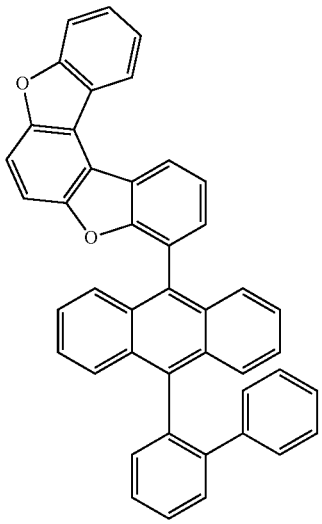
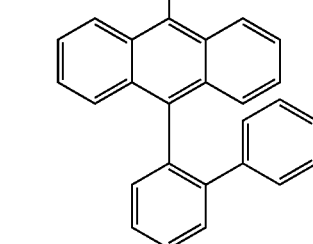

213
-continued
214
-continued
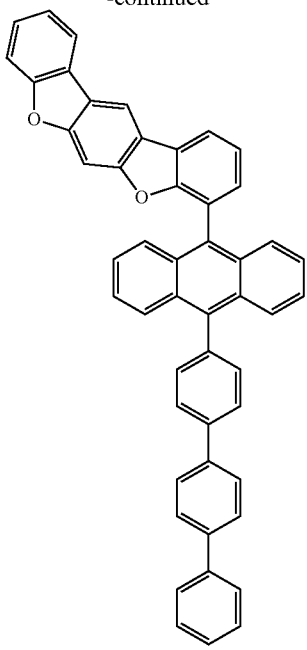
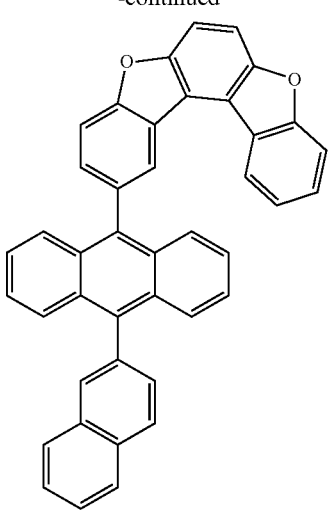
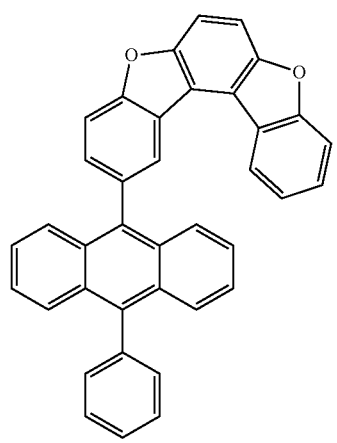
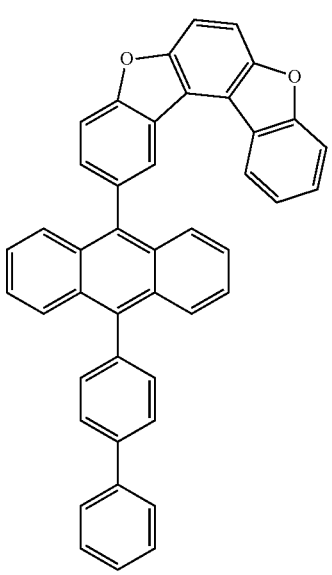
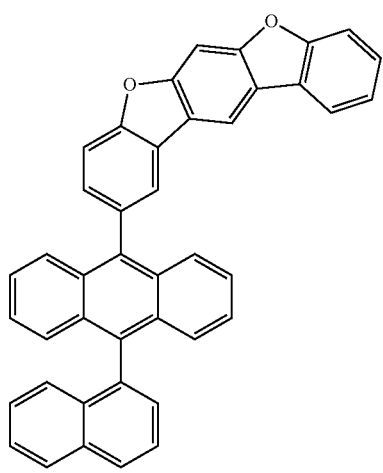
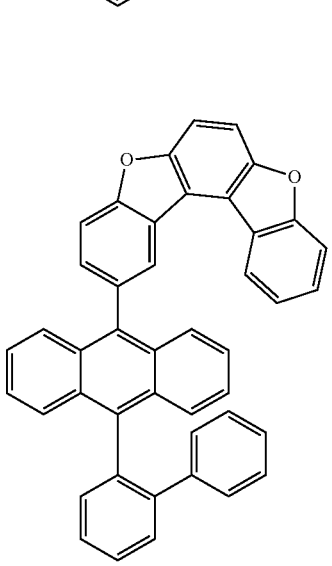

215
-continued
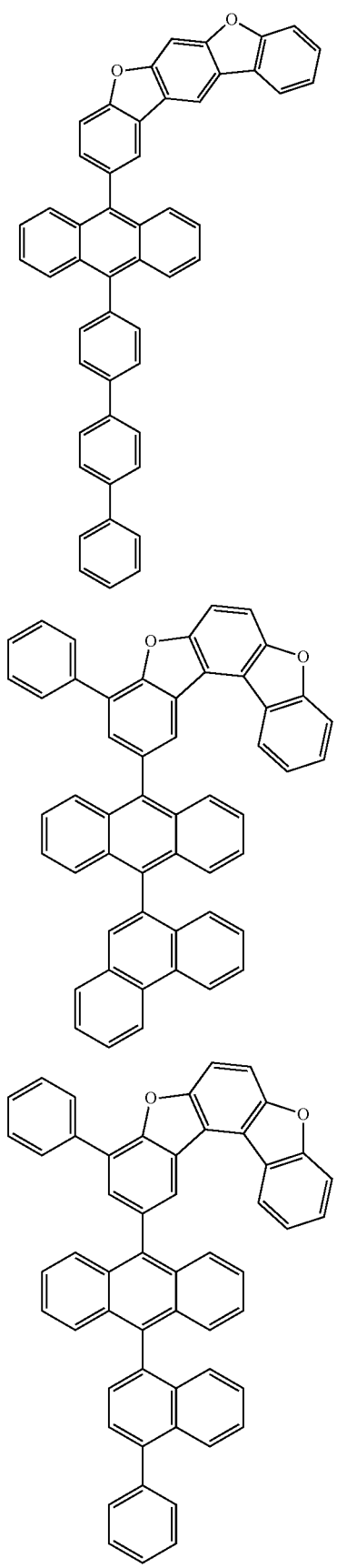
216
-continued
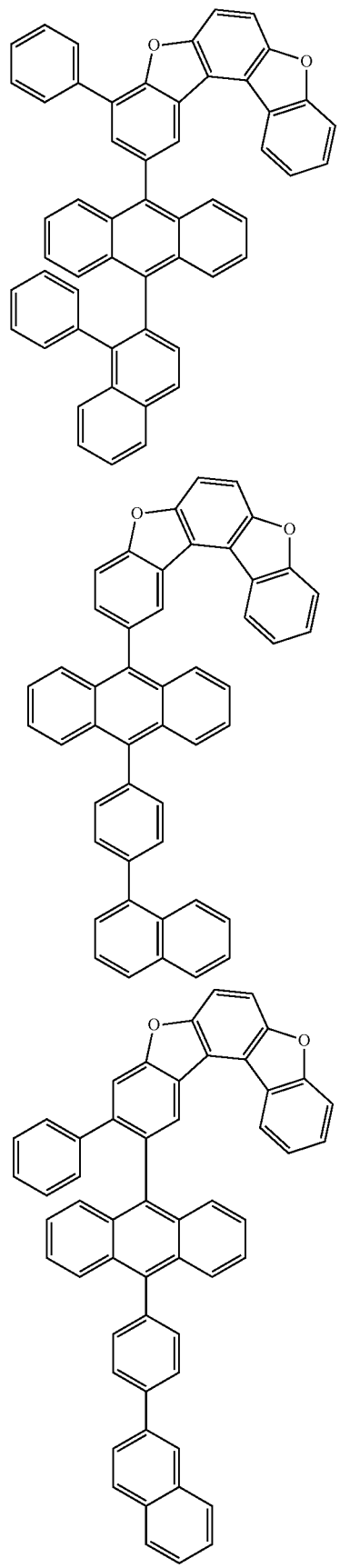

217
-continued
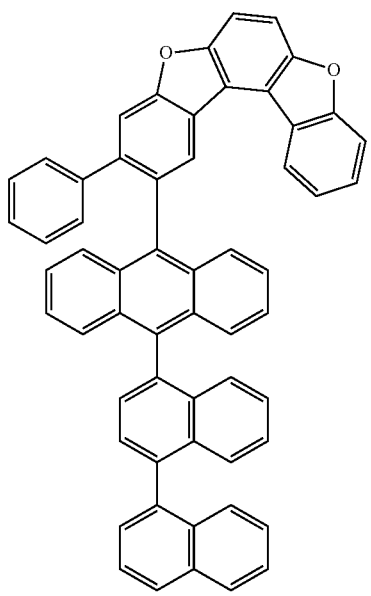
218
-continued
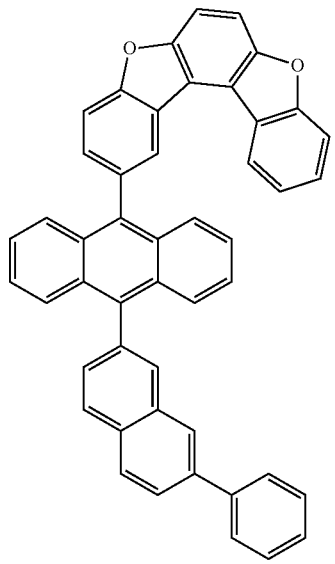
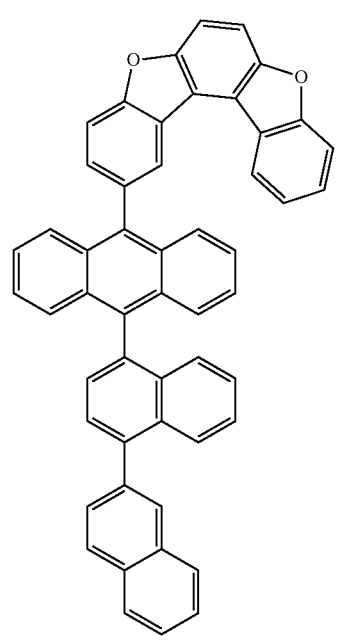
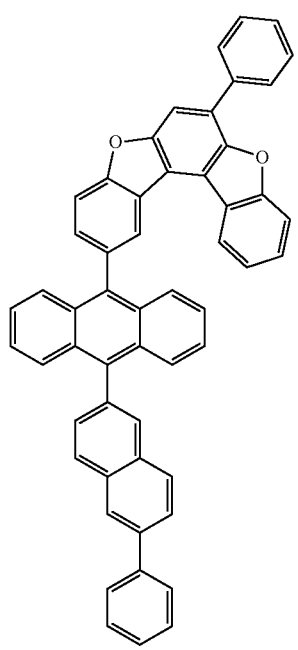

219
-continued
220
-continued
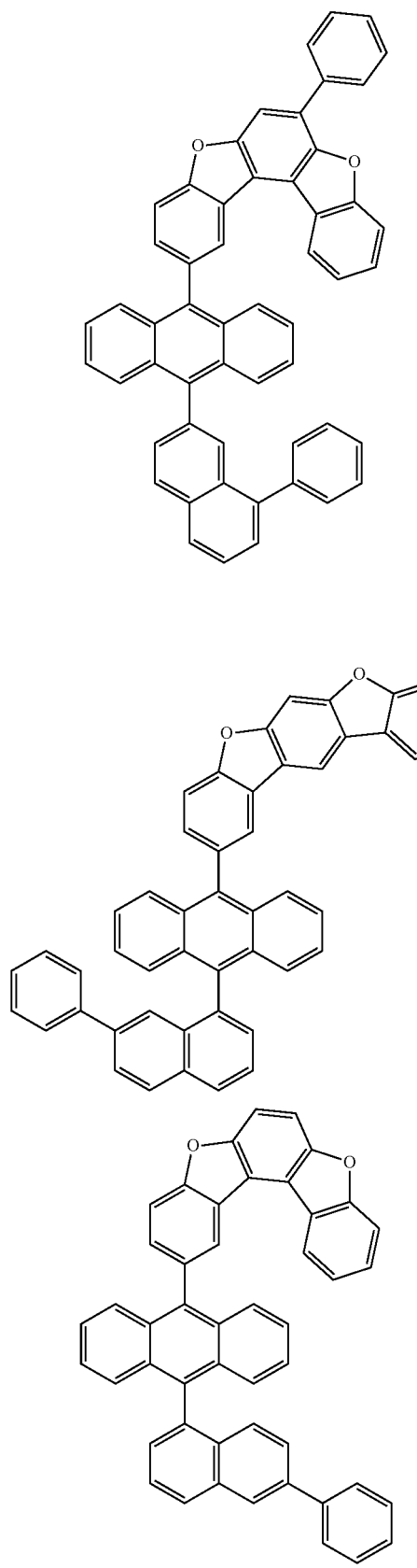
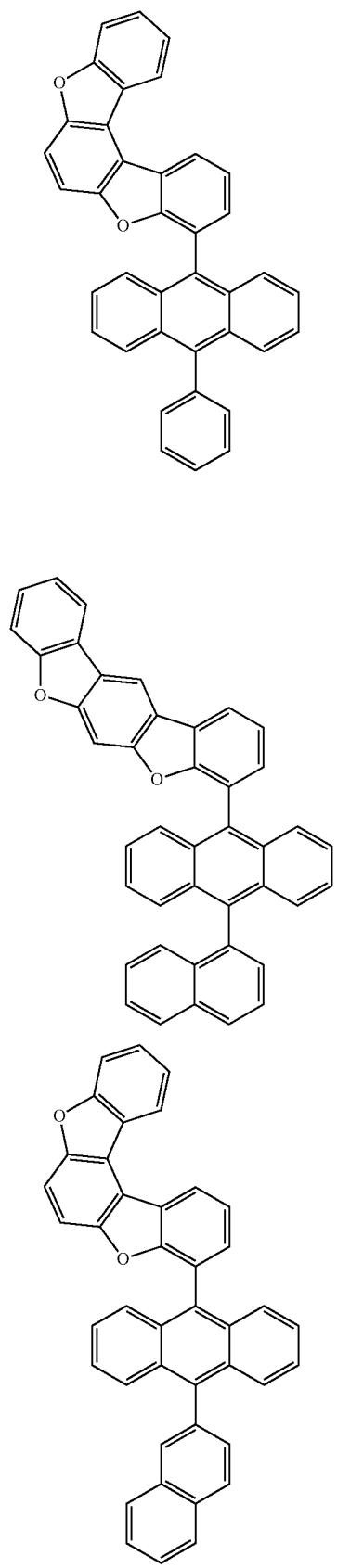

221
-continued
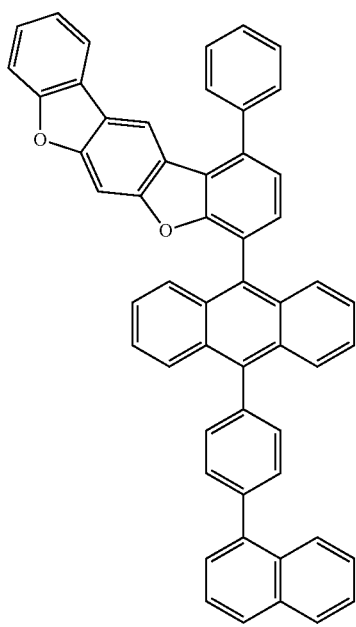
222
-continued
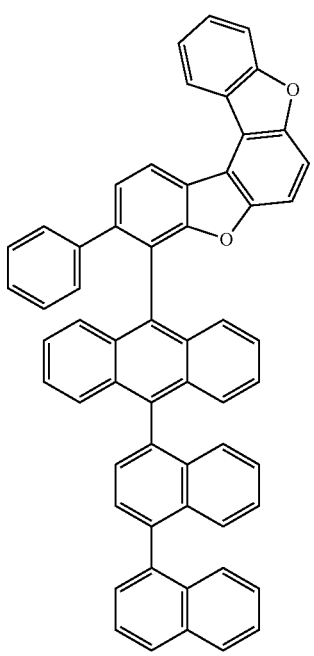
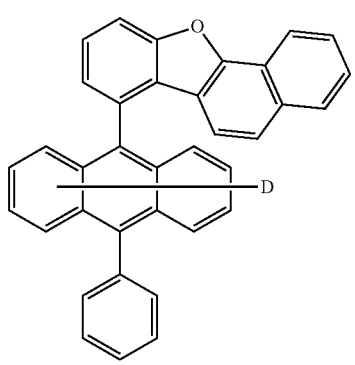
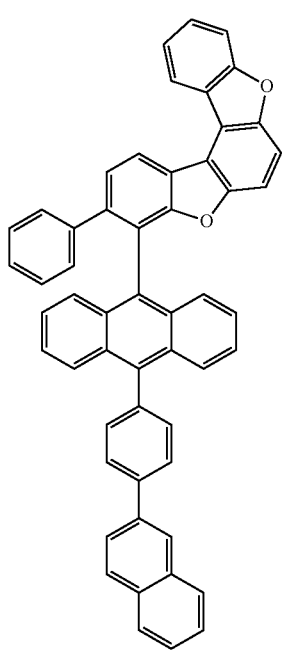
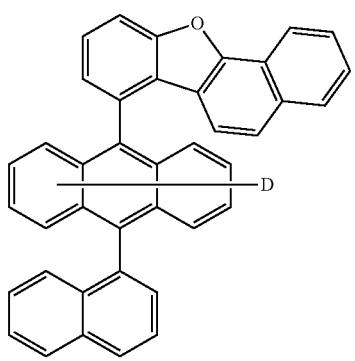

223
-continued
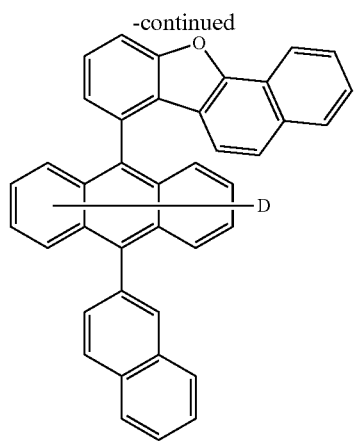
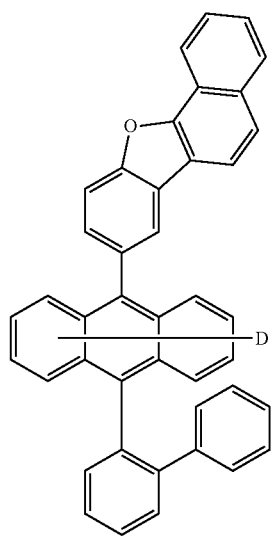
224
-continued
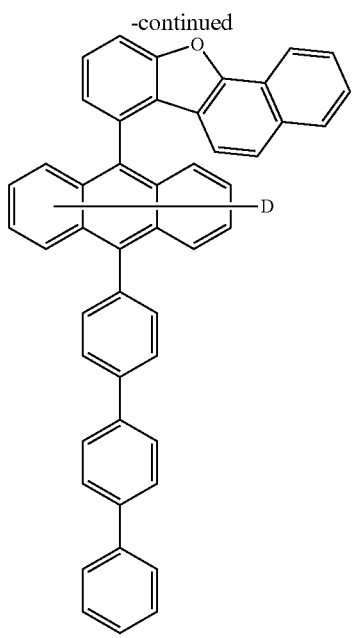
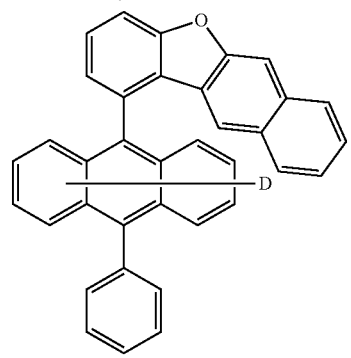
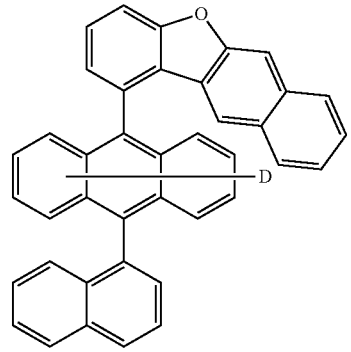
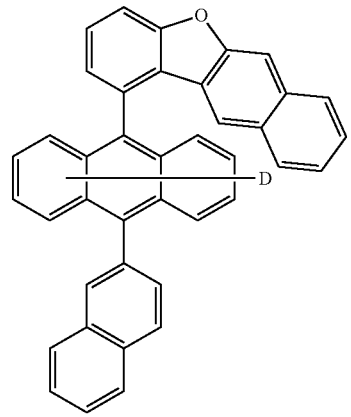

225
-continued
226
-continued
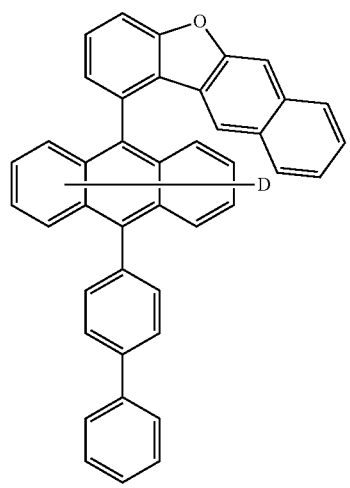
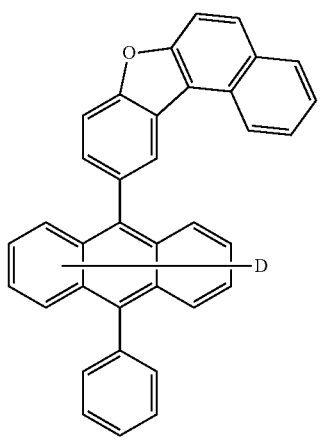
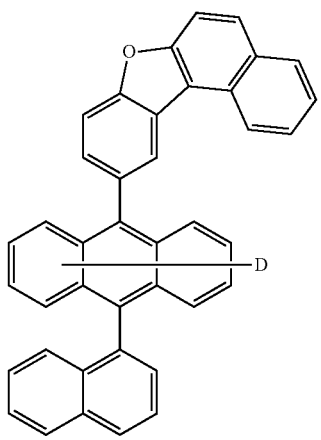
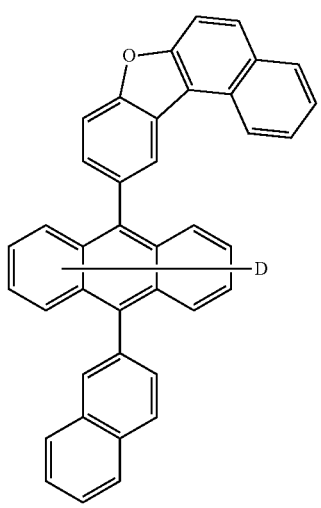

227
-continued
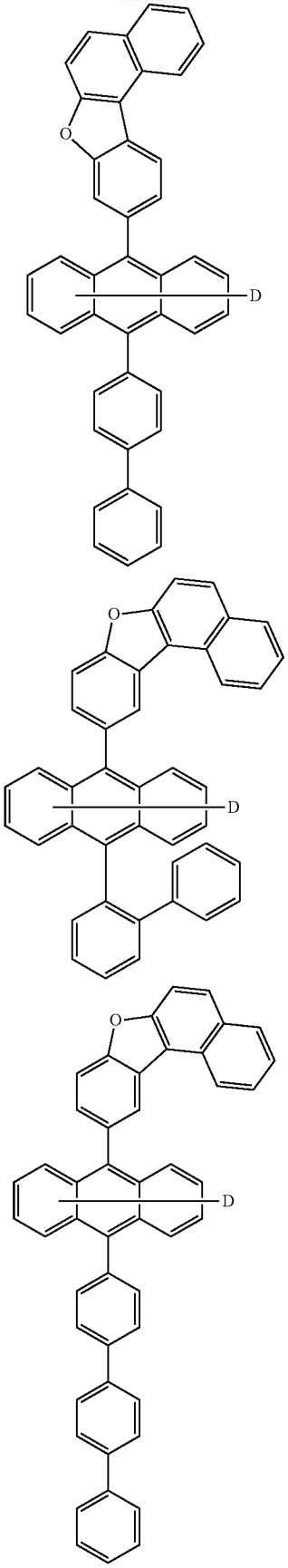
228
-continued

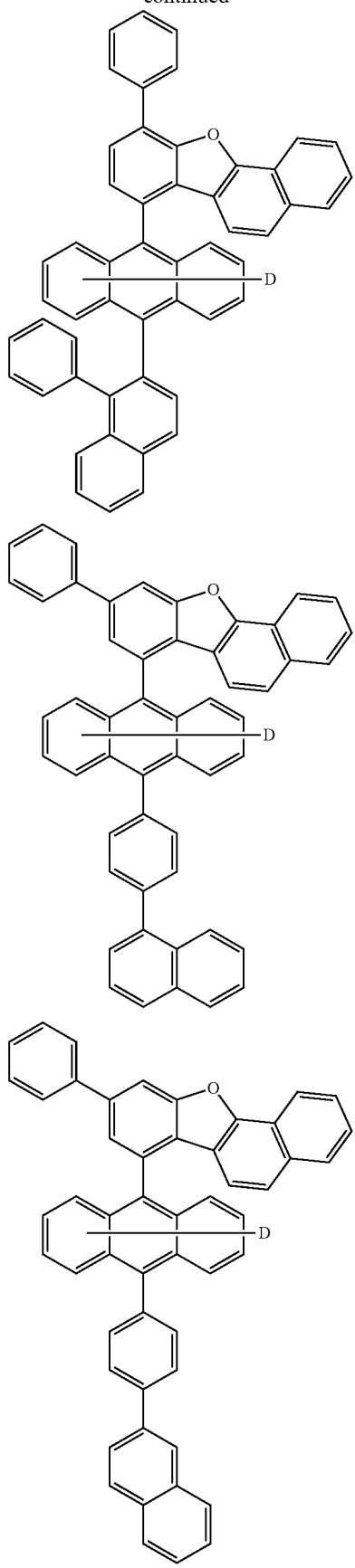
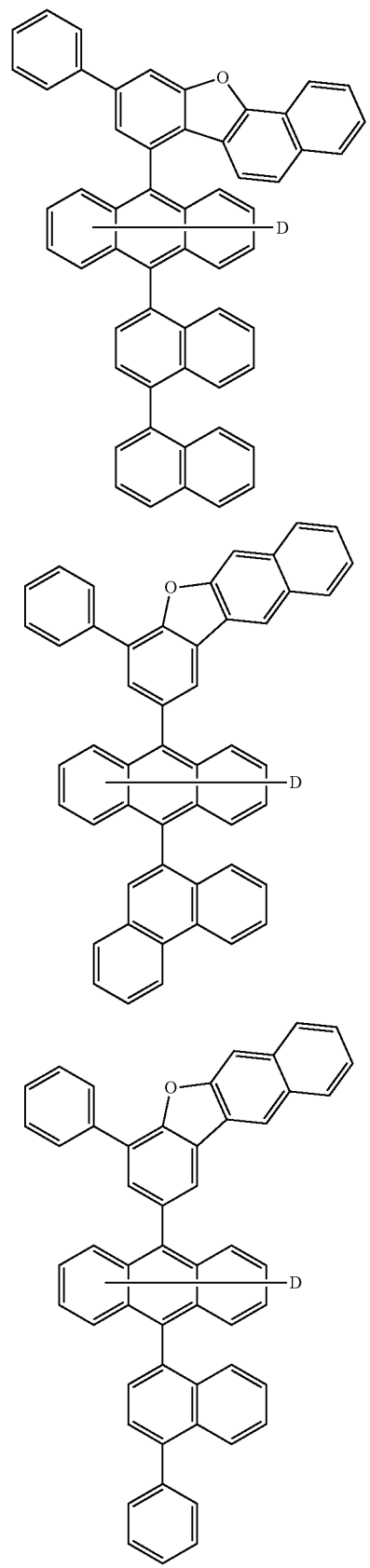

231
-continued
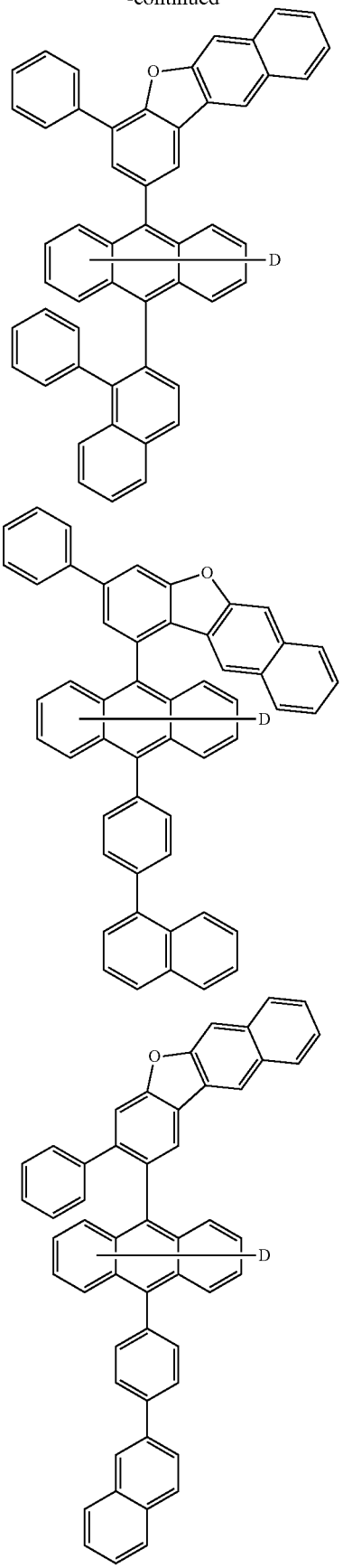
232
-continued
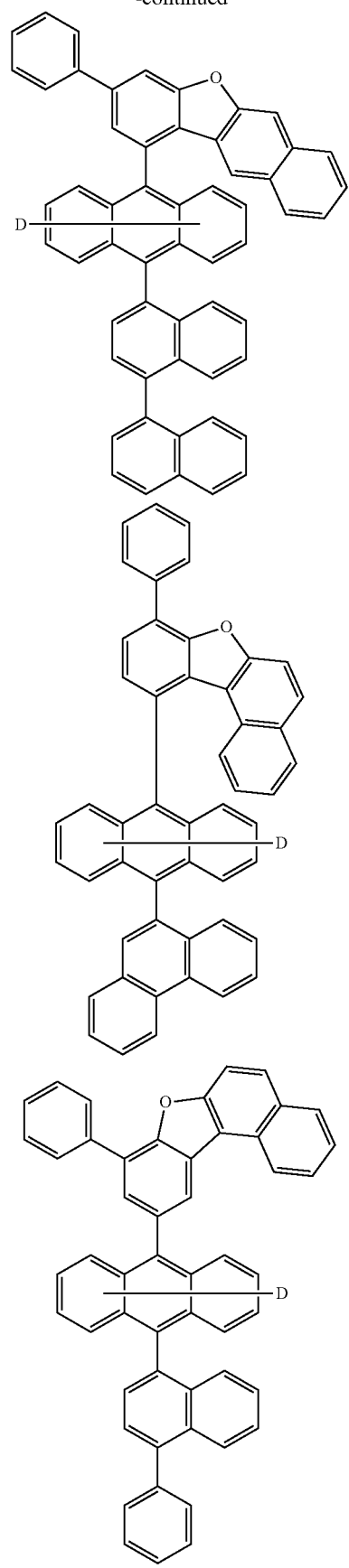

233
-continued
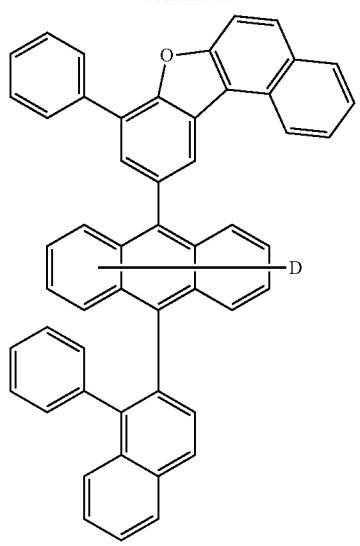
234
-continued
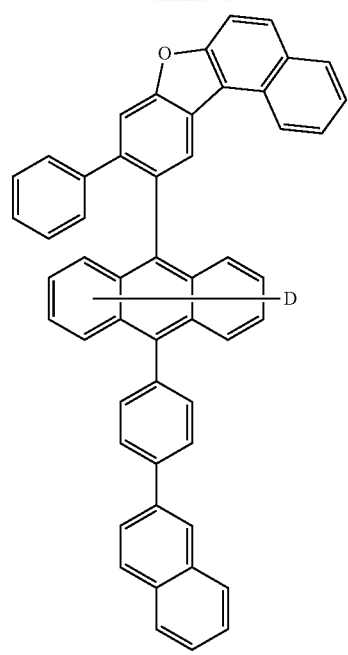
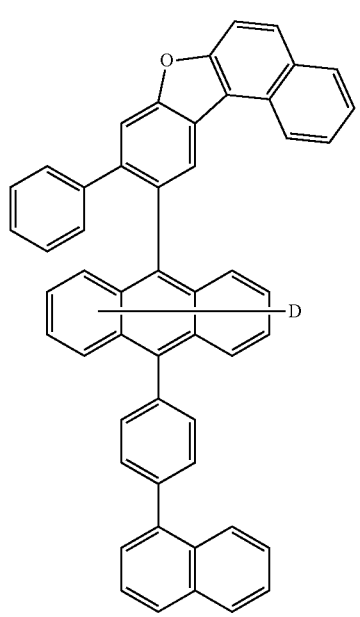
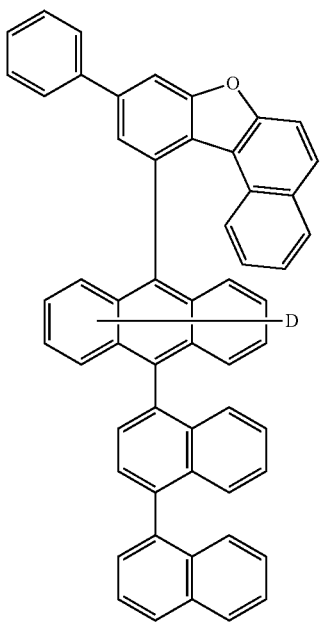

235
-continued
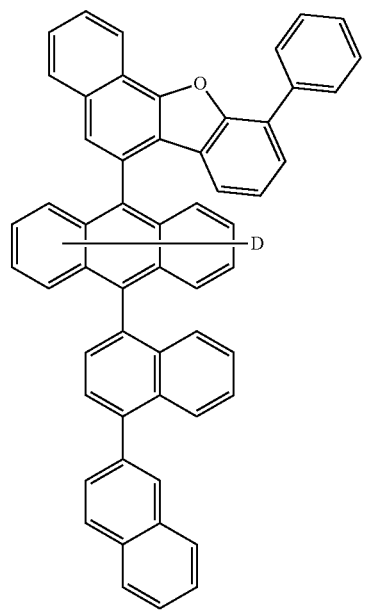
236
-continued
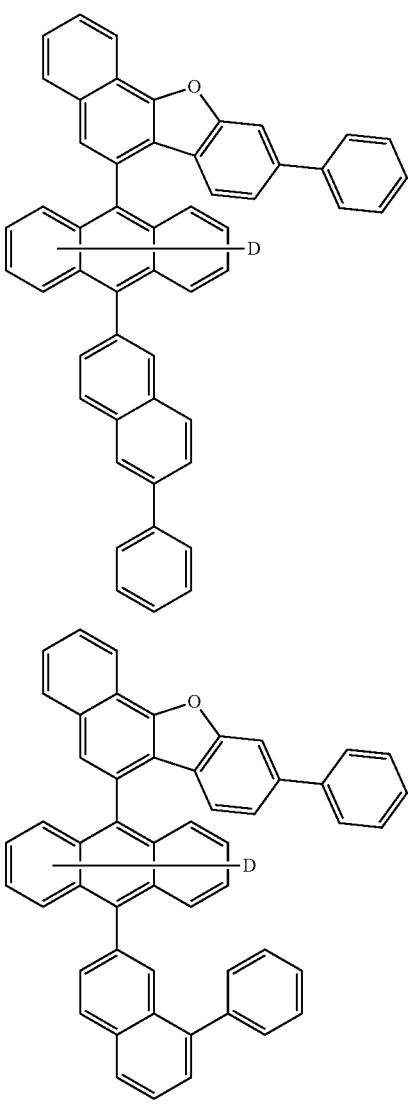
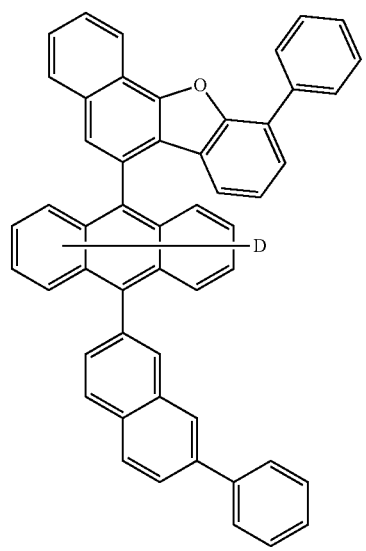
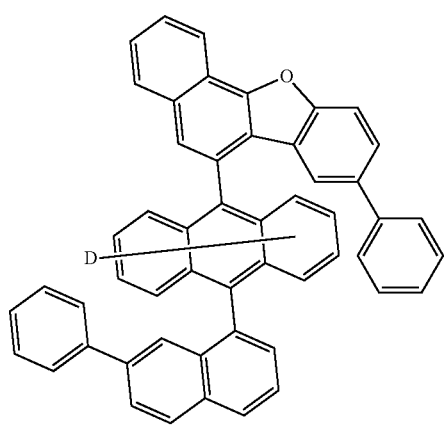

237
-continued
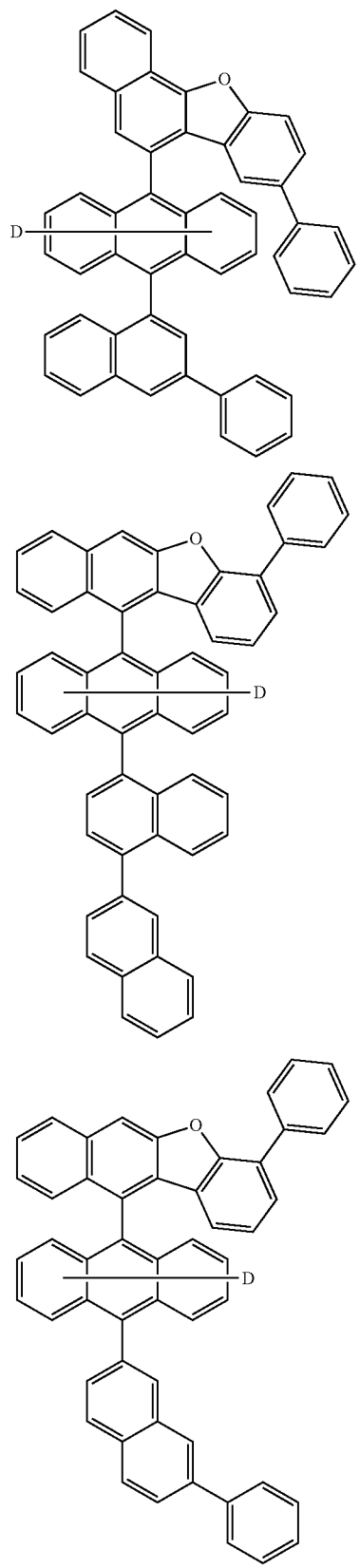
238
-continued
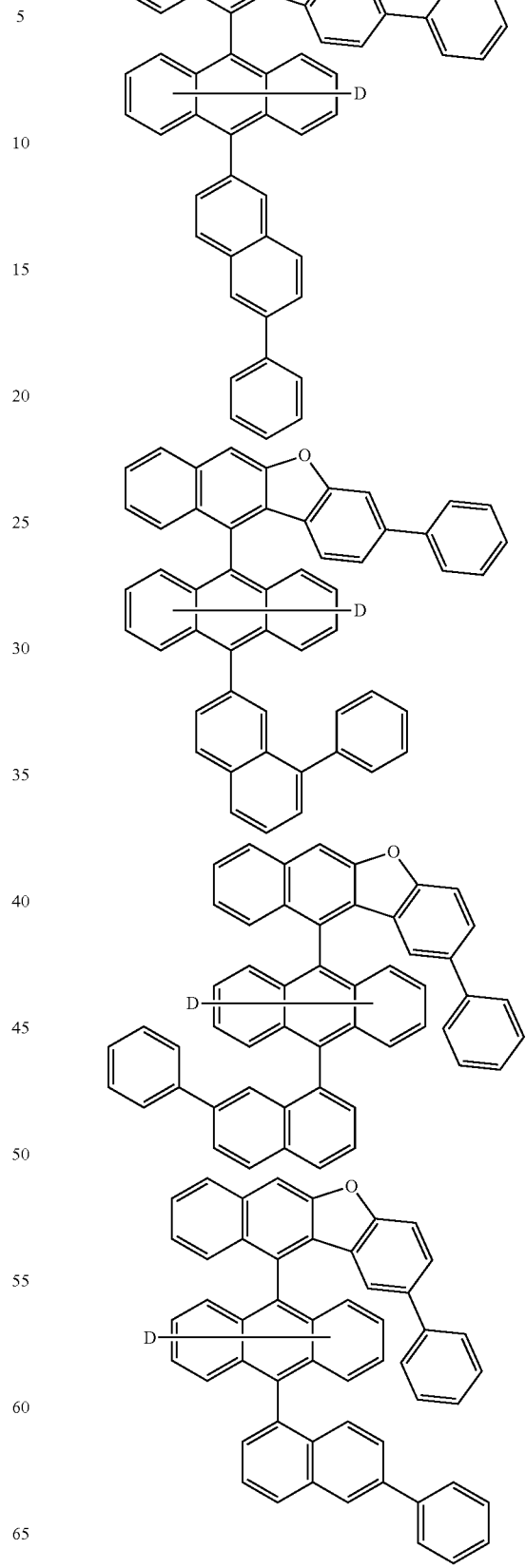

-continued
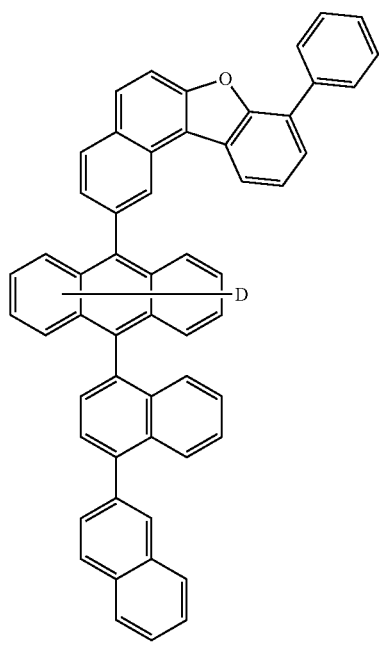
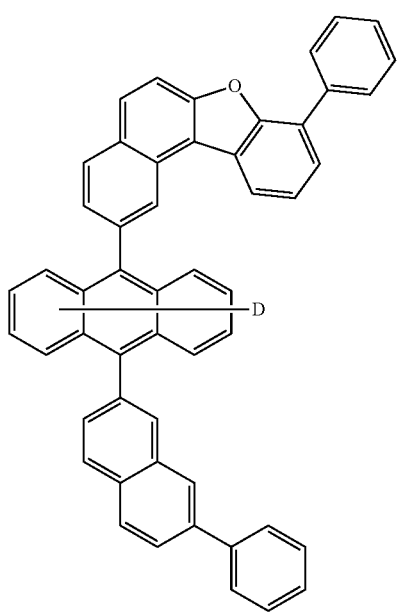
-continued
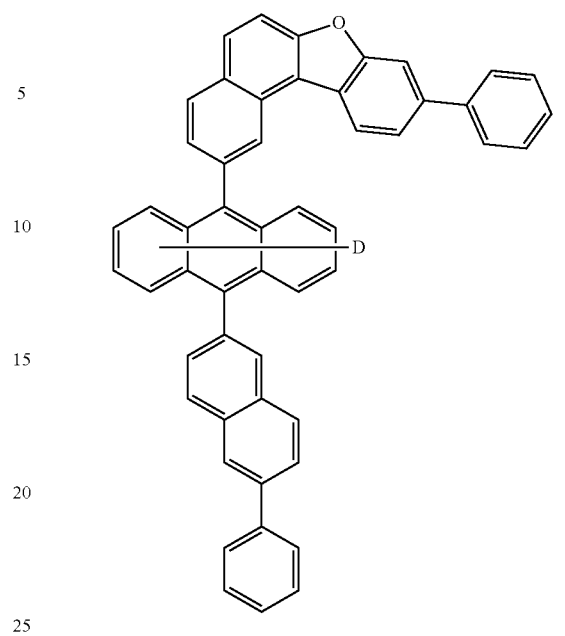
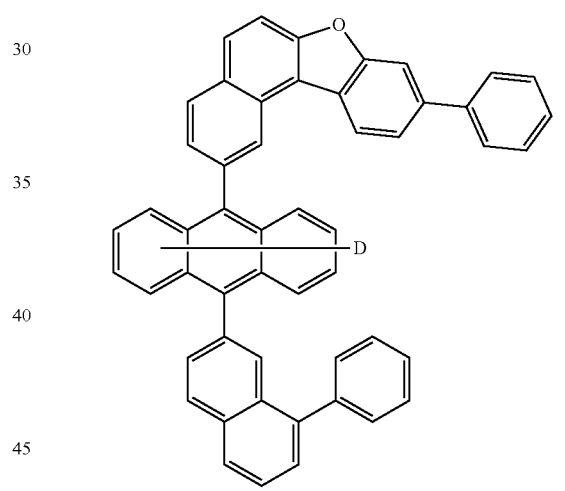
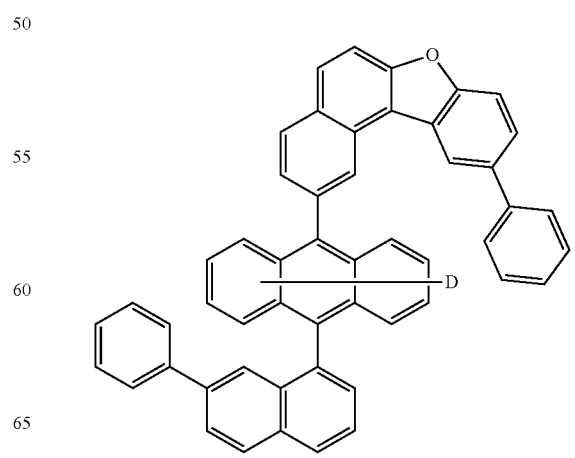

241
-continued
242
-continued
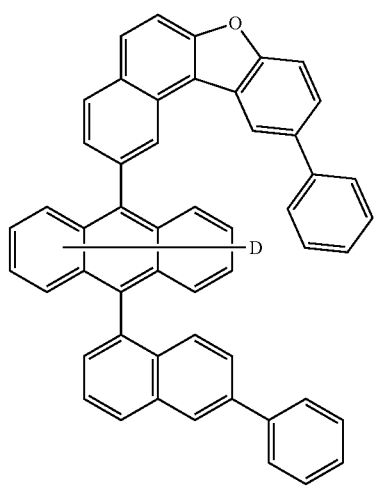
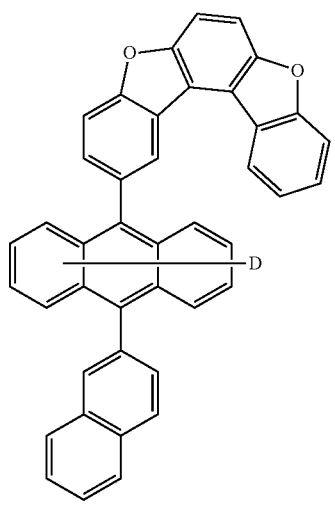
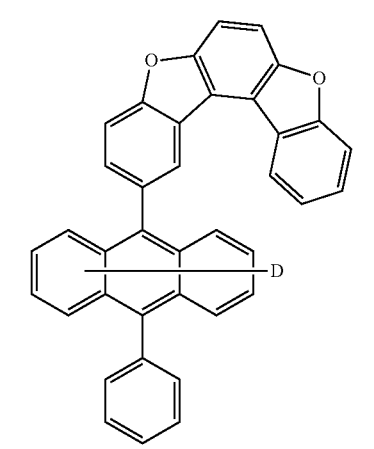
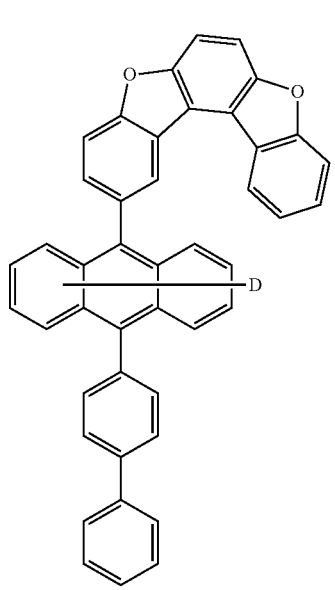
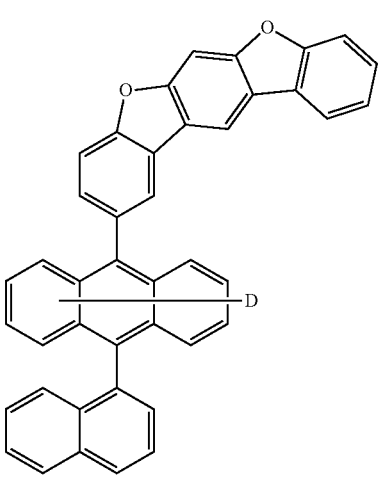
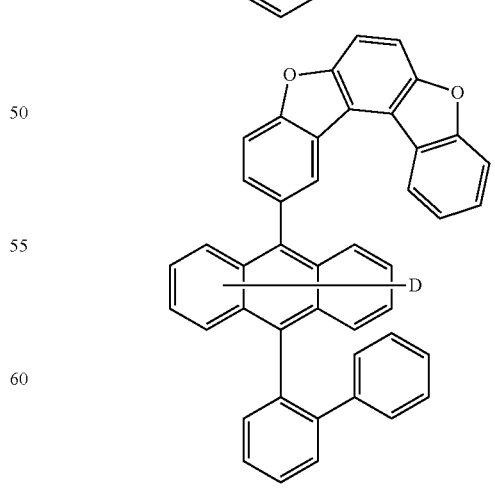

243
-continued
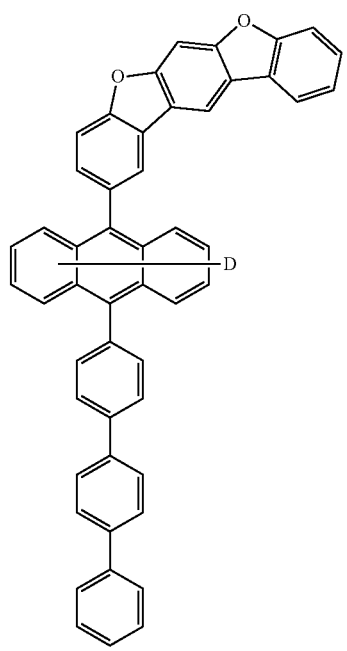
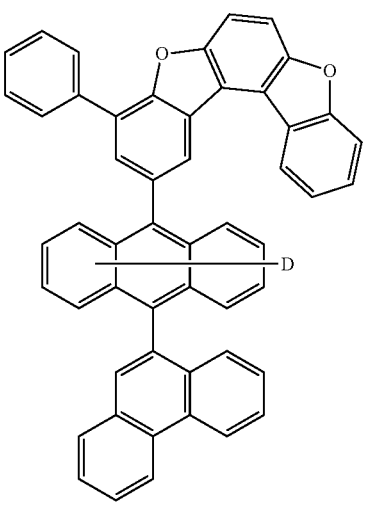
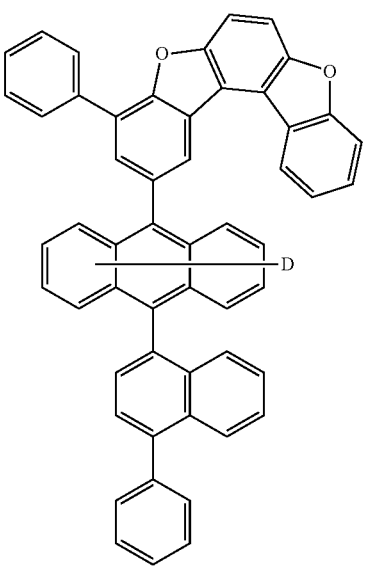
244
-continued
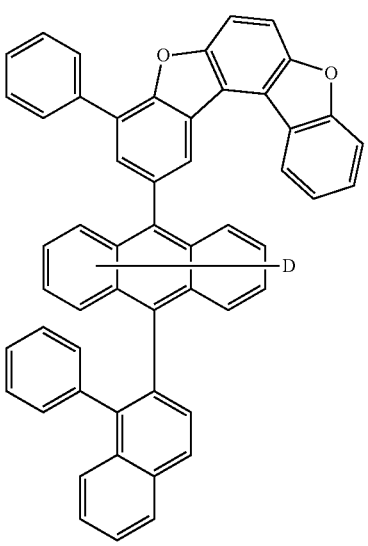
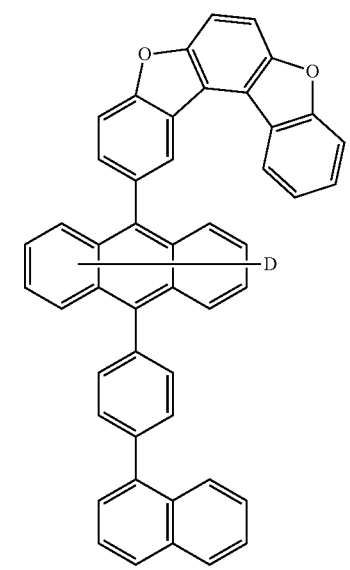

245
-continued
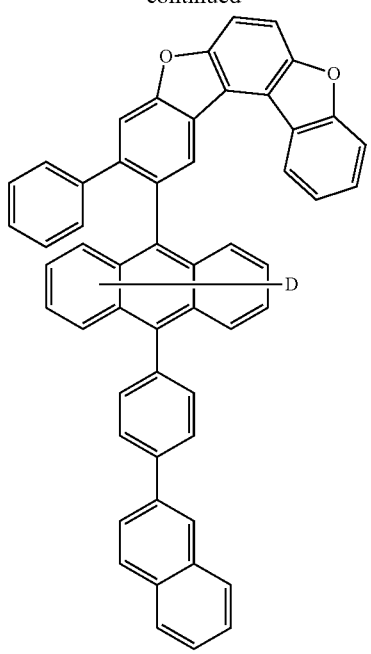
246
-continued
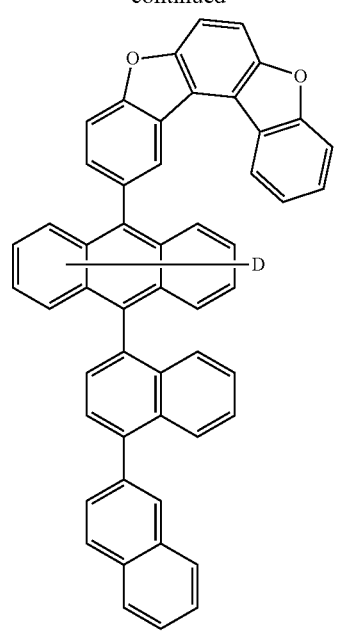
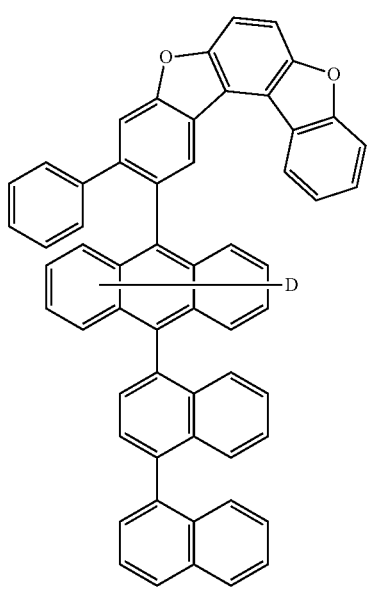
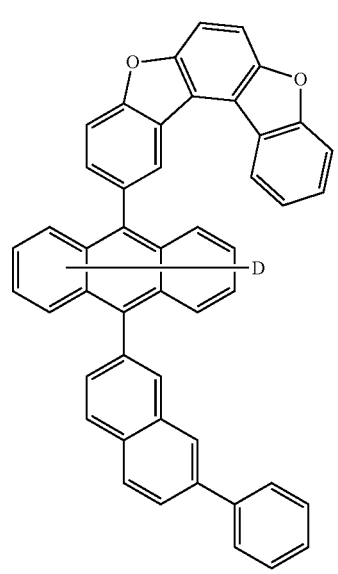

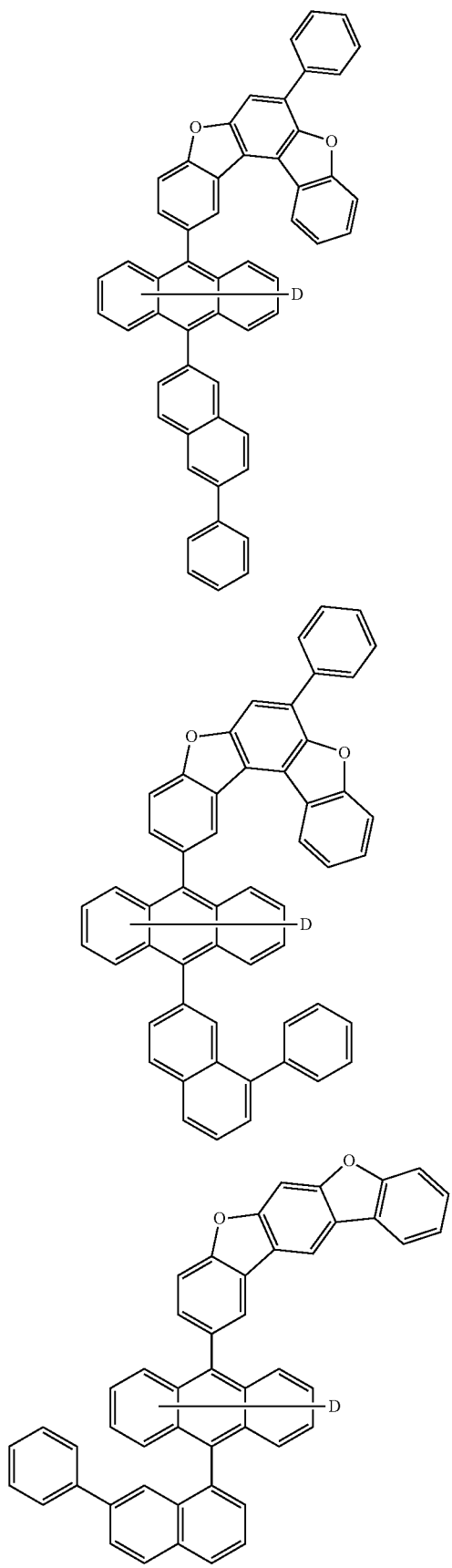
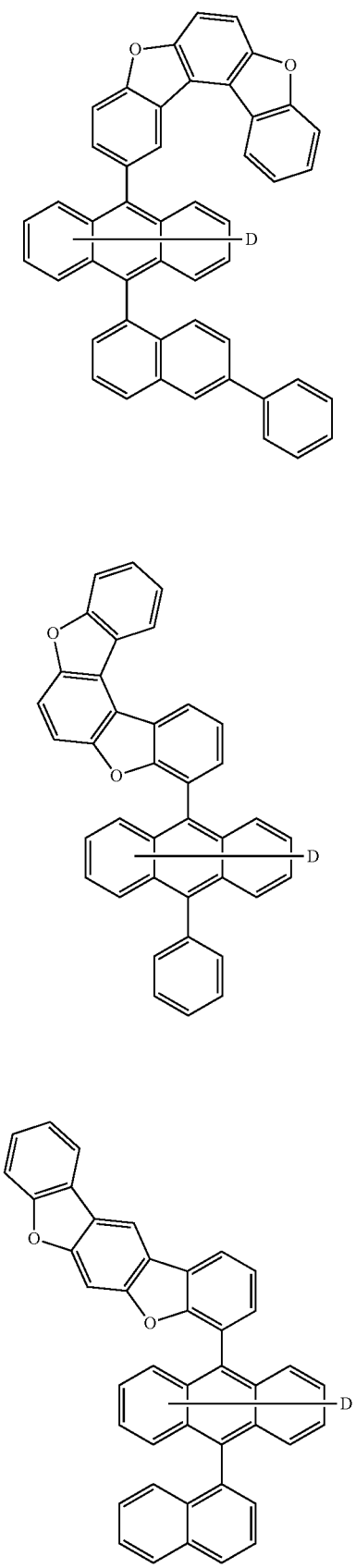

249
-continued
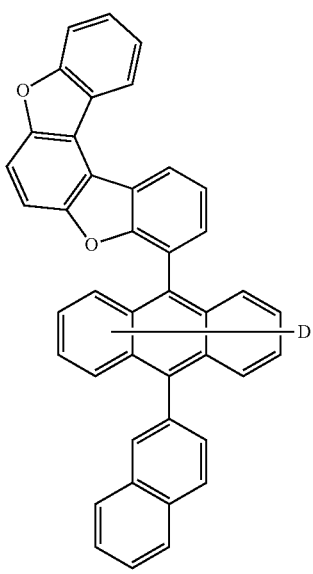
250
-continued
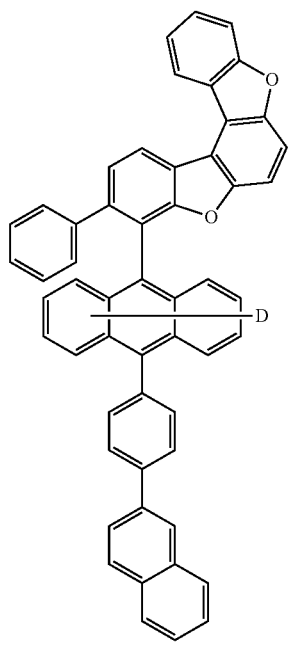
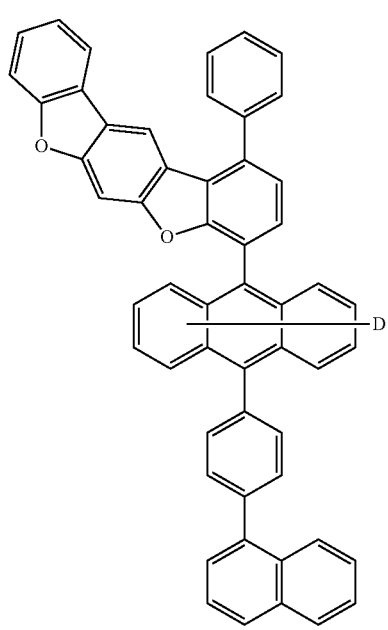
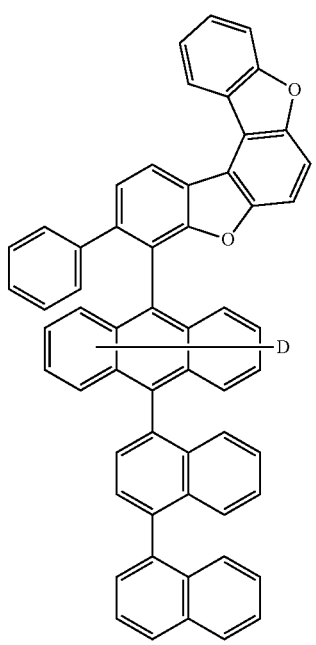

251
-continued
252
-continued
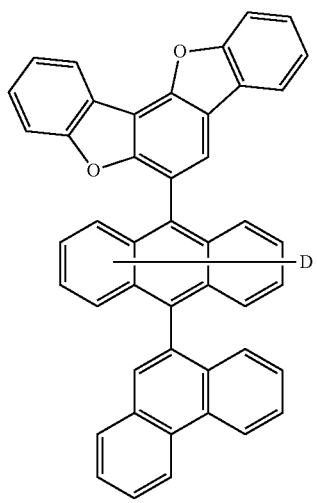
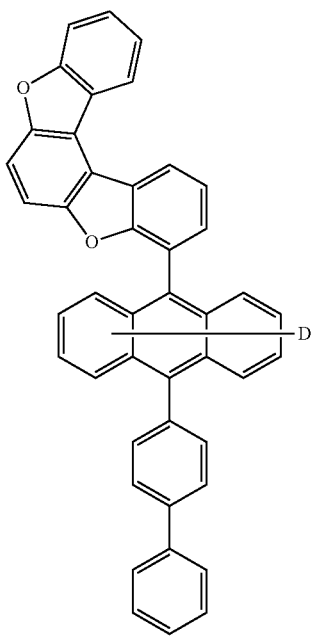
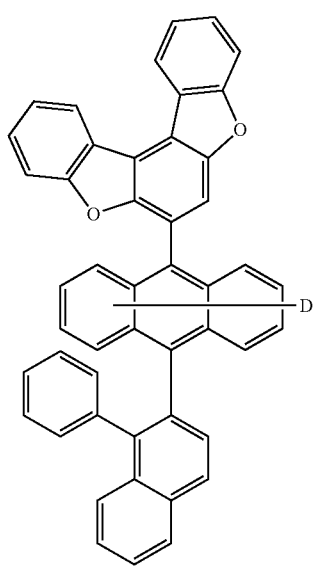

253
-continued
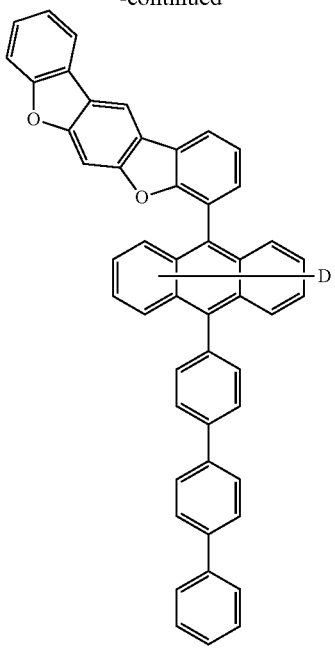
wherein in the compounds, D means deuterium, and when the corresponding structure is substituted with deuterium, 30% or more of the corresponding structure is substituted with deuterium.
8. The organic light emitting device of claim 1, wherein the compound of Formula 2 is selected from among the following compounds:
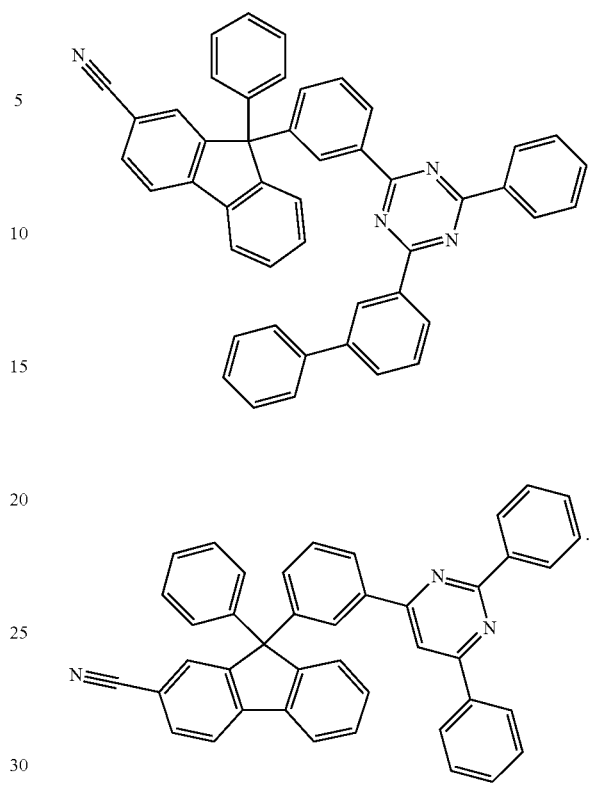
* * * * *